(12) United States Patent
Barbier et al.

(10) Patent No.: US 8,580,809 B2
(45) Date of Patent: *Nov. 12, 2013

(54) FILAMIN A-BINDING ANTI-INFLAMMATORY ANALGESIC

(75) Inventors: Lindsay Burns Barbier, Palo Alto, CA (US); Hoau-Yan Wang, Philadelphia, PA (US); Nan-Horng Lin, Vernon Hills, IL (US); Andrei Blasko, San Bruno, CA (US)

(73) Assignee: Pain Therapeutics, Inc., Austin, TX (US)

( * ) Notice: Subject to any disclaimer, the term of this patent is extended or adjusted under 35 U.S.C. 154(b) by 497 days.

This patent is subject to a terminal disclaimer.

(21) Appl. No.: 12/719,589

(22) Filed: Mar. 8, 2010

(65) Prior Publication Data

US 2011/0105547 A1    May 5, 2011

Related U.S. Application Data

(63) Continuation-in-part of application No. 12/609,518, filed on Oct. 30, 2009.

(51) Int. Cl.
A01N 43/42      (2006.01)
A61K 31/44      (2006.01)
C07D 471/10     (2006.01)
C07D 471/20     (2006.01)

(52) U.S. Cl.
USPC .................................. 514/278; 546/20

(58) Field of Classification Search
USPC .................................. 514/278; 546/20
See application file for complete search history.

(56) References Cited

U.S. PATENT DOCUMENTS

| | | | |
|---|---|---|---|
| 5,852,029 A | 12/1998 | Fisher et al. | |
| 5,869,496 A | 2/1999 | Hale et al. | |
| 6,060,469 A | 5/2000 | Baker et al. | |
| 7,049,321 B2 | 5/2006 | Fisher et al. | |
| 7,560,468 B2 * | 7/2009 | Sundermann et al. | 514/278 |
| 7,951,815 B2 | 5/2011 | Sundermann et al. | |
| 2004/0192916 A1 | 9/2004 | Buschmann et al. | |
| 2007/0015783 A1 | 1/2007 | Sundermann et al. | |
| 2007/0117824 A1 | 5/2007 | Berk et al. | |
| 2011/0105487 A1 | 5/2011 | Barbier et al. | |
| 2012/0083476 A1 | 4/2012 | Breitenbucher et al. | |

FOREIGN PATENT DOCUMENTS

WO    WO 2010/051476 A1    5/2010

OTHER PUBLICATIONS

ZINC12342403 Coumpound Summary—NCBI PubChem Chemical Database, (Nov. 2007).
Restriction mailed Mar. 31, 2011.
Office Action mailed Jul. 20, 2011 in U.S. Appl. No. 12/610,091.
Final Office Action mailed Jan. 11, 2012.
Advisory Action Mailed Mar. 8, 2012.
Office Action mailed May 22, 2012.
Noller, *Chemistry of Organic Compounds*, .W.B. Saunders Co., Philadelphia, 1951, p. 35.
Anderson (Chem and Biol 10:787-797, 2003).
Thiel (Nature Biotechnol 2:513-519, 2004).
Written Opinion and Preliminary Report for PCT/US2009/062823 (May 3, 2011).
Written Opinion and Preliminary Report for PCT/US2009/062860 (May 3, 2011).
Art 1965:29665 CAPLUS; Doc. No. 62:29665 (1965).
Art CAS RN 10708056-65-0 (Nov. 4, 2008).
STN Search Report (Accession No. 2007:564923) (2007).
Action in U.S. Appl. No. 12/609,518 Mailed Dec. 20, 2012.
U.S. Appl. No. 12/609,518 Notice of Allowance, Aug. 6, 2013.
Eliel et al., *Stereochemistry of Organic Compounds*, John Wiley & Sons, New York, (1994) pp. 11-15.
J. McMurry, *Organic Chemistry*, 6th ed., Brooks/Cole-Thomson Learning, Belmont, CA, (2004) pp. 75-77.

* cited by examiner

*Primary Examiner* — Kendra D Carter
(74) *Attorney, Agent, or Firm* — Husch Blackwell, LLP

(57) ABSTRACT

A compound, its pharmaceutically acceptable salt, a composition containing the same and method of treatment that can provide analgesia and/or reduce inflammation are disclosed. A contemplated compound has a structure that corresponds to Formula A, wherein G, W, Q, Z, D, E, F, K, Y, d, e, f, k, n, m, and circle B and all R groups are defined within.

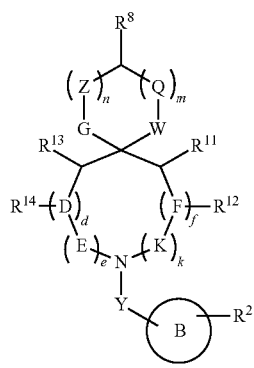

8 Claims, No Drawings

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial sequence
<220> FEATURE:
<223> OTHER INFORMATION: chemically synthesized FLNA sequence that
      corresponds to amino acid residue positions 2561-2565 of the
      FLNA protein

<400> SEQUENCE: 1

Val Ala Lys Gly Leu
1               5
```

FILAMIN A-BINDING ANTI-INFLAMMATORY ANALGESIC

CROSS-REFERENCE TO RELATED APPLICATION

This application is a continuation-in-part of application Ser. No. 12/609,518, filed on Oct. 30, 2009 that claims priority from application Ser. No. 12/263,257 that was filed on Oct. 31, 2008, and application Ser. No. 12/435,304 that was filed on May 4, 2009, whose disclosures are incorporated herein by reference.

TECHNICAL FIELD

This invention contemplates a composition and related method for providing long-lasting analgesia and reducing inflammation. More particularly, a compound, composition and method are described that utilize a small molecule to bind filamin A, to reduce inflammation and to preserve Gi/o signaling by the mu opioid receptor, known to interact with filamin A. Preferably, the compound reduces inflammation, preserves mu opioid receptor—Gi/o signaling and also functions as a mu opioid receptor agonist. Most preferably, the compound binds filamin A with picomolar or sub-picomolar affinity.

BACKGROUND OF THE INVENTION

Best known for cross-linking cytoplasmic actin into dynamic scaffolds to control cell motility, filamins are large cytoplasmic proteins increasingly found to regulate cell signaling by interacting with over 30 different receptors and signaling molecules (Feng et al., 2004 *Nat Cell Biol* 6:1034-1038; Stossel et al., 2001 *Nature* 2:138-145), including the mu opioid receptor (MOR) (Onoprishvili et al, 2003 *Mol Pharmacol* 64:1092-1100). Filamins are dimerized through the last carboxy-terminal repeat near the transmembrane regions, allowing an intracellular V-shaped structure that is critical for function. There are three mammalian isoforms: filamin A (FLNA), B and C.

FLNA controls cell motility by controlling the cycle of actin polymerization and depolymerization, allowing cells to move and to migrate. As actin depolymerization is linked to the inflammatory response, binding to FLNA suppresses inflammation by slowing actin polymerization and cell motility. Femtomolar naloxone and its inactive isomer, both known to bind FLNA (Wang et al., 2008 *PLoS One* 3:e1554), have been shown to reduce the microglial inflammatory response; i.e., pro-inflammatory factors and reactive oxygen species, of lipopolysaccaride-activated microglial cells (Liu et al, 2000 *JPET* 293:607-617; Qin et al., 2005 *FASEB J* 19:550-557). The glial inflammatory response has been implicated in neuropathic pain (Hutchinson et al., 2008 *Eur J Neurosci* 28:20-29) as well as the inflammatory neurotoxicity of neurodegenerative disease (Liu et al., 2003 *JPET* 304:1-7).

A second function of binding to FLNA is a beneficial regulation of opioid receptor signaling; i.e., a maintenance of coupling to Gi and Go proteins. MOR preferentially couples to pertussis toxin-sensitive G proteins, Gi/o (inhibitory/other), and inhibits the adenylyl cyclase/cAMP pathway (Laugwitz et al., 1993 *Neuron* 10:233-242; Connor et al., 1999 *Clin Exp Pharmacol Physiol* 26:493-499). Analgesia results from these MOR-linked inhibitory G protein (Gi/o) signaling cascades and related ion channel interactions that suppress cellular activities by hyperpolarization.

Adaptive responses of opioid receptors contribute to the development of analgesic tolerance and physical dependence, and possibly also to components of opioid addiction. A critical adaptive response of the MOR is a switch in G protein coupling from its native Gi/o proteins to stimulatory Gs proteins, resulting in opposite effects on the cell upon activation as well as analgesic tolerance and physical dependence (Wang et al., 2005 *Neuroscience* 135:247-261). Prevention of this G protein coupling switch by agents that bind filamin A (Wang et al, 2008 *PLoS One* 3:e1554), a scaffolding protein known to interact with MOR, can alleviate unwanted adaptive responses to continued opioid administration.

A chronic opioid-induced switch to Gs coupling by MOR can cause excitatory signaling, by activation of adenylyl cyclase, in place of the usual inhibitory signaling or inhibition of adenylyl cyclase (Crain et al., 1992 *Brain Res* 575:13-24; Crain et al., 2000 *Pain* 84:121-131; Gintzler et al., 2001 *Mol Neurobiol* 21:21-33; Wang et al., 2005 *Neuroscience* 135:247-261). This switch in G protein coupling from Gi/o to Gs (Wang et al., 2005 *Neuroscience* 135:247-261; Chakrabarti et al., 2005 *Mol Brain Res* 135:217-224) may be a result of the decreased efficiency of coupling to the native G proteins, the usual index of desensitization (Sim et al., 1996 *J Neurosci* 16:2684-2692) and still commonly considered the reason for analgesic tolerance.

The chronic opioid-induced MOR-G protein coupling switch is accompanied by stimulation of adenylyl cyclase II and IV by MOR-associated Gβγ dimers (Chakrabarti et al., 1998 *Mol Pharmacol* 54:655-662; Wang et al., 2005 *Neuroscience* 135:247-261). The interaction of the Gβγ dimer with adenylyl cyclase had previously been postulated to be the sole signaling change underlying the excitatory effects of opiates (Gintzler et al., 2001 *Mol Neurobiol* 21:21-33). It has further been shown that the Gβγ that interacts with adenylyl cyclases originates from the Gs protein coupling to MOR and not from the Gi/o proteins native to MOR (Wang et al., 2006 *J Neurobiol* 66:1302-1310).

Thus, MORs are normally inhibitory G protein-coupled receptors that couple to Gi or Go proteins to inhibit adenylyl cyclase and decrease production of the second messenger cAMP, as well as to suppress cellular activities via ion channel-mediated hyperpolarization. Opioid analgesic tolerance and dependence are also associated with that switch in G protein coupling by MOR from Gi/o to Gs (Wang et al., 2005 *Neuroscience* 135:247-261). This switch results in activation of adenylyl cyclase that provides essentially opposite, stimulatory, effects on the cell.

Controlling this switch in G protein coupling by MOR is the scaffolding protein FLNA, and compounds that bind a particular segment of FLNA with high affinity, like naloxone (NLX) and naltrexone (NTX), can prevent this switch (Wang et al, 2008 *PLoS One* 3:e1554) and the associated analgesic tolerance and dependence (Wang et al., 2005 *Neuroscience* 135:247-261). This switch in G protein coupling also occurs acutely, though transiently, and is potentially linked to the acute rewarding or addictive effects of opioid drugs, through CREB activation as a result of increased cAMP accumulation (Wang et al., 2009 *PLoS ONE* 4(1):e4282).

Ultra-low-dose NLX or NTX have been shown to enhance opioid analgesia, minimize opioid tolerance and dependence (Crain et al., 1995 *Proc Natl Acad Sci USA* 92:10540-10544; Powell et al. 2002. *JPET* 300:588-596), as well as to attenuate the addictive properties of opioids (Leri et al., 2005 *Pharmacol Biochem Behav* 82:252-262; Olmstead et al., 2005 *Psychopharmacology* 181:576-581). An ultra-low dose of opioid antagonist was an amount initially based on in vitro studies of nociceptive dorsal root ganglion neurons and on in vivo mouse studies. It has long been hypothesized that ultra-low-dose opioid antagonists enhance analgesia and alleviate tolerance/dependence by blocking the excitatory signaling opioid receptors that underlie opioid tolerance and hyperalgesia (Crain et al., 2000 *Pain* 84:121-131). Later research has shown that the attenuation of opioid analgesic tolerance, dependence and addictive properties by ultra-low-dose, defined herein, naloxone or naltrexone, occurs by preventing the MOR-Gs coupling that results from chronic opiate administration (Wang et al., 2005 *Neuroscience* 135:247-261), and that the prevention of MOR-Gs coupling is a result of NLX or NTX binding to filamin A at approximately 4 picomolar affinity (Wang et al, 2008 *PLoS One* 3:e1554).

Found in all cells of the brain, CREB is a transcription factor implicated in addiction as well as learning and memory and several other experience-dependent, adaptive (or maladaptive) behaviors (Carlezon et al., 2005 *Trends Neurosci* 28:436-445). In general, CREB is inhibited by acute opioid treatment, an effect that is completely attenuated by chronic opioid treatment, and activated during opioid withdrawal (Guitart et al., 1992 *J Neurochem* 58:1168-1171). However, a regional mapping study showed that opioid withdrawal activates CREB in locus coeruleus, nucleus accumbens and amygdala but inhibits CREB in lateral ventral tegemental area and dorsal raphe nucleus (Shaw-Luthman et al., 2002 *J Neurosci* 22:3663-3672).

In the striatum, CREB activation has been viewed as a homeostatic adaptation, attenuating the acute rewarding effects of drugs (Nestler, 2001 *Am J Addict* 10:201-217; Nestler, 2004 *Neuropharmacology* 47:24-32). This view is supported by nucleus accumbens overexpression of CREB or a dominant-negative mutant respectively reducing or increasing the rewarding effects of opioids in the conditioned place preference test (Barot et al., 2002 *Proc Natl Acad Sci USA* 99:11435-11440). In conflict with this view, however, is the finding that reducing nucleus accumbens CREB via antisense attenuated cocaine reinforcement as assessed in self-administration (Choi et al., 2006 *Neuroscience* 137:373-383). Clearly, CREB activation is implicated in addiction, but whether it directly contributes to the acute rewarding effects of drugs or initiates a homeostatic regulation thereof appears less clear.

The several-fold increase in pS$^{133}$CREB reported by Wang et al., 2009 *PLoS ONE* 4(1):e4282 following acute, high-dose morphine may indicate acute dependence rather than acute rewarding effects. However, the transient nature of the MOR-Gs coupling correlating with this CREB activation suggests otherwise. In fact, the correlation of pS$^{133}$CREB with the Gs coupling by MOR following this acute high-dose morphine exposure, as well as the similar treatment effects on both, suggest that this alternative signaling mode of MOR can contribute to the acute rewarding or addictive effects of opioids. This counterintuitive notion can explain the apparent paradox that ultra-low-dose NTX, while enhancing the analgesic effects of opioids, decreases the acute rewarding or addictive properties of morphine or oxycodone as measured in conditioned place preference or self-administration and reinstatement paradigms.

In considering analgesic tolerance, opioid dependence, and opioid addiction together as adaptive regulations to continued opioid exposure, a treatment that prevents MOR's signaling adaptation of switching its G protein partner can logically attenuate these seemingly divergent behavioral consequences of chronic opioid exposure.

Even though ultra-low-dose NTX blocks the conditioned place preference to oxycodone or morphine (Olmstead et al., 2005 *Psychopharmacology* 181:576-581), its co-self-administration only reduces the rewarding potency of these opioids but does not abolish self-administration outright (Leri et al., 2005 *Pharmacol Biochem Behav* 82:252-262). It is possible that a direct stimulatory effect on VTA neurons, as opposed to the proposed disinhibition via inhibition of GABA interneurons (Spanagel et al., 1993 *Proc Natl Acad Sci USA* 89:2046-2050), can play some role in opioid reward. A MOR-Gs coupling mediation of reward, increasing with increasing drug exposure, is in keeping with current theories that the escalation of drug use signifying drug dependence can not indicate a "tolerance" to rewarding effects but instead a sensitization to rewarding effects (Zernig et al., 2007 *Pharmacology* 80:65-119).

The results reported in Wang et al., 2009 *PLoS ONE* 4(1): e4282 demonstrated that acute, high-dose morphine causes an immediate but transient switch in G protein coupling by MOR from Go to Gs similar to the persistent switch caused by chronic morphine. Ultra-low-dose NLX or NTX prevented this switch and attenuated the chronic morphine-induced coupling switch by MOR. The transient nature of this acute altered coupling suggests the receptor eventually recovers and couples to its native G protein.

With chronic opioid exposure, the receptor can lose the ability to recover and continue to couple to Gs, activating the adenylyl cyclase/cAMP pathway, upregulating protein kinase A, and phosphorylating CREB as one downstream effector example. The persistently elevated phosphorylated CREB can then shape the expression of responsive genes including those closely related to drug addiction and tolerance. Importantly, the equivalent blockade of Gs coupling and pS$^{133}$CREB by the pentapeptide binding site of naloxone (NLX) and naltrexone (NTX) on FLNA further elucidates the mechanism of action of ultra-low-dose NLX and NTX in their varied effects.

These data further strengthen the regulation of MOR-Gs coupling by FLNA and that binding to FLNA or using a FLNA peptide decoy for MOR can prevent the altered MOR coupling, thereby attenuating tolerance, dependence and addictive properties associated with opioid drugs.

The combination of ultra-low-dose opioid antagonists with opioid agonists formulated together in one medication has been shown to alleviate many of these undesirable aspects of opioid therapy (Burns, 2005 *Recent Developments in Pain Research* 115-136, ISBN: 81-308-0012-8). This approach shows promise for an improvement in analgesic efficacy, and animal data suggests reduced addictive potential. The identification of the cellular target of ultra-low-dose NLX or NTX in their inhibition of mu opioid receptor—Gs coupling as a pentapeptide segment of filamin A (Wang et al., 2008 PLoS ONE 3(2):e1554) has led to development of assays to screen against this target to create a new generation of pain therapeutics that can provide long-lasting analgesia with minimal tolerance, dependence and addictive properties. Importantly, the non-opioid cellular target of ultra-low-dose NLX or NTX, FLNA, provides potential for developing either a therapeutic combination of which one component is not required to be ultra-low-dose, or a single-entity novel analgesic.

Sundermann et al. U.S. Pat. No. 7,560,468 discloses a vast number of substituted 1,4,9-triazaspiro[4,5]decan-2-one compounds that correspond in structure to the formula below, wherein the

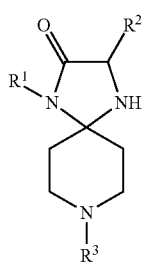

various R groups can provide compounds similar to but different from some of those disclosed hereinafter. In particular, each of $R^1$ and $R^2$ can be hydrogen or any of a large number of substituents, whereas $R^3$ must be a —S(=O)$_2$—$R^4$, —C(=S)NH—$R^5$ or —C(=O)NH—$R^6$; i.e., part of a sulfonamide, thiourea or urea substituent. The compounds are said to be useful for treating and/or preventing almost a complete printed patent column of ailments from various types of pain, inflammation, allergies, multiple sclerosis, rheumatoid arthritis, lupus erythematosis, Tourette's syndrome, various ischemias, blood poisoning, diabetes, sepsis, cancer, particularly leukemia and/or cerebral tumor, and several other diseases.

Published US Patent application No. 20090105290 A1 teaches substituted 1-oxa-3,8-diazaspiro[4,5]decan-2-one compounds that correspond in structure to the formula below, in which the

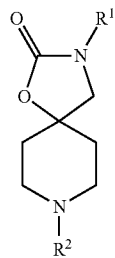

R groups can provide a huge number of possible compounds that are somewhat similar to, but are different from some of those disclosed hereinafter. The list of ailments for which the compounds of this application are said to be useful is almost as long as that of U.S. Pat. No. 7,560,468. Included among the disease states for published application No. 20090105290 A1 are the following: pain, preferably of pain selected from the group consisting of acute pain, chronic pain, visceral pain and neuropathic pain; for the prevention and/or treatment of one or more diseases selected from the group consisting of disorders of food intake, preferably selected from the group consisting of bulimia, anorexia, obesity and cachexia; water retention conditions; migraine; chronic paroxysmal hemicrania; depression; urinary incontinence; coughing; asthma; glaucoma; tinnitus; inflammation; neurodegenerative diseases, preferably selected from the group consisting of Parkinson's disease, Huntington's chorea, Alzheimer's disease and multiple sclerosis; cognitive dysfunction, preferably memory disorders; cognitive deficiency states (attention deficit syndrome, ADS); epilepsy; catalepsy; narcolepsy; diarrhea; gastritis; stomach ulcer; pruritus; anxiety states; panic attacks; schizophrenia; cerebral ischemic episodes; muscle spasms; cramps; gastro-esophageal reflux syndrome; alcohol and/or drug abuse, preferably nicotine and/or cocaine abuse, and/or abuse of medicines; alcohol and/or drug dependency, preferably nicotine and/or cocaine dependency, and the like.

Sundermann et al. U.S. Pat. No. 7,560,468 discloses a vast number of substituted 1,4,9-triazaspiro[4,5]decan-2-one compounds that correspond in structure to the formula below, wherein the

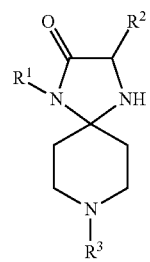

various R groups can provide compounds similar to but different from some of those disclosed hereinafter. In particular, each of $R^1$ and $R^2$ can be hydrogen or any of a large number of substituents, whereas $R^3$ must be a —S(=O)$_2$—$R^4$, —C(=S)NH—$R^5$ or —C(=O)NH—$R^6$; i.e., part of a sulfonamide, thiourea or urea substituent. The compounds are said to be useful for treating and/or preventing almost a complete printed patent column of ailments from various types of pain, inflammation, allergies, multiple sclerosis, rheumatoid arthritis, lupus erythematosis, Tourette's syndrome, various ischemias, blood poisoning, diabetes, sepsis, cancer, particularly leukemia and/or cerebral tumor, and several other diseases.

Published US Patent application No. 20090105290 A1 teaches substituted 1-oxa-3,8-diazaspiro[4,5]decan-2-one compounds that correspond in structure to the formula below, in which the

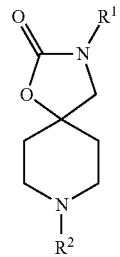

R groups can provide a huge number of possible compounds that are somewhat similar to, but are different from some of those disclosed hereinafter. The list of ailments for which the compounds of this application are said to be useful is almost as long as that of U.S. Pat. No. 7,560,468. Included among the disease states for published application No. 20090105290 A1 are the following: pain, preferably of pain selected from the group consisting of acute pain, chronic pain, visceral pain and neuropathic pain; for the prevention and/or treatment of one or more diseases selected from the group consisting of disorders of food intake, preferably selected from the group consisting of bulimia, anorexia, obesity and cachexia; water retention conditions; migraine; chronic paroxysmal hemicrania; depression; urinary incontinence; coughing; asthma; glaucoma; tinnitus; inflammation; neurodegenerative diseases, preferably selected from the group consisting of Parkinson's disease, Huntington's chorea, Alzheimer's disease and multiple sclerosis; cognitive dysfunction, preferably memory disorders; cognitive deficiency states (attention deficit syndrome, ADS); epilepsy; catalepsy; narcolepsy; diarrhea; gastritis; stomach ulcer; pruritus; anxiety states; panic attacks; schizophrenia; cerebral ischemic episodes; muscle spasms; cramps; gastro-esophageal reflux syndrome; alcohol and/or drug abuse, preferably nicotine and/or cocaine abuse, and/or abuse of medicines; alcohol and/or drug dependency, preferably nicotine and/or cocaine dependency, and the like.

The present invention identifies a compound that binds to filamin A (FLNA; the high-affinity binding site of naloxone [NLX] and naltrexone [NTX]), to reduce cell motility and inflammation as well as to prevent the Gi/o-to-Gs coupling switch of MOR and is similar to or more active than DAMGO in activating MOR.

BRIEF SUMMARY OF THE INVENTION

The present invention contemplates an analgesic compound, a composition containing that compound and a method of reducing pain in a host mammal in need thereof by administering a composition containing such a compound. A contemplated compound corresponds in structure to Formula A

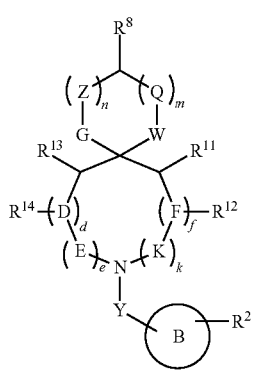

In Formula A,
Q is $CHR^9$ or C(O);
Z is $CHR^{10}$ or C(O), but only one of Q and Z is C(O);
each of m and n is zero or one and the sum of m+n is 1 or 2;
G and W are selected from the group consisting of $NR^{20}$, $NR^7$, S and O, where $R^7$ is H, $C_1$-$C_{12}$ hydrocarbyl, or $C_1$-$C_{12}$ hydrocarboyl(acyl) and $R^{20}$ is a group X-circle A-$R^1$ as defined hereinafter, with the provisos that;
 i) only one of G and W is $NR^{20}$,
 ii) one of G and W must be $NR^{20}$,
 iii) one of G and W is other than $NR^7$ in which $R^7$ is H or an aliphatic $C_1$ hydrocarbyl; i.e., methyl, when (a) the sum of m+n is 1, and (b) the other of G and W is $NR^{20}$ bonded to a Z or Q, respectively, that is C(O), and
 iv) when X and Y are both $SO_2$, W is O, Q is $CH_2$, n is zero, and d and f are both 1, $R^1$ and $R^2$ are other than (a) both H, methoxy, or $C_1$-$C_3$-hydrocarbyl, (b) H, halogen and $C_1$-$C_3$-hydrocarbyl, (c) H and $C_1$-$C_3$-hydrocarbyl, (d) halogen and $C_1$-$C_3$-hydrocarbyl, or (e) H and halogen;
X and Y are the same or different and are $SO_2$, C(O), $CH_2$, $CD_2$, C(O)O, C(NH)NH or C(O)NH; each of d, e, f and k is either zero or one and the sum of (d+e+f+k)=2, e is zero when d is zero, and k is zero when f is zero; D and F are the same or different and are CH or CD; E and K are the same or different and are $CH_2$, CHD or $CD_2$;

the circles A and B are the same or different aromatic or heteroaromatic ring systems containing one ring or two fused rings. Groups $R^1$ and $R^2$ are the same or different and each can be hydrogen or represent up to three substituents other than hydrogen that themselves can be the same or different; i.e., $R^{1a}$, $R^{1b}$, and $R^{1c}$, and $R^{2a}$, $R^{2b}$, and $R^{2c}$. Each of those six groups, $R^{1a-c}$ and $R^{2a-c}$, is separately selected from the group consisting of H, $C_1$-$C_6$ hydrocarbyl, $C_1$-$C_6$ hydrocarbyloxy, $C_1$-$C_6$ hydrocarbyloxycarbonyl, trifluoromethyl, trifluoromethoxy, $C_1$-$C_7$ hydrocarboyl (acyl), hydroxy-, trifluoromethyl-(—$CF_3$) or halogen-substituted $C_1$-$C_7$ hydrocarboyl, $C_1$-$C_6$ hydrocarbylsulfonyl, $C_1$-$C_6$ hydrocarbyloxysulfonyl, halogen, nitro, phenyl, cyano, carboxyl, $C_1$-$C_7$ hydrocarbyl carboxylate [C(O)O—$C_1$-$C_7$ hydrocarbyl], carboxamide [C(O)$NR^3R^4$] or sulfonamide [S(O)$_2NR^3R^4$] wherein the amido nitrogen in either group has the formula $NR^3R^4$ wherein $R^3$ and $R^4$ are the same or different and are H, $C_1$-$C_4$ hydrocarbyl, or $R^3$ and $R^4$ together with the depicted nitrogen form a 5-7-membered ring that optionally contains 1 or 2 additional hetero atoms that independently are nitrogen, oxygen or sulfur, MAr, where M is —$CH_2$—, —O— or —N=N— and Ar is a single-ringed aryl group, and $NR^5R^6$ wherein $R^5$ and $R^6$ are the same or different and are H, $C_1$-$C_4$ hydrocarbyl, $C_1$-$C_4$ acyl, $C_1$-$C_4$ hydrocarbylsulfonyl, or $R^5$ and $R^6$ together with the depicted nitrogen form a 5-7-membered ring that optionally contains 1 or 2 additional hetero atoms that independently are nitrogen, oxygen or sulfur;
$R^8$, $R^9$, and $R^{10}$ are each H, or two of $R^8$, $R^9$, and $R^{10}$ are H and one is a $C_1$-$C_8$ hydrocarbyl group that is unsubstituted or is substituted with up to three atoms that are the same or different and are oxygen or nitrogen atoms; and
$R^{11}$, $R^{12}$, $R^{13}$ and $R^{14}$ are all H, or $R^{11}$ and $R^{13}$ are H and $R^{12}$ and $R^{14}$ are H or D, or one of the pair $R^{11}$ and $R^{12}$ or the pair $R^{13}$ and $R^{14}$ together with the depicted ring form a saturated or unsaturated 6-membered ring, and the other pair are each H or they are H and D as recited above in this subparagraph.

A pharmaceutically acceptable salt of a compound of Formula A and all of the remaining formulas disclosed herein is also contemplated. A contemplated compound or its pharmaceutically acceptable salt can optionally be present in one or more forms. Illustratively, some of the contemplated compounds or their salts can be in the form of an individual enantiomer or diastereoisomer. A contemplated compound or its salt can also be present in the form of a mixture of stereoisomers. A contemplated compound or salt can also be present in the form of a racemic mixture.

A preferred embodiment of a compound of Formula A corresponds in structure to Formula I

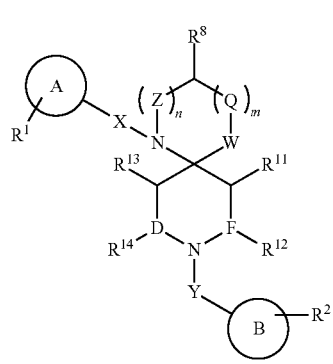

In Formula I, substituents that have the same designations (names) as those of Formula A or B, have the same definitions as in those formulas, unless the formula as shown precludes part of a definition provided for a compound of Formulas A or B. The provisos recited previously are somehat different here. Thus, for Formula I, i) W is other than $NR^7$ in which $R^7$ is H or an aliphatic $C_1$ hydrocarbyl; i.e., methyl, when (a) the sum of m+n is 1, and (b) Z is C(O), and ii) when X and Y are both $SO_2$, W is O, Q is $CH_2$ and n is zero, $R^1$ and $R^2$ are other than (a) both H, methoxy, or $C_1$-$C_3$-hydrocarbyl, (b) H, halogen and $C_1$-$C_3$-hydrocarbyl, (c) H and $C_1$-$C_3$-hydrocarbyl, (d) halogen and $C_1$-$C_3$-hydrocarbyl, or (e) H and halogen;

A pharmaceutical composition is also contemplated. That composition comprises an above compound of Formula A or its pharmaceutically acceptable salt, except for a compound in which $R^1$ and $R^2$ are both methoxy when X and Y are both $SO_2$, W is O, Q is $CH_2$ and n is zero, dissolved or dispersed in a physiologically tolerable carrier. The compound is present in an effective analgesic amount. The composition is preferably in solid form as in a tablet of capsule.

A method of reducing pain and inflammation in a host mammal in need thereof is also contemplated. That method comprises administering to that host mammal a pharmaceutical composition containing a compound of Formula A as disclosed above. The host mammal for such a method is selected from the group consisting of a primate, a laboratory rodent, a companion animal, and a food animal. A composition can be administered a plurality of times over a period of days, as well as administered a plurality of times in one day. That administration can be perorally or parenterally.

The present invention has several benefits and advantages.

One benefit is anti-inflammatory action combined with analgesia by a compound with a novel mechanism of action for both that does not have a narcotic structure.

An advantage of the invention is that analgesia can be provided by administration of a contemplated composition either perorally or parenterally.

A further benefit of the invention is that as indicated by the initial data, a contemplated compound provides the analgesic effects characteristic of opioid drugs but does not cause analgesic tolerance or dependence.

Another advantage of the invention as also indicated by the initial data is that a contemplated compound provides the analgesic effects characteristic of opioid drugs and does not have the addictive potential of opioid drugs.

Still further benefits and advantages will be apparent to a skilled worker from the description that follows.

ABBREVIATIONS AND SHORT FORMS

The following abbreviations and short forms are used in this specification.

"MOR" means μ-opioid receptor
"FLNA" means filamin A
"NLX" means naloxone
"NTX" means naltrexone
"Gαi/o" means G protein alpha subunit—inhibitory/other conformation, inhibits adenylyl cyclase
"Gαs" means G protein alpha subunit—stimulatory conformation stimulates adenylyl cyclase
"Gβγ" means G protein beta gamma subunit
"cAMP" means cyclic adenosine monophosphate
"CREB" means cAMP Response Element Binding protein
"IgG" means Immunoglobulin G

DEFINITIONS

In the context of the present invention and the associated claims, the following terms have the following meanings:

The articles "a" and "an" are used herein to refer to one or to more than one (i.e., to at least one) of the grammatical object of the article. By way of example, "an element" means one element or more than one element.

As used herein, the term "hydrocarbyl" is a short hand term for a non-aromatic group that includes straight and branched chain aliphatic as well as alicyclic groups or radicals that contain only carbon and hydrogen. Inasmuch as alicyclic groups are cyclic aliphatic groups, such substituents are deemed hereinafter to be subsumed within the aliphatic groups. Thus, alkyl, alkenyl and alkynyl groups are contemplated, whereas aromatic hydrocarbons such as phenyl and naphthyl groups, which strictly speaking are also hydrocarbyl groups, are referred to herein as aryl groups, substituents, moieties or radicals, as discussed hereinafter. An aralkyl substituent group such as benzyl is deemed an aromatic group as being an aromatic ring bonded to an X or Y group, where X or Y is $CH_2$. A substituent group containing both an aliphatic ring and an aromatic ring portion such as tetralin (tetrahydronaphthalene) that is linked via an aliphatic or aromatic carbon atom to the depicted ring containing the W group is deemed a non-aromatic, hydrocarbyl group. Where a specific aliphatic hydrocarbyl substituent group is intended, that group is recited; i.e., $C_1$-$C_4$ alkyl, methyl or dodecenyl. Exemplary hydrocarbyl groups contain 1 to about 12 carbon atoms, and preferably 1 to about 8 carbon atoms, and more preferably 1 to 6 carbon atoms of an alkyl group. A hydrocarbyl group can be straight or branched chain or cyclic.

A particularly preferred hydrocarbyl group is an alkyl group. As a consequence, a generalized, but more preferred substituent can be recited by replacing the descriptor "hydrocarbyl" with "alkyl" in any of the substituent groups enumerated herein.

Examples of alkyl radicals include methyl, ethyl, n-propyl, isopropyl, n-butyl, isobutyl, sec-butyl, tert-butyl, pentyl, isoamyl, hexyl, octyl, decyl, dodecyl and the like. Examples of suitable alkenyl radicals include ethenyl (vinyl), 2-propenyl, 3-propenyl, 1,4-pentadienyl, 1,4-butadienyl, 1-butenyl, 2-butenyl, 3-butenyl, decenyl and the like. Examples of alkynyl radicals include ethynyl, 2-propynyl, 3-propynyl, decynyl, 1-butynyl, 2-butynyl, 3-butynyl, and the like.

Usual chemical suffix nomenclature is followed when using the word "hydrocarbyl" except that the usual practice of removing the terminal "yl" and adding an appropriate suffix is not always followed because of the possible similarity of a resulting name to one or more substituents. Thus, a hydrocarbyl ether is referred to as a "hydrocarbyloxy" group rather than a "hydrocarboxy" group as may possibly be more proper when following the usual rules of chemical nomenclature. Illustrative hydrocarbyloxy groups include methoxy, ethoxy, and cyclohexenyloxy groups.

On the other hand, a hydrocarbyl group containing a —C(O)O— functionality is referred to as a hydrocarboyl (acyl) or hydrocarboyloxy group inasmuch as there is no ambiguity. Exemplary hydrocarboyl and hydrocarboyloxy groups include acyl and acyloxy groups, respectively, such as acetyl and acetoxy, acryloyl and acryloyloxy.

Carboxyl-related linking groups between the central spiro ring system and an aromatic or heteroaromatic ring system, circle A, include several types of ester and amide bonds. Illustrative of such bonds are sulfonamide, sulfonate and thiosulfonate esters that can be formed between a $SO_2$-containing group and an amine, oxygen or sulfur atom, respectively. Amide, ester and thioester links can be formed between an aromatic or heteroaromatic ring containing a C(O) group and a nitrogen, oxygen or sulfur atom, respectively. Similarly, a guanidino linker can be formed between an aromatic or heteroaromatic ring containing a NHC(NH) group and a nitrogen, a urethane, carbonate or thiocarbonate can be formed between an aromatic or heteroaromatic ring containing a OC(O) group and a nitrogen, oxygen or sulfur, respectively. A compound containing a urea linker, urethane linker or isothiourea linker [NHC(O)S] can be formed between an aromatic or heteroaromatic ring containing a NHC(O) group and a nitrogen, oxygen or sulfur, respectively.

A "carboxyl" substituent is a —C(O)OH group. A $C_1$-$C_6$ hydrocarbyl carboxylate is a $C_1$-$C_6$ hydrocarbyl ester of a carboxyl group. A carboxamide is a —C(O)$NR^3R^4$ substituent, where the R groups are defined hereinafter. Similarly, a sulfonamide is a —S(O)$_2NR^3R^4$ substituent, where the R groups are defined hereinafter. Illustrative $R^3$ and $R^4$ groups that together with the depicted nitrogen of a carboxamide form a 5-7-membered ring that optionally contains 1 or 2 additional hetero atoms that independently are nitrogen, oxygen or sulfur, include morpholinyl, piperazinyl, oxathiazolyl, 1,2,3-triazolyl, 1,2,4-triazolyl, pyrazolyl, 1,2,4-oxadiazinyl and azepinyl groups.

As a skilled worker will understand, a substituent that cannot exist such as a $C_1$ alkenyl or alkynyl group is not intended to be encompassed by the word "hydrocarbyl", although such substituents with two or more carbon atoms are intended.

The term "aryl", alone or in combination, means a phenyl or naphthyl radical that optionally carries one or more substituents selected from hydrocarbyl, hydrocarbyloxy, halogen, hydroxy, amino, nitro and the like, such as phenyl, p-tolyl, 4-methoxyphenyl, 4-(tert-butoxy)phenyl, 4-fluorophenyl, 4-chlorophenyl, 4-hydroxyphenyl, and the like. The term "arylhydrocarbyl", alone or in combination, means a hydrocarbyl radical as defined above in which one hydrogen atom is replaced by an aryl radical as defined above, such as benzyl, 2-phenylethyl and the like. The term "arylhydrocarbyloxycarbonyl", alone or in combination, means a radical of the formula —C(O)—O— arylhydrocarbyl in which the term "arylhydrocarbyl" has the significance given above. An example of an arylhydrocarbyloxycarbonyl radical is benzyloxycarbonyl. The term "aryloxy" means a radical of the formula aryl-O— in which the term aryl has the significance given above. The term "aromatic ring" in combinations such as substituted-aromatic ring sulfonamide, substituted-aromatic ring sulfinamide or substituted-aromatic ring sulfenamide means aryl or heteroaryl as defined above.

As used herein, the term "binds" refers to the adherence of molecules to one another, such as, but not limited to, peptides or small molecules such as the compounds disclosed herein, and opioid antagonists, such as naloxone or naltrexone.

As used herein, the term "selectively binds" refers to binding as a distinct activity. Examples of such distinct activities include the independent binding to filamin A or a filamin A binding peptide, and the binding of a compound discussed above to a µ opioid receptor.

As used herein, the term "FLNA-binding compound" refers to a compound that binds to the scaffolding protein filamin A, or more preferably to a polypeptide comprising residues -Val-Ala-Lys-Gly-Leu- (SEQ ID NO:1) of the FLNA sequence that correspond to amino acid residue positions 2561-2565 of the FLNA protein sequence as noted in the sequence provided at the web address: UniProtKB/Swiss-Prot entry P21333, FLNA-HUMAN, Filamin-A protein sequence. A FLNA-binding compound can inhibit the MOR-Gs coupling caused by agonist stimulation of the µ opioid receptor via interactions with filamin A, preferably in the $24^{th}$ repeat region. When co-administered with an opioid agonist, a FLNA-binding compound can enhance the analgesic effects and improve the treatment of pain.

As used herein, the term "candidate FLNA-binding compound" refers to a substance to be screened as a potential FLNA-binding compound. In preferred instances a FLNA-binding compound is also an opioid agonist. Additionally, a FLNA-binding compound can function in a combinatory manner similar to the combination of an opioid agonist and ultra-low-dose antagonist, wherein both FLNA and the mu-opioid receptor are targeted by a single entity.

As used herein, the term "opioid receptor" refers to a G protein coupled receptor, located in the central nervous system that interacts with opioids. More specifically, the µ opioid receptor is activated by morphine causing analgesia, sedation, nausea, and many other side effects known to one of ordinary skill in the art.

As used herein, the term "opioid agonist" refers to a substance that upon binding to an opioid receptor can stimulate the receptor, induce G protein coupling and trigger a physiological response. More specifically, an opioid agonist is a morphine-like substance that interacts with MOR to produce analgesia.

As used herein, the term "opioid antagonist" refers to a substance that upon binding to an opioid receptor inhibits the function of an opioid agonist by interfering with the binding of the opioid agonist to the receptor.

As used herein an "analgesia effective amount" refers to an amount sufficient to provide analgesia or pain reduction to a recipient host.

As used herein the term "ultra-low-dose" or "ultra-low amount" refers to an amount of compound that when given in combination with an opioid agonist is sufficient to enhance the analgesic potency of the opioid agonist. More specifically, the ultra-low-dose of an opioid antagonist admixed with an opioid agonist in mammalian cells is an amount about 1000- to about 10,000,000-fold less, and preferably between about 10,000- and to about 1,000,000-fold less than the amount of opioid agonist.

As used herein an "FLNA-binding effective amount" refers to an amount sufficient to perform the functions described herein, such as inhibition of MOR-Gs coupling, prevention of the cAMP desensitization measure, inhibition of CREB $S^{133}$ phosphorylation and inhibition of any other cellular indices of opioid tolerance and dependence, which functions can also be ascribed to ultra-low-doses of certain opioid antagonists such as naloxone or naltrexone. When a polypeptide or FLNA-binding compound of the invention interacts with FLNA, an FLNA-binding effective amount can be an ultra-low amount or an amount higher than an ultra-low-dose as the polypeptide or FLNA-binding compound will not antagonize the opioid receptor and compete with the agonist, as occurs with known opioid antagonists such as naloxone or naltrexone in amounts greater than ultra-low-doses. More preferably, when a polypeptide or VAKGL-binding compound of the present invention both interacts with FLNA and is an agonist of the mu opioid receptor, an FLNA-binding effective amount is an amount higher than an ultra-low-dose and is a sufficient amount to activate the mu opioid receptor.

As used herein the phrase "determining inhibition of the interaction of a mu opioid receptor with a Gs protein" refers to monitoring the cellular index of opioid tolerance and dependence caused by chronic or high-dose administration of opioid agonists to mammalian cells. More specifically, the mu opioid receptor—Gs coupling response can be identified by measuring the presence of the Gαs (stimulatory) subunit, the interaction of MOR with the G protein complexes and formation of Gs-MOR coupling, the interaction of the Gβγ protein with adenylyl cyclase types II and IV, loss of inhibition or outright enhancement of cAMP accumulation, and the activation of CREB via phosphorylation of $S^{133}$.

As used herein the term "naloxone/naltrexone positive control" refers to a positive control method comprising steps discussed in a method embodiment, wherein the candidate FLNA-binding compound is a known opioid antagonist administered in an ultra-low amount, preferably naloxone or naltrexone.

As used herein the term "FLNA-binding compound negative control" refers to a negative control method comprising steps discussed in a method embodiment, wherein the candidate FLNA-binding compound is absent and the method is carried out in the presence of only opioid agonist.

As used herein the term "pharmacophore" is not meant to imply any pharmacological activity. The term refers to chemical features and their distribution in three-dimensional space that constitutes and epitomizes the preferred requirements for molecular interaction with a receptor (U.S. Pat. No. 6,034,066).

DETAILED DESCRIPTION OF THE INVENTION

It should be understood that the present disclosure is to be considered as an exemplification of the present invention, and is not intended to limit the invention to the specific embodiments illustrated. It should be further understood that the title of this section of this application ("Detailed Description of the Invention") relates to a requirement of the United States Patent Office, and should not be found to limit the subject matter disclosed herein.

The present invention contemplates a compound that binds to FLNA and also stimulates the µ opioid receptor (MOR), a composition containing that compound and method of its use to provide analgesia and reduce inflammation. A contemplated compound can suppress inflammation and inhibit MOR-Gs coupling through interactions with FLNA and/or the µ opioid receptor (MOR).

In another aspect of the present invention, a contemplated compound prevents the morphine-induced Gs protein coupling by MOR. That prevention of MOR-Gs coupling is believed to occur by preventing the interaction of filamin A and MOR. Downstream effects of preventing the MOR-Gs coupling include inhibition of cAMP accumulation and of cAMP Response Element Binding protein (CREB) activation in a manner resembling the activity of ultra-low-dose opioid antagonists naloxone and naltrexone.

In another aspect of the present invention, a FLNA-binding compound prevents the MOR-Gs coupling while itself activating MOR.

The data collected in organotypic striatal slice cultures demonstrate that after 7 days of twice daily 1-hour exposures to oxycodone, µ opioid receptors in striatum switch from Go to Gs coupling (compare vehicle to oxycodone conditions). In contrast, a compound contemplated herein did not cause a switch to Gs coupling despite its ability to stimulate µ opioid receptors as previously assessed by GTPγS binding that is blocked by beta-funaltrexamine, a specific MOR antagonist. These data imply that these compounds provide the analgesic effects characteristic of opioid drugs but do not cause analgesic tolerance or dependence, and do not have the addictive potential of opioid drugs.

A compound contemplated by the present invention binds to an above-defined FLNA polypeptide as well as stimulates the µ opioid receptor (MOR). A contemplated compound corresponds in structure to Formula A

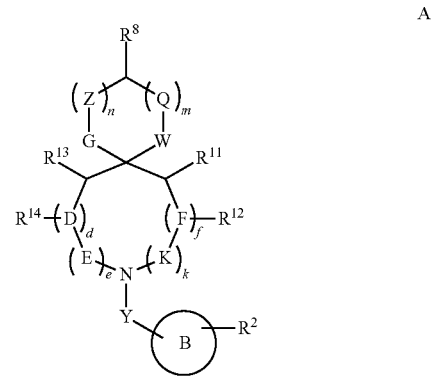

In Formula A,

Q is $CHR^9$ or C(O);

Z is $CHR^{10}$ or C(O), but only one of Q and Z is C(O);

each of m and n is zero or one and the sum of m+n is 1 or 2;

G and W are selected from the group consisting of $NR^{20}$, $NR^7$, S and O, where $R^7$ is H, $C_1$-$C_{12}$ hydrocarbyl, or $C_1$-$C_{12}$ hydrocarboyl(acyl) and $R^{20}$ is a group X-circle A-$R^1$ as defined hereinafter, with the provisos that:

i) only one of G and W is $NR^{20}$, ii) one of G and W must be $NR^{20}$, iii) one of G and W is other than $NR^7$ in which $R^7$ is H or an aliphatic $C_1$ hydrocarbyl; i.e., methyl, when (a) the sum of m+n is 1, and (b) the other of G and W is $NR^{20}$ bonded to a Z or Q, respectively, that is C(O), and iv) when X and Y are both $SO_2$, W is O, Q is $CH_2$, n is zero, and d and f are both 1, $R^1$ and $R^2$ are other than (a) both H, methoxy, or $C_1$-$C_3$-hydrocarbyl, (b) H, halogen and $C_1$-$C_3$-hydrocarbyl, (c) H and $C_1$-$C_3$-hydrocarbyl, (d) halogen and $C_1$-$C_3$-hydrocarbyl, or (e) H and halogen;

X and Y are the same or different and are $SO_2$, C(O), $CH_2$, $CD_2$, C(O)O, C(NH)NH or C(O)NH; each of d, e, f and k is either zero or one and the sum of (d+e+f+k)=2, e is zero when d is zero, and k is zero when f is zero; D and F are the same or different and are CH or CD; E and K are the same or different and are $CH_2$, CHD or $CD_2$; the circles A and B are the same or different aromatic or heteroaromatic ring systems. Groups $R^1$ and $R^2$ are the same or different and each can be hydrogen or represent up to three substituents other than hydrogen that themselves can be the same or different; i.e., $R^{1a}$, $R^{1b}$, and $R^{1c}$, and $R^{2a}$, $R^{2b}$, and $R^{2c}$. Each of those six groups, $R^{1a-c}$ and $R^{2a-c}$, is separately selected from the group consisting of H, $C_1$-$C_6$ hydrocarbyl, $C_1$-$C_6$ hydrocarbyloxy, $C_1$-$C_6$ hydrocarbyloxycarbonyl, trifluoromethyl, trifluoromethoxy, $C_1$-$C_7$ hydrocarboyl(acyl), hydroxy-, trifluoromethyl-(—$CF_3$) or halogen-substituted $C_1$-$C_7$ hydrocarboyl, $C_1$-$C_6$ hydrocarbylsulfonyl, $C_1$-$C_6$ hydrocarbyloxysulfonyl, halogen, nitro, phenyl, cyano, carboxyl, $C_1$-$C_7$ hydrocarbyl carboxylate [C(O)O—$C_1$-$C_7$ hydrocarbyl], carboxamide [C(O)NR$^3$R$^4$] or sulfonamide [S(O)$_2$NR$^3$R$^4$] wherein the amido nitrogen in either group has the formula NR$^3$R$^4$ wherein R$^3$ and R$^4$ are the same or different and are H, $C_1$-$C_4$ hydrocarbyl, or R$^3$ and R$^4$ together with the depicted nitrogen form a 5-7-membered ring that optionally contains 1 or 2 additional hetero atoms that independently are nitrogen, oxygen or sulfur, MAr, where M is —CH$_2$—, —O— or —N=N— and Ar is a single-ringed aryl group, and NR$^5$R$^6$ wherein R$^5$ and R$^6$ are the same or different and are H, $C_1$-$C_4$ hydrocarbyl, $C_1$-$C_4$ acyl, $C_1$-$C_4$ hydrocarbylsulfonyl, or R$^5$ and R$^6$ together with the depicted nitrogen form a 5-7-membered ring that optionally contains 1 or 2 additional hetero atoms that independently are nitrogen, oxygen or sulfur;

R$^8$, R$^9$, and R$^{10}$ are each H, or two of R$^8$, R$^9$, and R$^{10}$ are H and one is a $C_1$-$C_8$ hydrocarbyl group that is unsubstituted or is substituted with up to three atoms that are the same or different and are oxygen or nitrogen atoms;

R$^{11}$, R$^{12}$, R$^{13}$ and R$^{14}$ are all H, or one of the pair R$^{11}$ and R$^{12}$ or the pair R$^{13}$ and R$^{14}$ together with the depicted ring form a saturated or unsaturated 6-membered ring, and the other pair are each H, or they are H and D as recited herein (in this subparagraph).

A pharmaceutically acceptable salt of a compound of Formula A and all of the remaining formulas disclosed herein is also contemplated.

A compound having an asymmetrical (chiral) carbon or a salt thereof can exist in the form of two enantiomers. The invention relates both to each individual enantiomer and to their mixture; i.e., to both enantiomeric forms and to their mixture. Additionally, where two or more chiral centers are present, diastereomers can form.

Where a contemplated compound or a pharmaceutically acceptable salt of Formula A or any of the other formulas herein is obtained in the form of a mixture of the stereoisomers, preferably in the form of the racemates or other mixtures of the various enantiomers and/or diastereoisomers, they can be separated and optionally isolated by conventional methods known to the person skilled in the art. Illustratively, for example, chromatographic separation processes are useful, particularly liquid chromatography processes under standard pressure or under elevated pressure, preferably MPLC and HPLC methods, and also methods involving fractional crystallization. This can particularly involve the separation of individual enantiomers, e.g., diastereoisomeric salts separated by means of HPLC in the chiral phase or by means of crystallization with chiral acids, for example (+)-tartaric acid, (−)-tartaric acid, or (+)-10-camphorsulfonic acid. An enantiomer separated by chiral salt formation can readily be converted into an achiral or racemic pharmaceutically acceptable salt for use.

A compound of Formula A or a pharmaceutically acceptable salt thereof is contemplated to be optionally present individually, in enantiomerically pure form; i.e., in (S) or (R) configuration or d and l forms, or in the form of a racemic mixture having a (S,R) or (d,l) configuration, or as one or more diastereomers, and mixtures thereof.

Thus, a contemplated compound or its pharmaceutically acceptable salt can optionally be present in one or more forms. Illustratively, the compound or its salt can be in the form of an individual enantiomer or diastereoisomer. A contemplated compound or its salt can also be present in the form of a mixture of stereoisomers. A contemplated compound or salt can also be present in the form of a racemic mixture.

An illustrative, compound of Formula A corresponds in structure to the formula

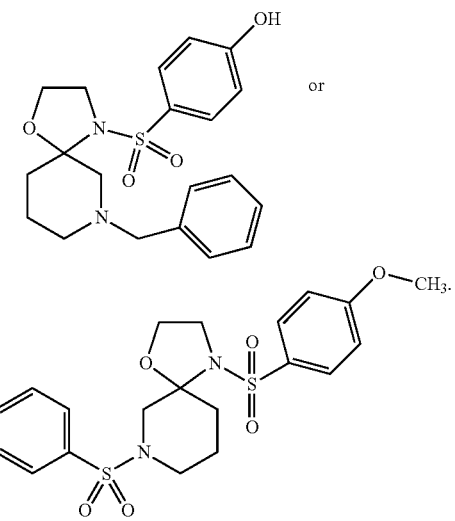

A preferred embodiment of a compound of Formula A corresponds in structure to Formula B

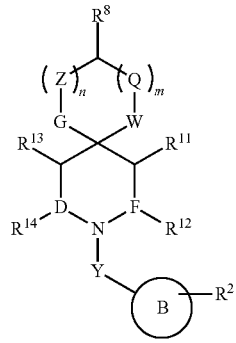

In Formula B, substituents that have the same designations (names) as those of Formula A have the same definitions, unless the formula as shown precludes part of a definition provided for a compound of Formula A. For example, e and k of Formula A are both zero in a compound of Formula B so that both of d and f are one and cannot be zero. Provisos i) through iv) that relate to Formula A also apply to Formula B. A pharmaceutically acceptable salt of a compound of Formula B is also contemplated.

In one preferred embodiment of a compound of Formula A, e and k are both zero and a compound of Formula A becomes a compound that corresponds in structure to Formula I

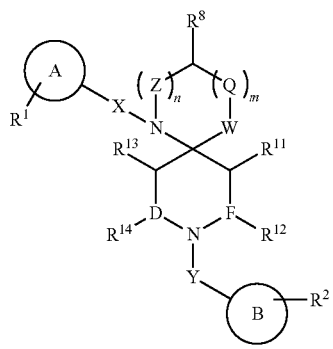

I

In Formula I, Q is $CHR^9$ or C(O);

Z is $CHR^{10}$ or C(O), but only one of Q and Z is C(O);

each of m and n is zero or one and the sum of m+n is 1 or 2;

X and Y are the same or different and are $SO_2$, C(O), $CH_2$, $CD_2$, C(O)O, C(NH)NH or C(O)NH; W is $NR^7$, S or O, where $R^7$ is H, $C_1$-$C_{12}$ hydrocarbyl, or $C_1$-$C_{12}$ hydrocarboyl(acyl), with the provisos that:

i) W is other than $NR^7$ in which $R^7$ is H or an aliphatic $C_1$ hydrocarbyl; i.e., methyl, when (a) the sum of m+n is 1, and (b) Z is C(O), and ii) when X and Y are both $SO_2$, W is O, Q is $CH_2$ and n is zero, $R^1$ and $R^2$ are other than (a) both H, methoxy, or $C_1$-$C_3$-hydrocarbyl, (b) H, halogen and $C_1$-$C_3$-hydrocarbyl, (c) H and $C_1$-$C_3$-hydrocarbyl, (d) halogen and $C_1$-$C_3$-hydrocarbyl, or (e) H and halogen;

D and F are the same or different and are CH or CD; the circles A and B are the same or different aromatic or heteroaromatic ring systems that contain one ring or two fused rings. Groups $R^1$ and $R^2$ are the same or different and each can be hydrogen or represent up to three substituents other than hydrogen that themselves can be the same or different; i.e., $R^{1a}$, $R^{1b}$, and $R^{1c}$, and $R^{2a}$, $R^{2b}$, and $R^{2c}$. Each of those six groups, $R^{1a-c}$ and $R^{2a-c}$, is separately selected from the group consisting of H, $C_1$-$C_6$ hydrocarbyl, $C_1$-$C_6$ hydrocarbyloxy, trifluoromethyl, trifluoromethoxy, $C_1$-$C_7$ hydrocarboyl (acyl), hydroxy-, trifluoromethyl-(—$CF_3$) or halogen-substituted $C_1$-$C_7$ hydrocarboyl, $C_1$-$C_6$ hydrocarbylsulfonyl, halogen, nitro, phenyl, cyano, carboxyl, $C_1$-$C_7$ hydrocarbyl carboxylate [C(O)O—$C_1$-$C_7$ hydrocarbyl], carboxamide [C(O)$NR^3R^4$] or sulfonamide [$SO_2NR^3R^4$] wherein the amido nitrogen of either group (the carboxamide or sulfonamide) has the formula $NR^3R^4$ wherein $R^3$ and $R^4$ are the same or different and are H, $C_1$-$C_4$ hydrocarbyl, or $R^3$ and $R^4$ together with the depicted nitrogen form a 5-7-membered ring that optionally contains 1 or 2 additional hetero atoms that independently are nitrogen, oxygen or sulfur, MAr, where M is where M is —$CH_2$—, —O— or —N=N— and Ar is a single-ringed aryl group, and $NR^5R^6$ wherein $R^5$ and $R^6$ are the same or different and are H, $C_1$-$C_4$ hydrocarbyl, $C_1$-$C_4$ acyl, $C_1$-$C_4$ hydrocarbylsulfonyl, or $R^5$ and $R^6$ together with the depicted nitrogen form a 5-7-membered ring that optionally contains 1 or 2 additional hetero atoms that independently are nitrogen, oxygen or sulfur;

$R^8$, $R^9$, and $R^{10}$ are each H, or two of $R^8$, $R^9$, and $R^{10}$ are H and one is a $C_1$-$C_8$ hydrocarbyl group that is unsubstituted or is substituted with up to three atoms that are the same or different and are oxygen or nitrogen atoms;

$R^{11}$, $R^{12}$, $R^{13}$ and $R^{14}$ are all H, or $R^{11}$ and $R^{13}$ are H and $R^{12}$ and $R^{14}$ are H or D, or one of the pair $R^{11}$ and $R^{12}$ or the pair $R^{13}$ and $R^{14}$ together with the depicted ring form a saturated or unsaturated 6-membered ring, and the other pair are each H or they are H and D as recited herein (in this subparagraph).

In preferred embodiments, X and Y are the same. X and Y are preferably both C(O) or $SO_2$, and more preferably are both $SO_2$. In those and other embodiments, W is preferably O. It is also preferred that n be zero. It is further preferred that $R^1$ and $R^2$ be the same, and that each is hydrogen or represents one substituent other than hydrogen. Some compounds of Formula B and of Formula I can be present a enantiomers as discussed previously.

A particularly preferred compound of Formula I includes a compound corresponding to a structural formula below:

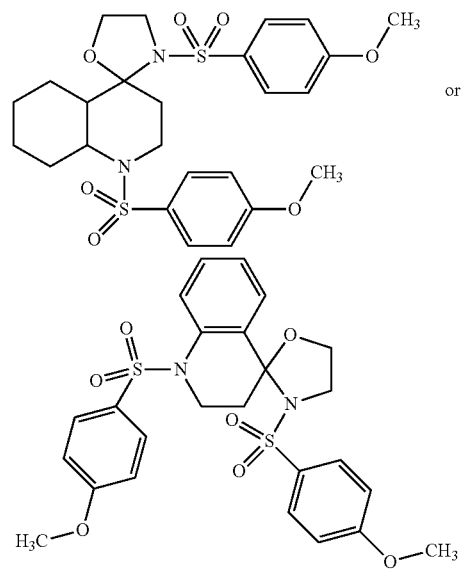

A contemplated aromatic or heteroaromatic ring system of circle A or circle B can contain one ring or two fused rings, and preferably contains a single aromatic ring. An illustrative aromatic or heteroaromatic ring system is selected from the group consisting of phenyl, pyridyl, pyrazinyl, pyrimidinyl, pyridazinyl, triazinyl[1,3,5-triazinyl, 1,2,4-triazinyl and 1,2,3-triazinyl], furanyl, thienyl, oxazolyl, isoxazolyl, thiazolyl, isothiazolyl, naphthyl, benzofuranyl, isobenzofuranyl, benzothiophenyl, isobenzothiophenyl, benzoxazolyl, benzisoxazole, quinolyl, isoquinolyl, quinazolyl, cinnolinyl, quinoxalinyl, naphthyridinyl, benzopyrimidinyl, and mixtures thereof. The mixtures of the previous sentence occur when circle A and circle B aromatic or heteroaromatic ring systems are different.

An illustrative single-ringed aryl group of substituent MAr is selected from the group consisting of phenyl, pyridyl, pyrazinyl, pyrimidinyl, pyridazinyl, triazinyl[1,3,5-triazinyl, 1,2,4-triazinyl and 1,2,3-triazinyl], furanyl, thienyl, oxazolyl, isoxazolyl, thiazolyl and isothiazolyl.

Phenyl is a preferred aromatic or heteroaromatic ring system of circle A and circle B. Phenyl, pyridinyl and furanyl are preferred single-ringed aryl groups, Ar, of a MAr substituent, with phenyl being particularly preferred.

There are several independent and separate preferences regarding the substituent R groups. Thus, $R^1$ and $R^2$ are preferably the same single substituent other than hydrogen, so that circle A and circle B both contain a single substituent other than hydrogen. The single substituent of $R^1$ and $R^2$ is preferably located at the same relative position in their respective ring systems. $R^1$ and $R^2$ preferably also have a Hammett sigma value for a para-position substituent that is greater than −0.2, and more preferably, a Hammett sigma value for a para-position substituent that is zero or positive (greater than zero).

Hammett sigma values are well known in organic chemistry and those values for para-position substituents reflect both electron donation and withdrawal via an inductive effect, but also are understood to reflect a resonance effect. It is noted that the recited para-position sigma value is utilized regardless of the actual position of the substituent on the aromatic or heteroaromatic ring. For Hammett sigma values see, for example, U.S. Pat. No. 7,473,477, U.S. Pat. No. 5,811,521, U.S. Pat. No. 4,746,651, and U.S. Pat. No. 4,548,905. A list of Hammett sigma values can be found in J. Hine, *Physical Organic Chemistry*, $2^{nd}$ ed., McGraw-Hill Book Co., Inc., New York page 87 (1962) and at the web site: wiredchemist-.com/chemistry/data/hammett_sigma_constants.

Thus, X and Y can form a sulfonamido, a carboxamido, a carbamido (urea), a guanidino or methylene linkage from the circle A or circle B ring system to a depicted nitrogen atom of the central spiro ring. A compound having a central ring that is a spiro 6,6-ring system or a spiro 5,6-ring system, along with one nitrogen and one oxygen or two nitrogens is contemplated. Illustrative central spiro rings are shown below where wavy lines are used to indicate the presence of covalent bonds to other entities, and where $R^7$ is defined above and $R^8$ is H.

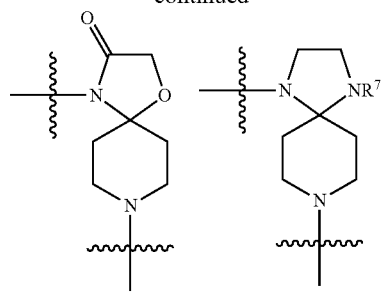

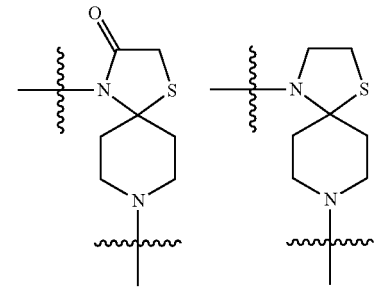

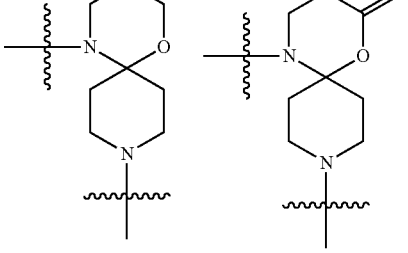

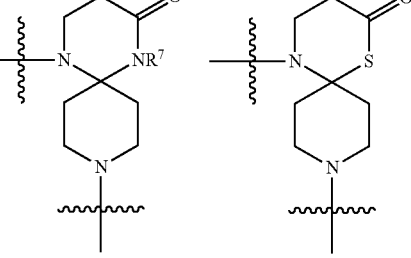

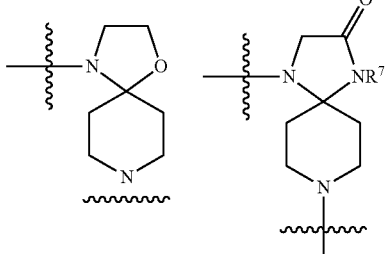

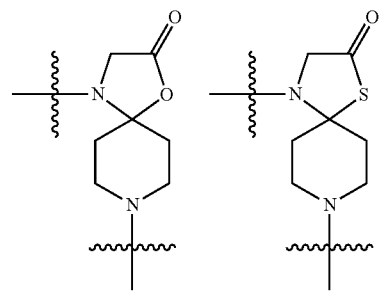

-continued

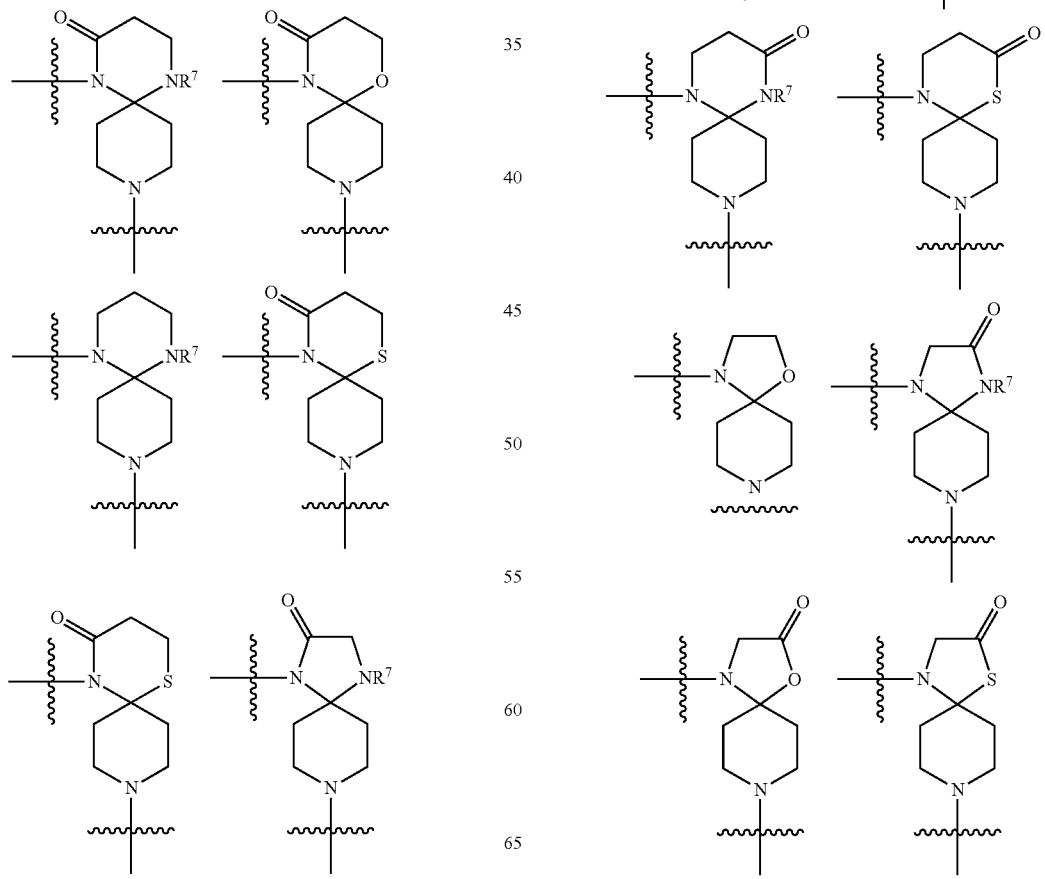

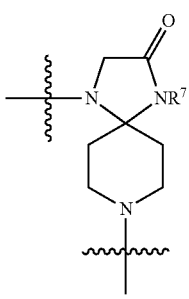

Illustrative compounds of Formula A in which d and e are each zero and $R^{11}$, $R^{12}$ and $R^{13}$ are each H have asymmetric spiro ring structures a few of which are shown below with wavy lines indicating the presence of covalent bonds to other entities, and $R^7$ is defined above and $R^8$ is H.

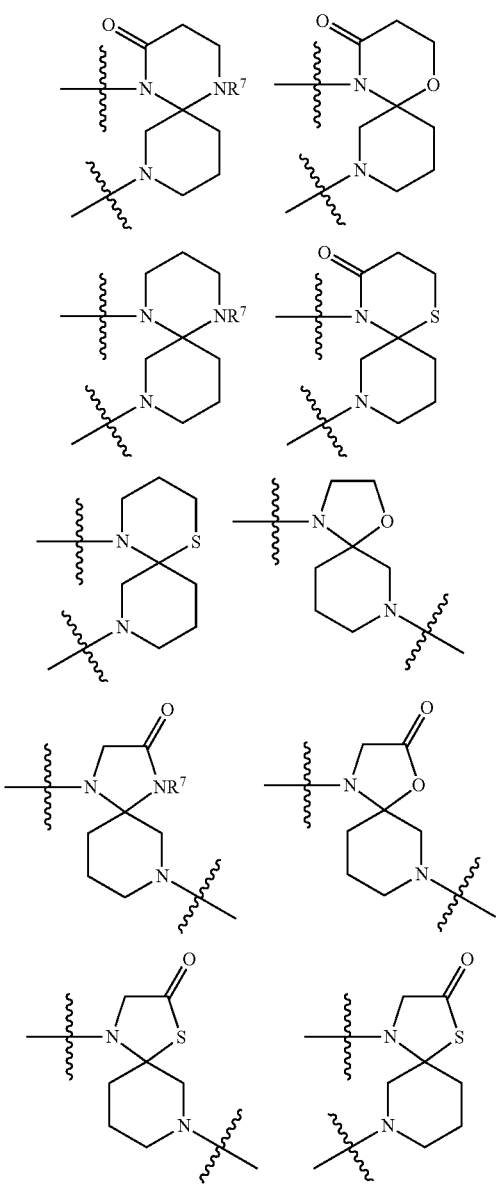

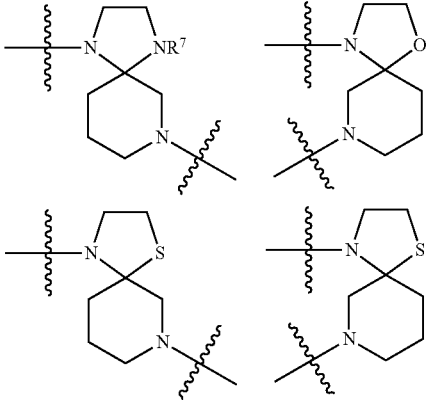

In preferred practice, n is zero, e and k are both zero and $R^{11}$, $R^{12}$ and $R^{13}$ are all H, so the central ring is a spiro 5,6-ring system whose 6-membered ring is unsubstituted and in which the spiro bonds are in the 4-position relative to the nitrogen of the 6-membered It is separately preferred that W be O. A compound in which X and Y are the same is preferred. It is also separately preferred that X and Y both be $SO_2$ (sulfonyl).

A particularly preferred compound of Formula A that embodies the above separate preferences is a compound of Formula II

II

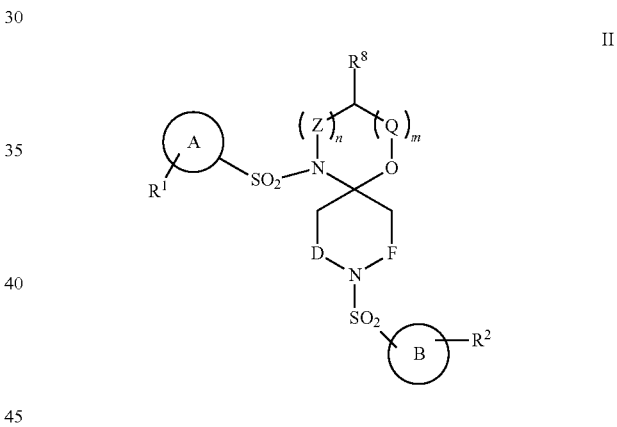

wherein
circle A and circle B, D, F, Z, Q, m, n, $R^1$, $R^2$ and $R^8$ are as described previously, unless the formula as shown precludes a definition provided for a compound of Formula A. Only one of the above provisos for Formulas A, B and I applies here, and that proviso is that when Q is $CH_2$ and n is zero, $R^1$ and $R^2$ are other than (a) both H, methoxy, or $C_1$-$C_3$-hydrocarbyl, (b) H, halogen and $C_1$-$C_3$-hydrocarbyl, (c) H and $C_1$-$C_3$-hydrocarbyl, (d) halogen and $C_1$-$C_3$-hydrocarbyl, or (e) H and halogen. It is preferred that the sum of m+n=1 so that the upper depicted ring contains 5-ring atoms.

It is more preferred that circle A and circle B are each phenyl, furanyl or pyridyl and $R^1$ and $R^2$ is each a single substituent. There are several independent and separate preferences regarding the substituent R groups. Thus, $R^1$ and $R^2$ are preferably the same. $R^1$ and $R^2$ are also preferably located at the same relative position in their respective rings. Thus, if $R^1$ is 4-cyano, $R^2$ is also 4-cyano.

$R^1$ and $R^2$ preferably also have a Hammett sigma value for a para-position substituent that is greater than −0.2, and more preferably, a Hammett sigma value for a para-position substituent that is positive (greater than zero).

Most of the compounds assayed having substituents with Hammett sigma values for a para-position substituent that are greater than −0.2 are more active than are assayed compounds with Hammett sigma values for a para-position substituent that are less than −0.2 (more negative). The most active compounds have substituents whose Hammett sigma values for a para-position substituent are positive; i.e., greater than zero. It is also noted that preferred $R^1$ and $R^2$ substituent groups do not themselves provide a positive or negative charge to a compound at a pH value of about 7.2-7.4.

A particularly preferred compound of Formula II that embodies the above separate preferences is selected from the group consisting of:

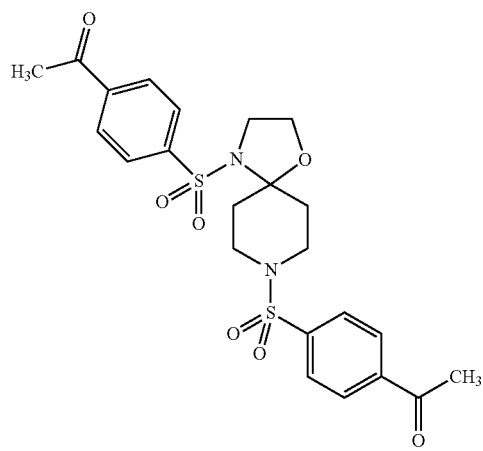

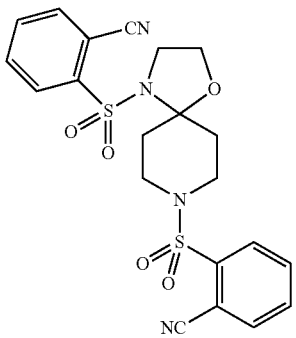

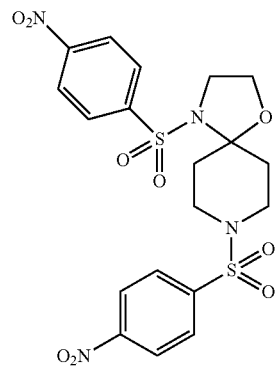

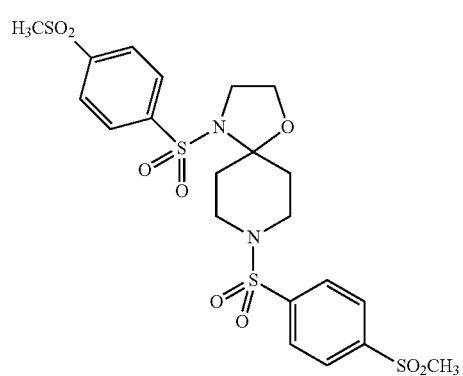

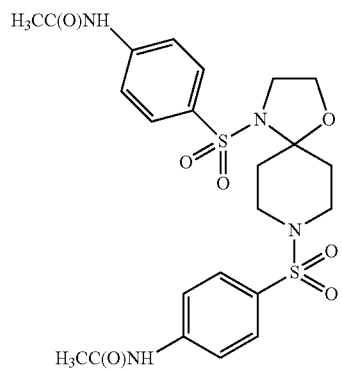

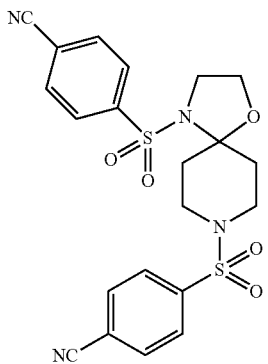

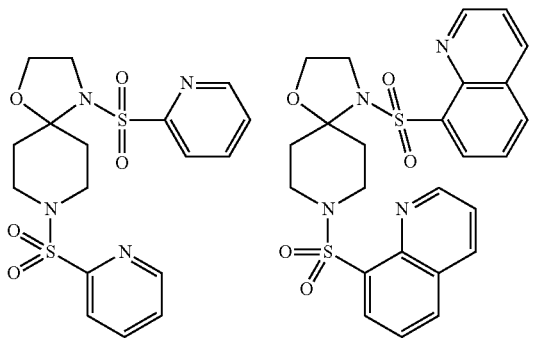

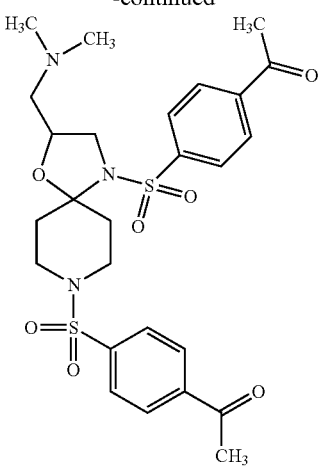

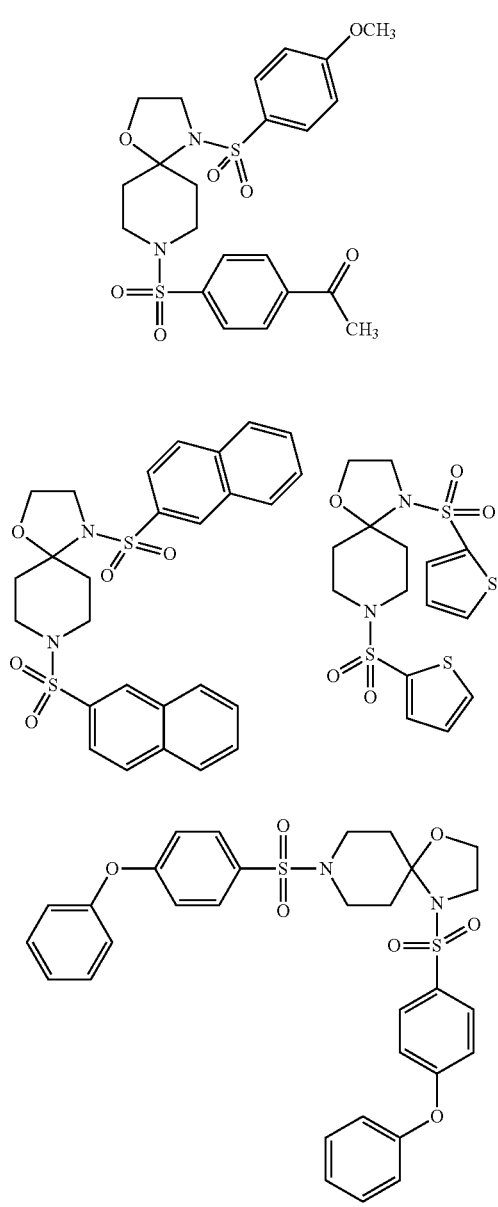

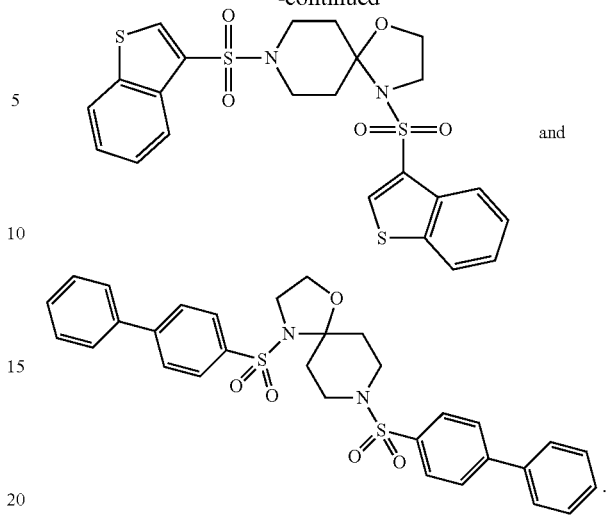

In other embodiments, a particularly preferred compound of Formula A is a compound of Formula III

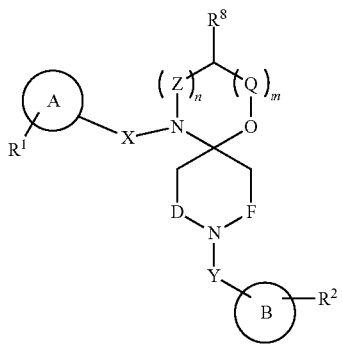

wherein
circle A and circle B, D, F, Z, Q, m, n, $R^1$, $R^2$ and $R^8$ are as described previously. X and Y are both CO, or X and Y are different and are $SO_2$, C(O), $CH_2$, $CD_2$, C(O)O, C(NH)NH or C(O)NH.

More preferably, circle A and circle B are each phenyl, furanyl or pyridyl. $R^1$ and $R^2$ are the same and are selected from the group consisting of trifluoromethyl, $C_1$-$C_6$ acyl, $C_1$-$C_4$ alkylsulfonyl, halogen, nitro, cyano, carboxyl, $C_1$-$C_4$ alkyl carboxylate, carboxamide wherein the amido nitrogen has the formula $NR^3R^4$ wherein $R^3$ and $R^4$ are the same or different and are H, $C_1$-$C_4$ alkyl, and $NR^5R^6$ wherein $R^5$ and $R^6$ are the same or different and are H, $C_1$-$C_4$ alkyl, $C_1$-$C_4$ acyl, $C_1$-$C_4$ alkylsulfonyl.

It is still more preferred that $R^1$ and $R^2$ each be a single substituent. There are several independent and separate preferences regarding the substituent R groups. $R^1$ and $R^2$ are preferably the same. $R^1$ and $R^2$ are also preferably located at the same relative position in their respective rings. Thus, if $R^1$ is 4-cyano, $R^2$ is also 4-cyano. It is also preferred that the sum of m+n=1, so that the upper depicted ring contains 5-ring atoms. $R^1$ and $R^2$ preferably also have a Hammett sigma value for a para-position substituent that is greater than −0.2, and more preferably, a Hammett sigma value for a para-position substituent that is positive (greater than zero).

A particular compound of Formula III is

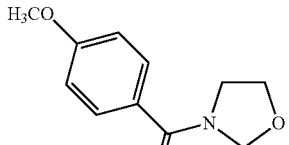
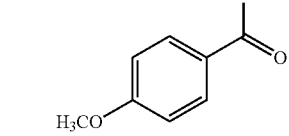
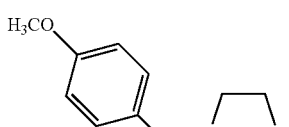
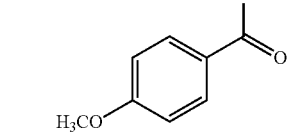

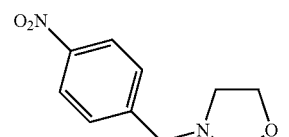
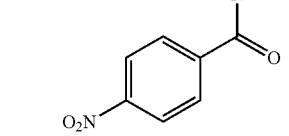
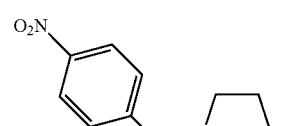
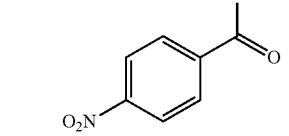

and

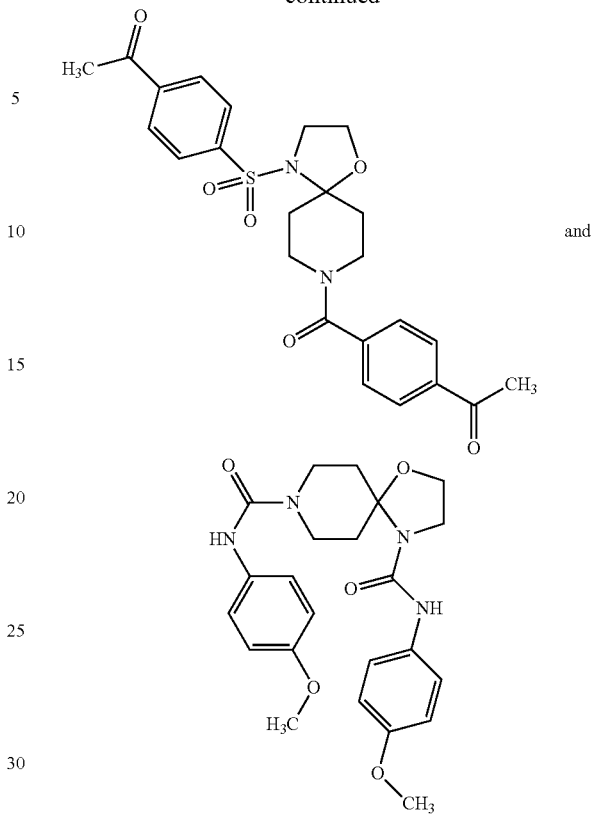

In still further embodiments, a particularly preferred compound of Formula A is a compound of Formula IV

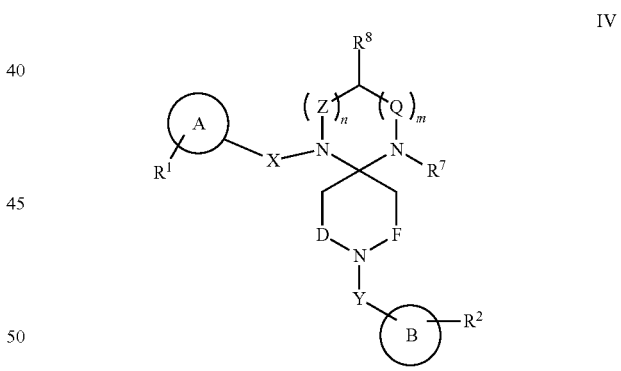

IV wherein
circle A and circle B, D, F, Z, Q, m, n, $R^1$, $R^2$, $R^7$ and $R^8$ are as described previously. X and Y are similarly as described previously, and are the same or different and are $SO_2$, C(O), $CH_2$, $CD_2$, C(O)O, C(NH)NH or C(O)NH.

More preferably, circle A and circle B are each phenyl, furanyl or pyridyl. $R^1$ and $R^2$ are the same and are selected from the group consisting of trifluoromethyl, $C_1$-$C_6$ acyl, $C_1$-$C_4$ alkylsulfonyl, halogen, nitro, cyano, carboxyl, $C_1$-$C_4$ alkyl carboxylate, carboxamide wherein the amido nitrogen has the formula $NR^3R^4$ wherein $R^3$ and $R^4$ are the same or different and are H, $C_1$-$C_4$ alkyl, and $NR^5R^6$ wherein $R^5$ and $R^6$ are the same or different and are H, $C_1$-$C_4$ alkyl, $C_1$-$C_4$ acyl, $C_1$-$C_4$ alkylsulfonyl.

It is still more preferred that $R^1$ and $R^2$ each be a single substituent. There are several independent and separate preferences regarding the substituent R groups. $R^1$ and $R^2$ are preferably the same. $R^1$ and $R^2$ are also preferably located at the same relative position in their respective rings. Thus, if $R^1$ is 4-cyano, $R^2$ is also 4-cyano. It is also preferred that the sum of m+n=1, so that the upper depicted ring contains 5-ring atoms. $R^1$ and $R^2$ preferably also have a Hammett sigma value for a para-position substituent that is greater than −0.2, and more preferably, a Hammett sigma value for a para-position substituent that is positive (greater than zero).

Particular compounds of Formula IV include

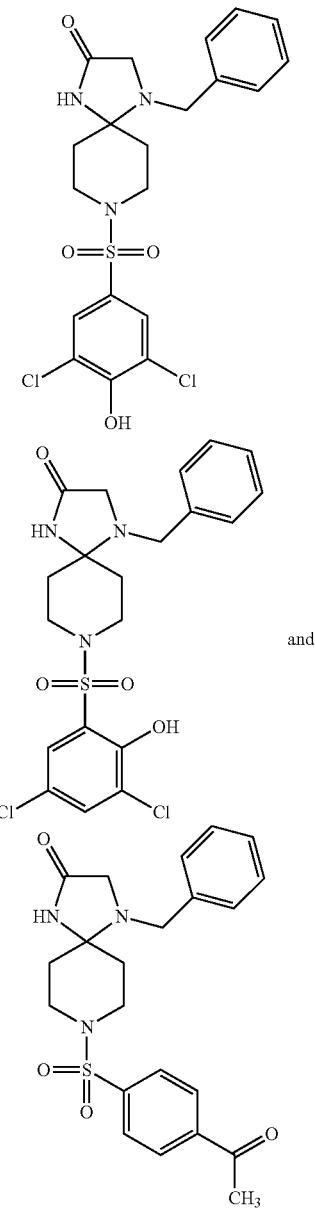

and

The present invention also contemplates a method of treatment to reduce pain in a treated mammal. A compound of Formula A, or of any of Formulas B, I, II, III and IV present in an analgesic effective amount dissolved or dispersed in a physiologically tolerable diluent can and preferably is used in such a treatment.

A compound of Formula C in an analgesic effective amount dissolved or dispersed in a physiologically tolerable diluent is also contemplated.

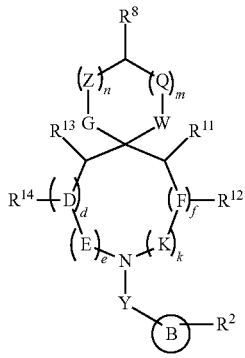

C

In Formula C,

Q is $CHR^9$ or C(O);

Z is $CHR^{10}$ or C(O), but only one of Q and Z is C(O);

each of m and n is zero or one and the sum of m+n is 1 or 2;

G and W are selected from the group consisting of $NR^{20}$, $NR^7$, S and O, where $R^7$ is H, $C_1$-$C_{12}$ hydrocarbyl, or $C_1$-$C_{12}$ hydrocarboyl(acyl) and $R^{20}$ is a group X-circle A-$R^1$ as defined hereinafter, with the provisos that:

i) only one of G and W is $NR^{20}$, ii) one of G and W must be $NR^{20}$, and iii) one of G and W is other than $NR^7$ in which $R^7$ is H or an aliphatic $C_1$ hydrocarbyl when (a) the sum of m+n is 1 and (b) the other of G and W is $NR^{20}$ bonded to a Z or Q, respectively, that is C(O);

X and Y are the same or different and are $SO_2$, C(O), $CH_2$, $CD_2$, C(O)O, C(NH)NH or C(O)NH; each of d, e, f and k is either zero or one and the sum of (d+e+f+k)=2, e is zero when d is zero, and g is zero when f is zero; D and F are the same or different and are CH or CD; E and K are the same or different and are $CH_2$, CHD or $CD_2$ the circles A and B are the same or different aromatic or heteroaromatic ring systems that contain one ring or two fused rings. Groups $R^1$ and $R^2$ are the same or different and each can be hydrogen or represent up to three substituents other than hydrogen that themselves can be the same or different; i.e., $R^{1a}$, $R^{1b}$, and $R^{1c}$, and $R^{2a}$, $R^{2b}$, and $R^{2c}$. Each of those six groups, $R^{1a-c}$ and $R^{2a-c}$, is separately selected from the group consisting of H, $C_1$-$C_6$ hydrocarbyl, $C_1$-$C_6$ hydrocarbyloxy, $C_1$-$C_6$ hydrocarbyloxycarbonyl, trifluoromethyl, trifluoromethoxy, $C_1$-$C_7$ hydrocarboyl (acyl), hydroxy-, trifluoromethyl-(—$CF_3$) or halogen-substituted $C_1$-$C_7$ hydrocarboyl, $C_1$-$C_6$ hydrocarbylsulfonyl, $C_1$-$C_6$ hydrocarbyloxysulfonyl, halogen, nitro, phenyl, cyano, carboxyl, $C_1$-$C_7$ hydrocarbyl carboxylate [C(O)O—$C_1$-$C_7$ hydrocarbyl], carboxamide [C(O)$NR^3R^4$] or sulfonamide [S(O)$_2NR^3R^4$] wherein the amido nitrogen in either group has the formula $NR^3R^4$ wherein $R^3$ and $R^4$ are the same or different and are H, $C_1$-$C_4$ hydrocarbyl, or $R^3$ and $R^4$ together with the depicted nitrogen form a 5-7-membered ring that optionally contains 1 or 2 additional hetero atoms that independently are nitrogen, oxygen or sulfur, MAr, where M is —$CH_2$—, —O— or —N=N— and Ar is a single-ringed aryl group, and $NR^5R^6$ wherein $R^5$ and $R^6$ are the same or different and are H, $C_1$-$C_4$ hydrocarbyl, $C_1$-$C_4$ acyl, $C_1$-$C_4$ hydrocarbylsulfonyl, or $R^5$ and $R^6$ together with the depicted nitrogen form a 5-7-membered ring that optionally contains 1 or 2 additional hetero atoms that independently are nitrogen, oxygen or sulfur;

$R^8$, $R^9$, and $R^{10}$ are each H, or two of $R^8$, $R^9$, and $R^{10}$ are H and one is a $C_1$-$C_8$ hydrocarbyl group that is unsubstituted or is substituted with up to three atoms that are the same or different and are oxygen or nitrogen atoms;

$R^{11}$, $R^{12}$, $R^{13}$ and $R^{14}$ are all H, or $R^{11}$ and $R^{13}$ are H and $R^{12}$ and $R^{14}$ are H or D, or one of the pair $R^{11}$ and $R^{12}$ or the pair $R^{13}$ and $R^{14}$ together with the depicted ring form a saturated or unsaturated 6-membered ring, and the other pair are each H or they are H and D as recited herein; i.e., in this subparagraph.

Again, a pharmaceutically acceptable salt of all of the compounds of Formulas A, B, C, and I-IV is contemplated. A compound of Formula A, B, C, and I-IV or its pharmaceutically acceptable salt can optionally be used in a process of the invention individually, in enantiomerically pure form; i.e., in (S) or (R) configuration or d and l forms, or in the form of a racemic mixture showing an (S,R) or (d,l) configuration, or as one or more diastereomers, and mixtures thereof.

Thus, a compound of Formula C encompasses compounds in addition to those of Formula A. In particular, $R^1$ and $R^2$ substituents of a compound of Formula C include $C_1$-$C_6$ hydrocarbyloxy and amino substituents $NR^5R^6$. These $R^1$ and $R^2$ groups have Hammett sigma values for the para-position that are less than −0.2. For example, the Hine text, cited above, lists appropriate para-position sigma values for methoxy and ethoxy groups as −0.268 and −0.24, respectively. The para-position sigma value for an unsubstituted amine is −0.66, whereas a dimethylamino group has a reported para-position sigma value of −0.83.

Aside from the inclusion of additional $R^1$ and $R^2$ groups, the preferences discussed above for a compound of Formula A also apply to a compound of Formula C. Thus, for example, W is preferably O, and X and Y are preferably the same and are $SO_2$.

In another aspect, a contemplated compound is selected in part using a method for determining the ability of a candidate FLNA-binding compound, other than naloxone or naltrexone, to inhibit the interaction of the mu opioid receptor with filamin A (FLNA) and thereby prevent the mu opioid receptor from coupling to Gs proteins (Gs). That method comprises the steps of: (a) admixing the candidate FLNA-binding compound (alone if such FLNA-binding compound also stimulates MOR or with a MOR agonist otherwise) with mammalian cells that contain the mu opioid receptor and FLNA in their native conformations and relative orientations, the opioid agonist being present in an agonist effective amount and/or being administered in a repeated, chronic manner the FLNA-binding compound being present in an FLNA-binding effective amount; and (b) determining inhibition of the interaction of the mu opioid receptor with the G protein by analysis of the presence or the absence of the Gαs subunit of Gs protein, wherein the absence of the Gαs subunit indicates inhibition of the interaction of the mu opioid receptor with the Gs protein.

In one aspect, the analysis of Gs protein coupling by the mu opioid receptor and downstream effects elicited by admixing mammalian cells with a before-defined compound can be conducted by any one or more of several methods such as for example co-immunoprecipitation of Gα proteins with MOR, Western blot detection of MOR in immunoprecipitates, and densitometric quantification of Western blots.

Pharmaceutical Composition

A compound of the invention can be provided for use by itself, or as a pharmaceutically acceptable salt. Although substituent groups can provide an acid functionality, a contemplated compound of any of Formulas A-C and Formulas I-IV is an amine and can typically be used in the form of an acid addition salt derived from an inorganic or organic acid. Exemplary salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate.

Other compounds useful in this invention that contain acid functionalities can also form salts. Examples include salts with alkali metals or alkaline earth metals, such as sodium, potassium, calcium or magnesium or with organic bases or basic quaternary ammonium salts.

The reader is directed to Berge, 1977 *J. Pharm. Sci.* 68(1):1-19 for lists of commonly used pharmaceutically acceptable acids and bases that form pharmaceutically acceptable salts with pharmaceutical compounds.

In some cases, the salts can also be used as an aid in the isolation, purification or resolution of the compounds of this invention. In such uses, the acid used and the salt prepared need not be pharmaceutically acceptable.

As can be seen from the above definitions, a contemplated compound can contain deuterated carbon atoms on either side of the "X" substituent. Deuterated compounds can be useful in studying the mechanism of drug interactions with living organisms for the elucidation of metabolic and biosynthetic pathways. Deuteration can also extend the half-life of a contemplated compound in vivo because a C-D bond is stronger than a C—H bond thereby requiring more energy input for bond cleavage. See, Blake et al., 1975 *J. Pharm. Sci.* 64(3):367-391; and Nelson et al., 2003 *Drug Metab. Dispos.* 31(12):1481-1498, and the citations therein. Contemplated deuterated compounds are prepared using well-known reactions.

A contemplated composition can be used in the manufacture of a medicament that is useful at least for lessening or reducing pain in a mammal that is in need, such as somatic, visceral, neuropathic or sympathetic pain, including musculoskeletal pain, inflammatory pain, burn pain, and pain from syndromes such as fibromyalgia and complex regional pain syndrome (CRPS). A contemplated composition can also be used in the manufacture of a medicament that is useful in reducing inflammation. Inasmuch as pain and inflammation are not always coincident, a contemplated composition is referred to as being used to reduce one or both of pain and inflammation, or a similar phrase.

A contemplated pharmaceutical composition contains an analgesia effective amount of a compound Formulas A, B or C and of Formulas I-IV or a pharmaceutically acceptable salt thereof dissolved or dispersed in a physiologically tolerable carrier. Such a composition can be administered to mammalian cells in vitro as in a cell culture, or in vivo as in a living, host mammal in need.

A contemplated composition is typically administered a plurality of times over a period of days. More usually, a contemplated composition is administered a plurality of times in one day.

As is seen from the data that follow, a contemplated compound is active in the assays studies at micromolar amounts.

In the laboratory mouse tail flick test, orally administered morphine exhibited an $A_{50}$ value of 61.8 (52.4-72.9) mg/kg, and a mean maximum antinociception amount of about 43% at 56 mg/kg at about 20 minutes. Orally administered compound C0011 (see the Table of Correspondence hereinafter for a correlation of structures and compound numbers) exhibited a mean maximum antinociception amount of about 70% at 56 mg/kg at about 10-20 minutes, whereas orally administered compound C0009 exhibited a mean maximum antinociception amount of about 50% at 56 mg/kg at about 10 minutes, compound C0022 exhibited a mean maximum antinociception amount of about 40% at 56 mg/kg at about 30 minutes, and compound C0148M exhibited a mean maximum antinociception amount of about 30% at 32 mg/kg at about 10 minutes. It is thus seen that the contemplated compounds are quite active and potent, and that a skilled worker can readily determine an appropriate dosage level to achieve a desired amount of pain reduction, particularly in view of the relative activity of a contemplated compound compared to orally administered morphine.

A contemplated composition described herein can be used in the manufacture of a medicament that is useful at least for lessening or reducing pain in a mammal that is in need.

A contemplated pharmaceutical composition can be administered orally (perorally), parenterally, by inhalation spray in a formulation containing conventional nontoxic pharmaceutically acceptable carriers, adjuvants, and vehicles as desired. The term parenteral as used herein includes subcutaneous injections, intravenous, intramuscular, intrasternal injection, or infusion techniques. Formulation of drugs is discussed in, for example, Hoover, John E., *Remington's Pharmaceutical Sciences*, Mack Publishing Co., Easton, Pa.; 1975 and Liberman, H. A. and Lachman, L., Eds., *Pharmaceutical Dosage Forms*, Marcel Decker, New York, N.Y., 1980.

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution, phosphate-buffered saline. Liquid pharmaceutical compositions include, for example, solutions suitable for parenteral administration. Sterile water solutions of an active component or sterile solution of the active component in solvents comprising water, ethanol, or propylene glycol are examples of liquid compositions suitable for parenteral administration.

In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents such as those discussed above are also useful.

Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

Solid dosage forms for oral administration can include capsules, tablets, pills, powders, and granules. In such solid dosage forms, the compounds of this invention are ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

A mammal in need of treatment and to which a pharmaceutical composition containing a contemplated compound is administered can be a primate such as a human, an ape such as a chimpanzee or gorilla, a monkey such as a cynomolgus monkey or a macaque, a laboratory animal such as a rat, mouse or rabbit, a companion animal such as a dog, cat, horse, or a food animal such as a cow or steer, sheep, lamb, pig, goat, llama or the like.

Where in vitro mammalian cell contact is contemplated, a CNS tissue culture of cells from an illustrative mammal is often utilized, as is illustrated hereinafter. In addition, a non-CNS tissue preparation that contains opioid receptors such as guinea pig ileumcan also be used.

Preferably, the pharmaceutical composition is in unit dosage form. In such form, the composition is divided into unit doses containing appropriate quantities of the active urea. The unit dosage form can be a packaged preparation, the package containing discrete quantities of the preparation, for example, in vials or ampules.

EXAMPLES

The present invention is described in the following examples which are set forth to aid in the understanding of the invention, and should not be construed to limit in any way the invention as defined in the claims which follow thereafter.

The experiments described herein were carried out on organotypic striatal slices from male Sprague Dawley rats (200 to 250 g) purchased from Taconic (Germantown, N.Y.). Rats were housed two per cage and maintained on a regular 12-hour light/dark cycle in a climate-controlled room with food and water available ad libitum and sacrificed by rapid decapitation. All data are presented as mean±standard error of the mean. Treatment effects were evaluated by two-way ANOVA followed by Newman-Keul's test for multiple comparisons. Two-tailed Student's t test was used for post hoc pairwise comparisons. The threshold for significance was $p<0.05$.

The following Table of Correspondence shows the structures of the compounds discussed herein and their identifying numbers.

TABLE OF CORRESPONDENCE
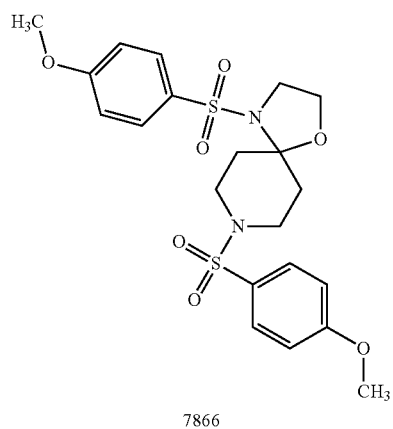
7866
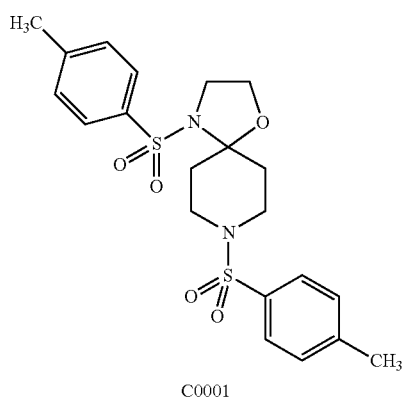
C0001
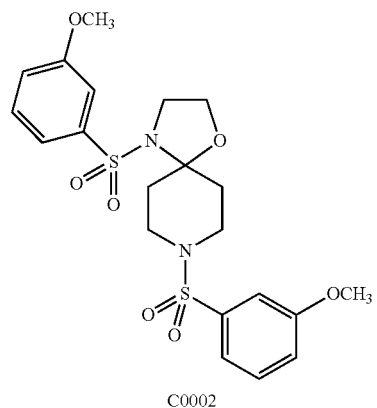
C0002
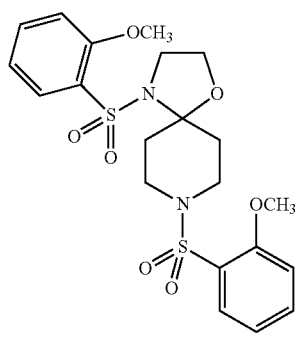 [SMILES: COc1ccccc1S(=O)(=O)N1CCC2(CC1)OCCN2S(=O)(=O)c1ccccc1OC]
C0003
TABLE OF CORRESPONDENCE-continued
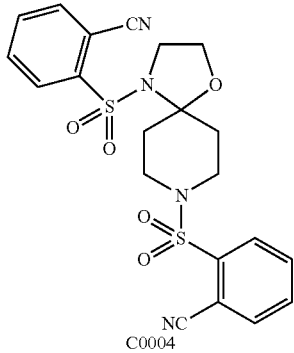
C0004
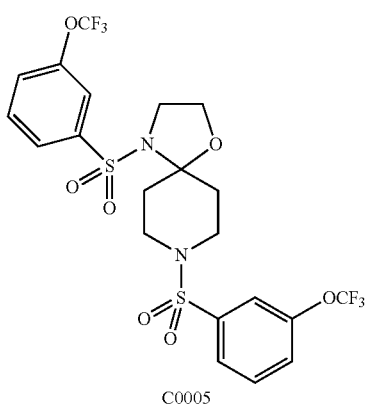
C0005
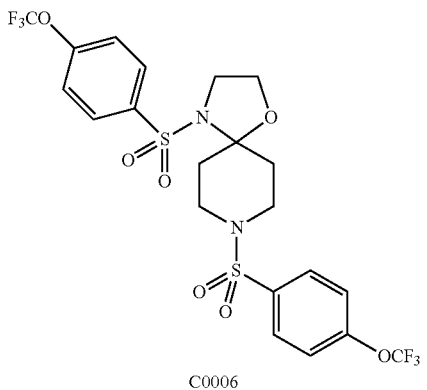
C0006
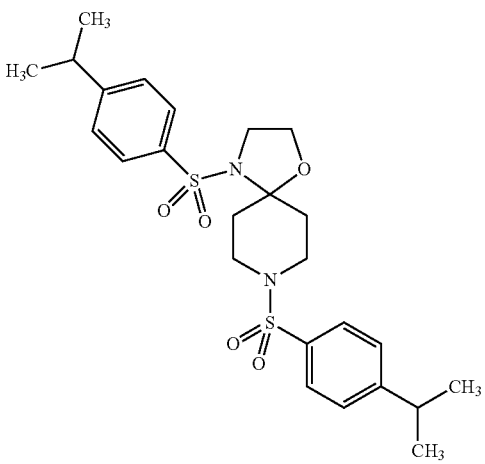 [SMILES: CC(C)c1ccc(S(=O)(=O)N2CCC3(CC2)OCCN3S(=O)(=O)c2ccc(C(C)C)cc2)cc1]
C0007

TABLE OF CORRESPONDENCE-continued
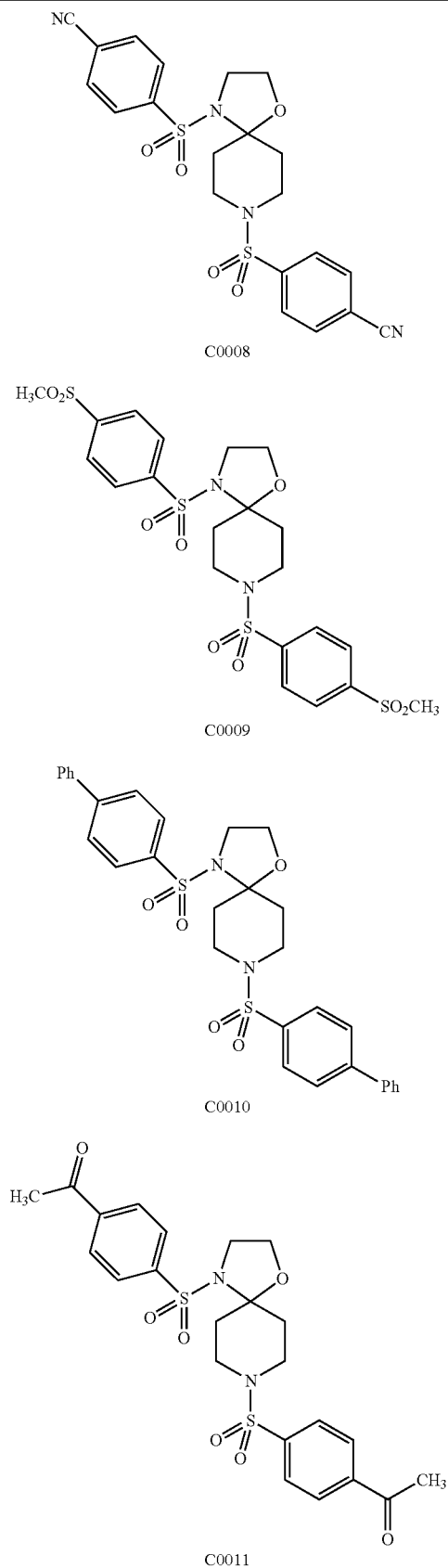
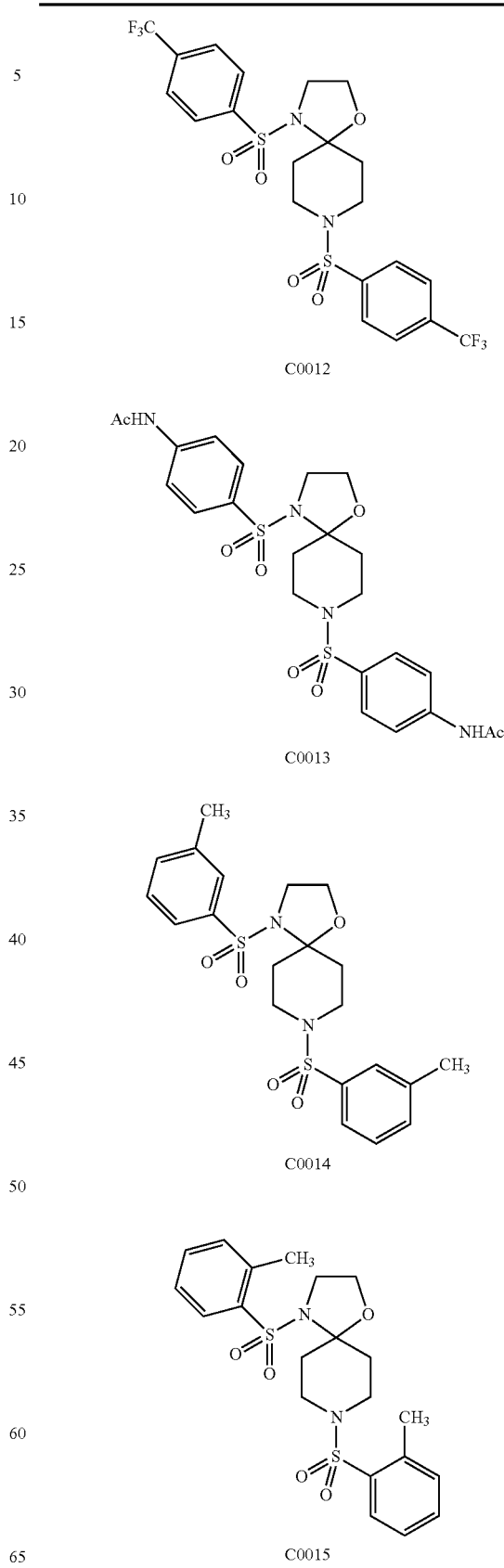

TABLE OF CORRESPONDENCE-continued
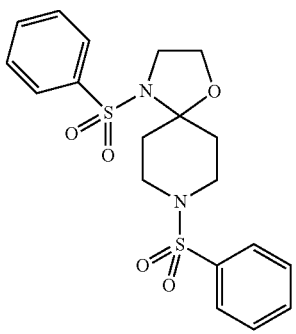 [SMILES: O=S(=O)(c1ccccc1)N1CCC2(CC1)OCCN2S(=O)(=O)c1ccccc1]
C0016
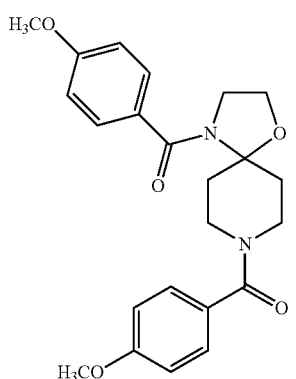
C0017
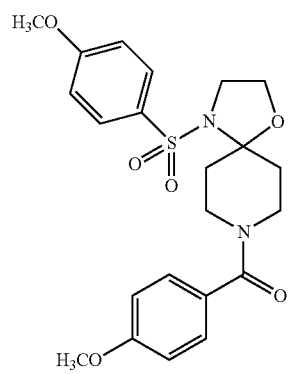 [SMILES: COc1ccc(C(=O)N2CCC3(CC2)OCCN3S(=O)(=O)c2ccc(OC)cc2)cc1]
C0018
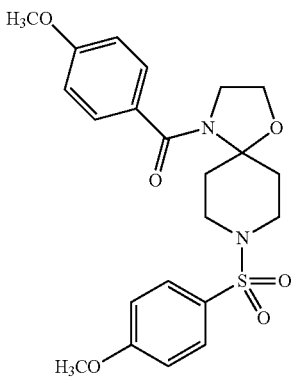 [SMILES: COc1ccc(C(=O)N2CCOC23CCN(S(=O)(=O)c2ccc(OC)cc2)CC3)cc1]
C0019
TABLE OF CORRESPONDENCE-continued
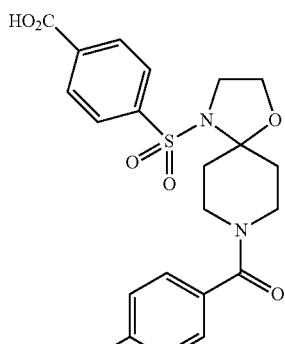
C0021
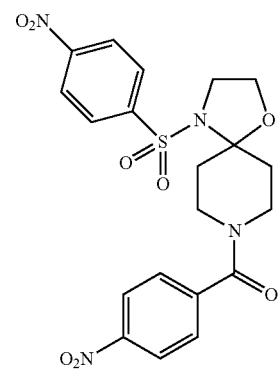 [SMILES: O=C(c1ccc([N+](=O)[O-])cc1)N1CCC2(CC1)OCCN2S(=O)(=O)c1ccc([N+](=O)[O-])cc1]
C0022
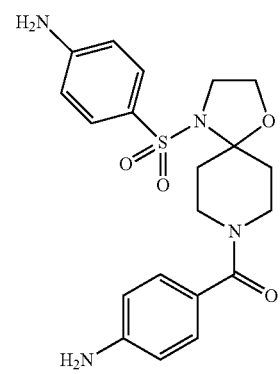
C0023
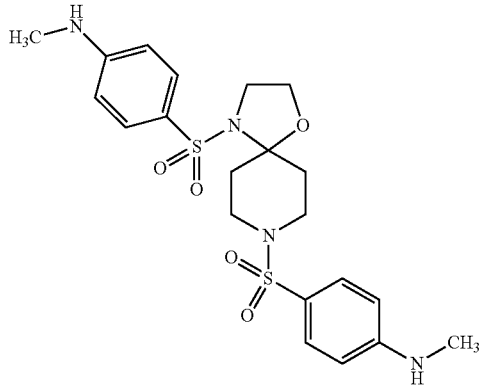
C0024

TABLE OF CORRESPONDENCE-continued
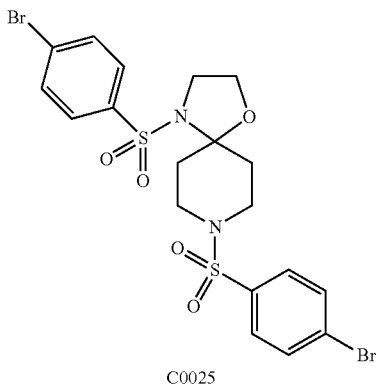
C0025
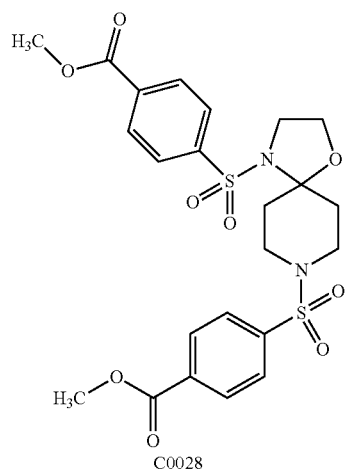
C0028
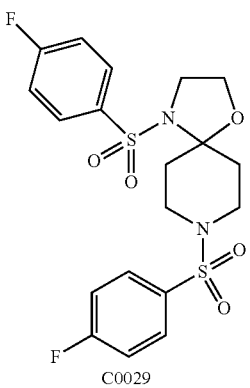
C0029
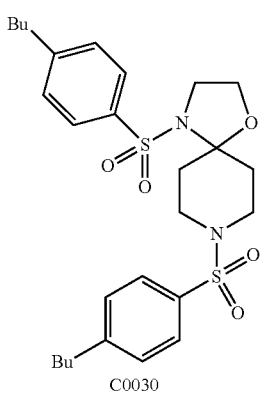
C0030
TABLE OF CORRESPONDENCE-continued
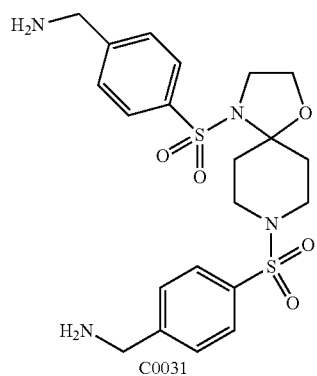
C0031
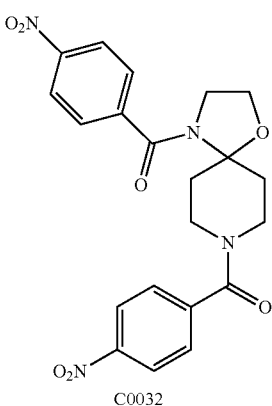
C0032
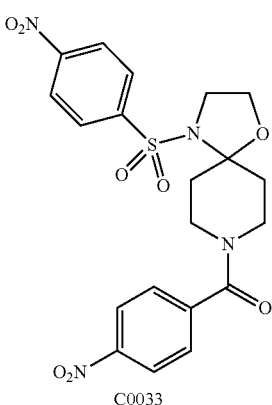
C0033
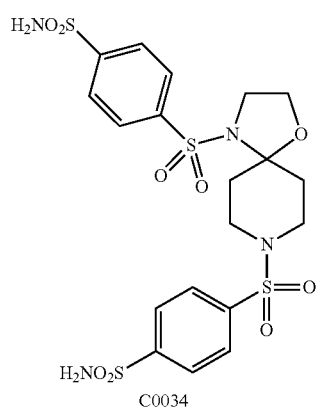
C0034

TABLE OF CORRESPONDENCE-continued
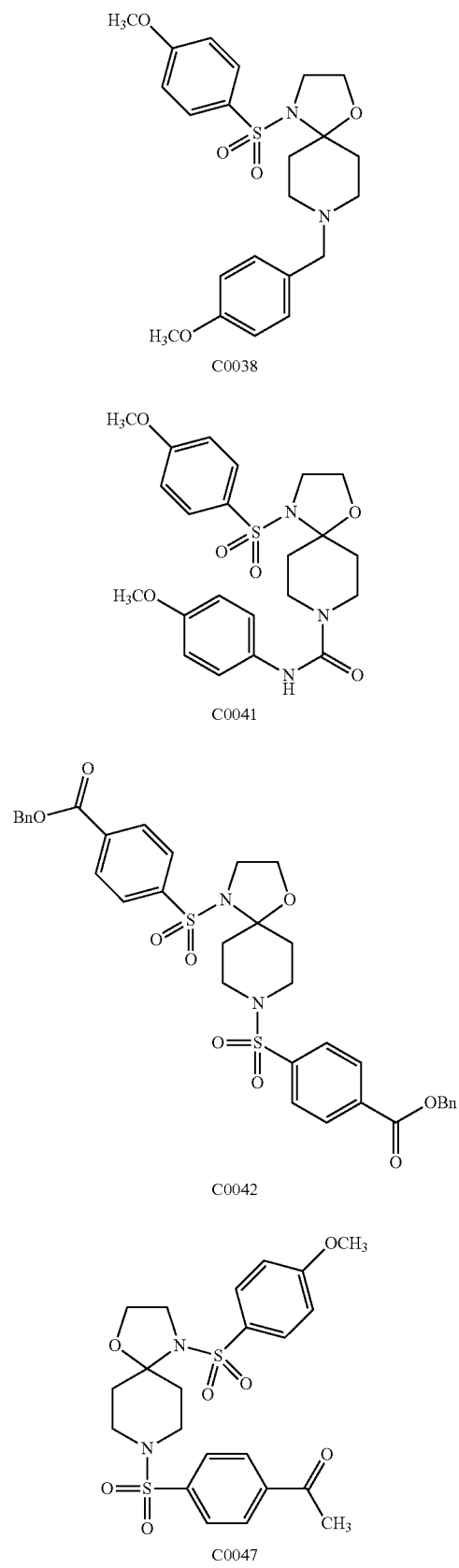
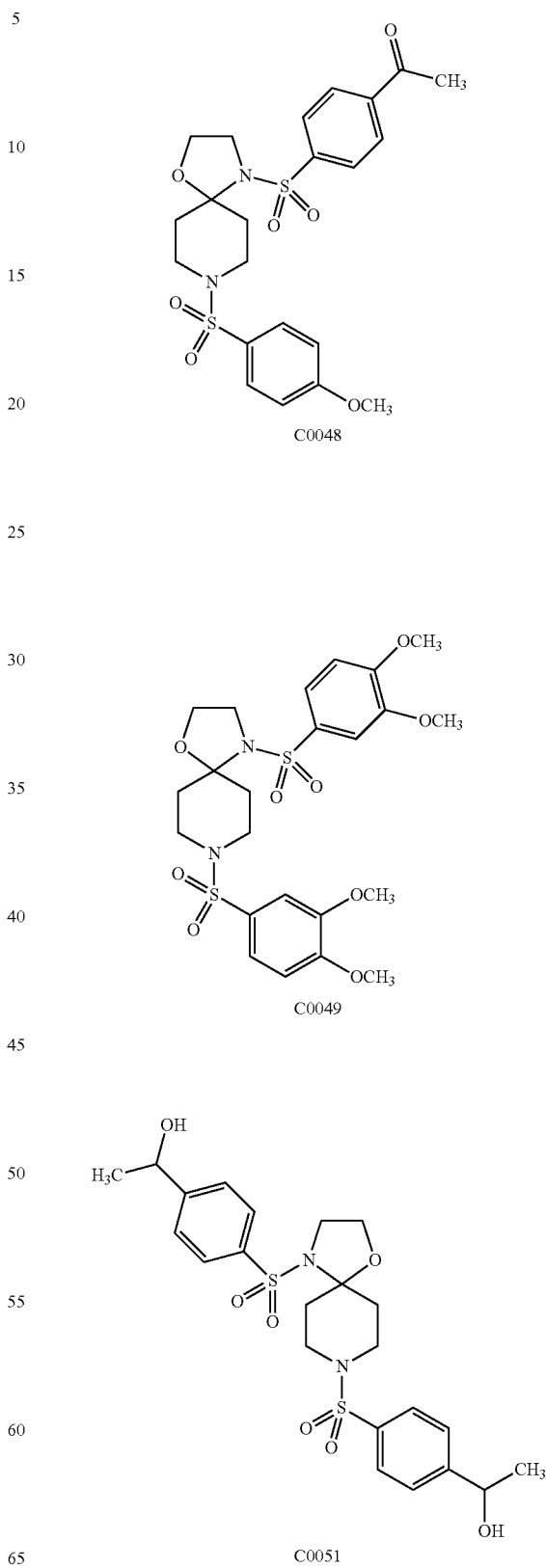

TABLE OF CORRESPONDENCE-continued
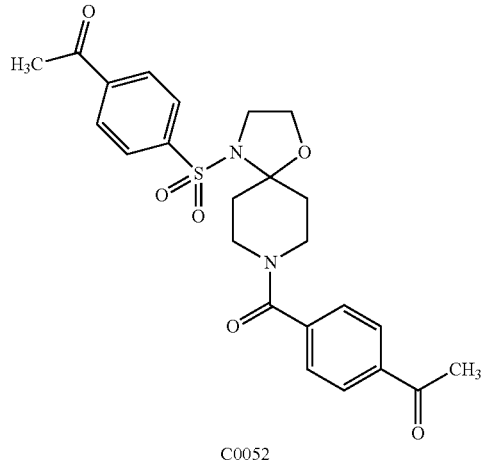
C0052
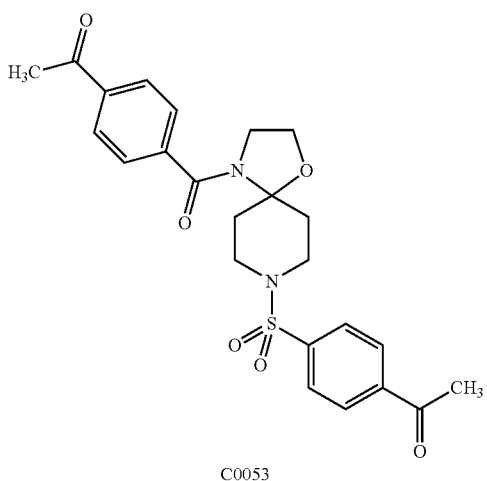
C0053
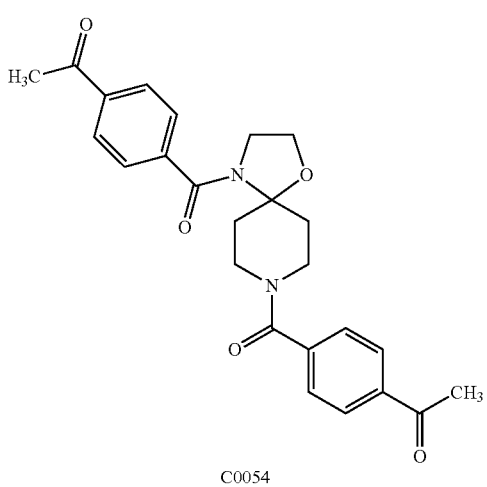
C0054
TABLE OF CORRESPONDENCE-continued
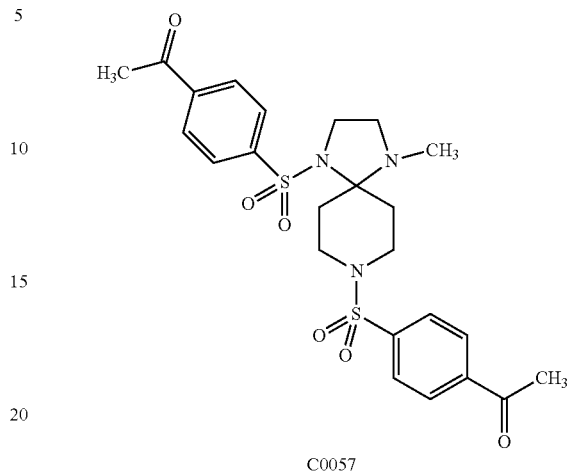
C0057
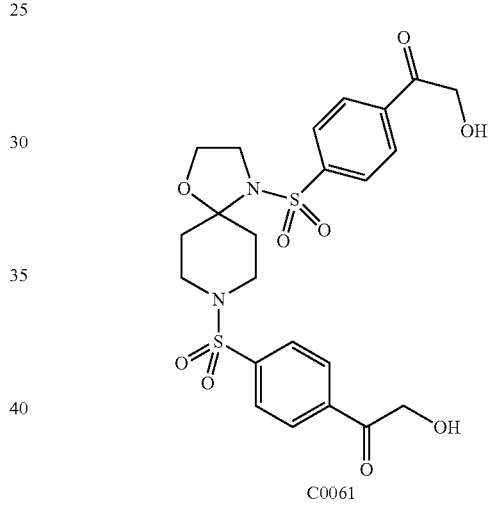
C0061
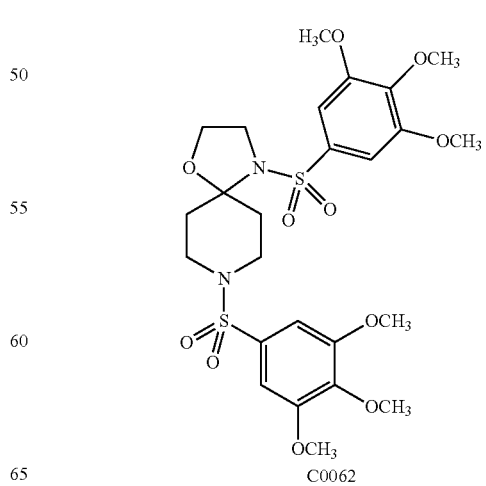
C0062

TABLE OF CORRESPONDENCE-continued
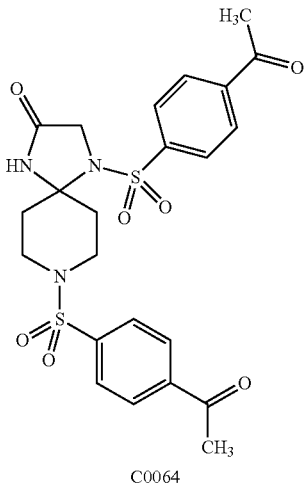
C0064
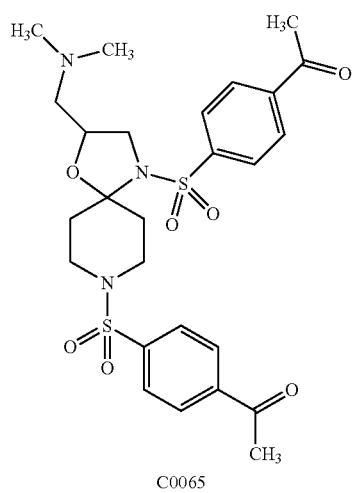
C0065
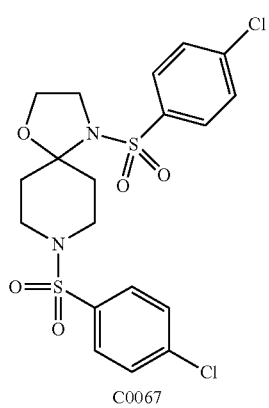
C0067
TABLE OF CORRESPONDENCE-continued
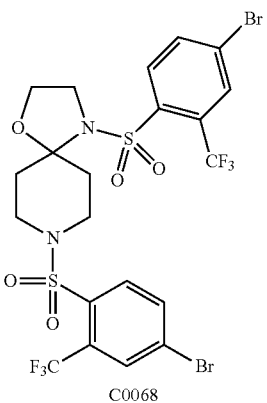
C0068
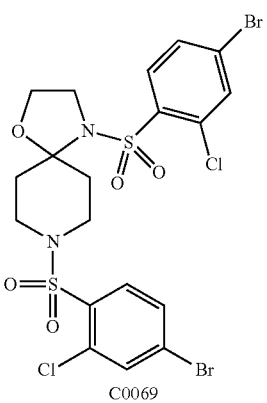
C0069
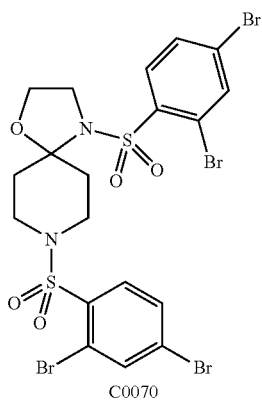
C0070
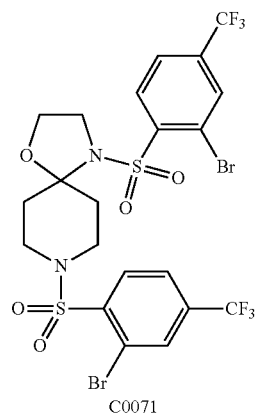
C0071

TABLE OF CORRESPONDENCE-continued
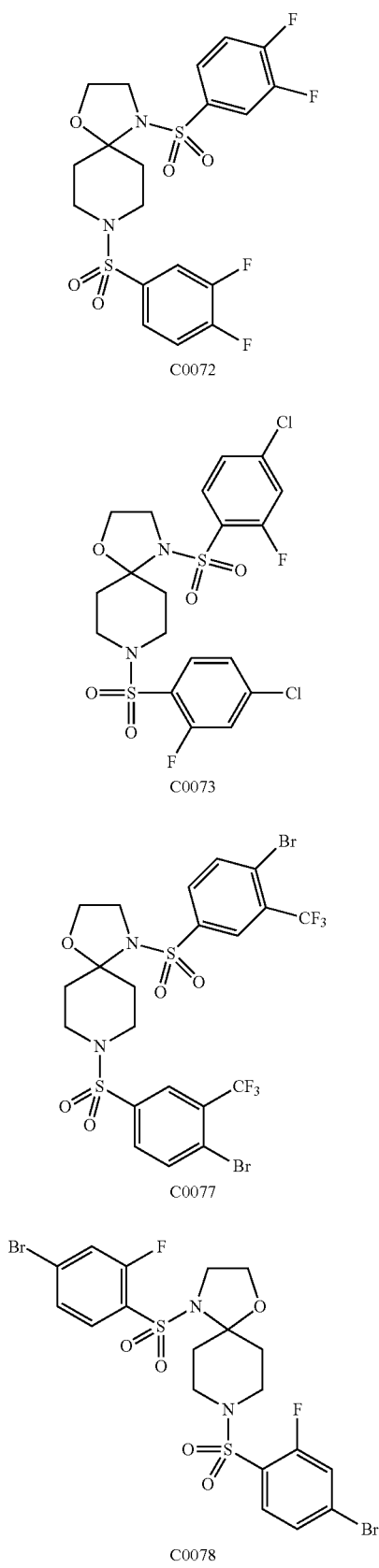
C0072
C0073
C0077
C0078
TABLE OF CORRESPONDENCE-continued
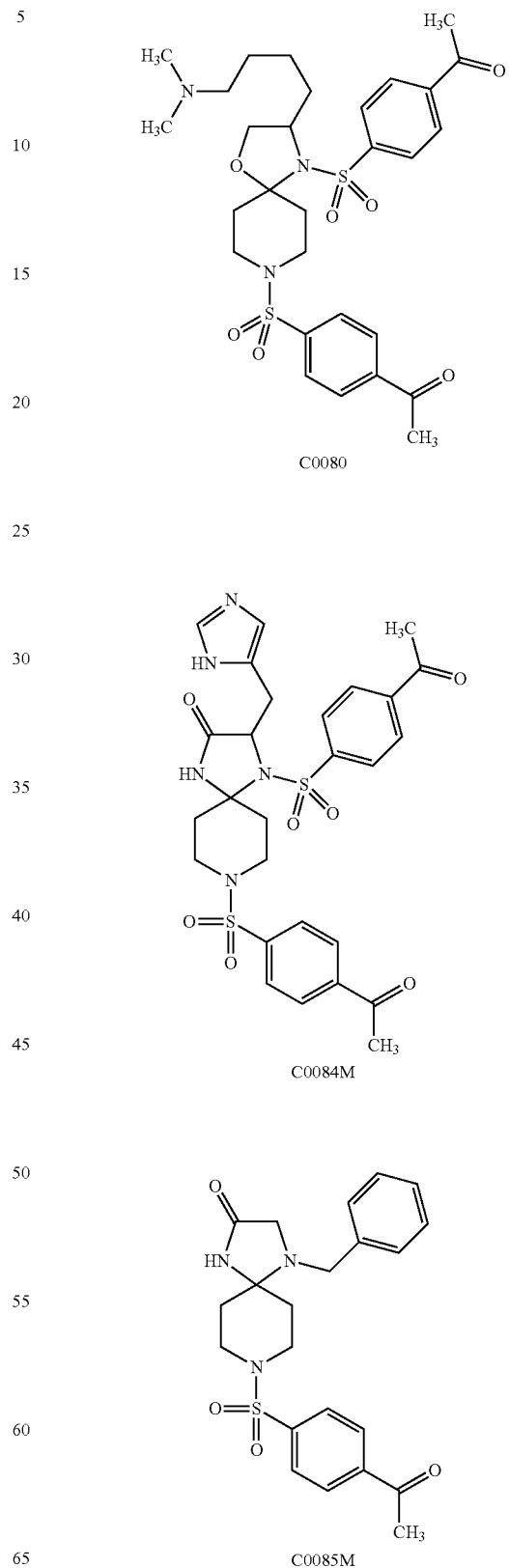
C0080
C0084M
C0085M TABLE OF CORRESPONDENCE-continued
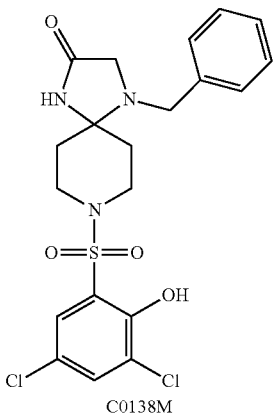
C0138M
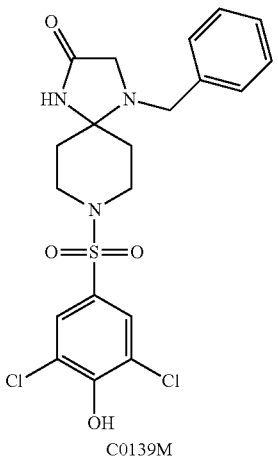
C0139M
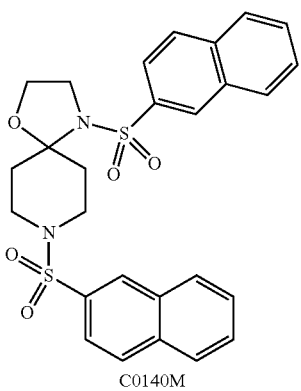
C0140M
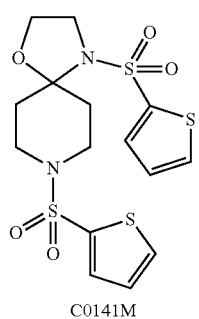
C0141M
TABLE OF CORRESPONDENCE-continued
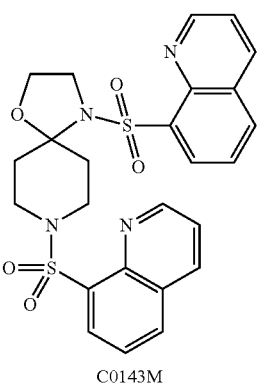
C0143M
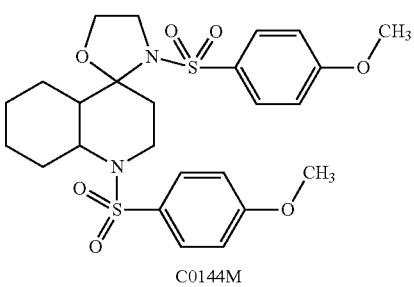
C0144M
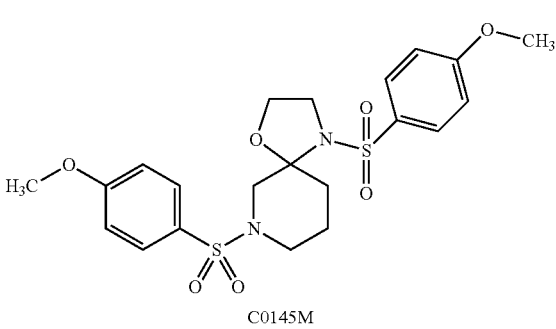
C0145M
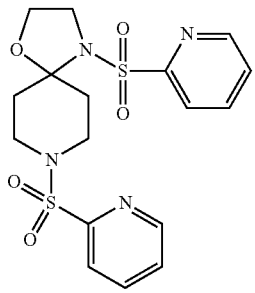 [SMILES: O=S(=O)(c1ccccn1)N1CCC2(CC1)OCCN2S(=O)(=O)c1ccccn1]
C0146M TABLE OF CORRESPONDENCE-continued

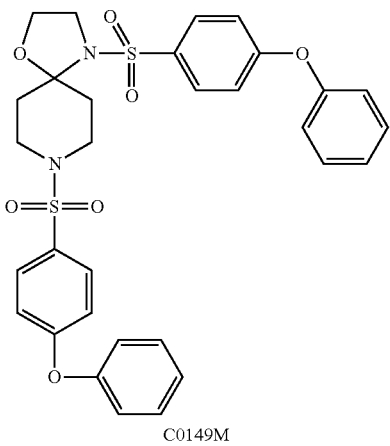

C0149M

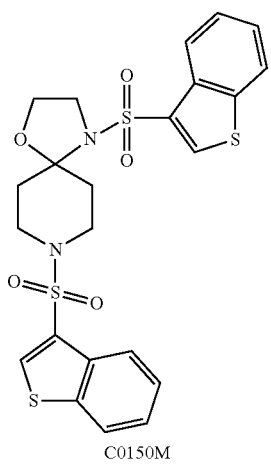

C0150M

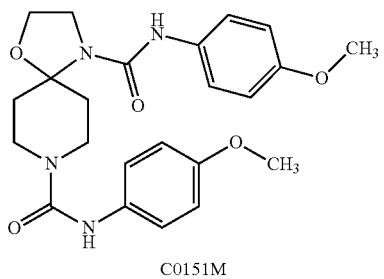

C0151M

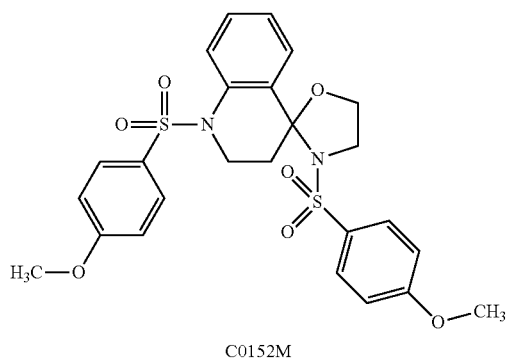

C0152M

TABLE OF CORRESPONDENCE-continued

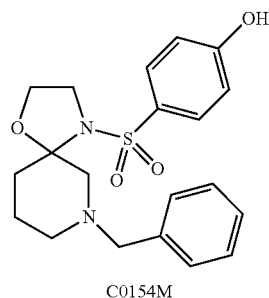

C0154M

Tables A-AG hereinafter illustrate several further contemplated compounds having various linking groups X and Y, central spiro ring systems and aromatic or heteroaromatic ring systems, circle A and Circle B. Substituents on the aromatic or heteroaromatic ring systems are omitted for added clarity with the understanding that one to three substituents, $R^{1a-c}$ and $R^{2a-c}$, can be present bonded to each of the ring systems as discussed previously.

TABLE A

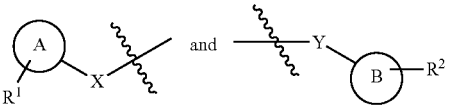

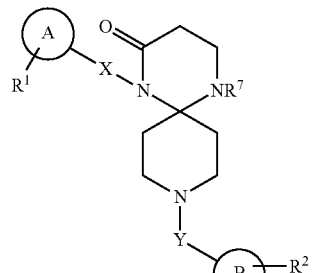

$R^1 = R^2 = H$

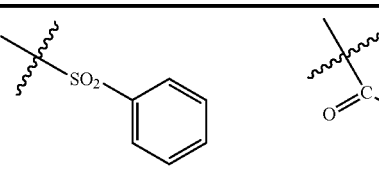

TABLE A-continued
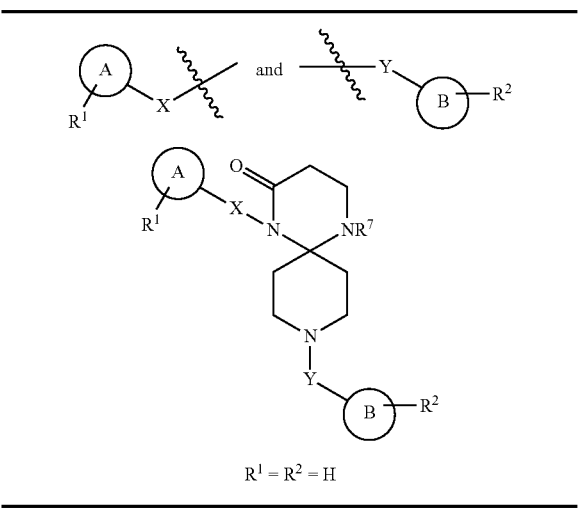
$R^1 = R^2 = H$
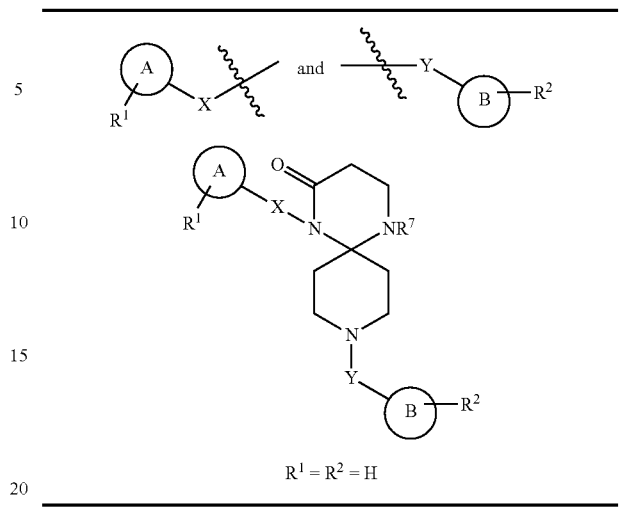
$R^1 = R^2 = H$
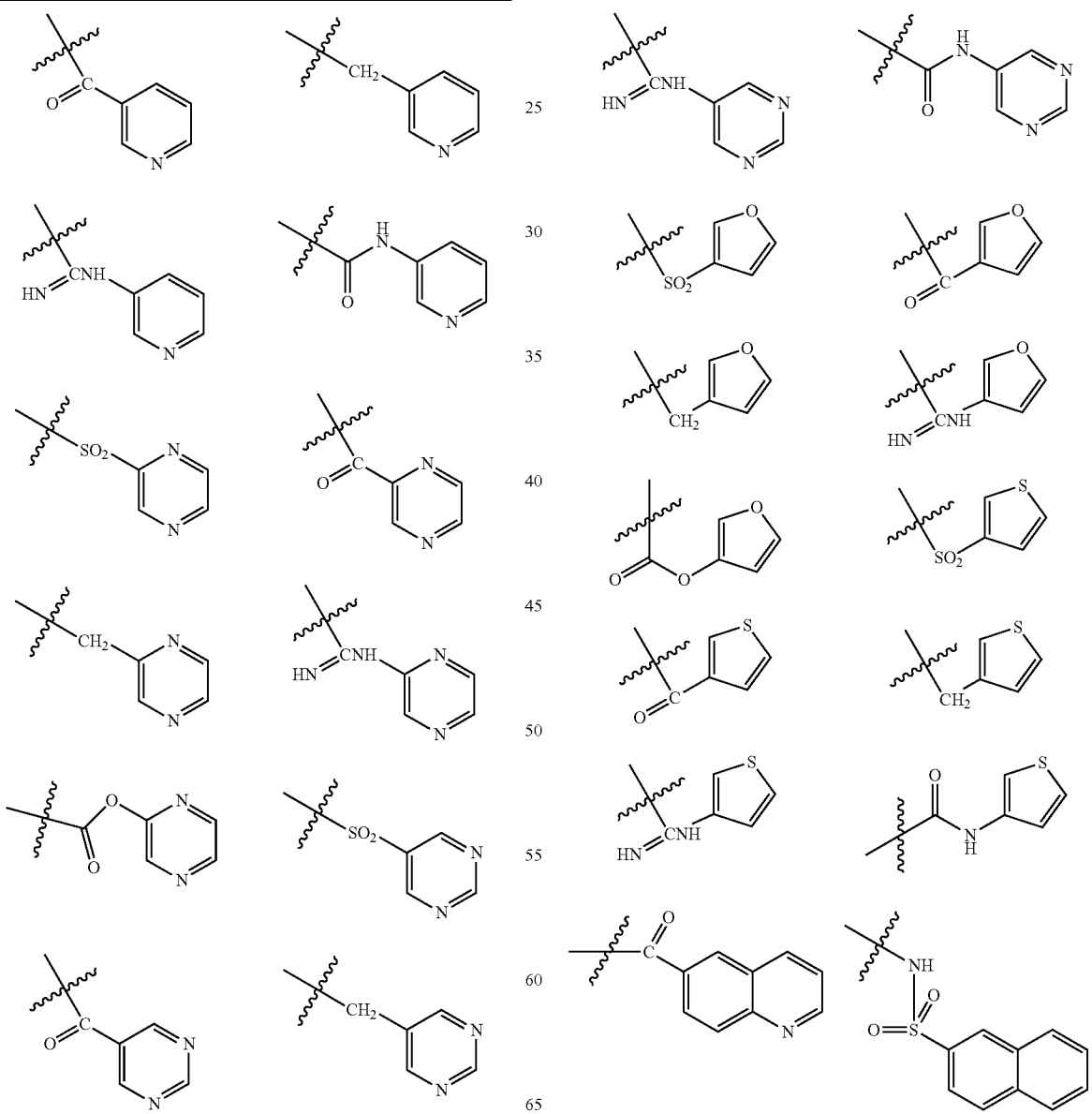

TABLE A-continued
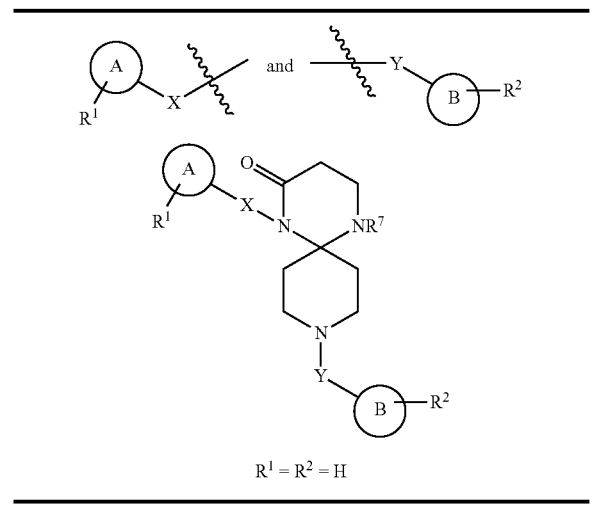
$R^1 = R^2 = H$
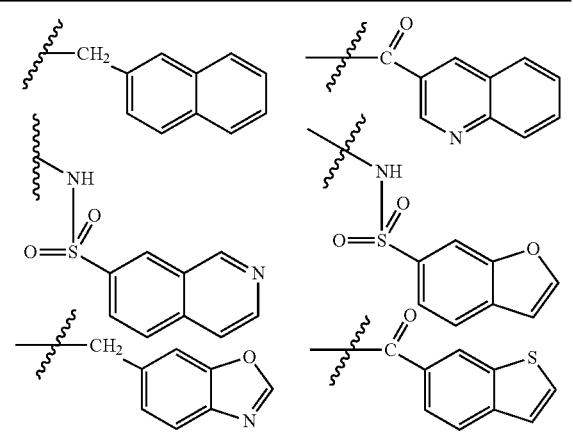
TABLE B
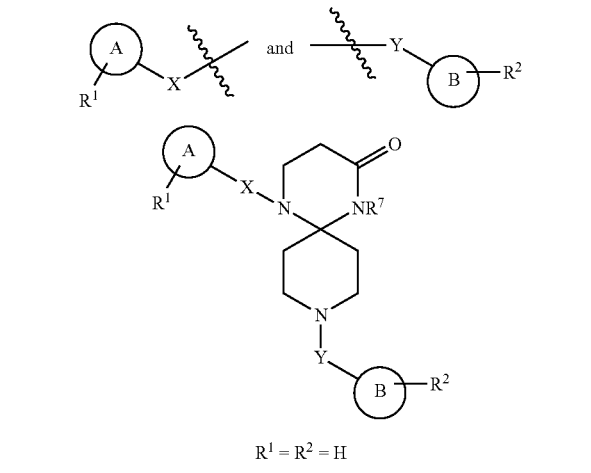
$R^1 = R^2 = H$
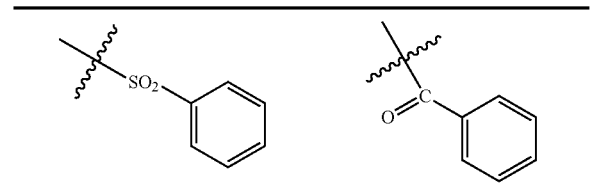
TABLE B-continued
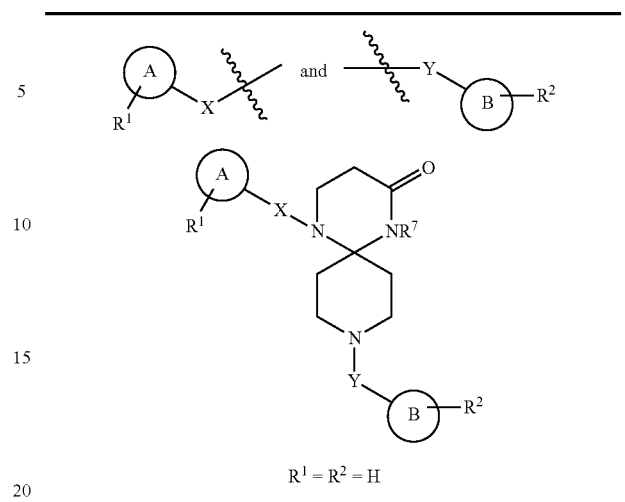
$R^1 = R^2 = H$
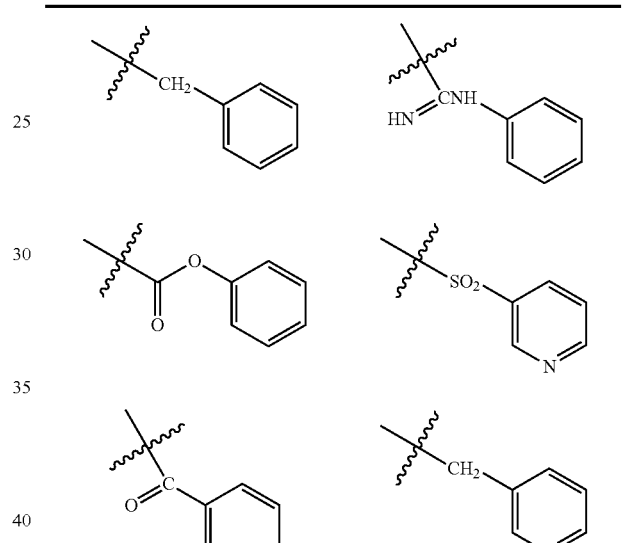
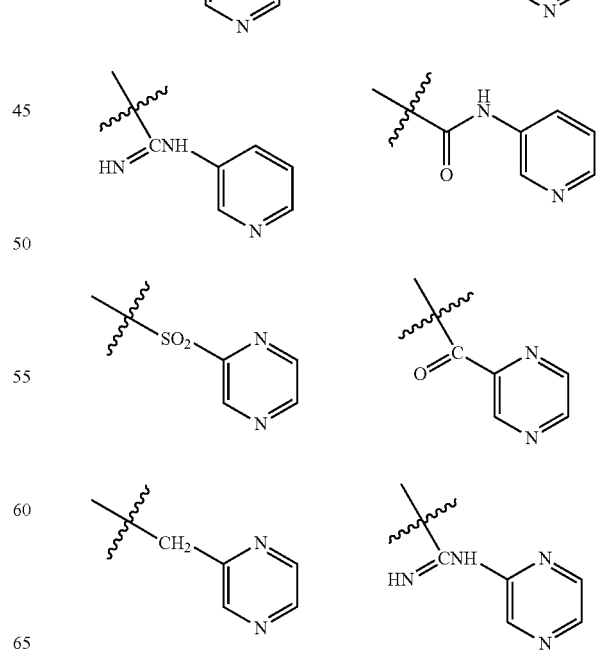

TABLE B-continued
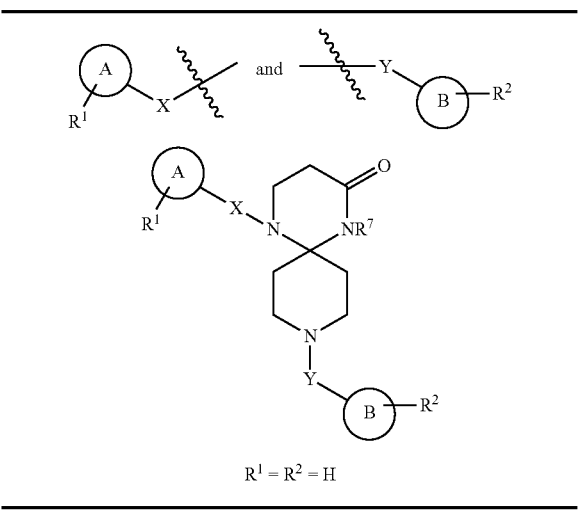
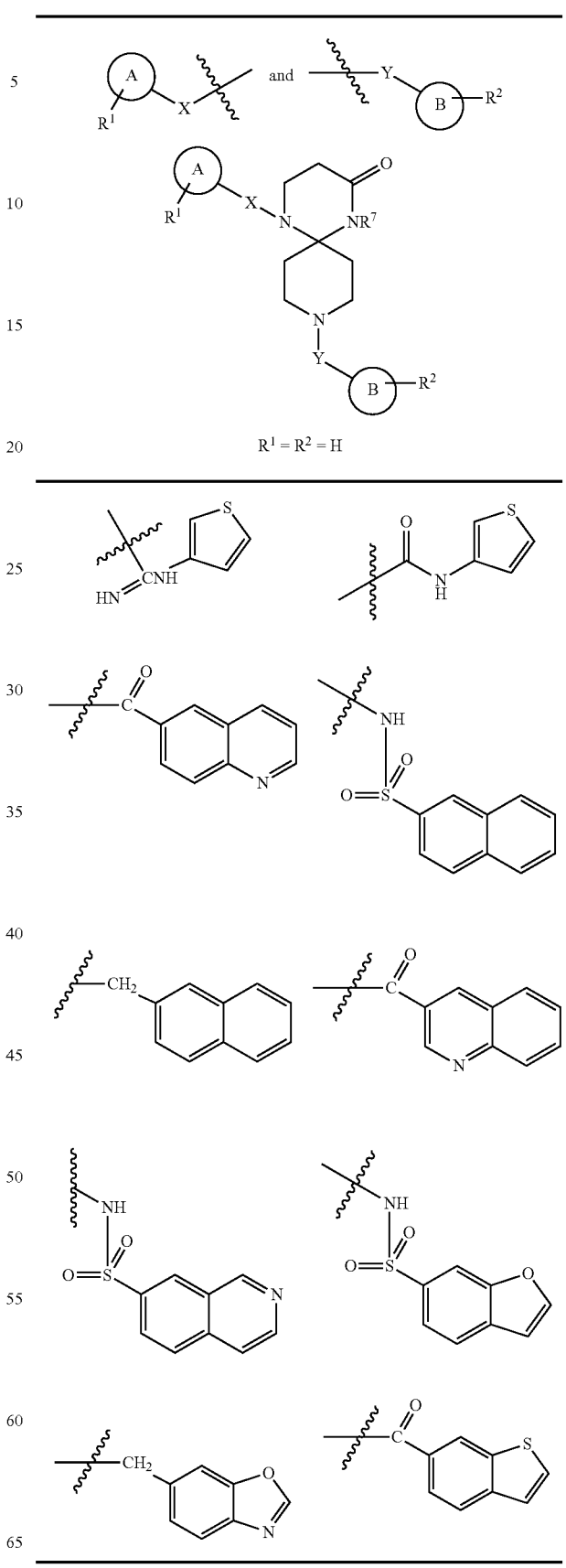

TABLE C
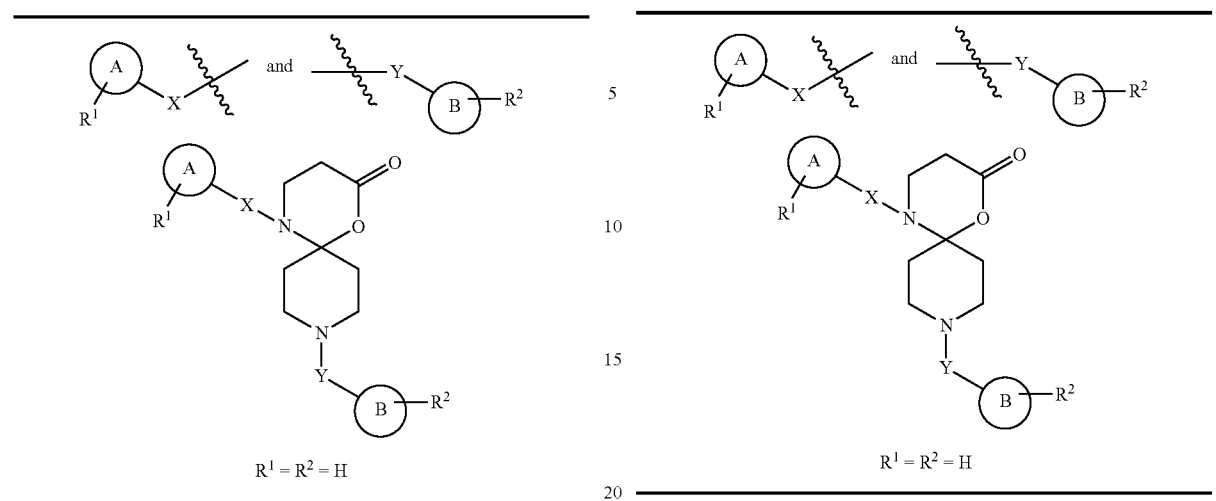
$R^1 = R^2 = H$
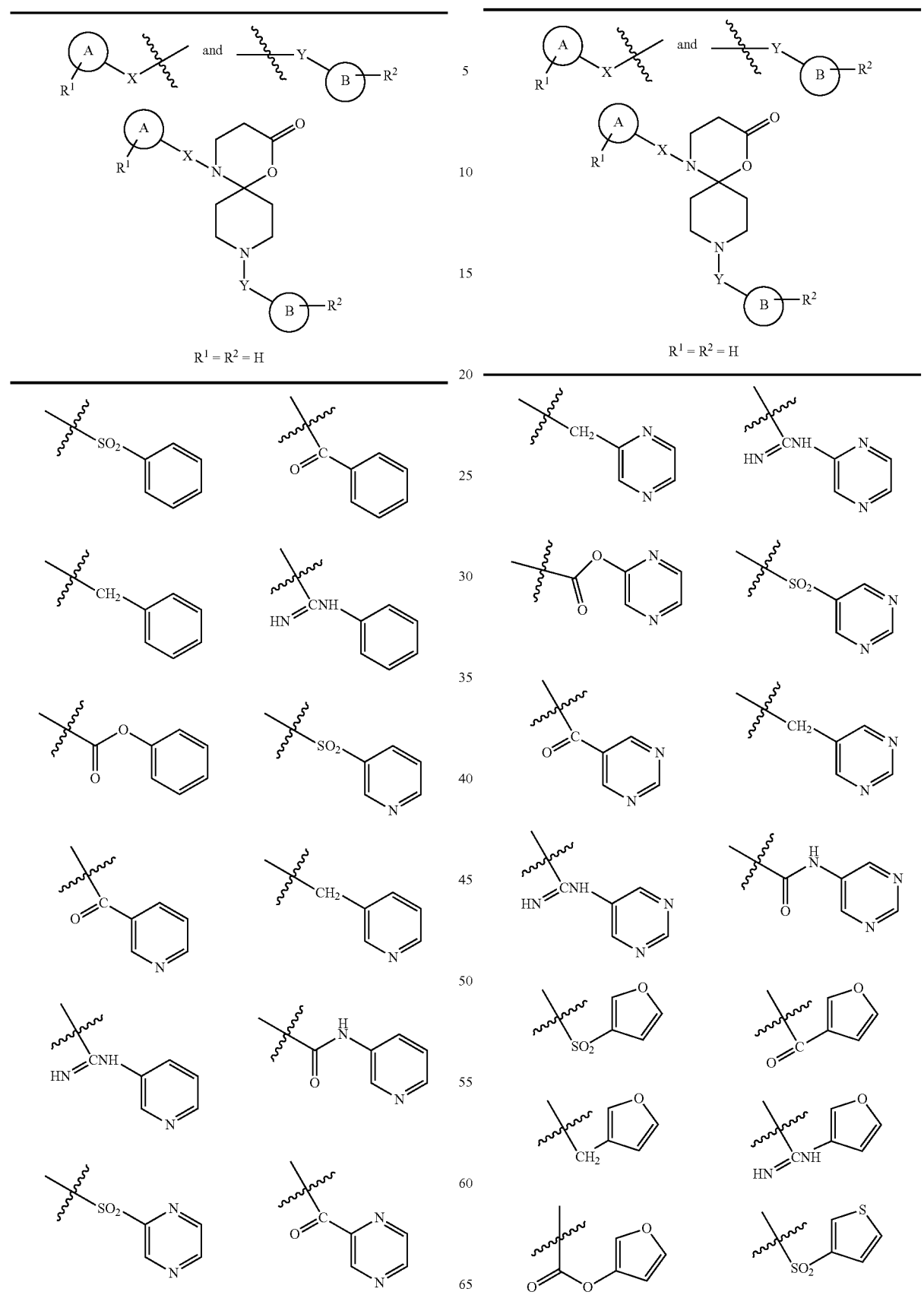

TABLE C-continued
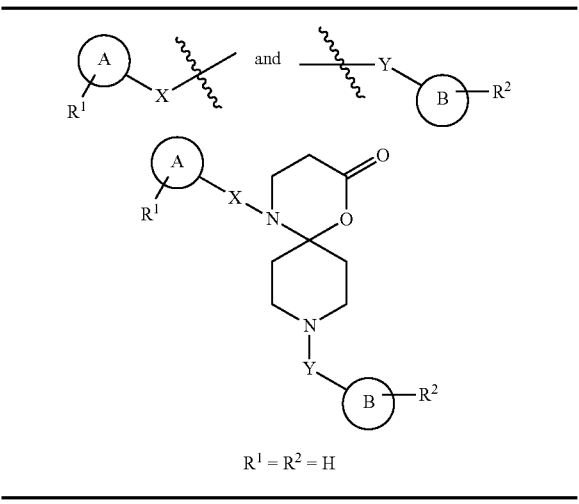
$R^1 = R^2 = H$
TABLE D
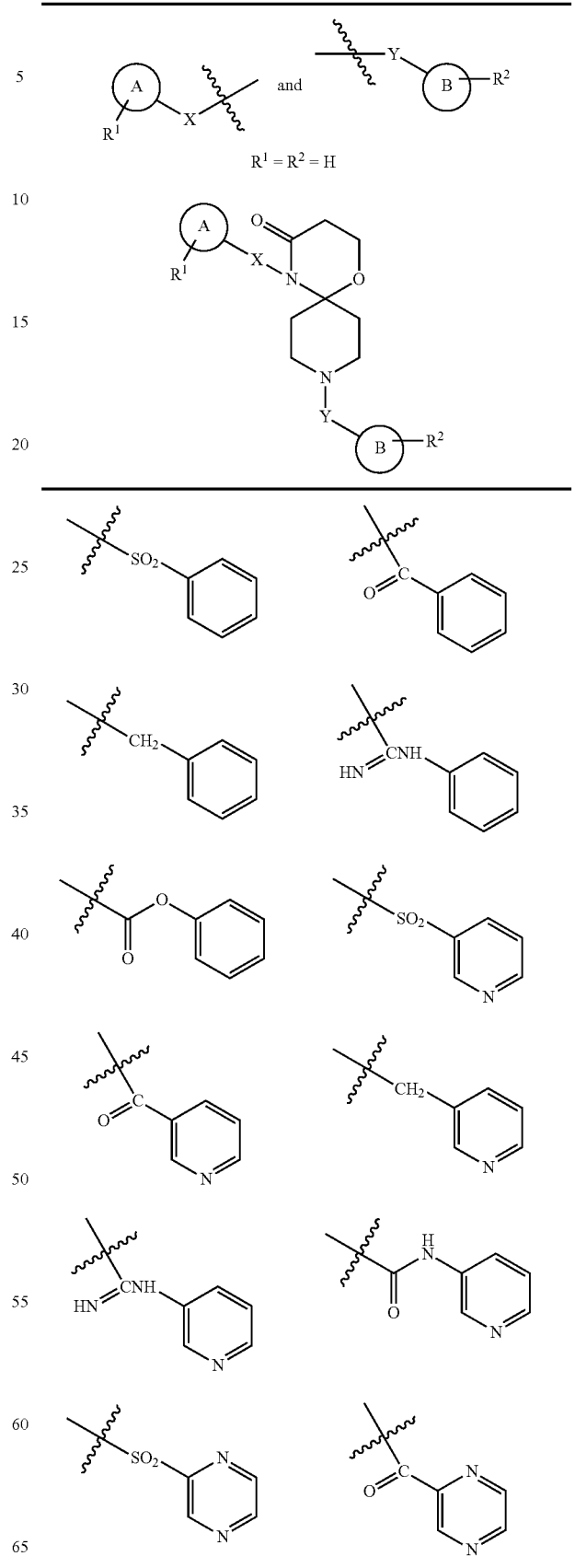
$R^1 = R^2 = H$ TABLE D-continued
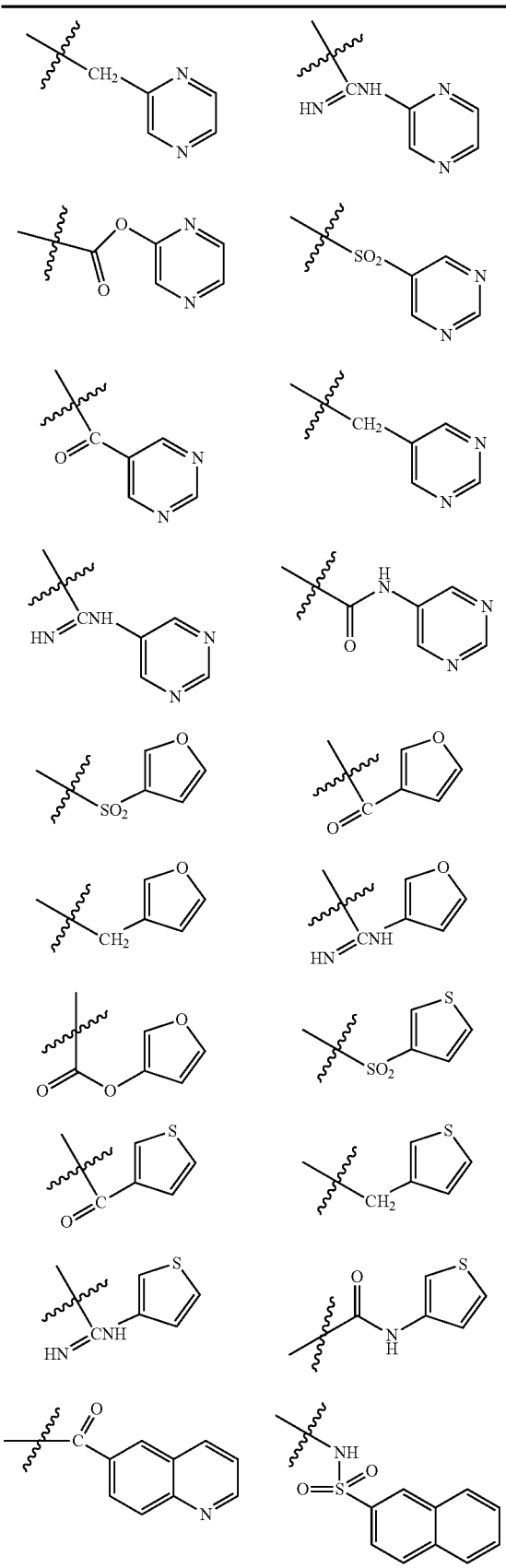
TABLE D-continued
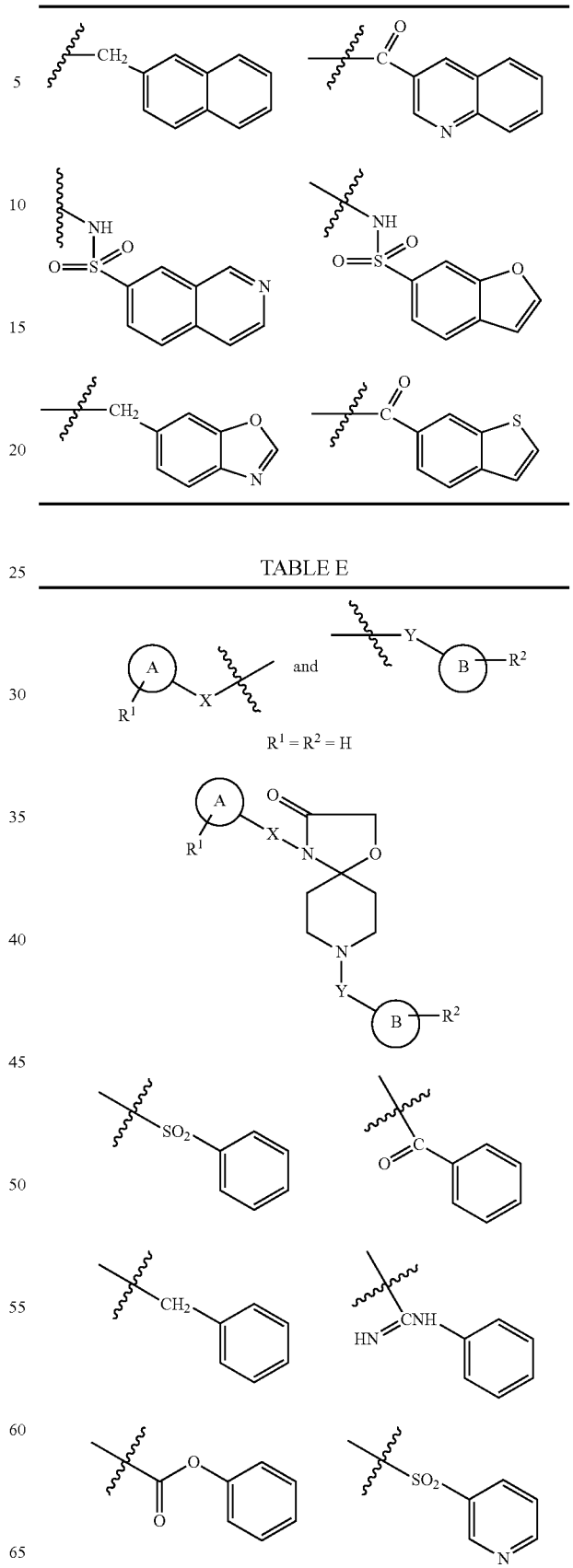
TABLE E TABLE E-continued
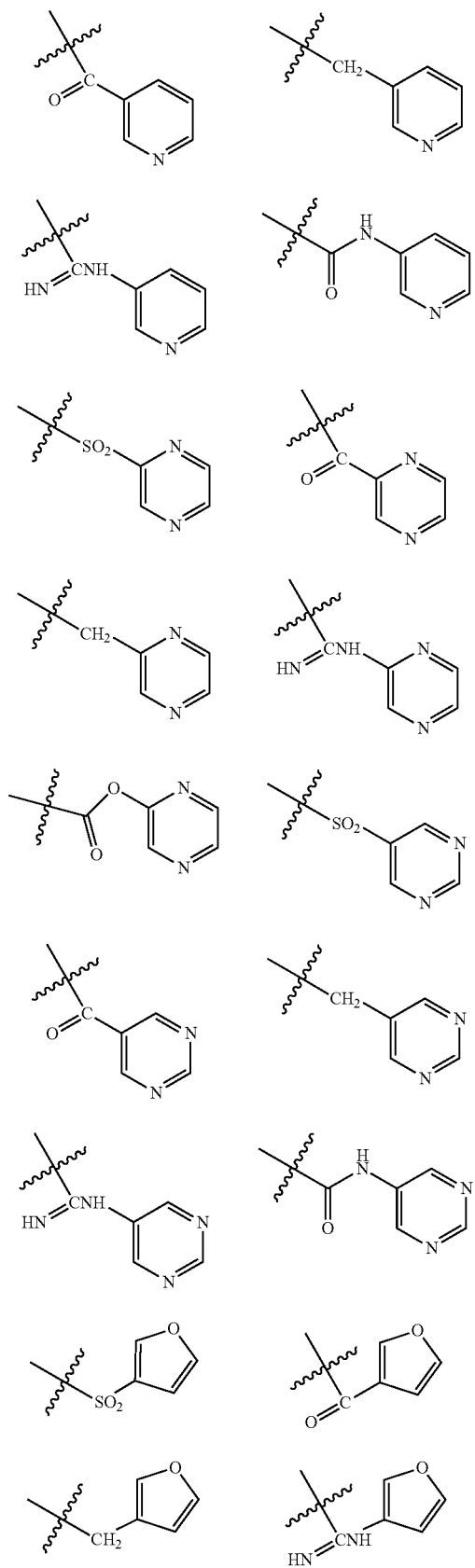
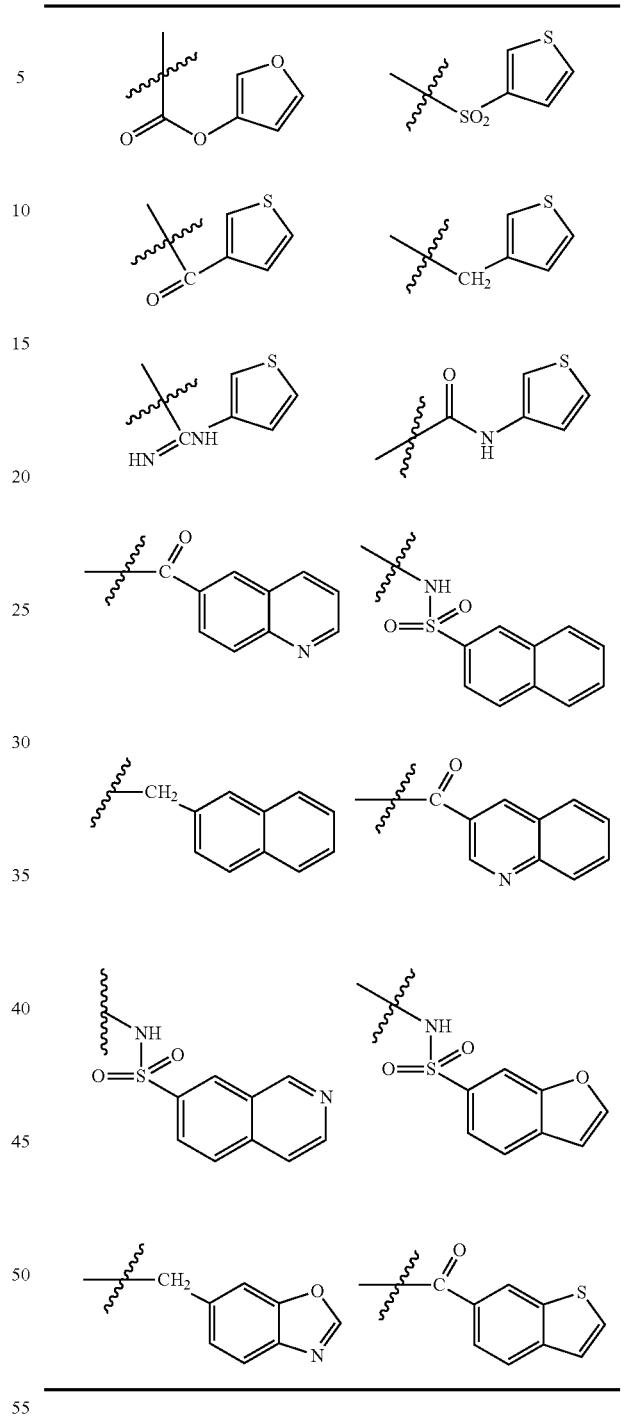
TABLE F
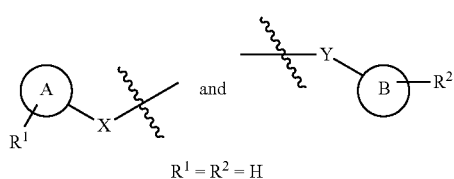
$R^1 = R^2 = H$ TABLE F-continued
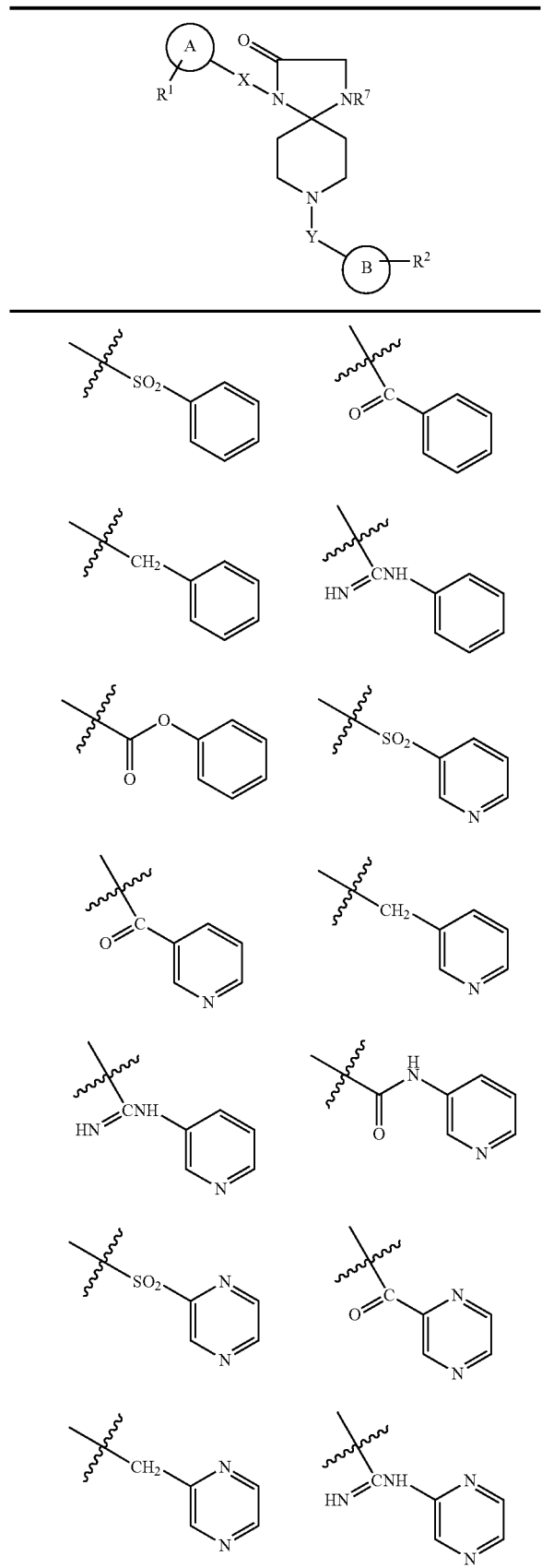
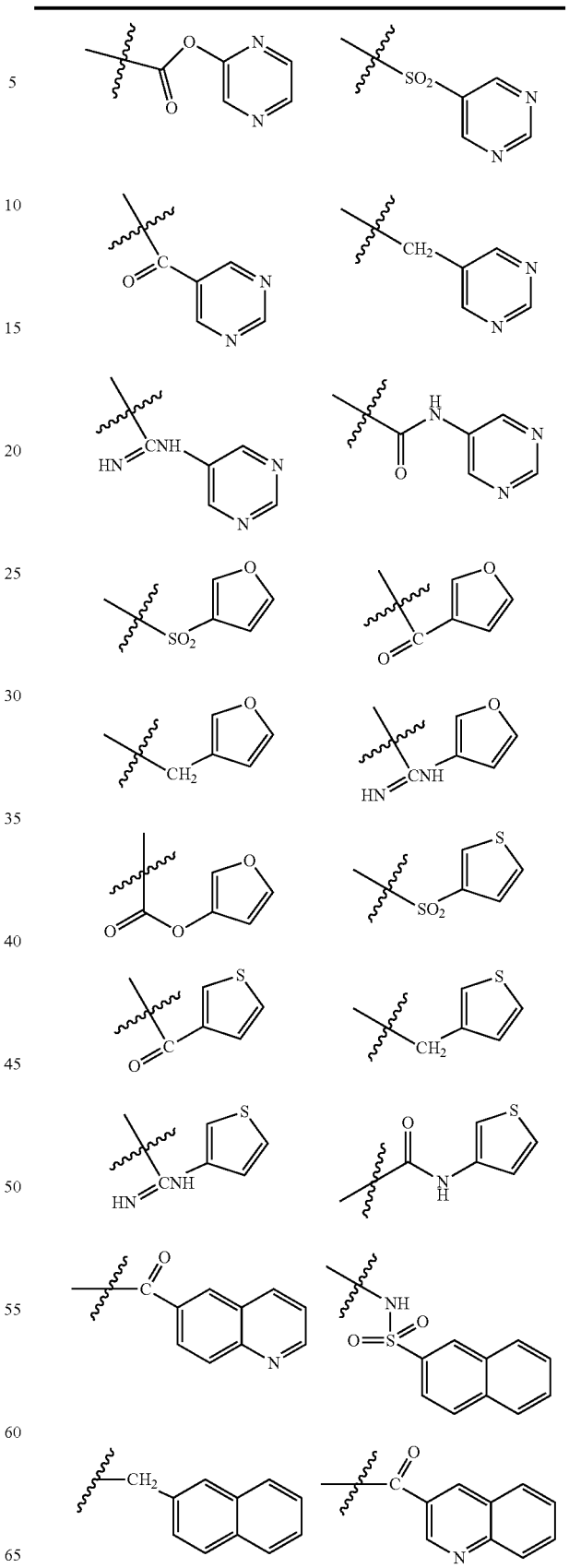

TABLE F-continued
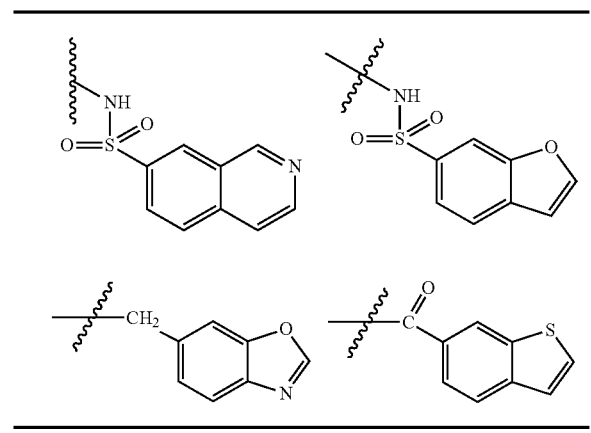
TABLE G
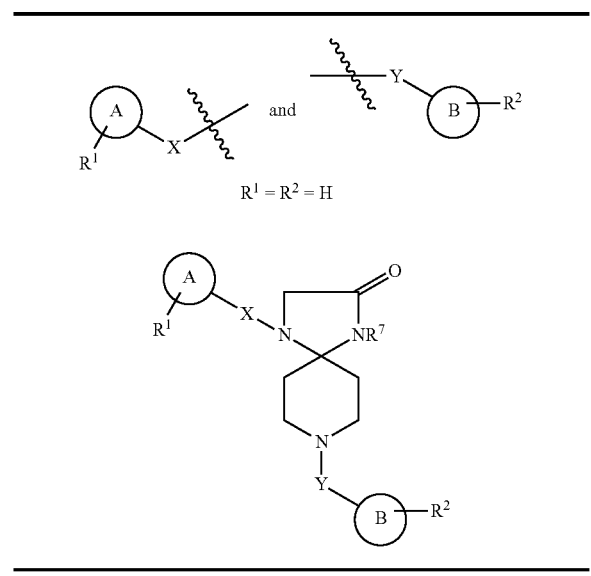
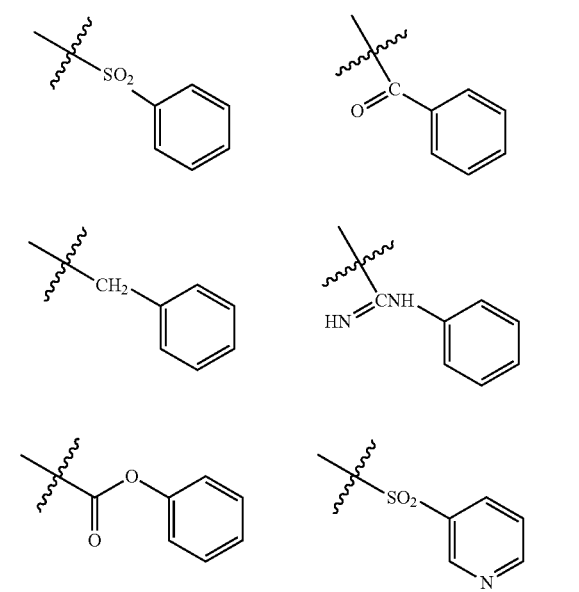
TABLE G-continued
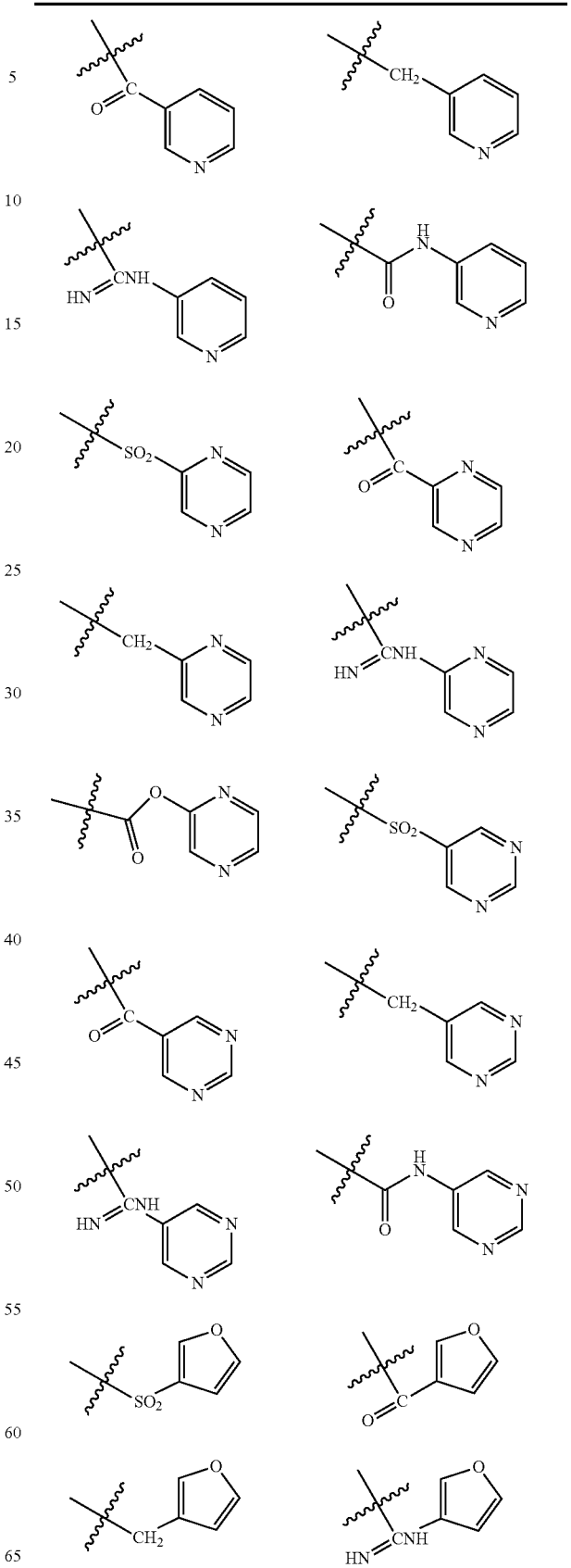

TABLE G-continued
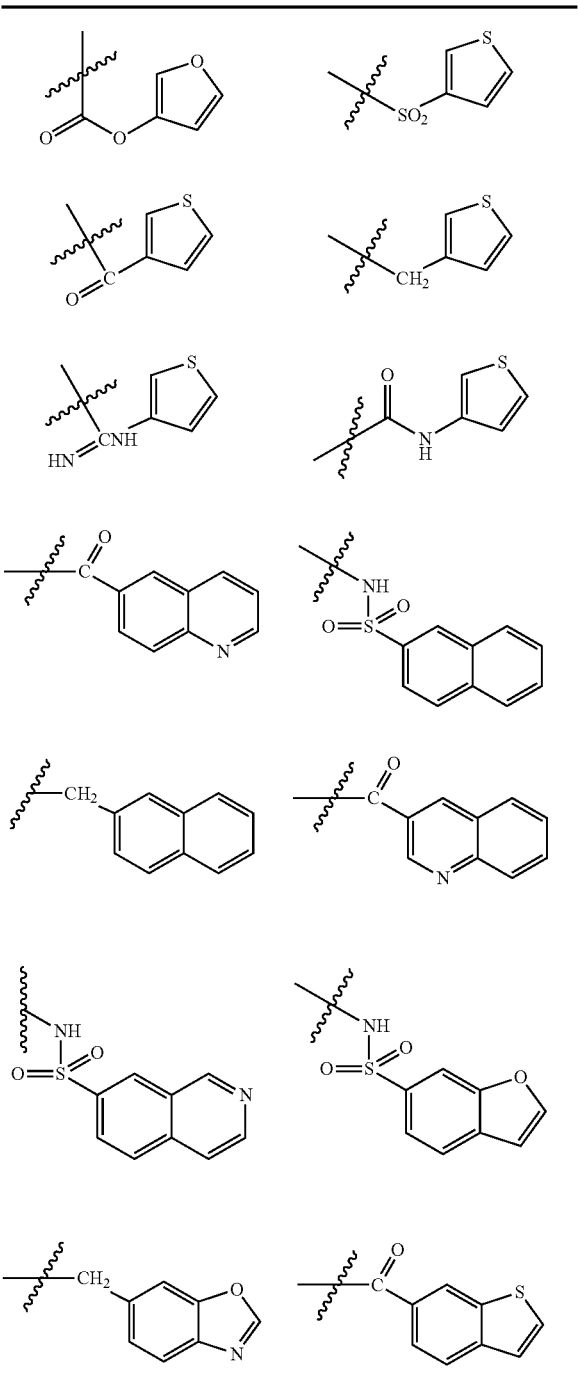
TABLE H
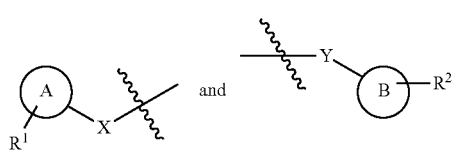
R¹ = R² = H
TABLE H-continued
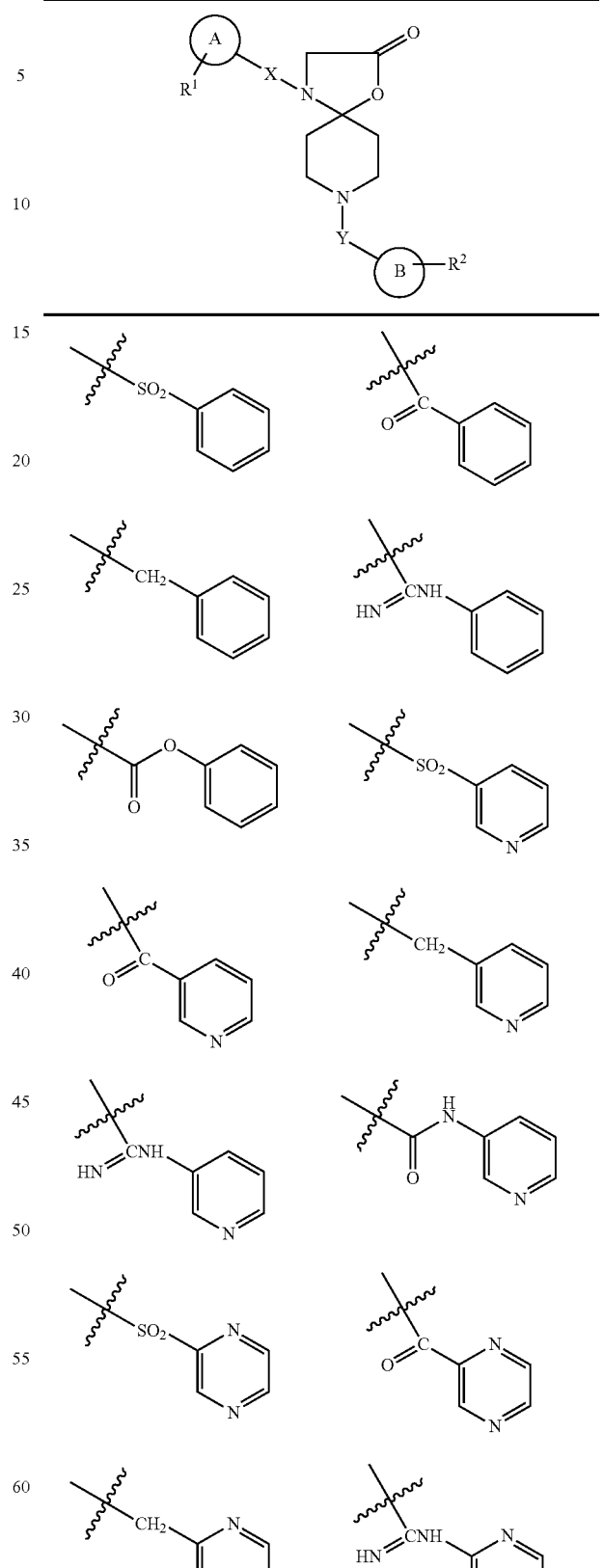

TABLE H-continued
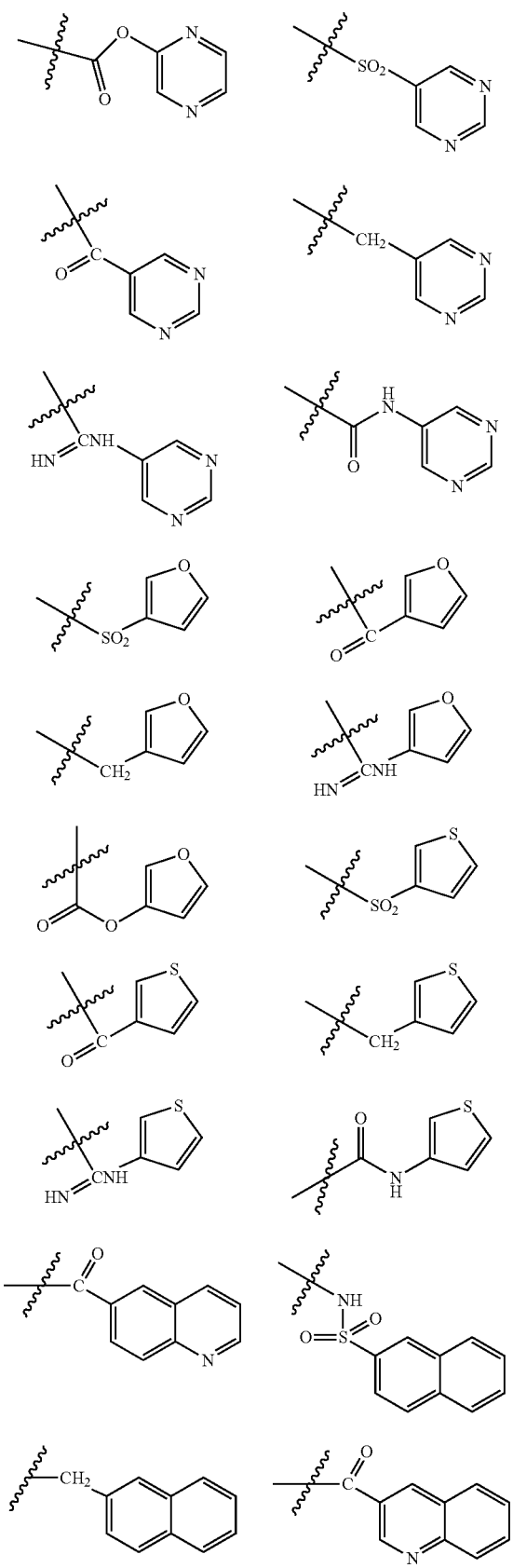
TABLE H-continued
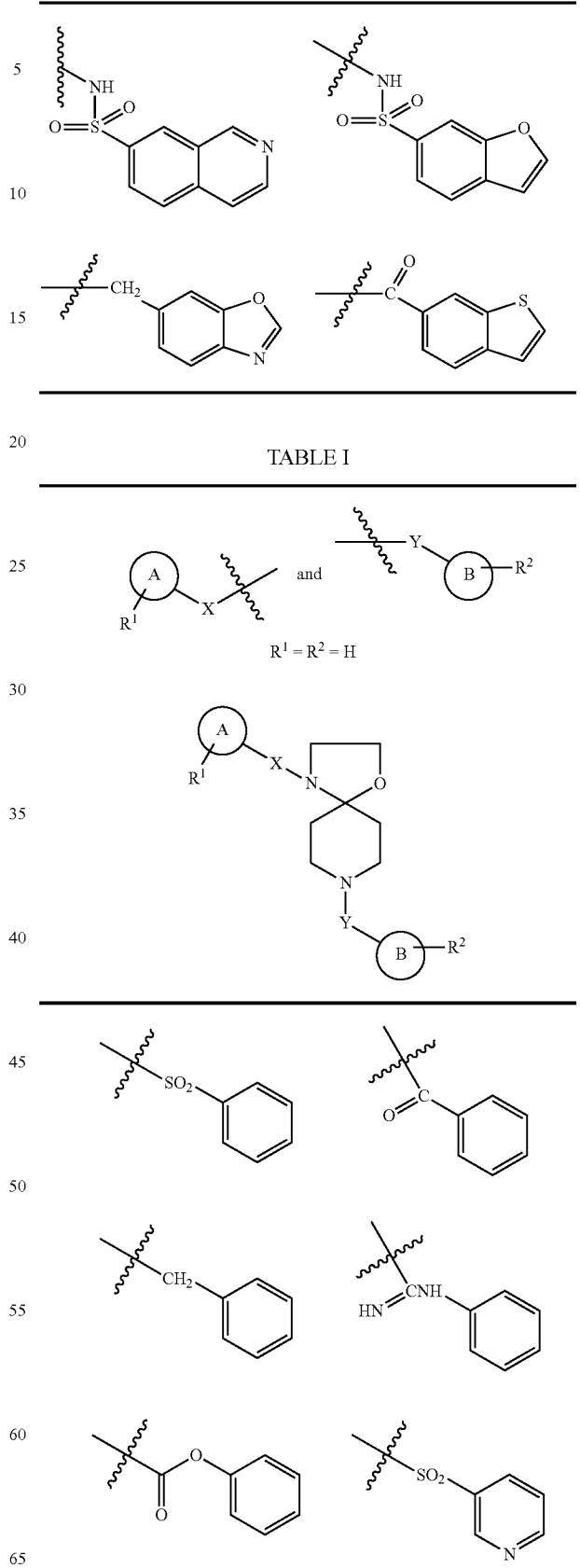
TABLE I
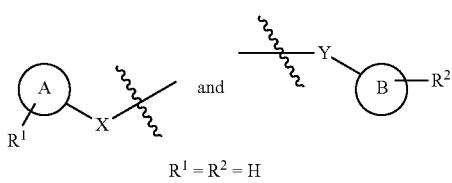
R[1] = R[2] = H
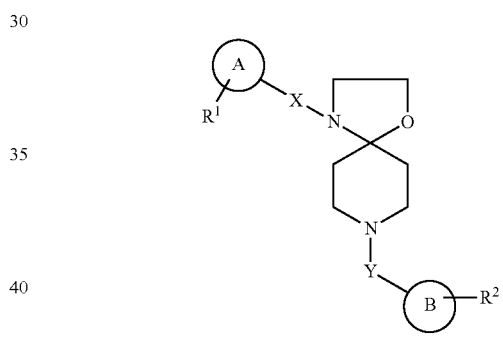
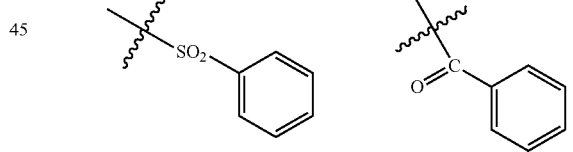
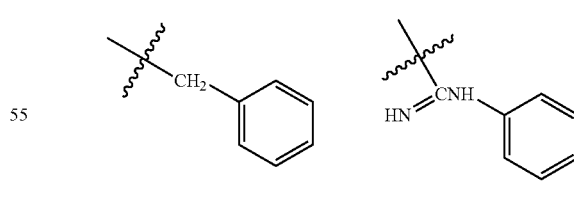
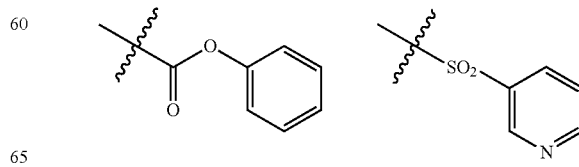

TABLE I-continued
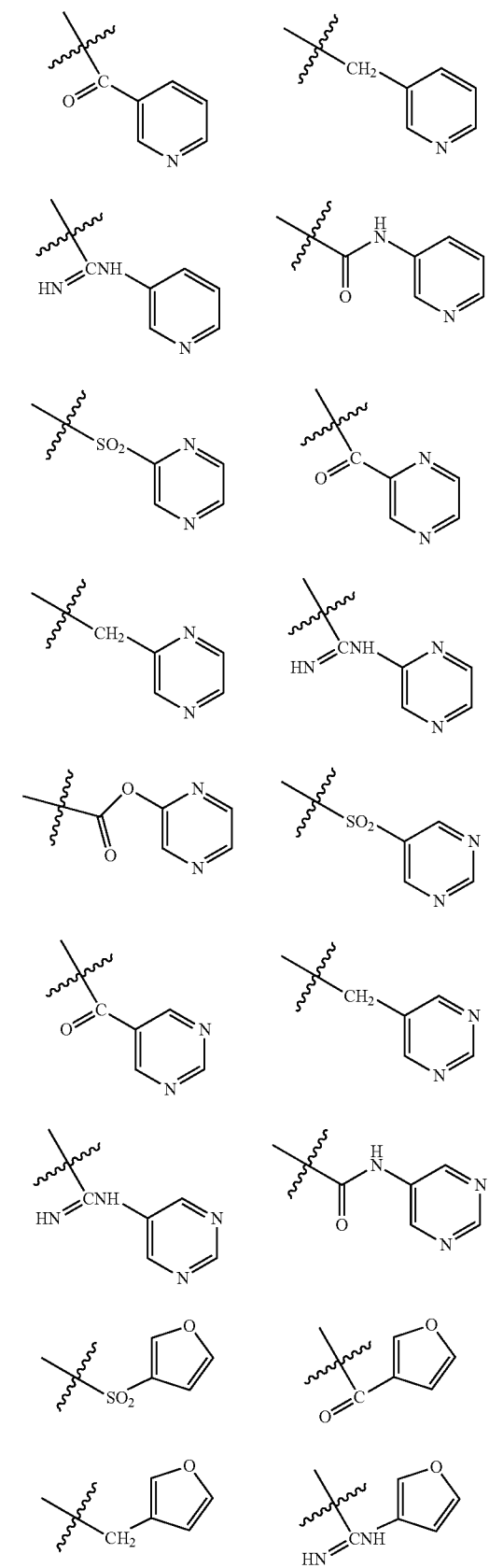
TABLE I-continued
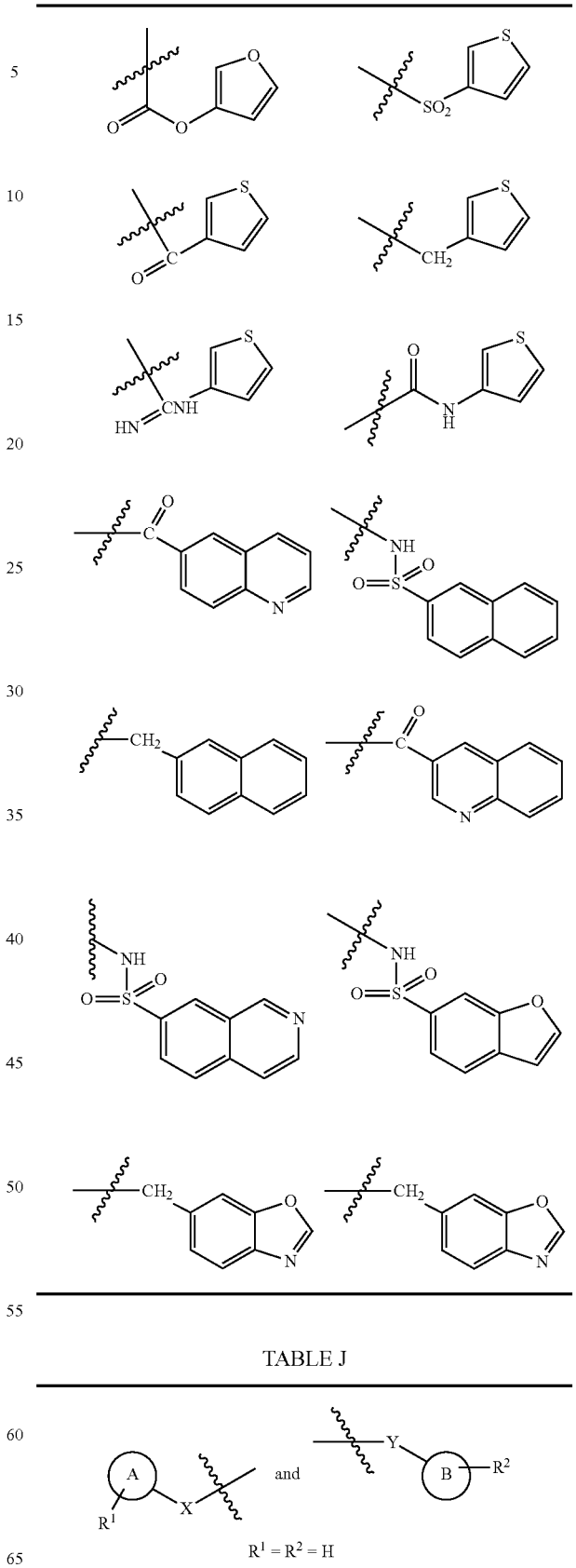
TABLE J

TABLE J-continued
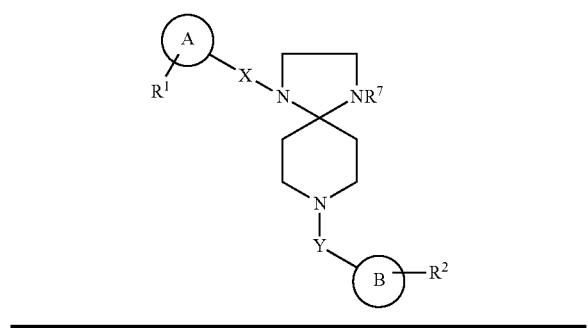
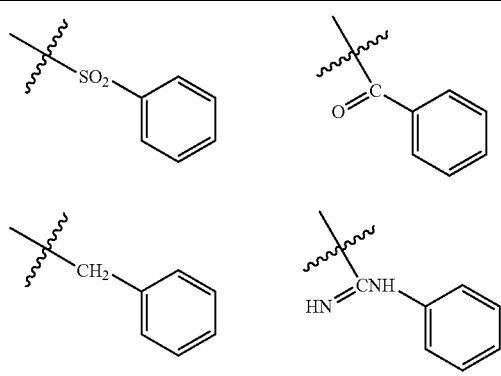
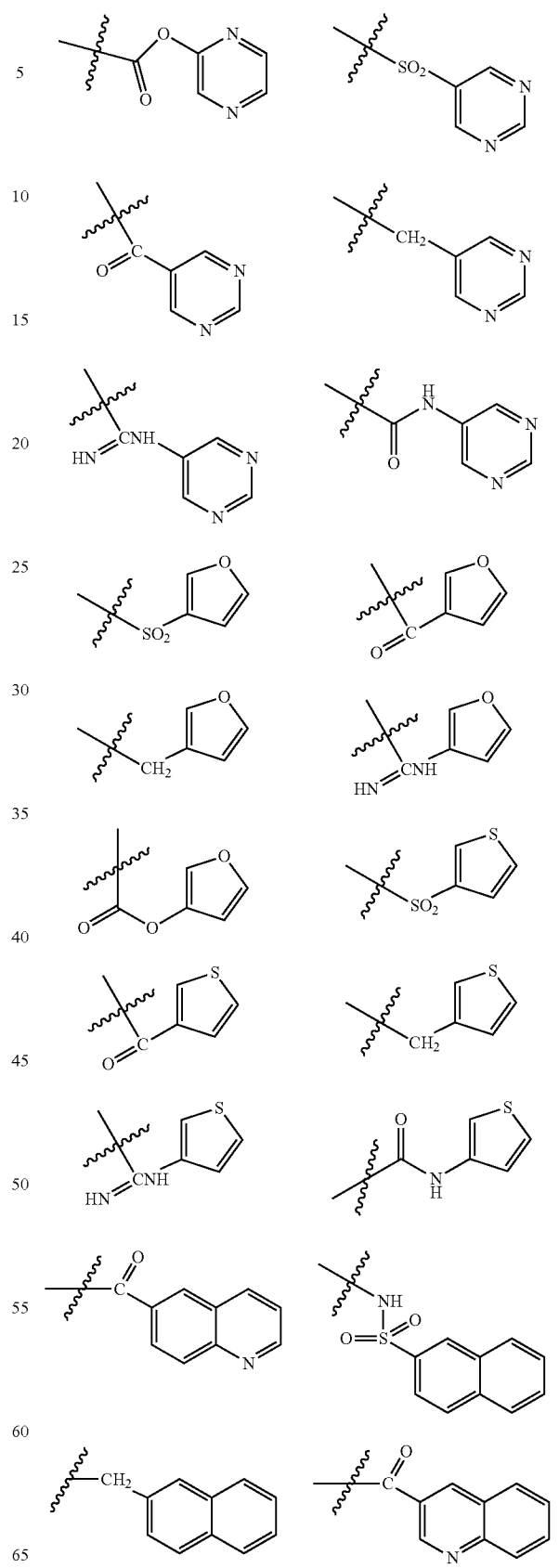

TABLE J-continued
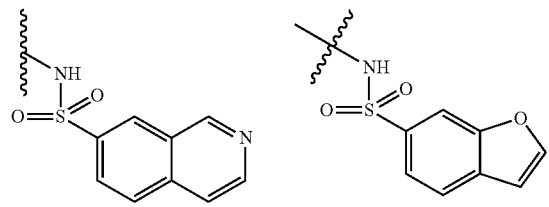
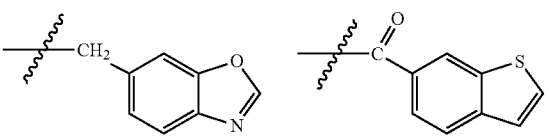
TABLE K
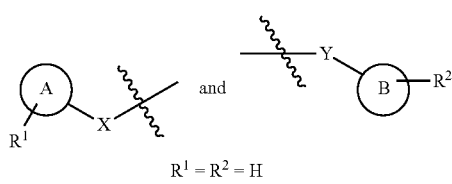
R¹ = R² = H
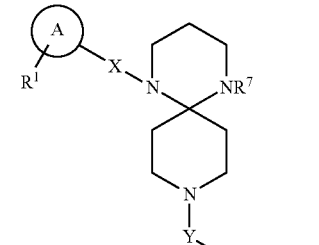
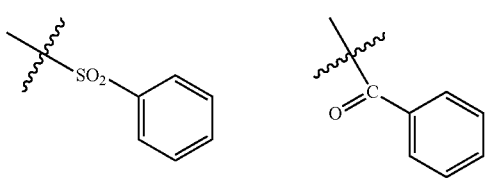
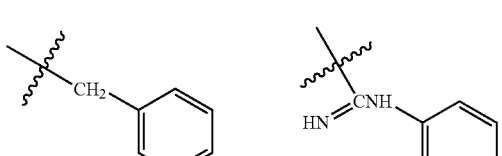
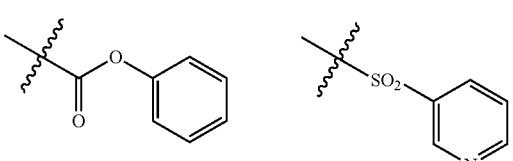
TABLE K-continued
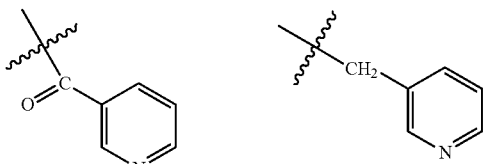
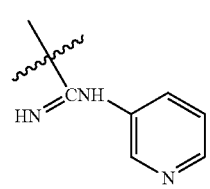
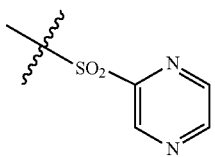 [SMILES: *S(=O)(=O)c1cnccn1]
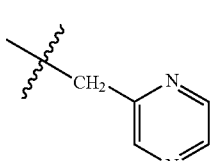
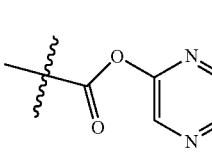
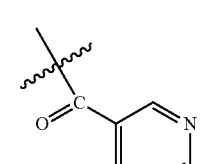
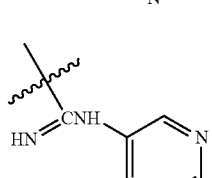
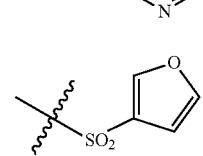
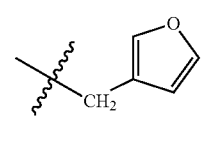

TABLE K-continued
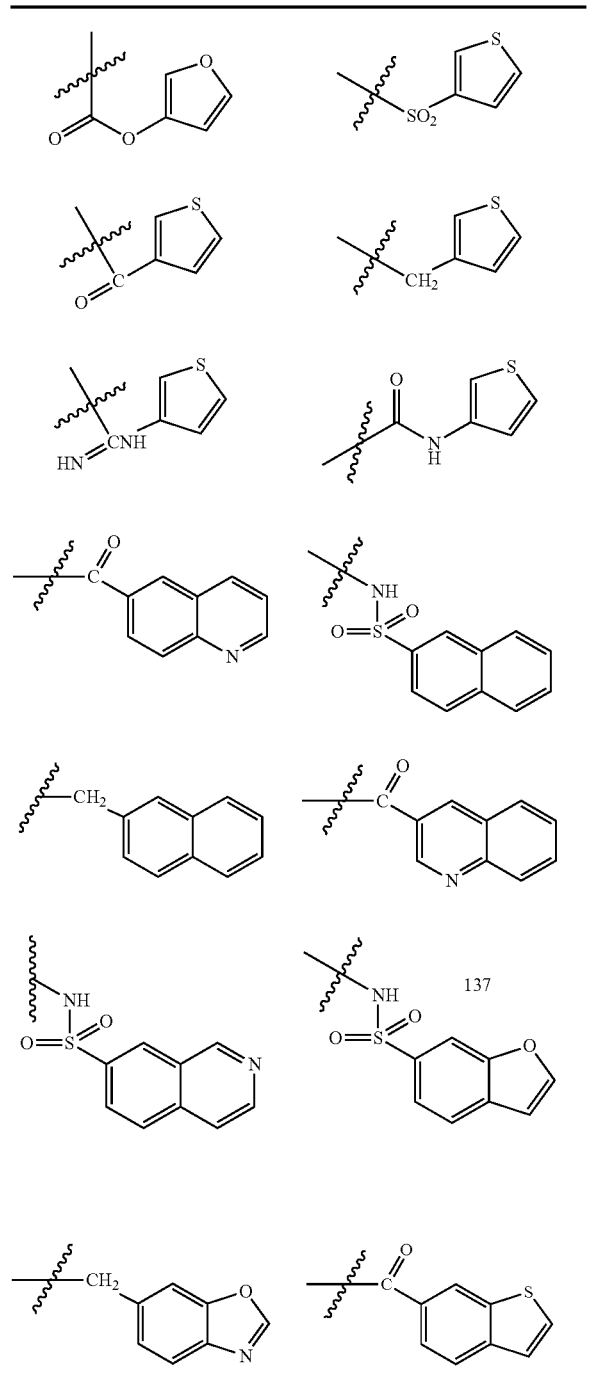
TABLE L
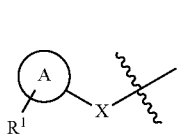 and 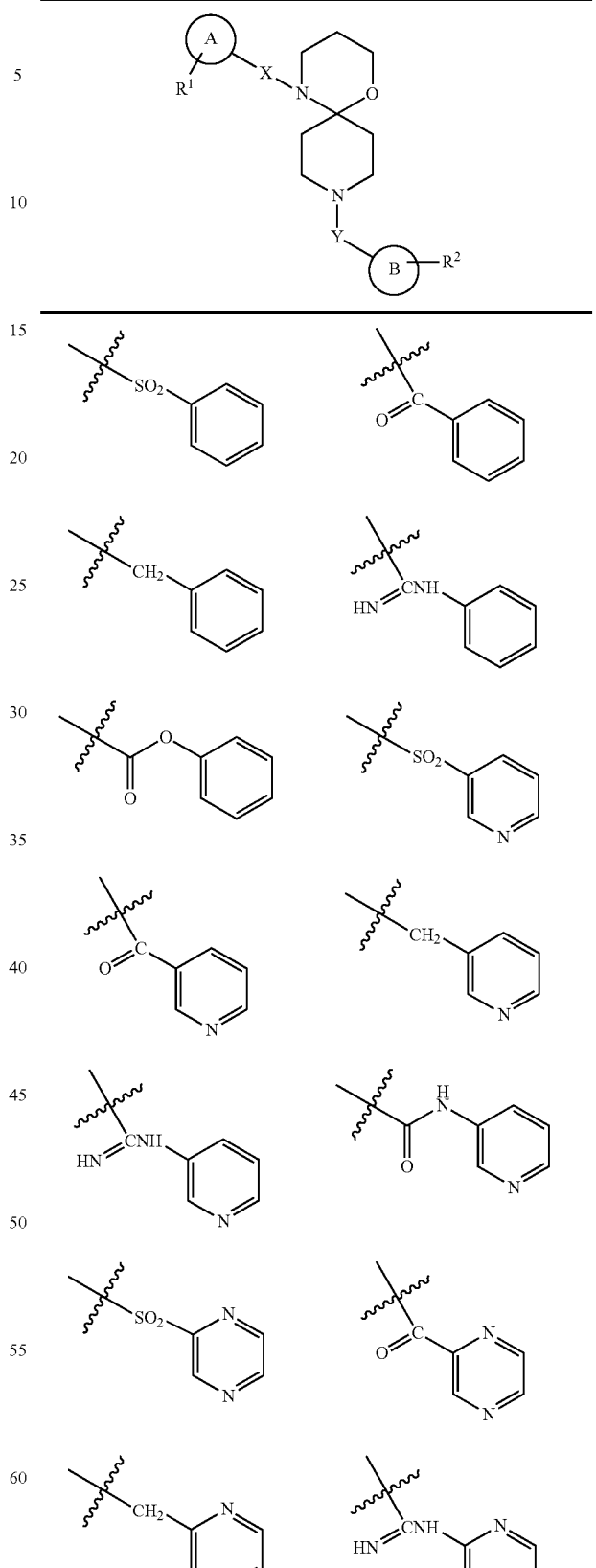
R¹ = R² = H

TABLE L-continued
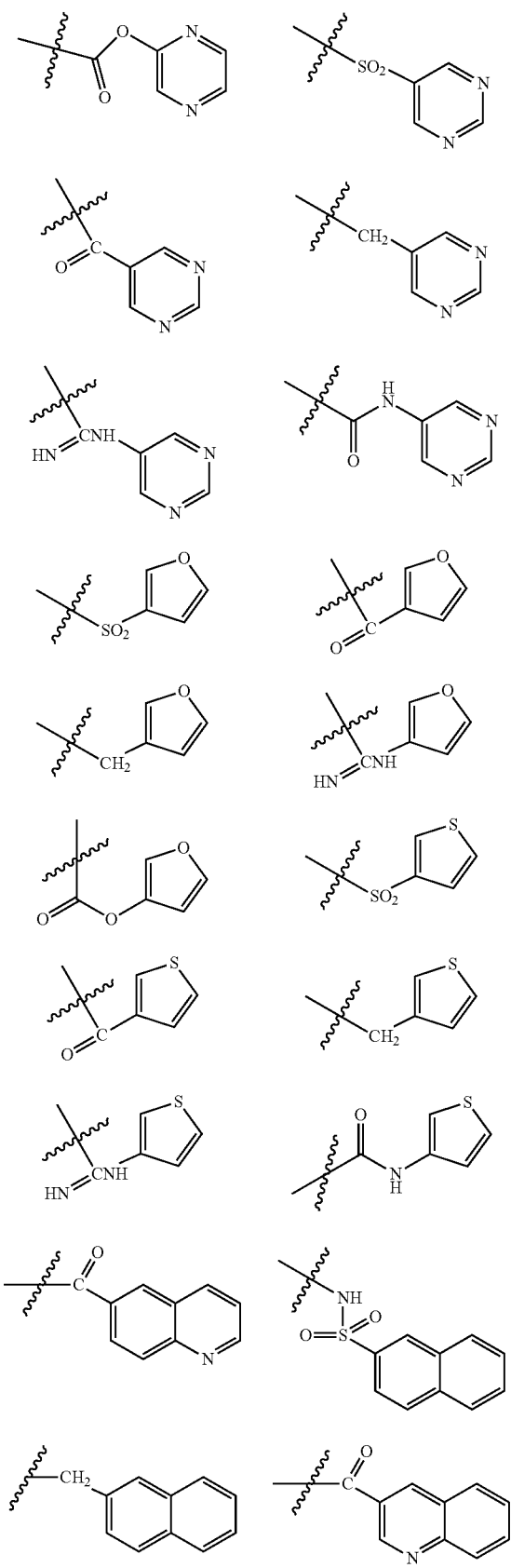
TABLE L-continued
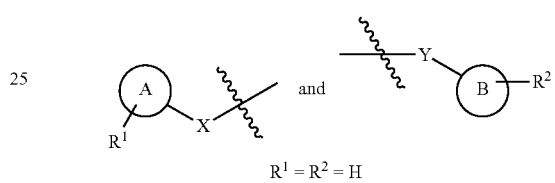
TABLE M
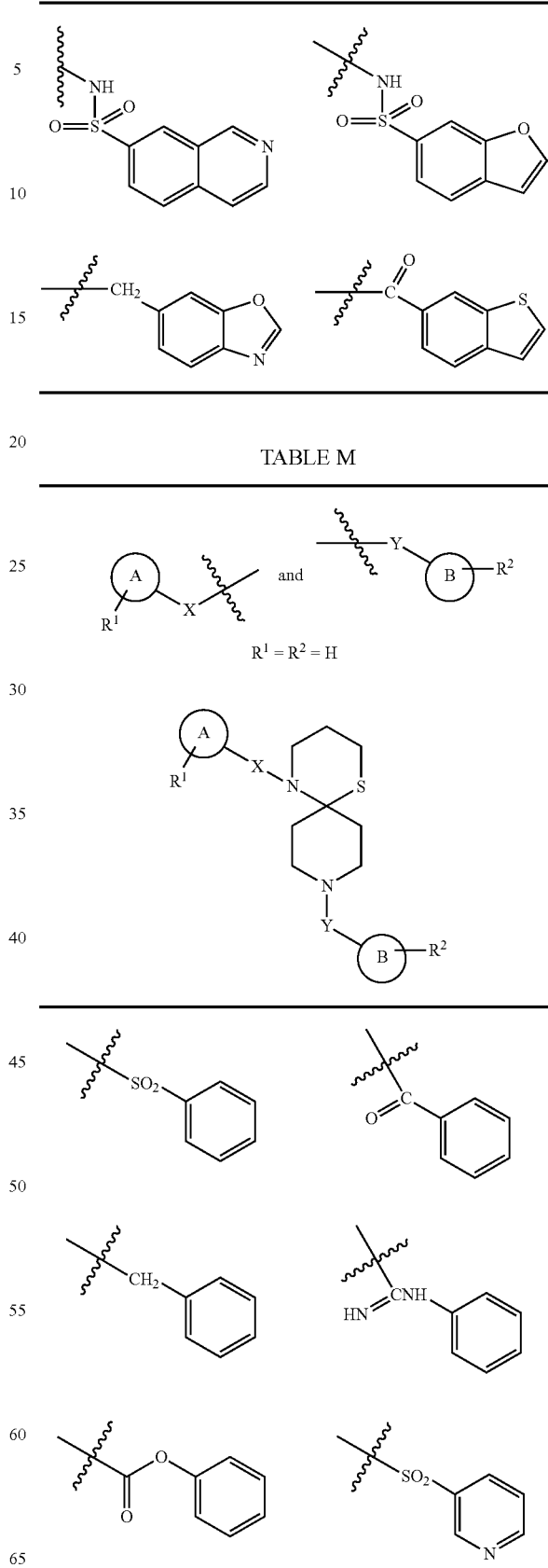

TABLE M-continued
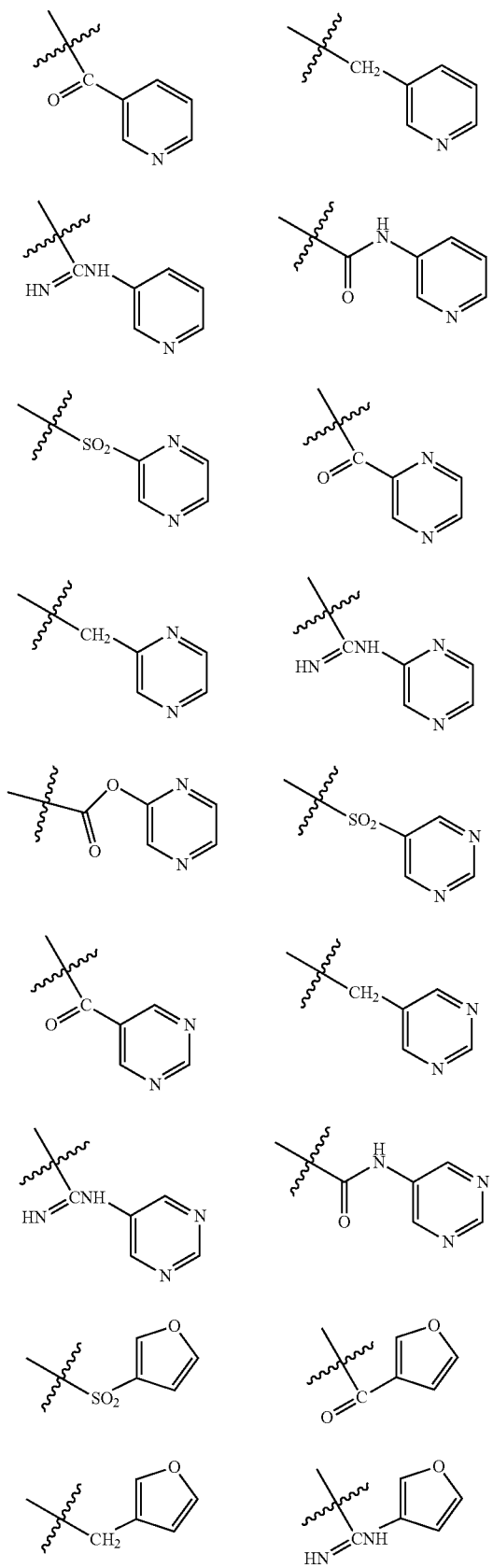
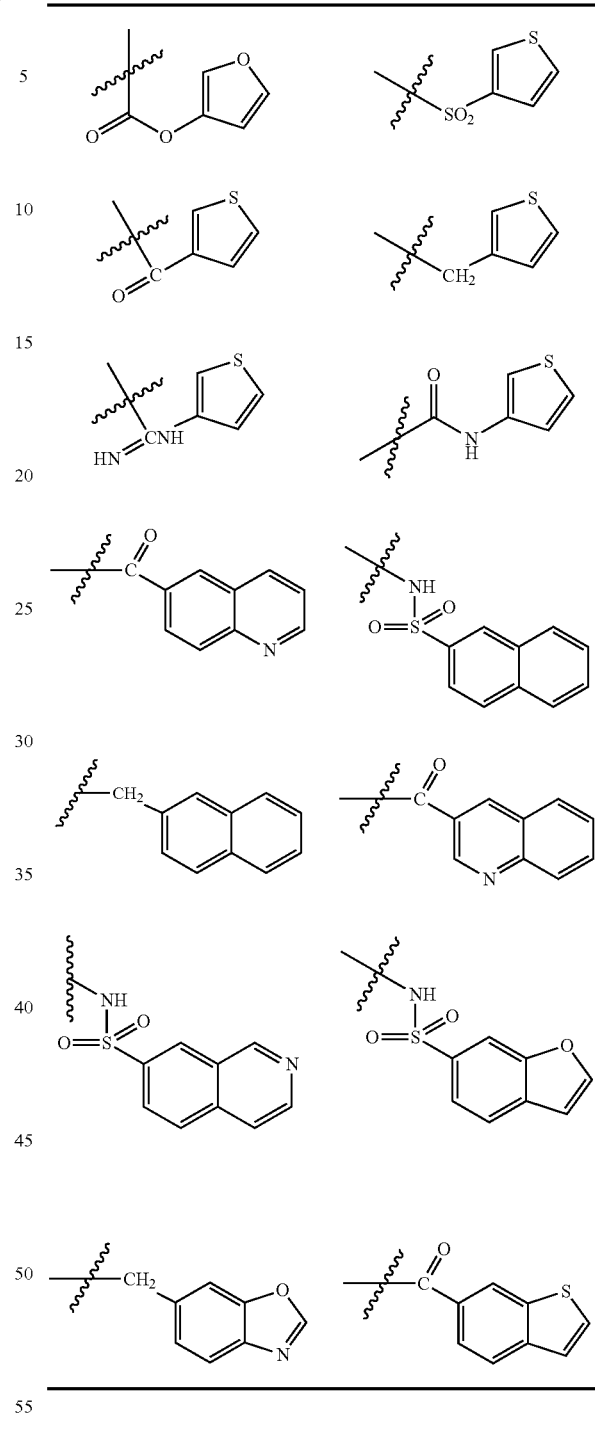
TABLE N
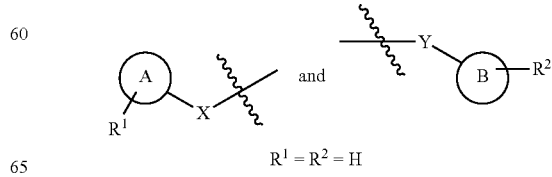
$R^1 = R^2 = H$

TABLE N-continued
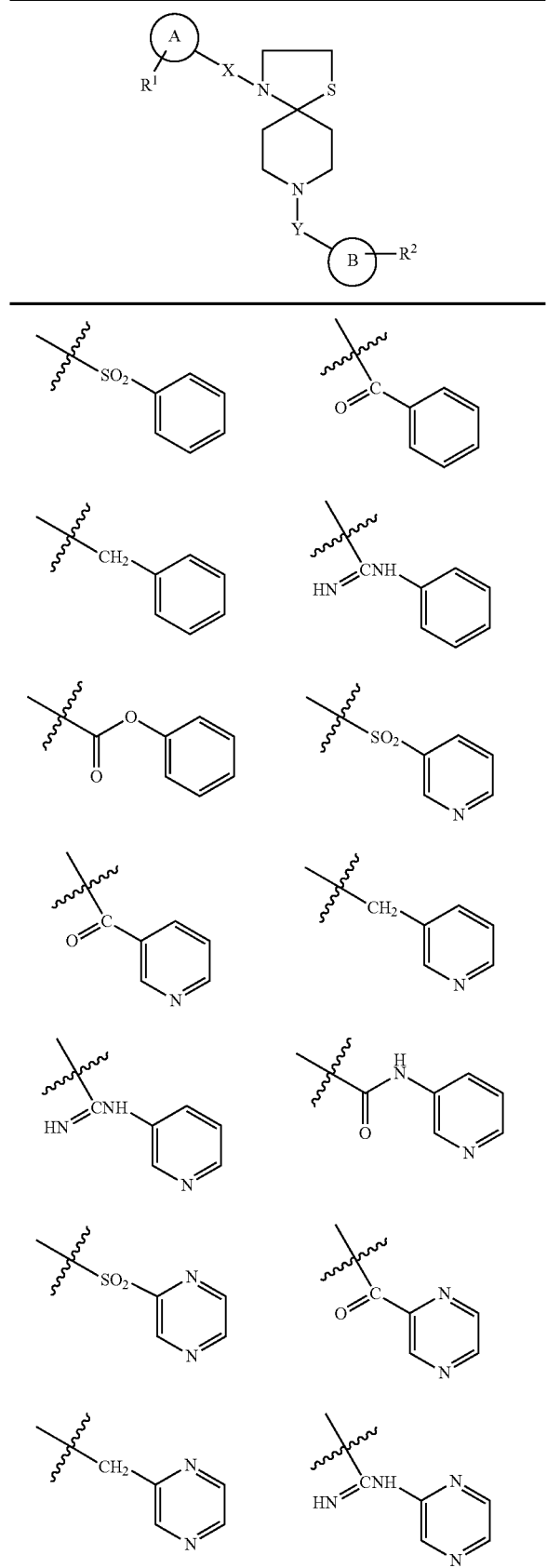
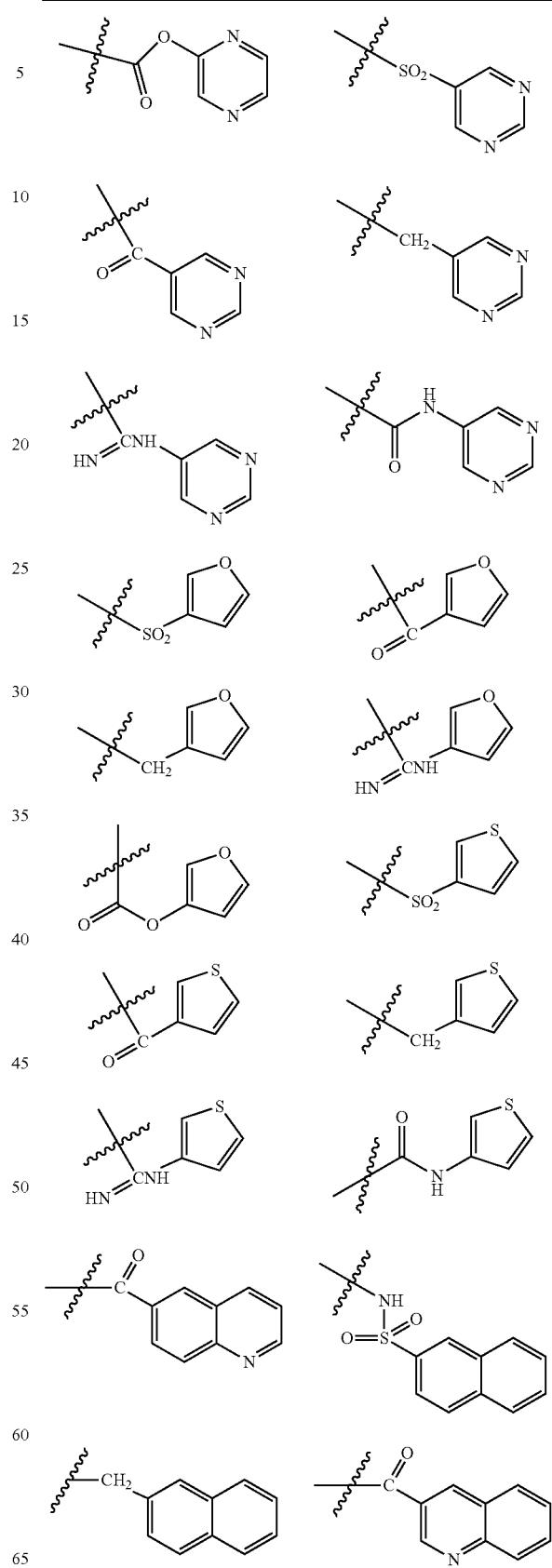

TABLE N-continued
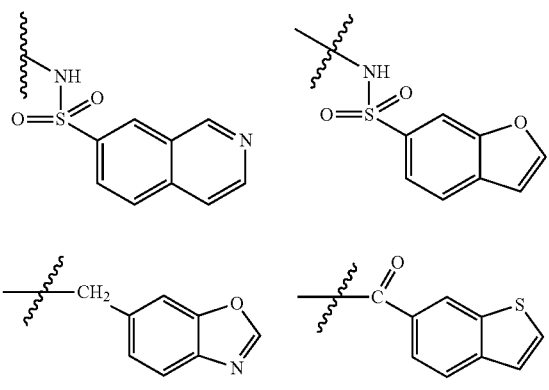
TABLE O
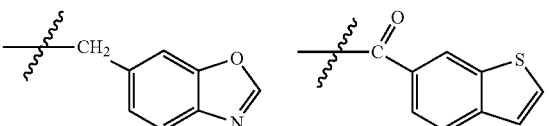
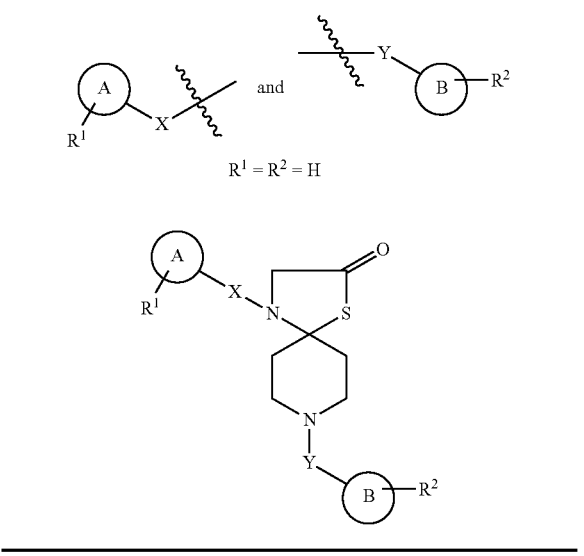
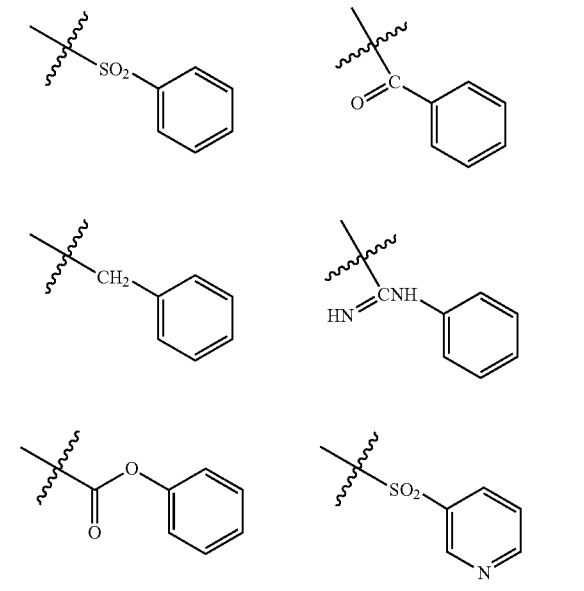
TABLE O-continued
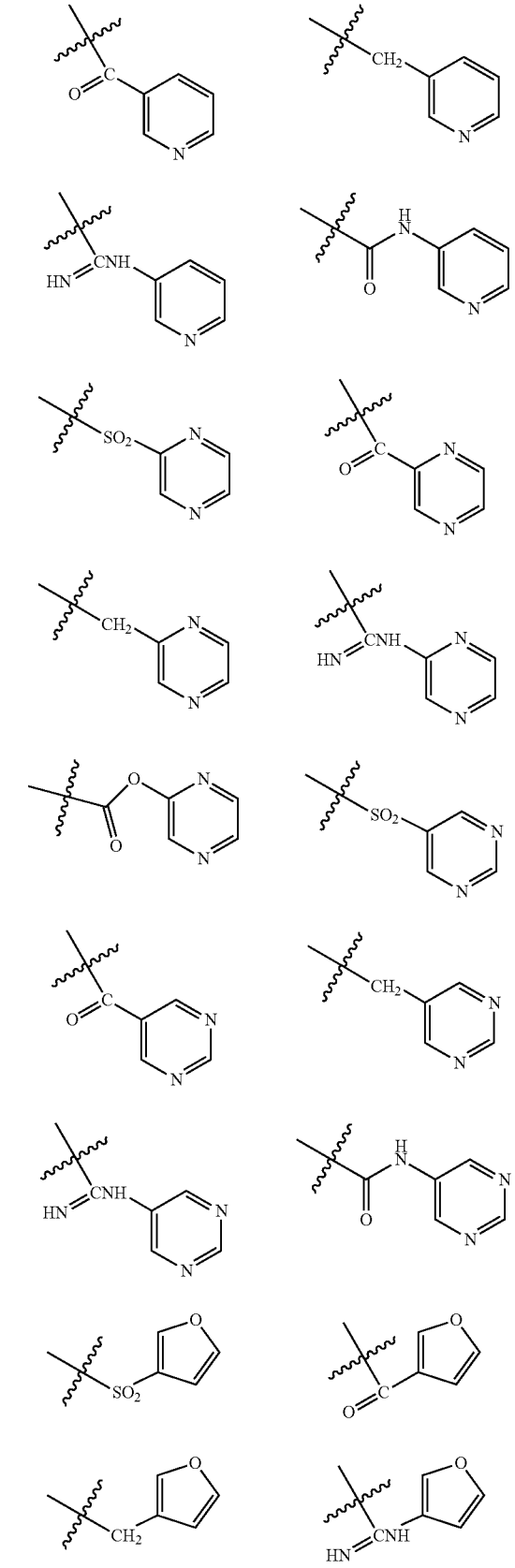

TABLE O-continued
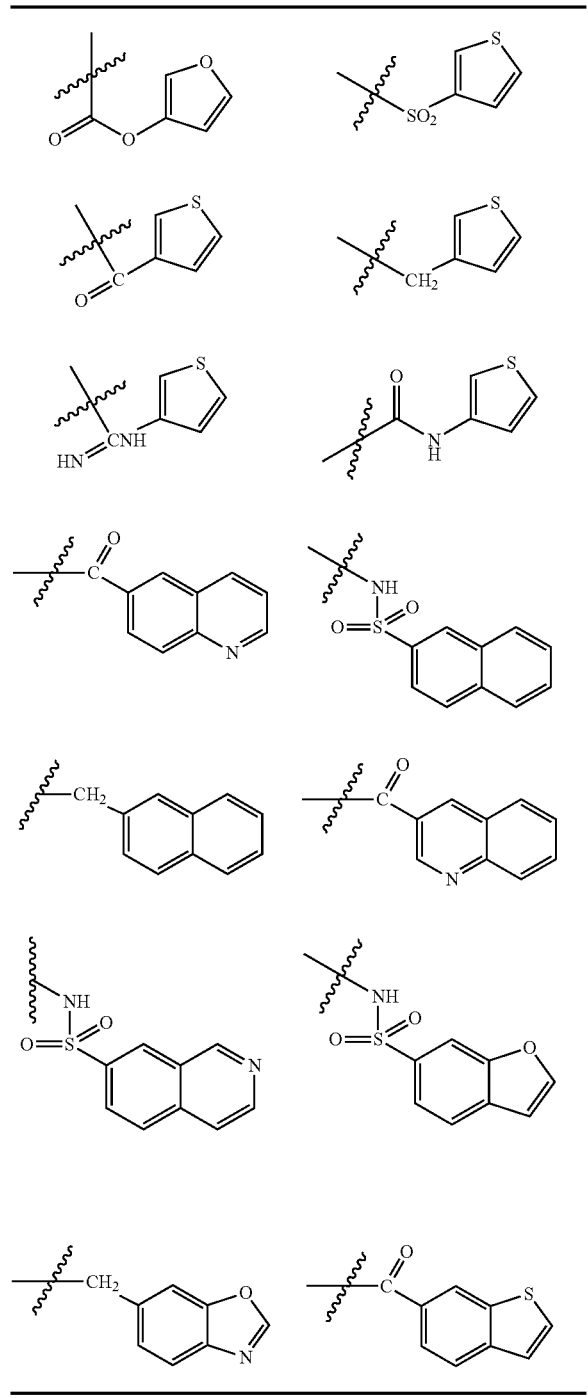
TABLE P
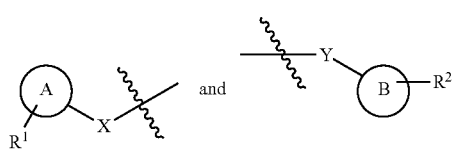
$R^1 = R^2 = H$
TABLE P-continued
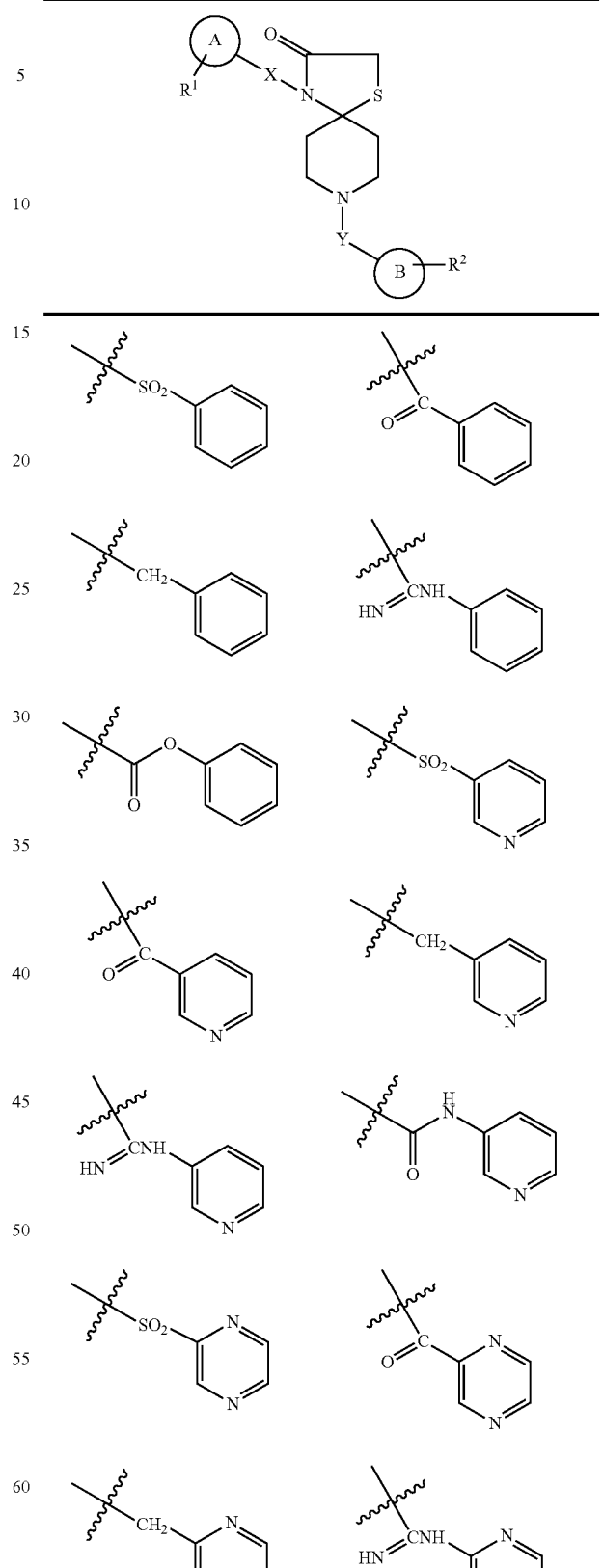
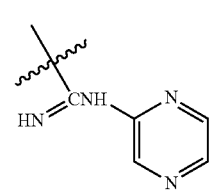

TABLE P-continued
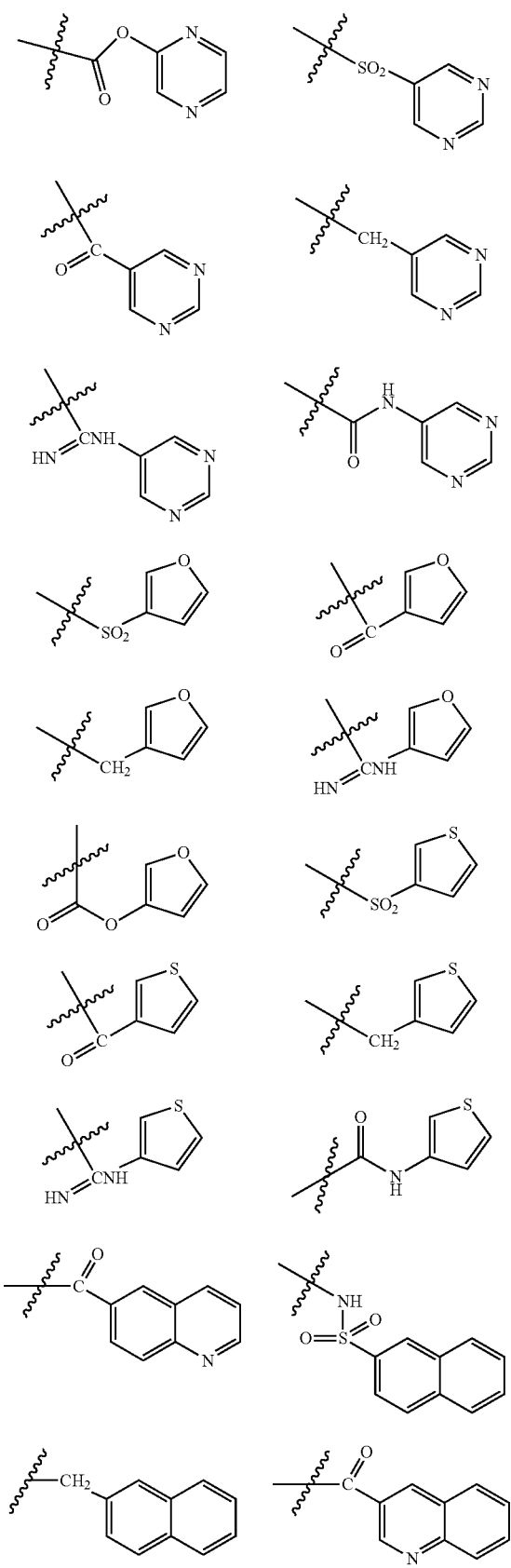
TABLE P-continued
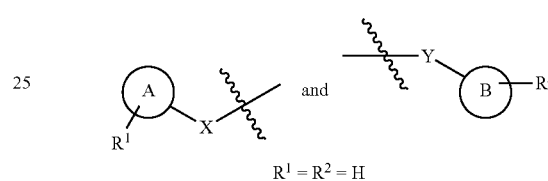
TABLE Q
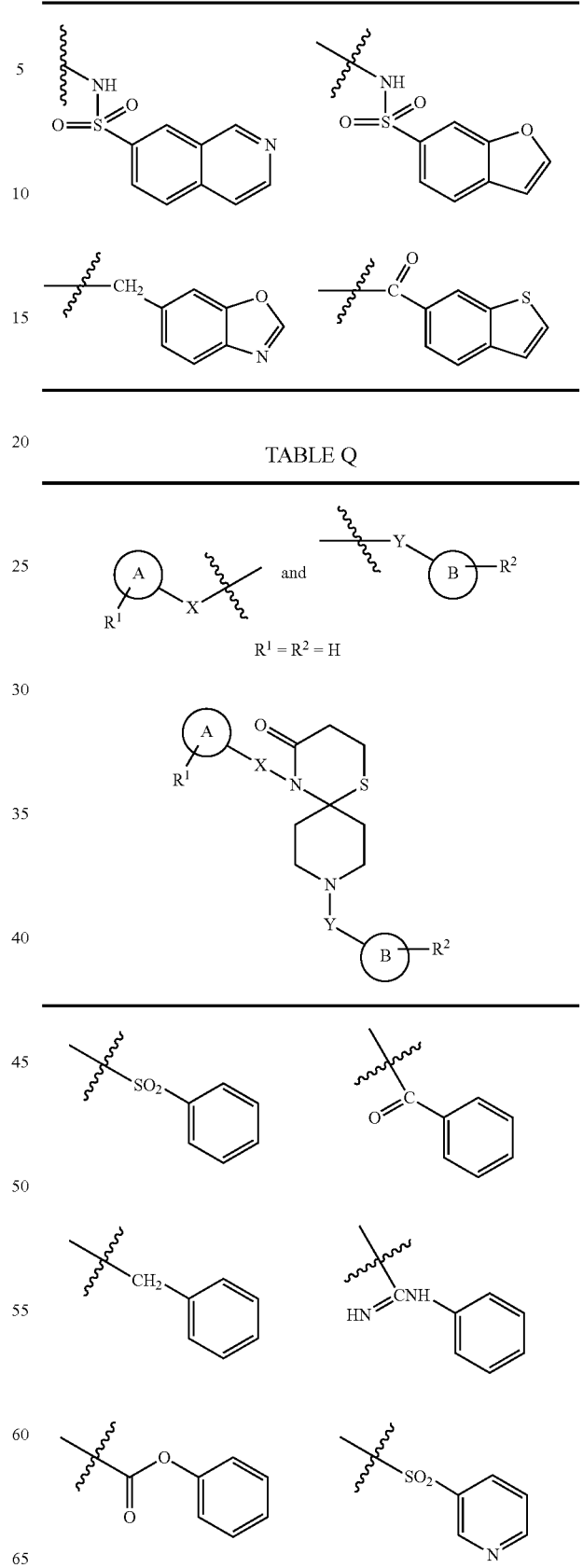

TABLE Q-continued
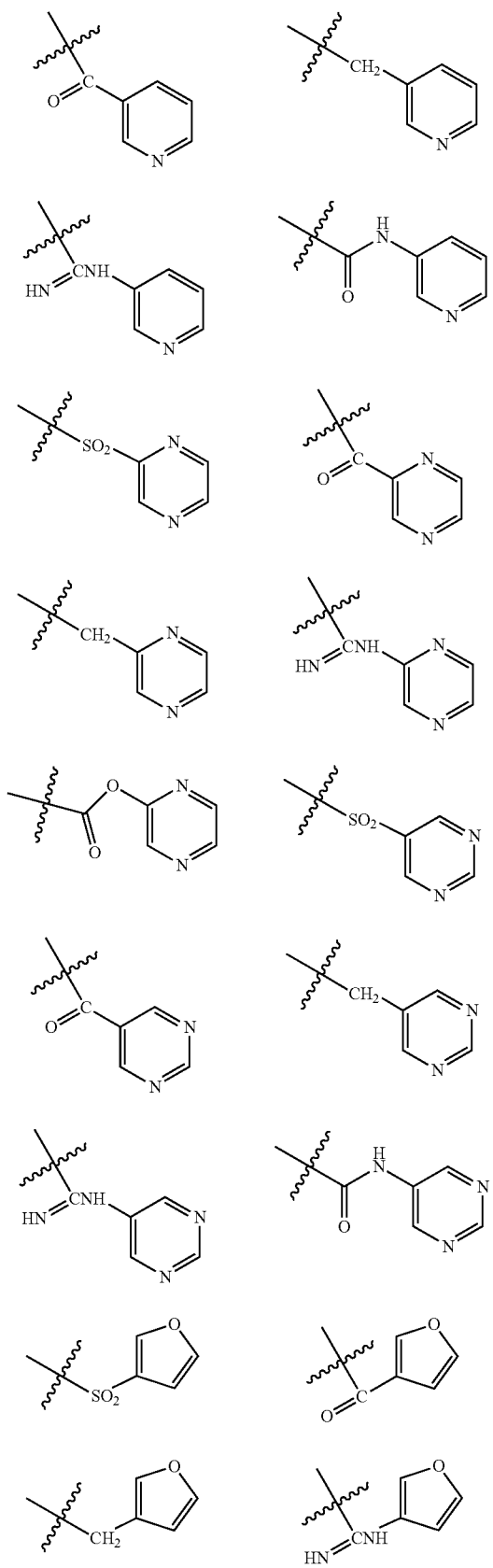
TABLE Q-continued
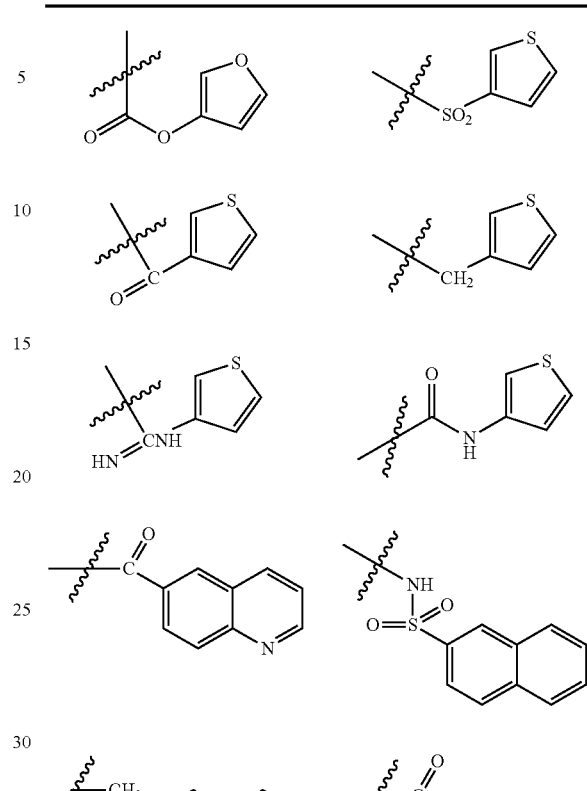
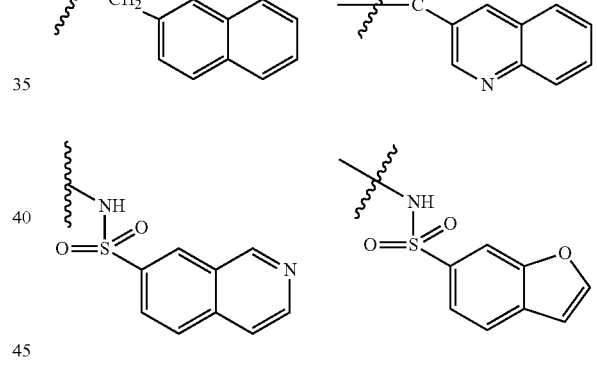
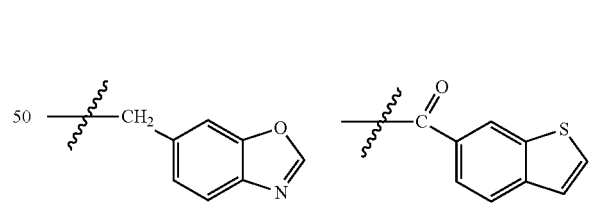
TABLE R
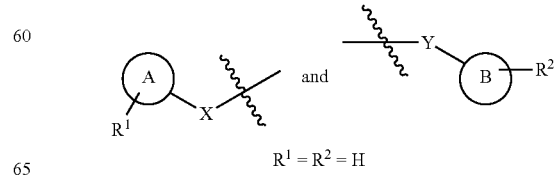
$R^1 = R^2 = H$ TABLE R-continued
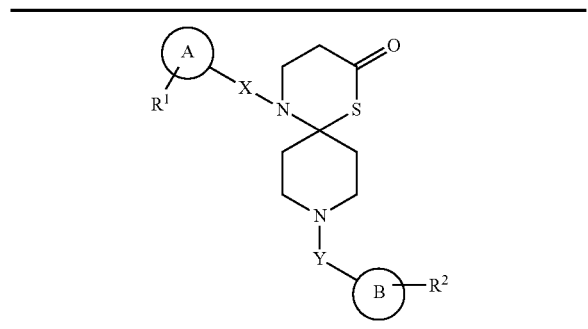
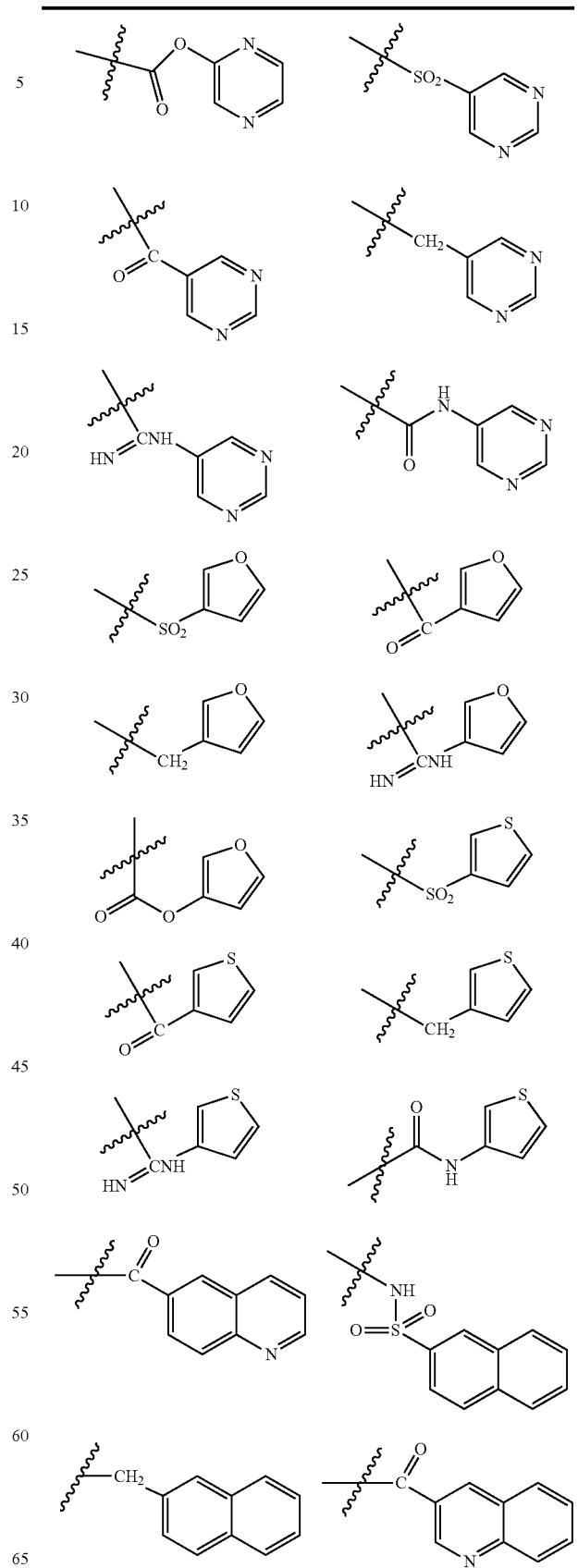

101
TABLE R-continued
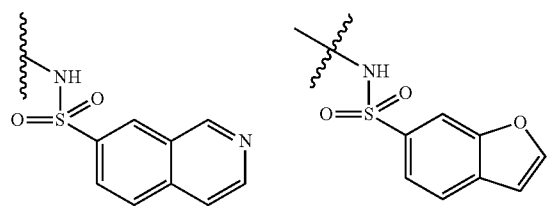
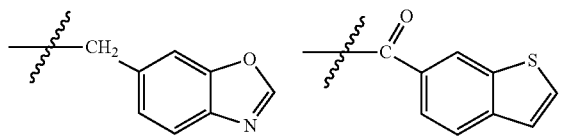
TABLE S
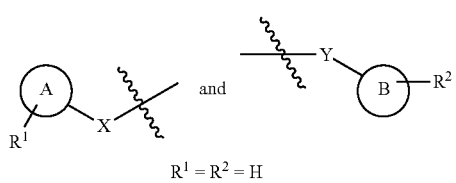
$R^1 = R^2 = H$
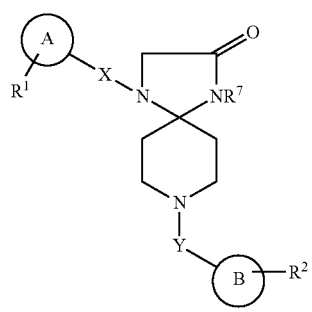
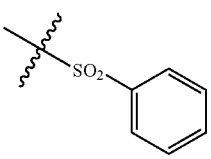 [SMILES: *S(=O)(=O)c1ccccc1] 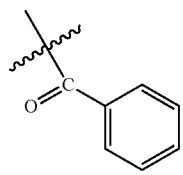 [SMILES: *C(=O)c1ccccc1]
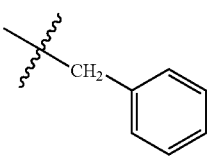 [SMILES: *Cc1ccccc1] 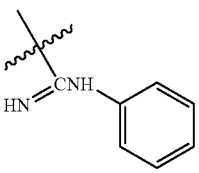
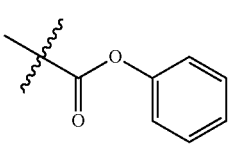 [SMILES: *C(=O)Oc1ccccc1] 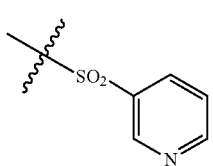 [SMILES: *S(=O)(=O)c1cccnc1]
102
TABLE S-continued
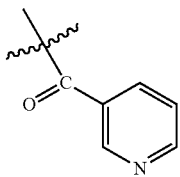 [SMILES: *C(=O)c1cccnc1] 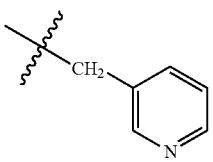 [SMILES: *Cc1cccnc1]
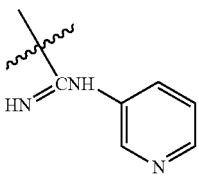 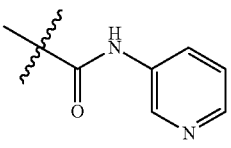 [SMILES: *C(=O)Nc1cccnc1]
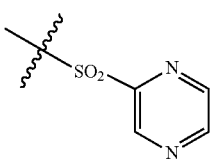 [SMILES: *S(=O)(=O)c1cnccn1] 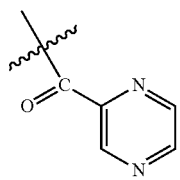
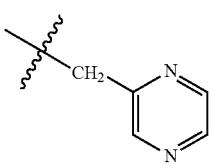 [SMILES: *Cc1cnccn1] 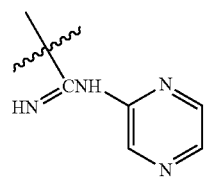
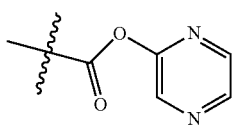 [SMILES: *C(=O)Oc1cnccn1] 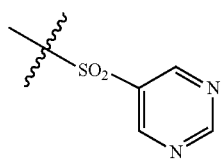 [SMILES: *S(=O)(=O)c1cncnc1]
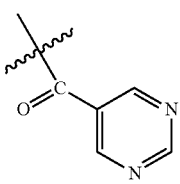 [SMILES: *C(=O)c1cncnc1] 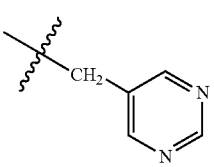 [SMILES: *Cc1cncnc1]
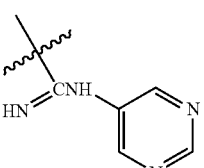 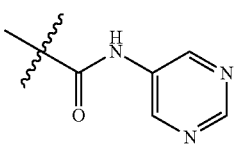
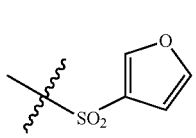 [SMILES: *S(=O)(=O)c1ccoc1] 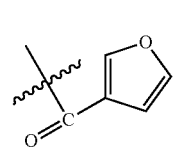
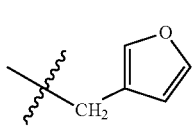 [SMILES: *Cc1ccoc1] 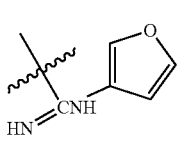

TABLE S-continued
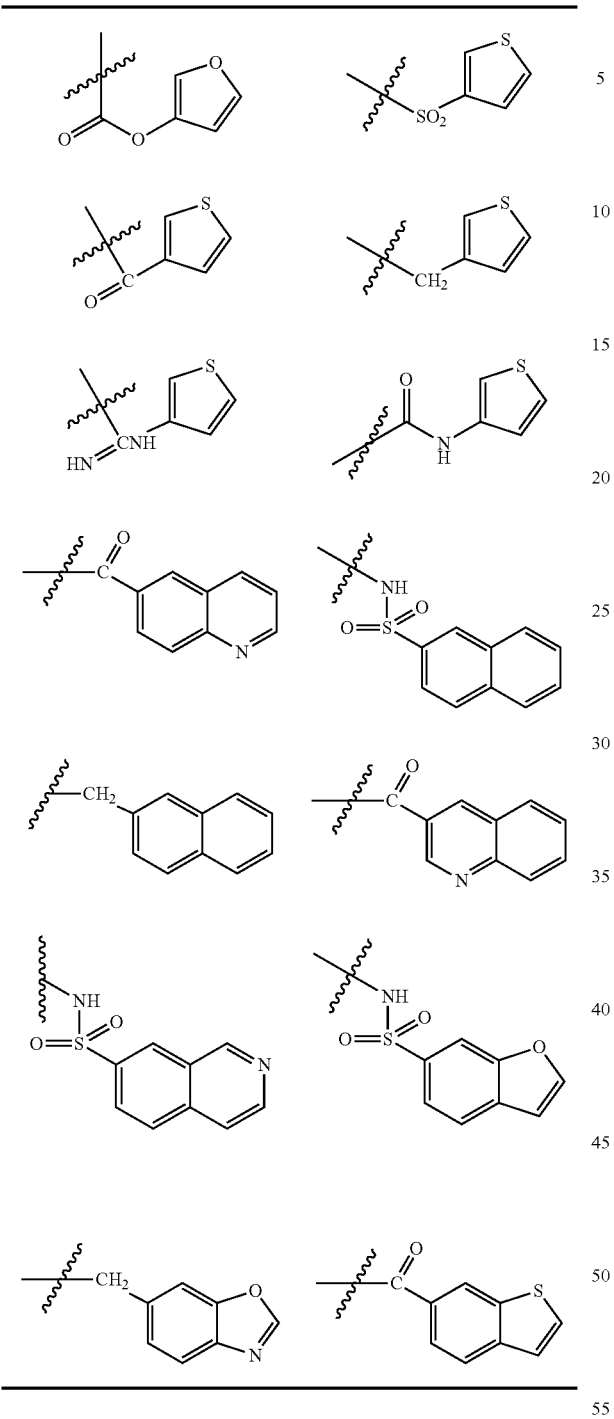
TABLE T
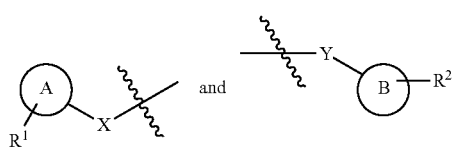
$R^1 = R^2 = H$
TABLE T-continued
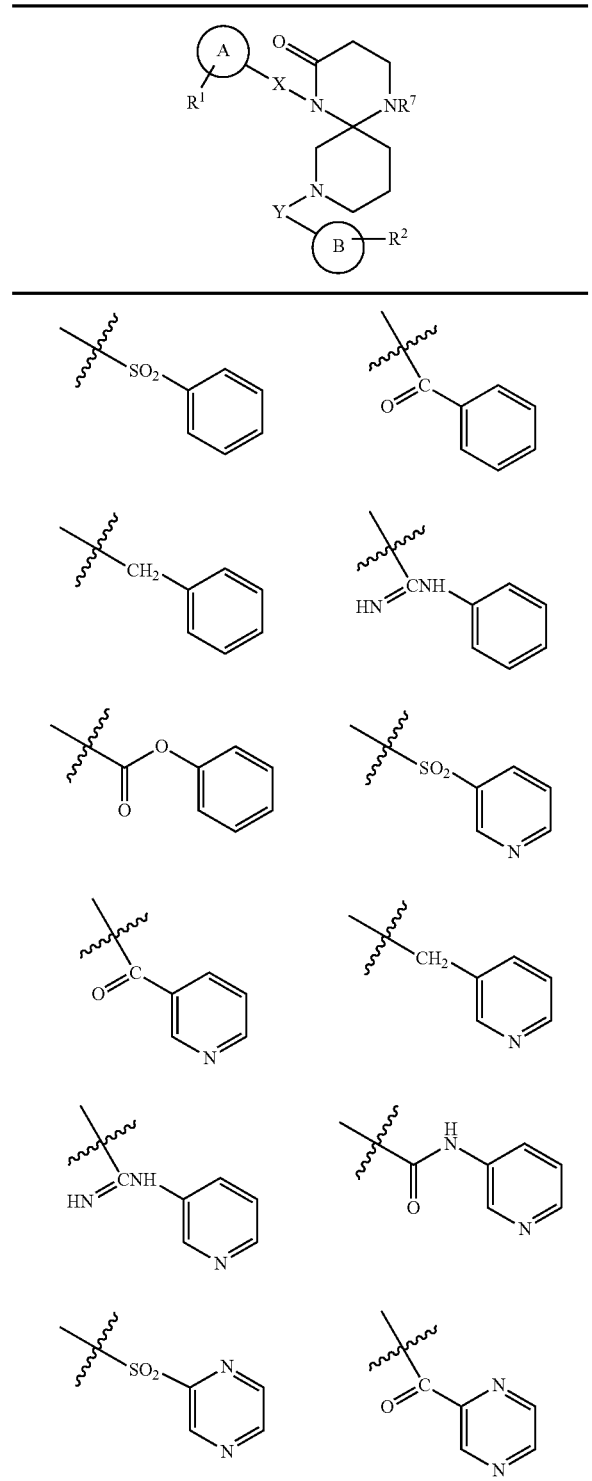

TABLE T-continued
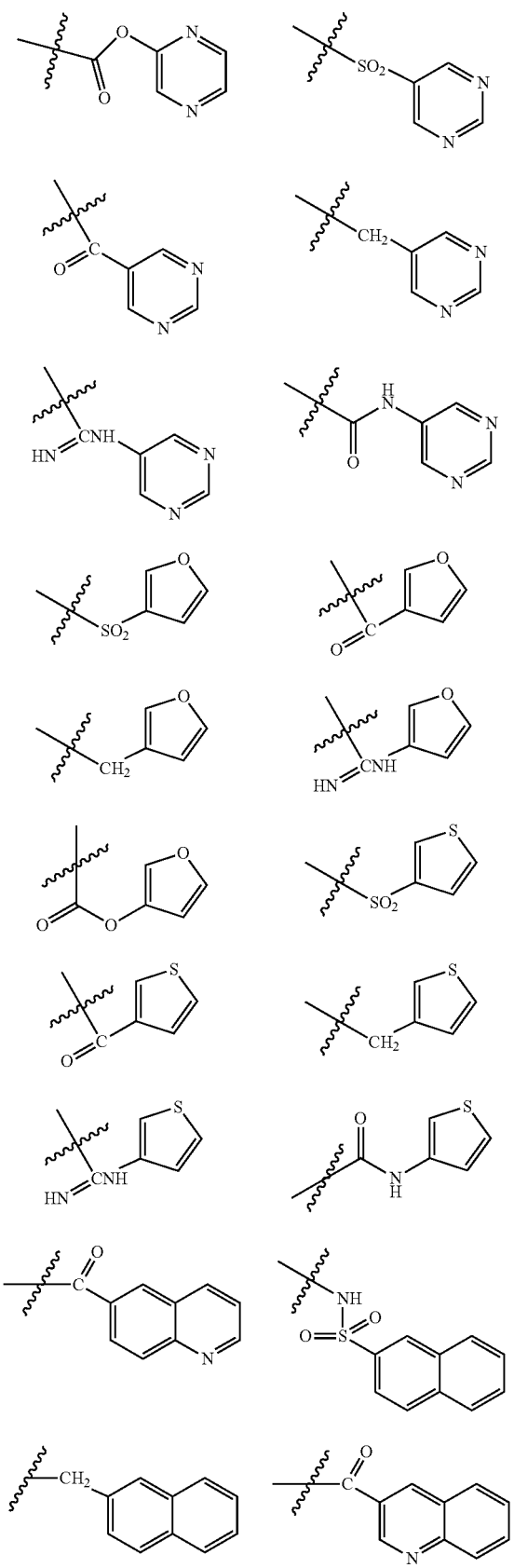
TABLE T-continued
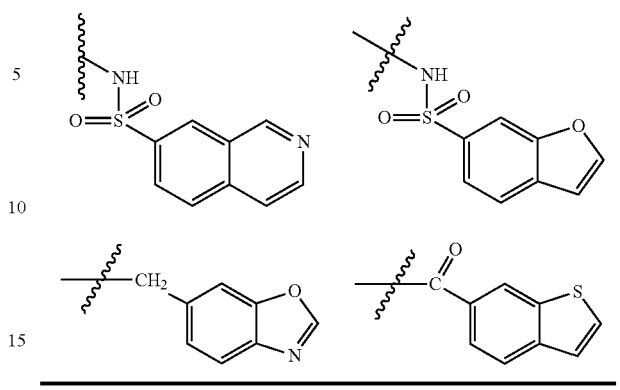
TABLE U
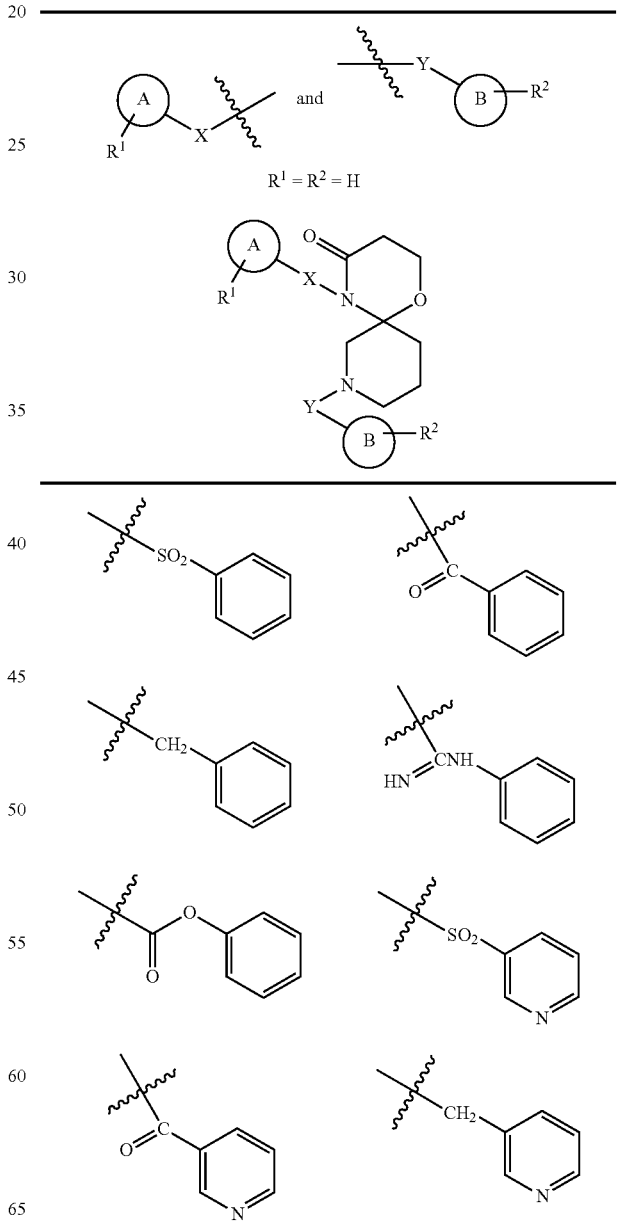

TABLE U-continued
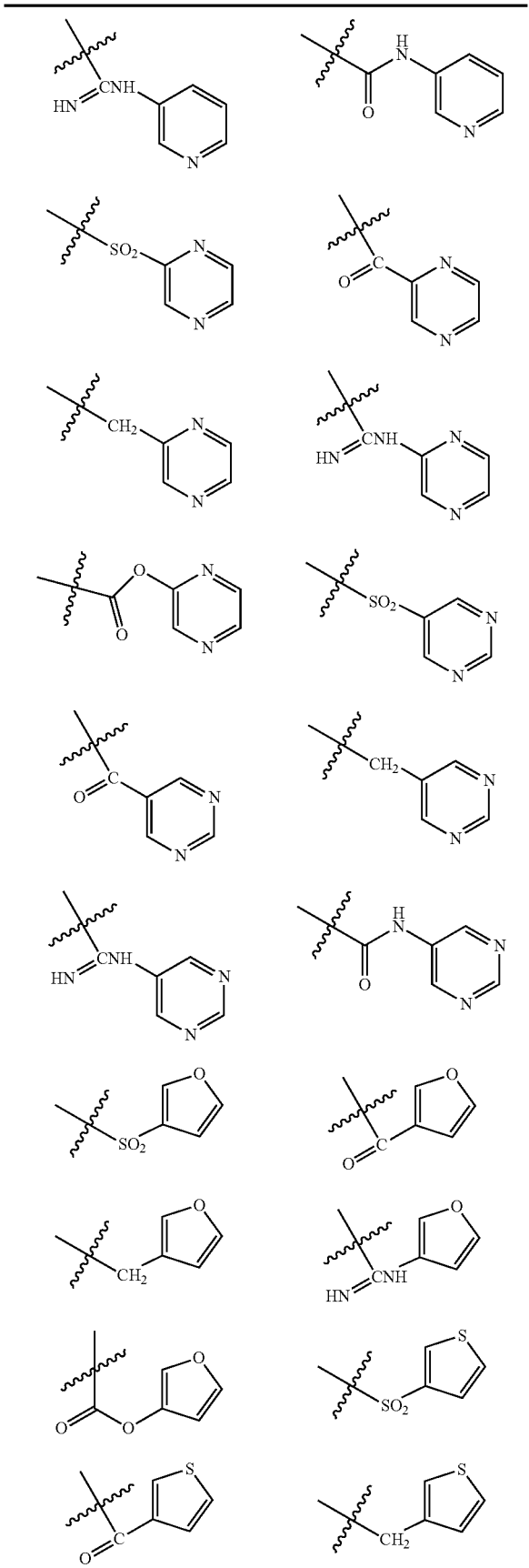
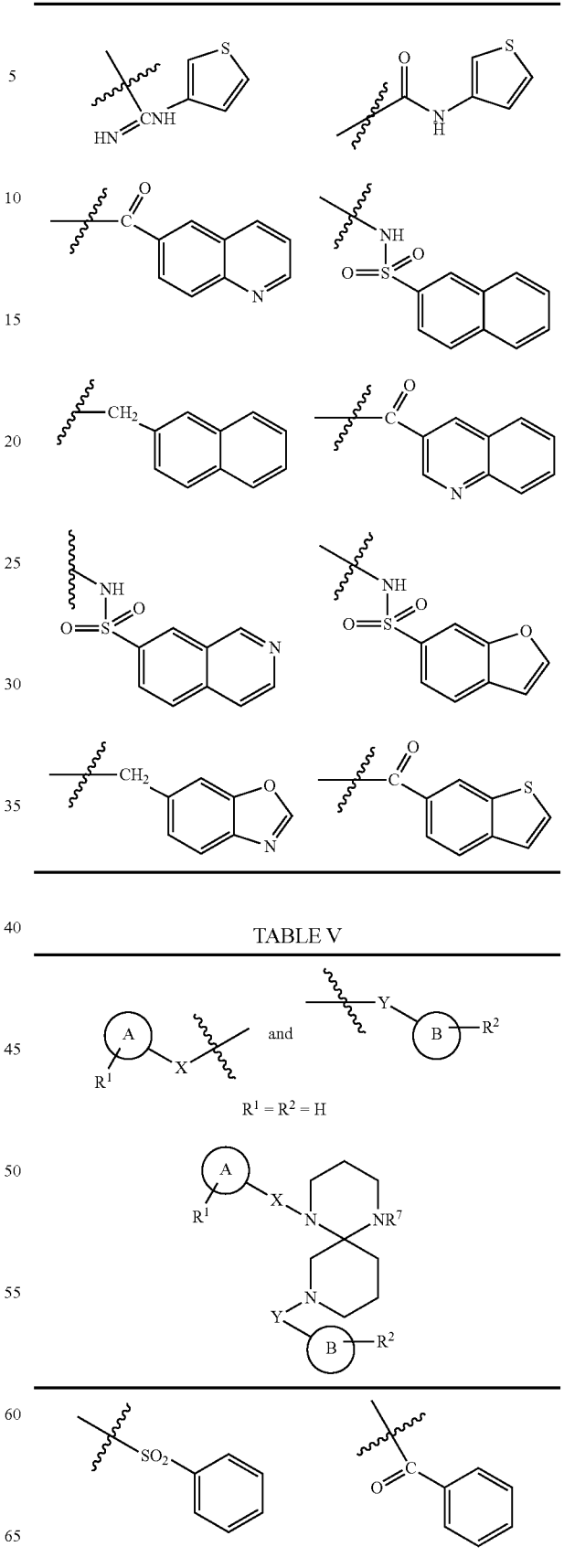
TABLE V
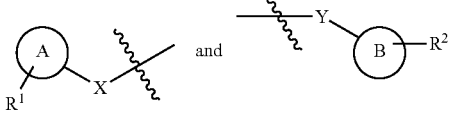
$R^1 = R^2 = H$
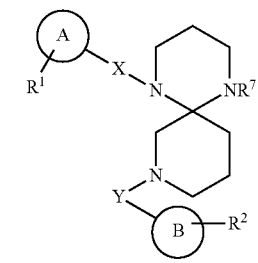
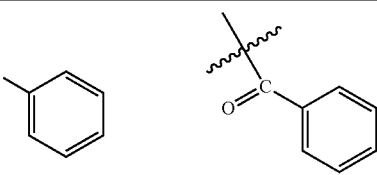

TABLE V-continued
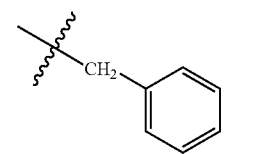 [SMILES: *Cc1ccccc1] 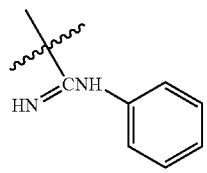
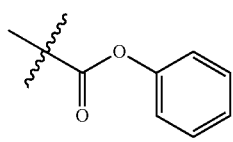 [SMILES: *C(=O)Oc1ccccc1] 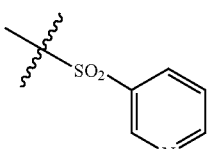
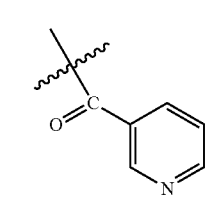 [SMILES: *C(=O)c1cccnc1] 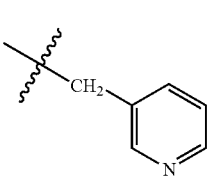 [SMILES: *Cc1cccnc1]
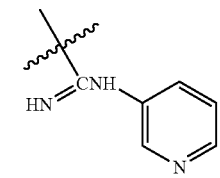 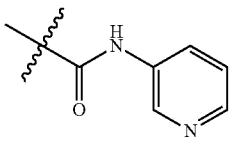 [SMILES: *C(=O)Nc1cccnc1]
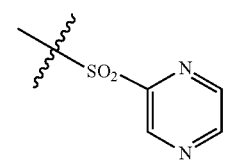 [SMILES: *S(=O)(=O)c1cnccn1] 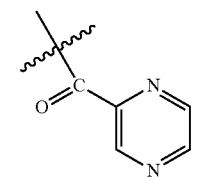 [SMILES: *C(=O)c1cnccn1]
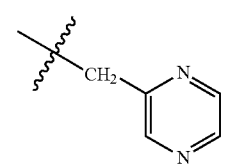 [SMILES: *Cc1cnccn1] 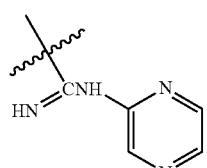
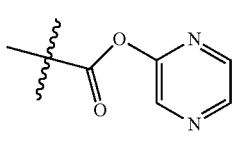 [SMILES: *C(=O)Oc1cnccn1] 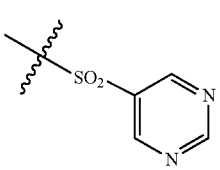
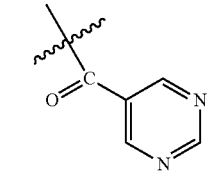 [SMILES: *C(=O)c1cncnc1] 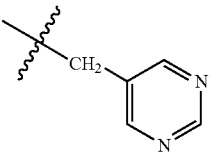 [SMILES: *Cc1cncnc1]
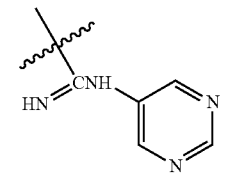 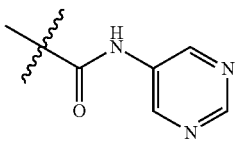 [SMILES: *C(=O)Nc1cncnc1]
TABLE V-continued
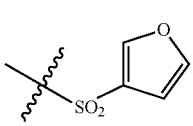 [SMILES: *S(=O)(=O)c1ccoc1] 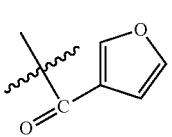 [SMILES: *C(=O)c1ccoc1]
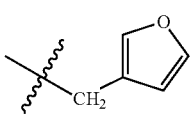 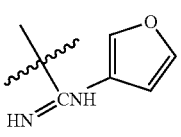
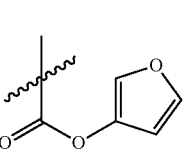 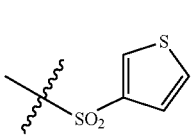
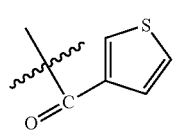 [SMILES: *C(=O)c1ccsc1] 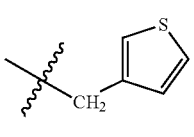 [SMILES: *Cc1ccsc1]
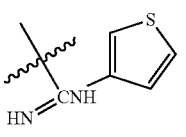 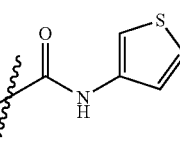
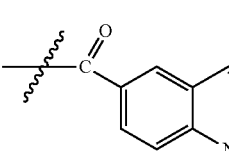 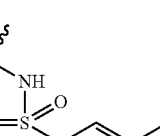
 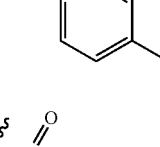
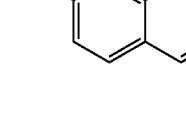 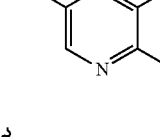
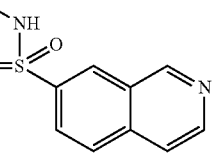 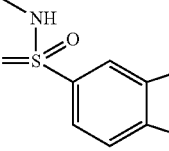
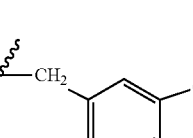 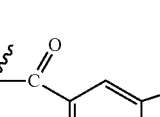
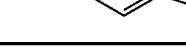 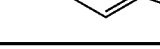

TABLE W
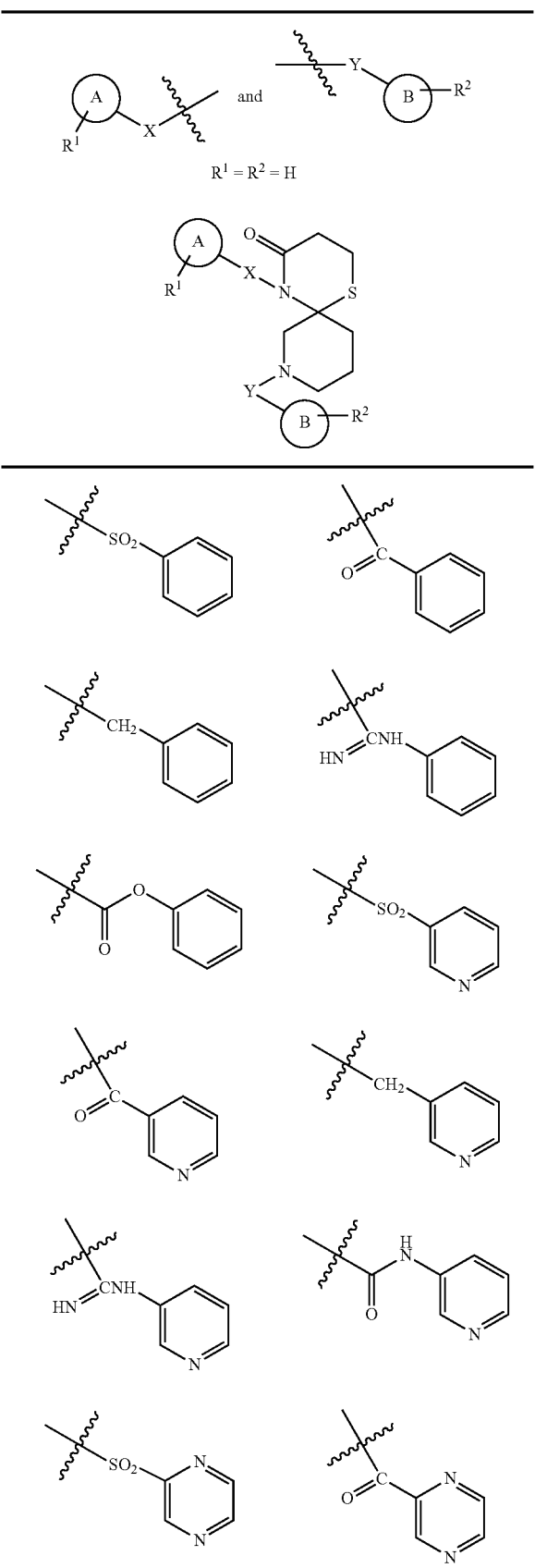
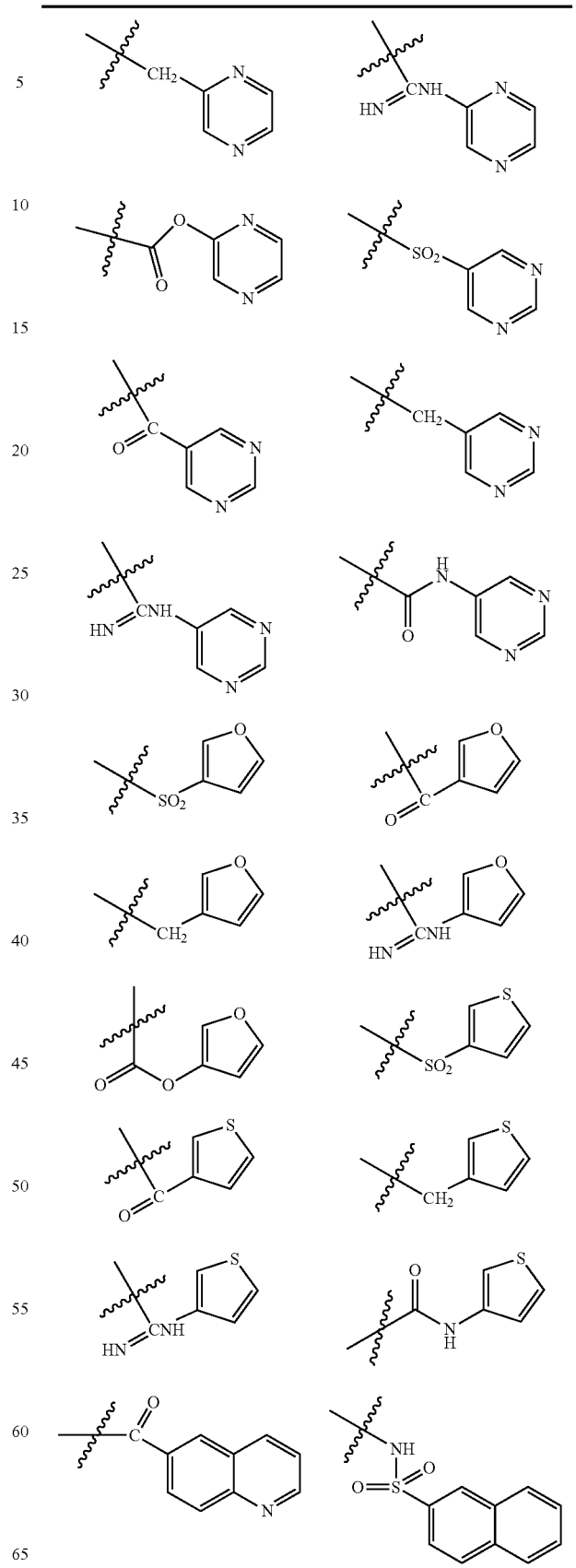

TABLE W-continued
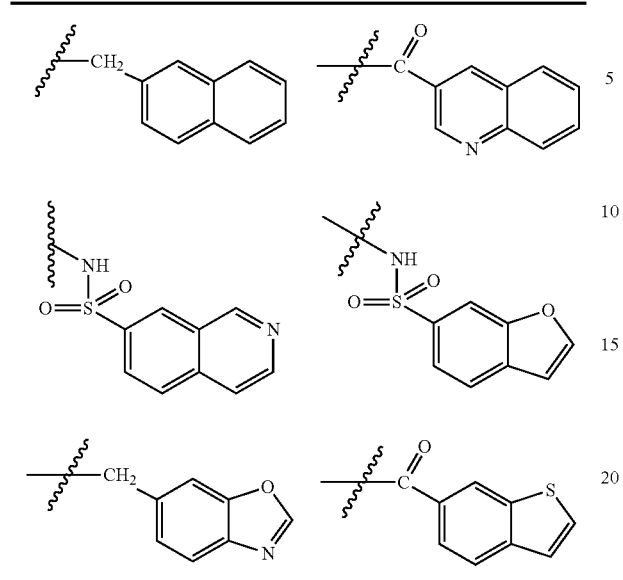
TABLE X
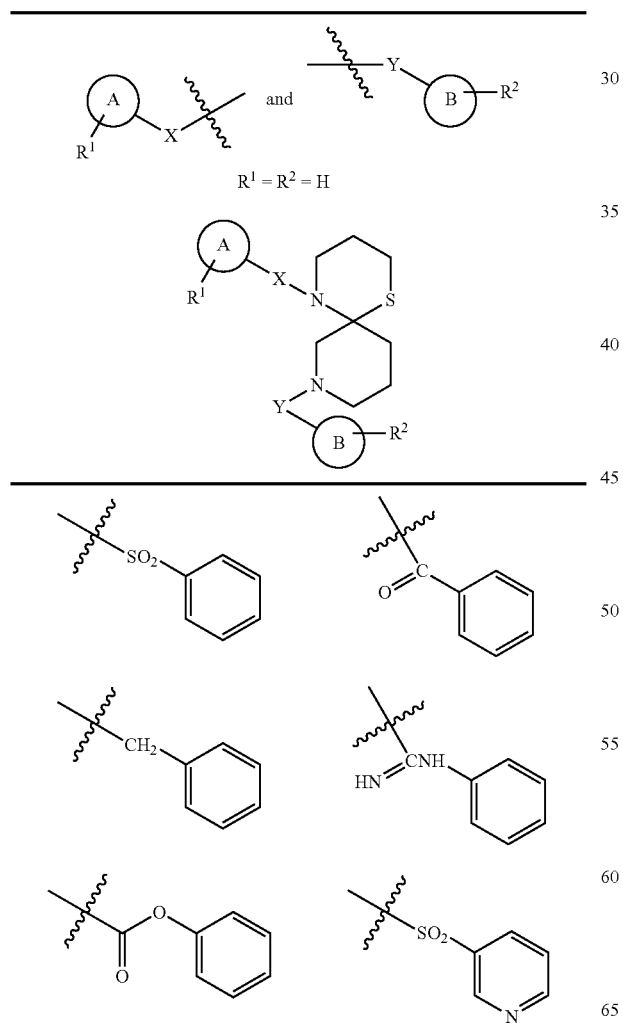
TABLE X-continued
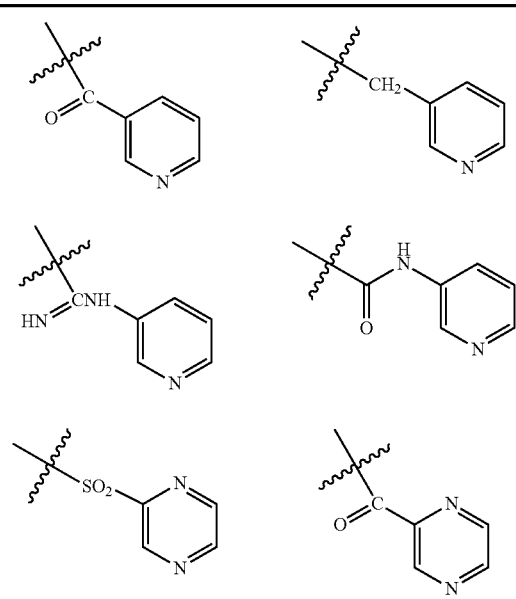
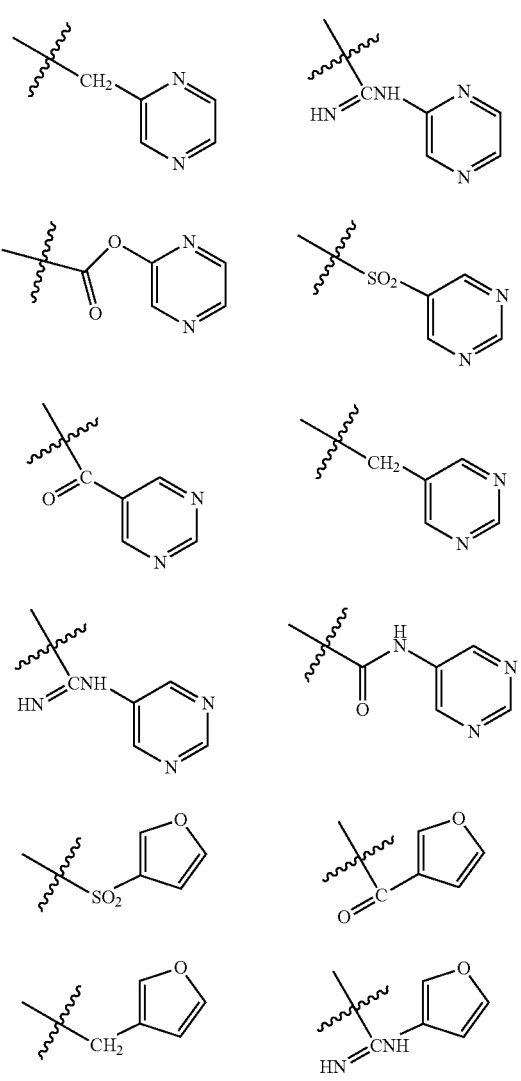

TABLE X-continued
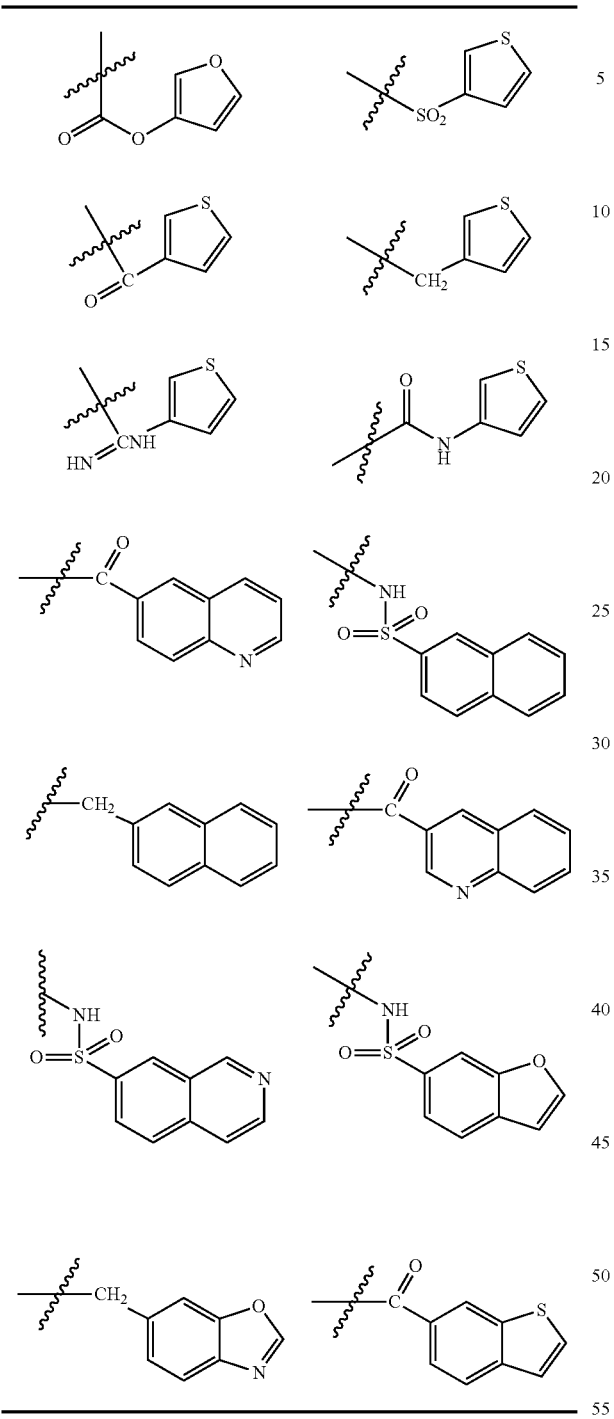
TABLE Y
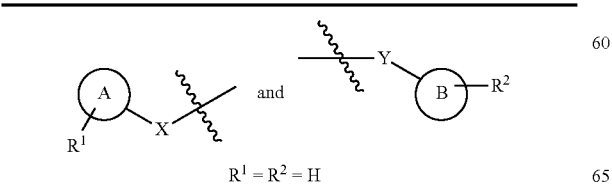
$R^1 = R^2 = H$
TABLE Y-continued
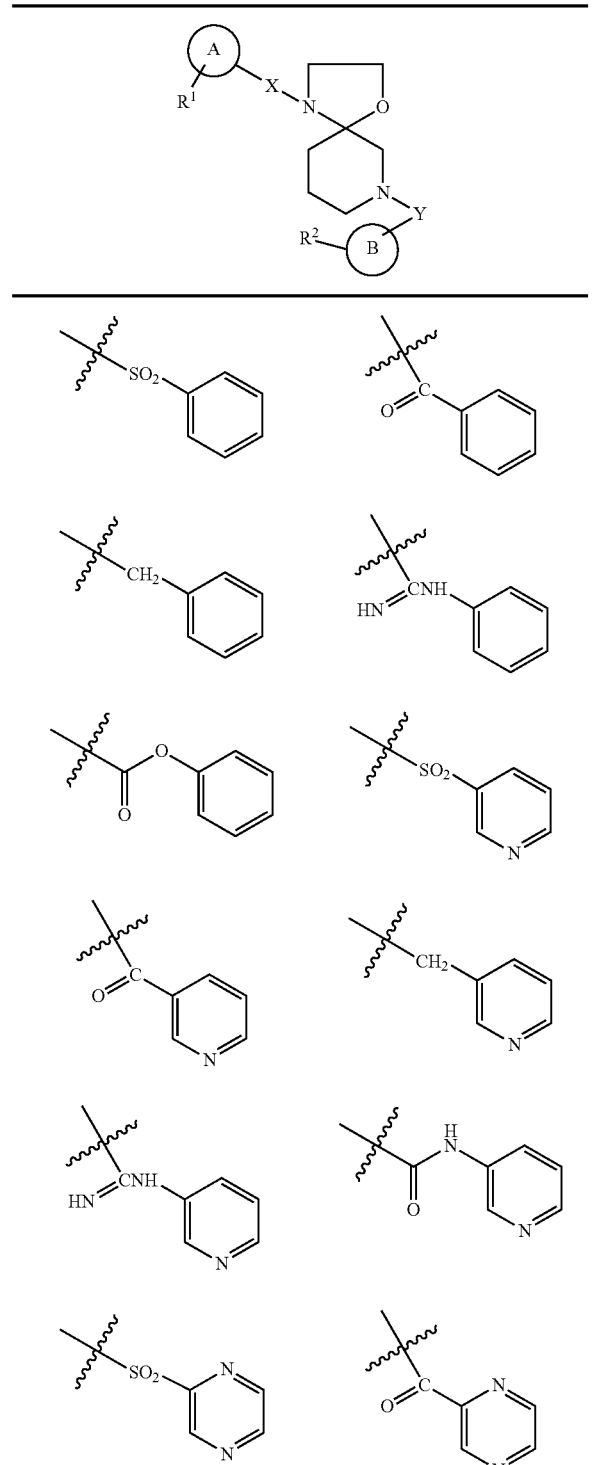

TABLE Y-continued
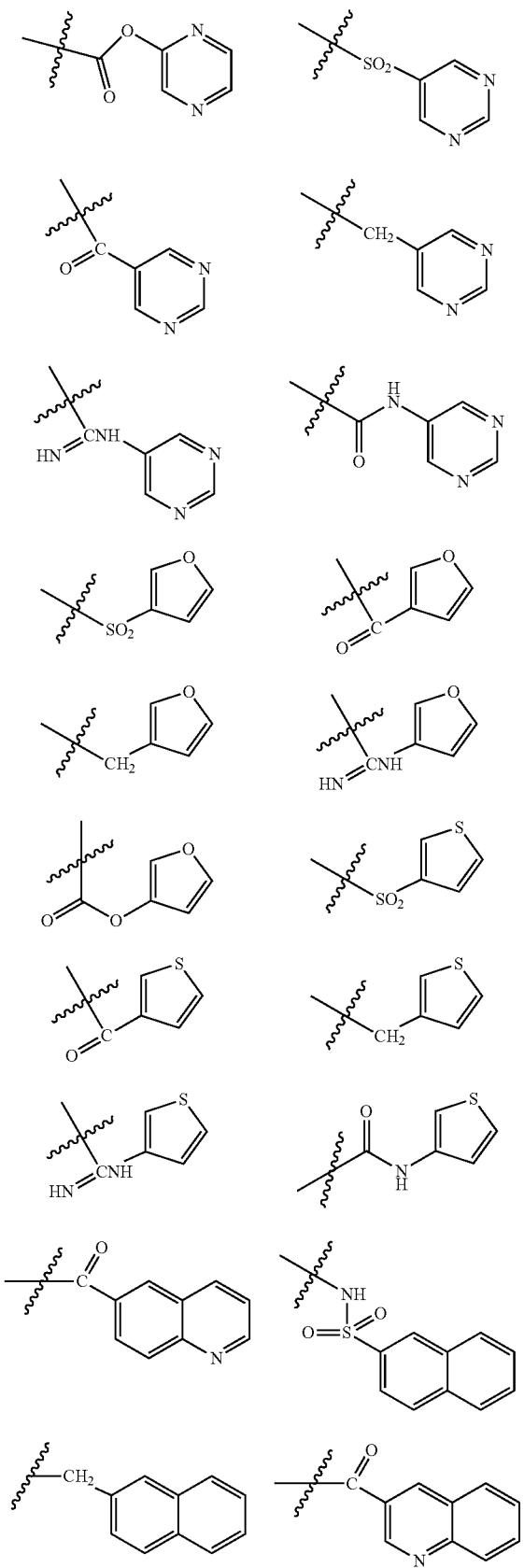
TABLE Y-continued
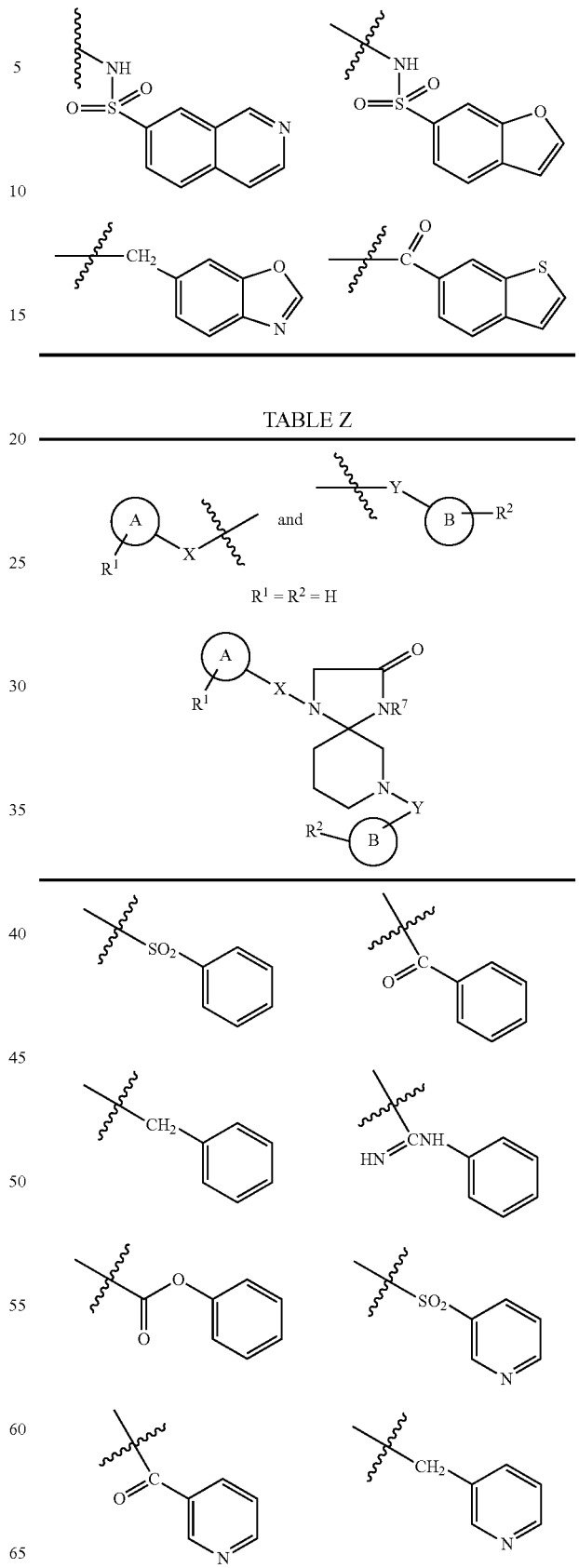

TABLE Z-continued
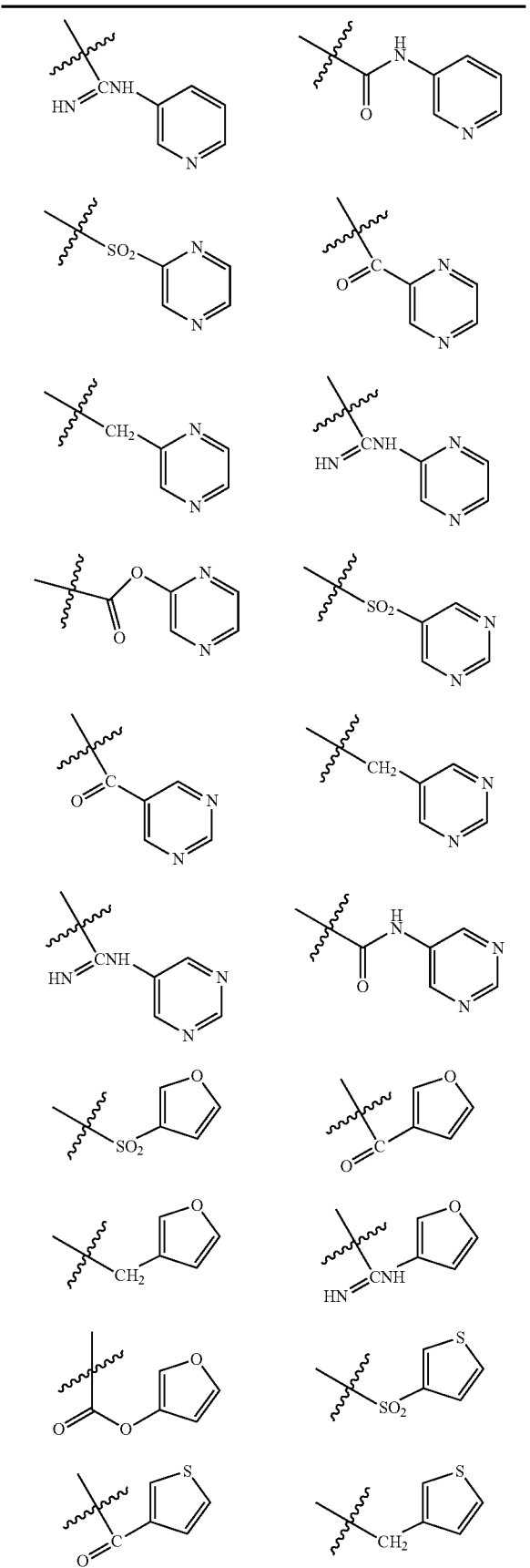
TABLE Z-continued
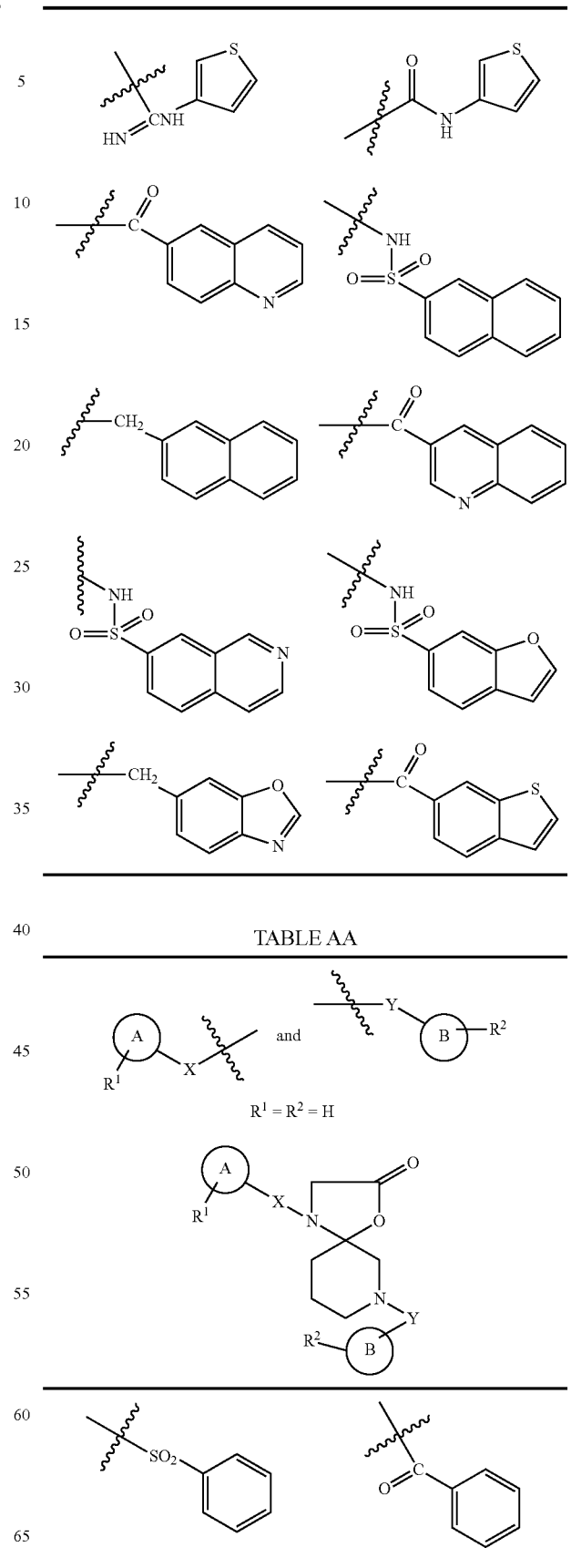

TABLE AA-continued
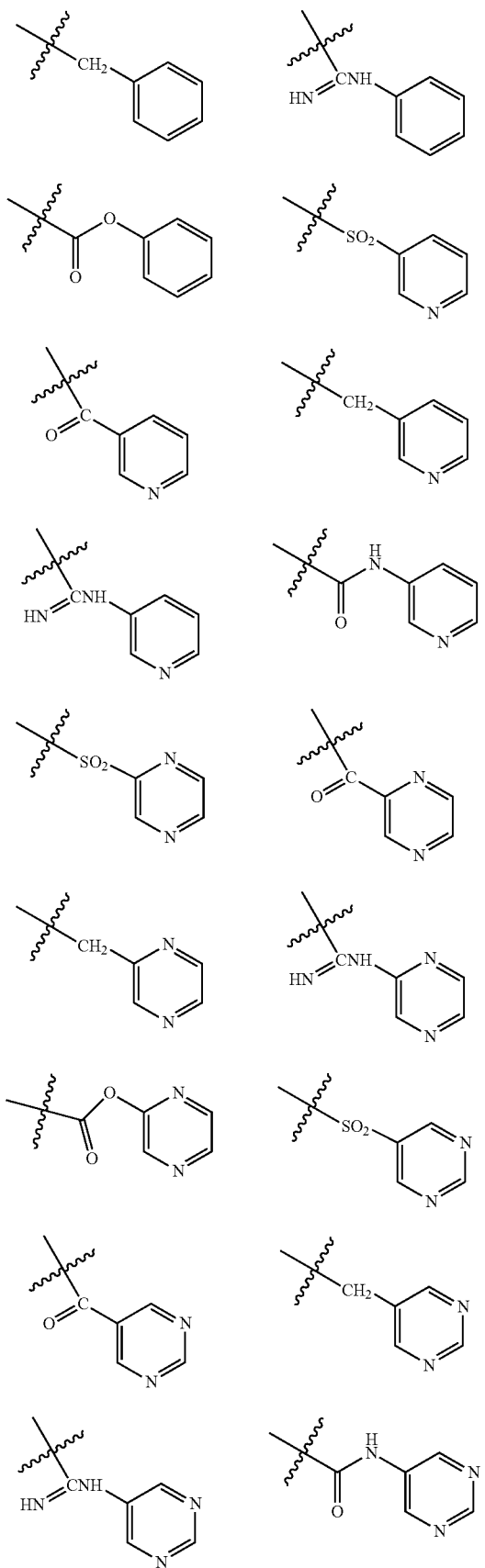
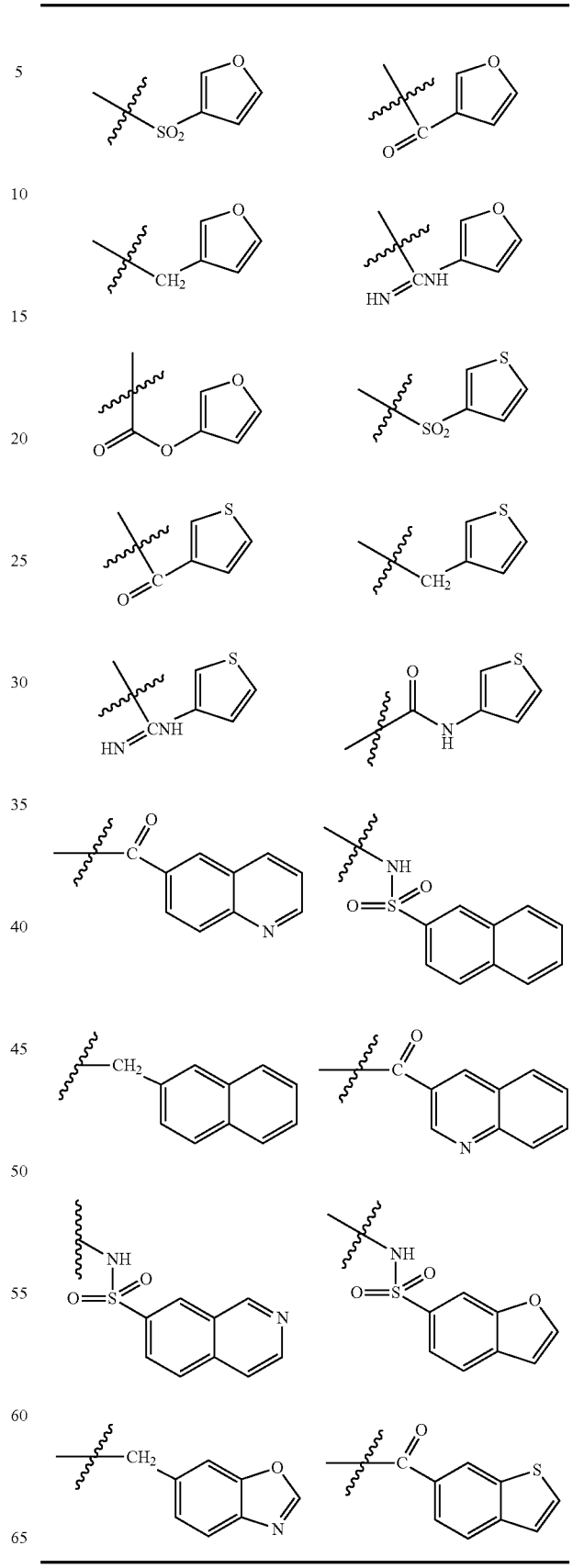

TABLE AB
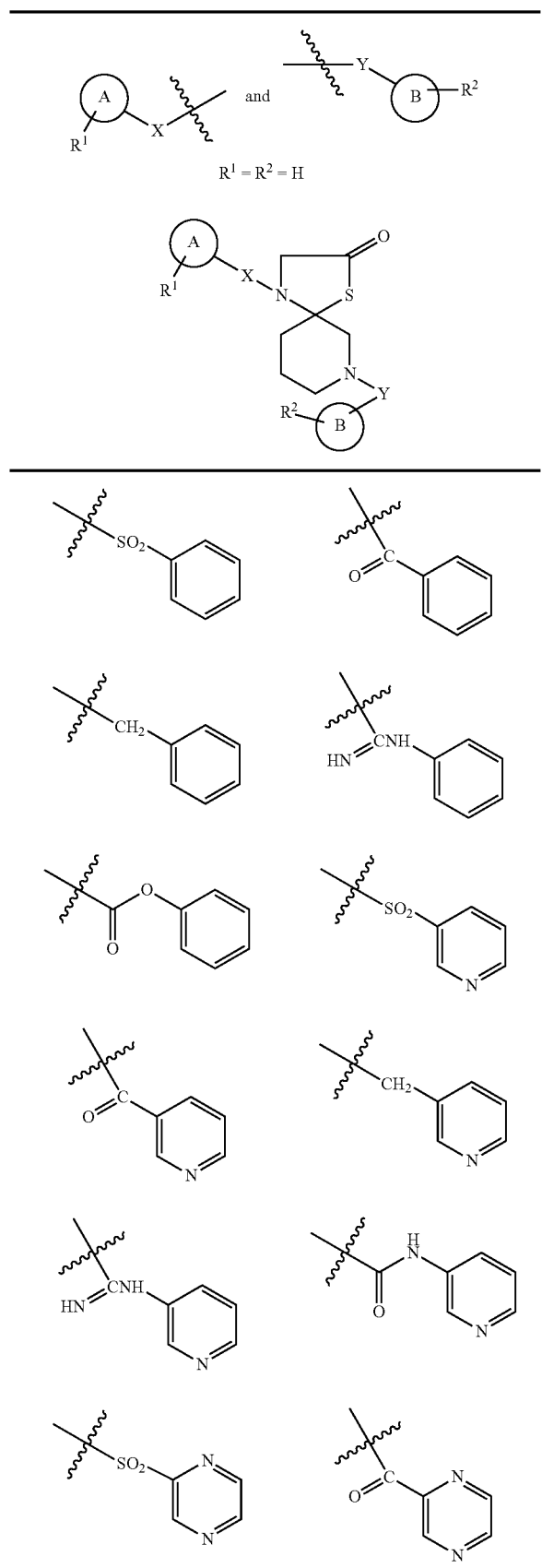
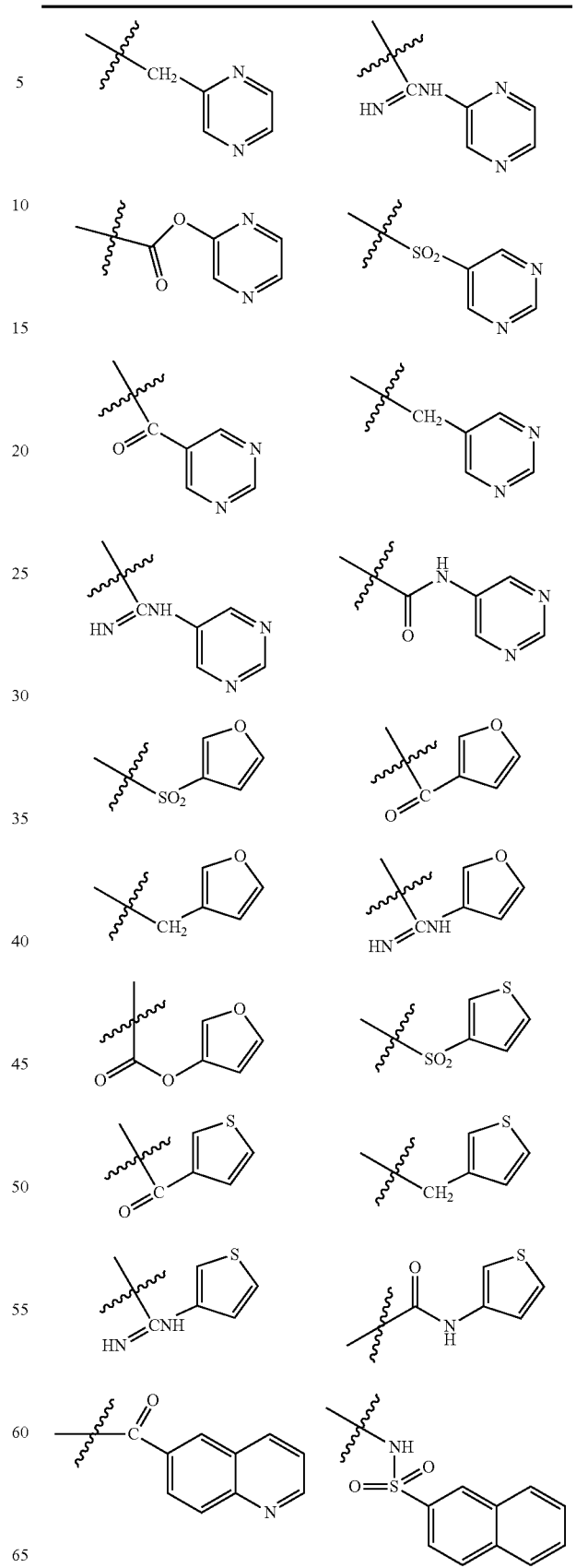

TABLE AB-continued
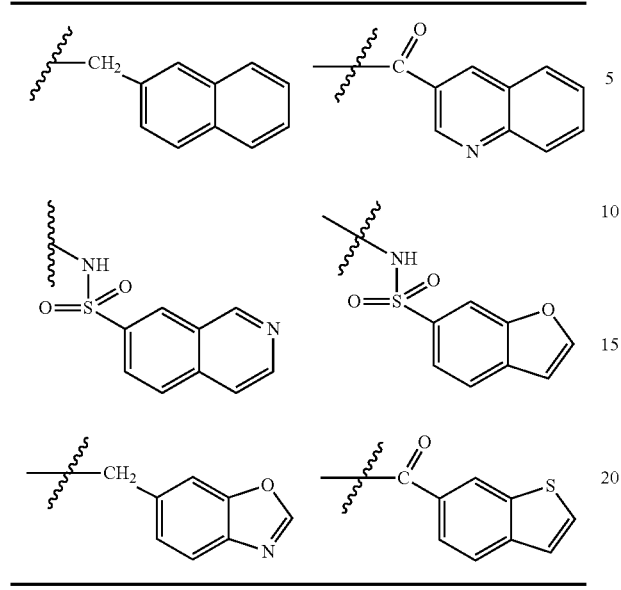
TABLE AC
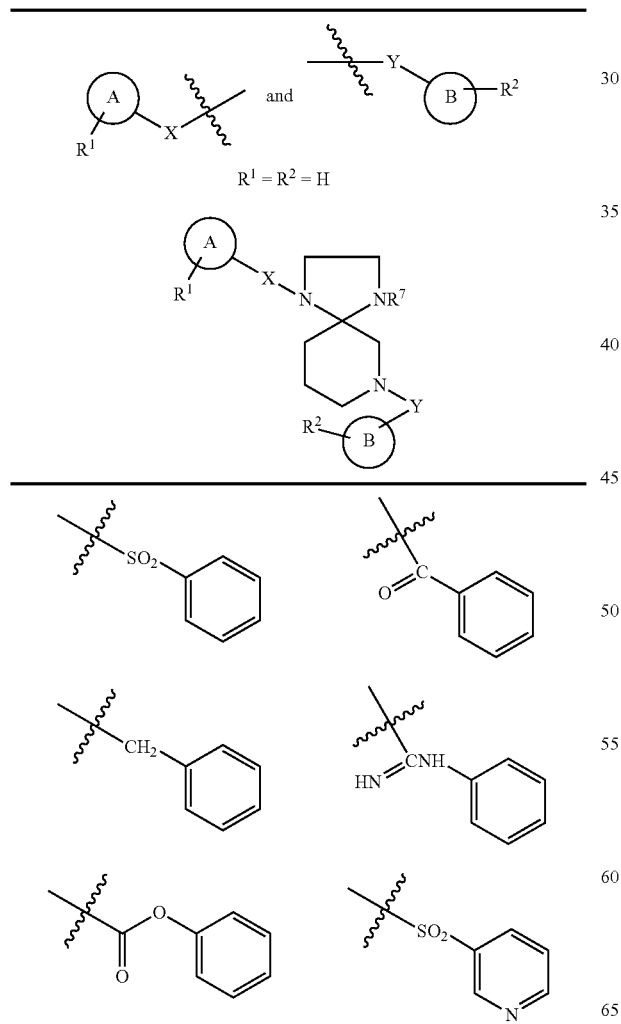
TABLE AC-continued
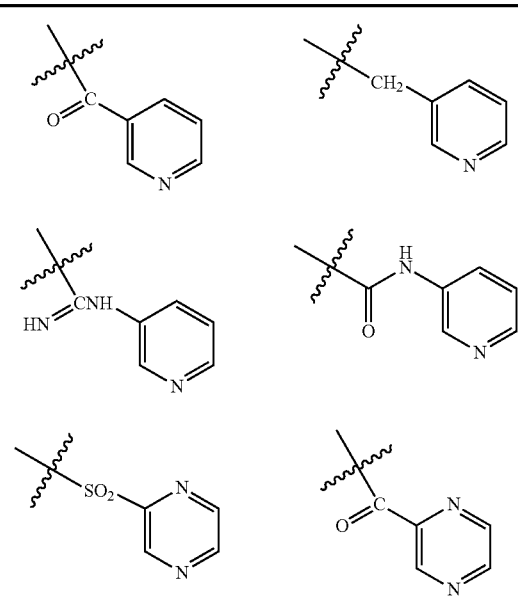
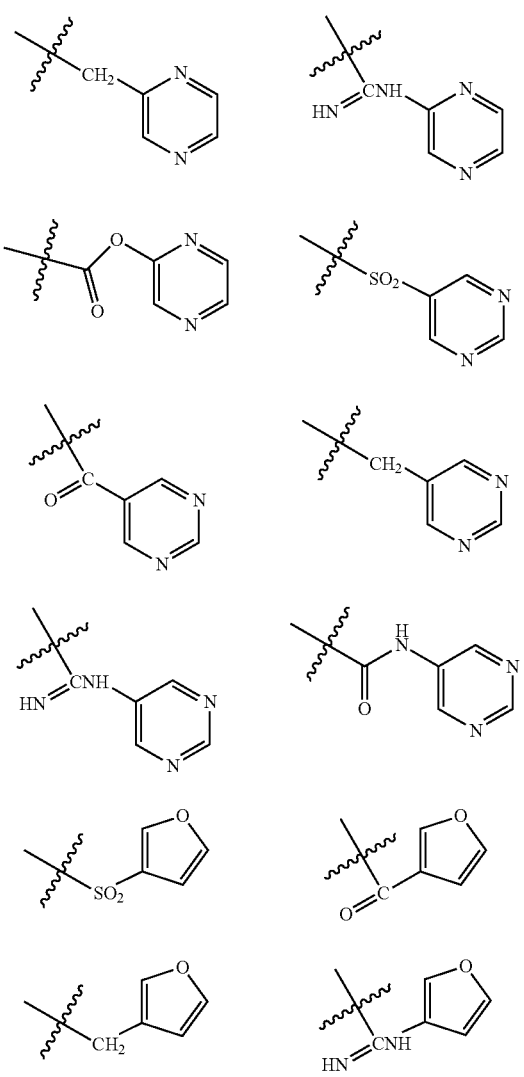

TABLE AC-continued
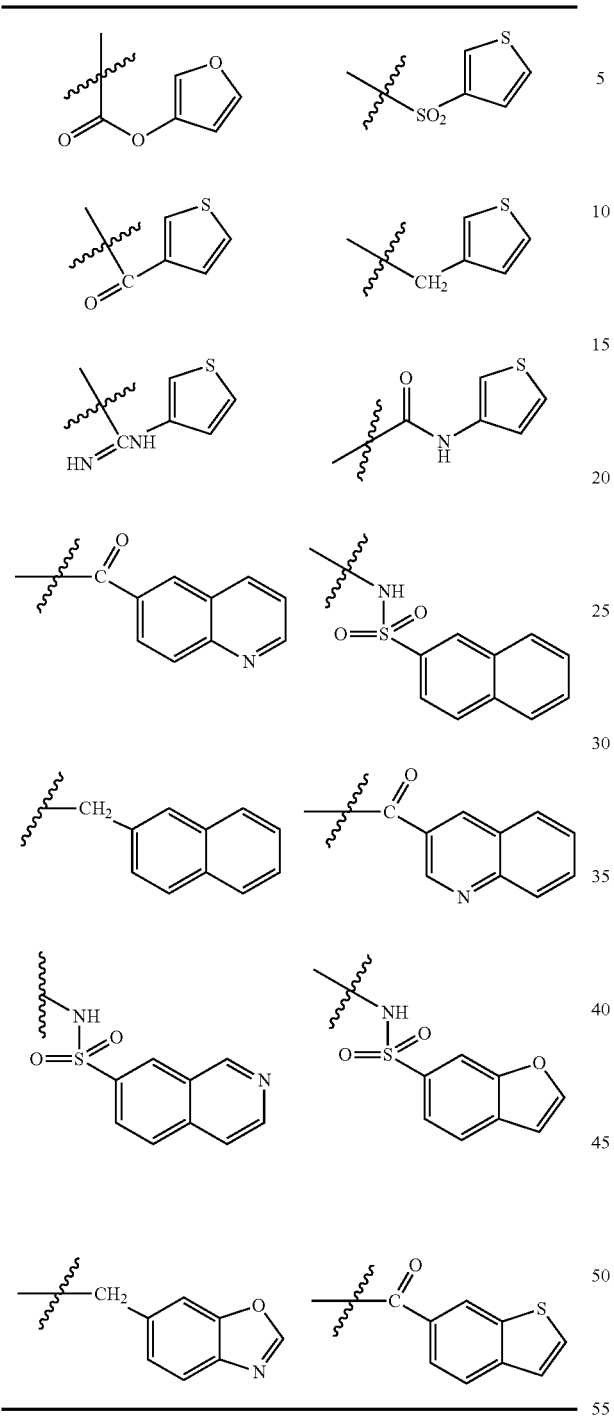
TABLE AD
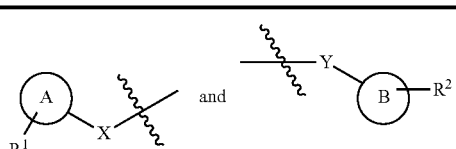
R¹ = R² = H
TABLE AD-continued
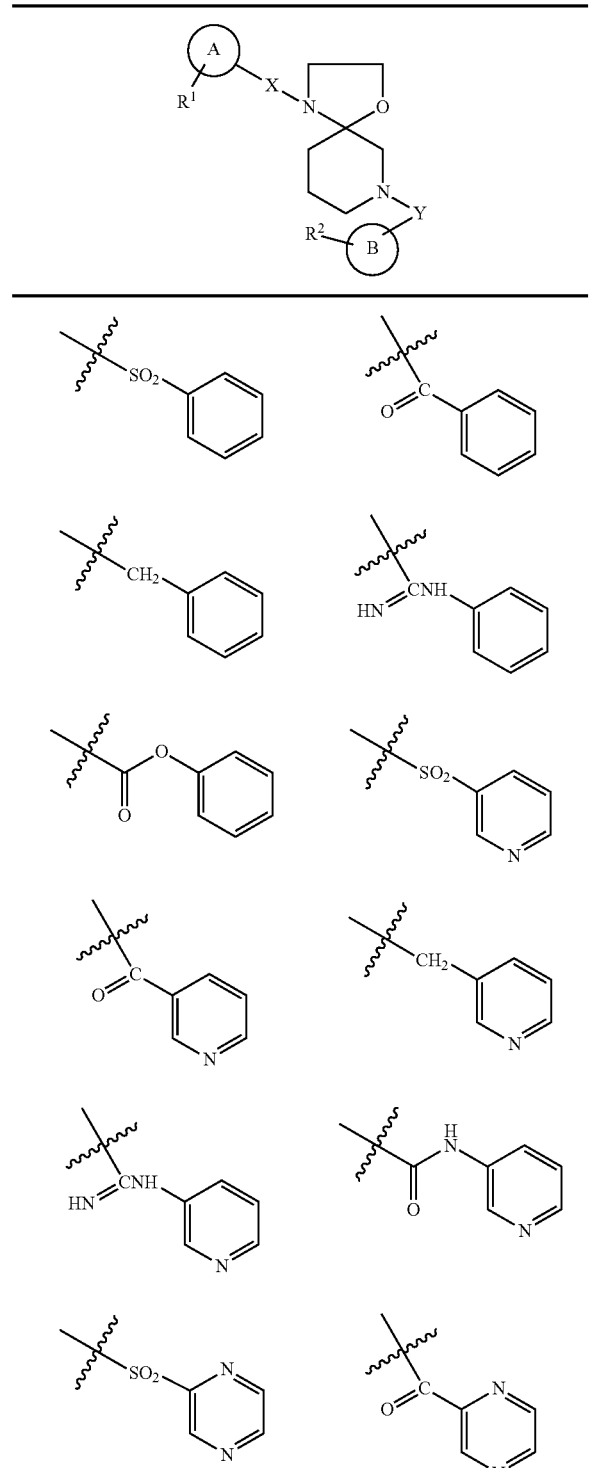

TABLE AD-continued
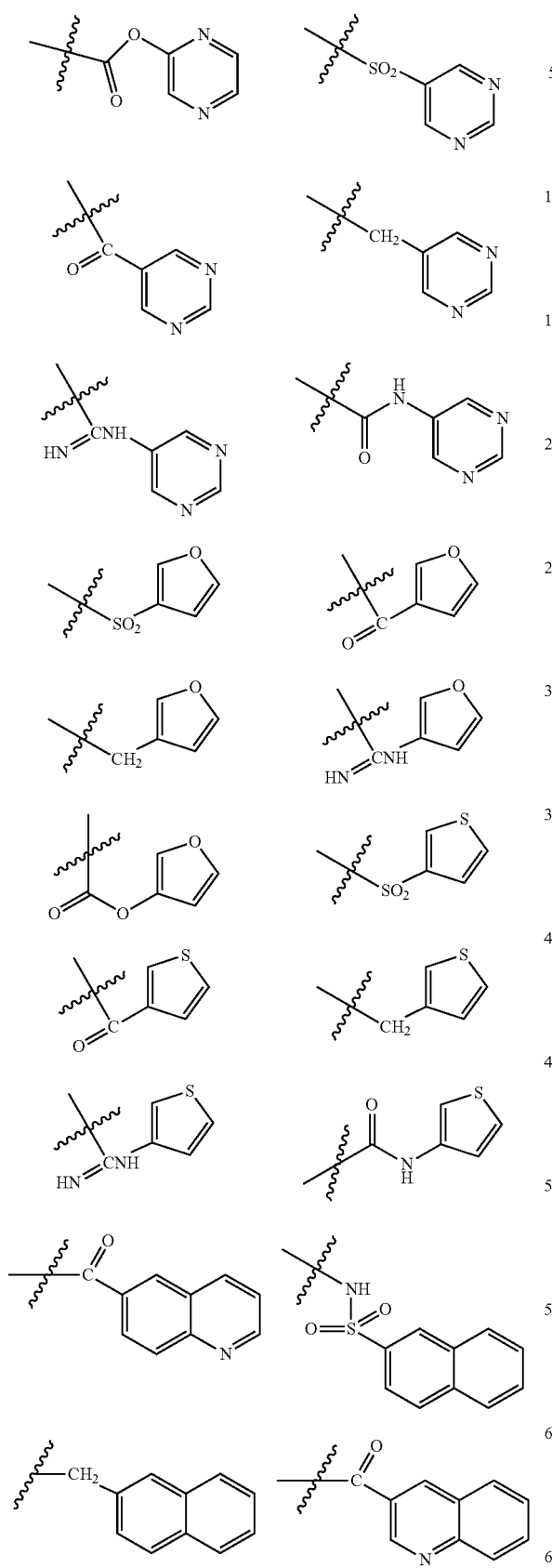
TABLE AD-continued
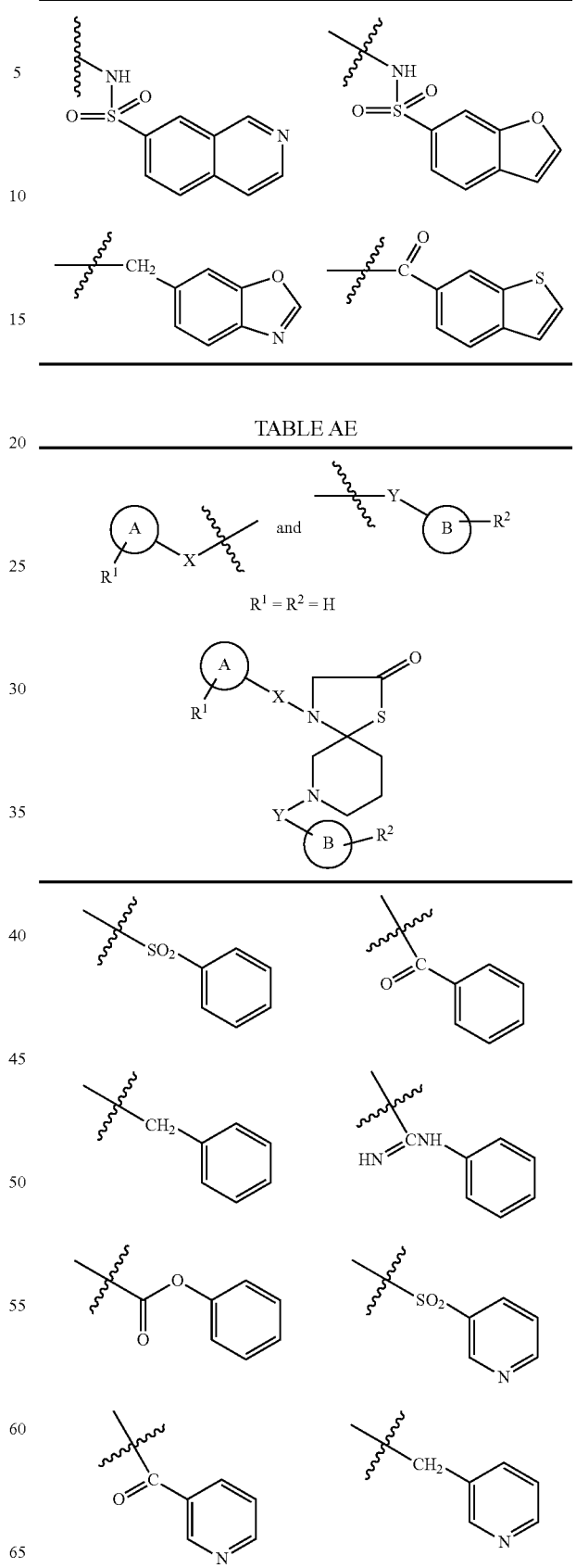
TABLE AE
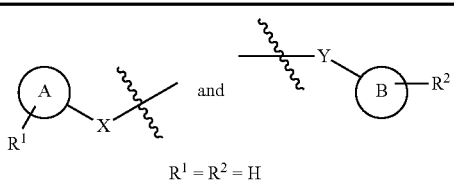
$R^1 = R^2 = H$
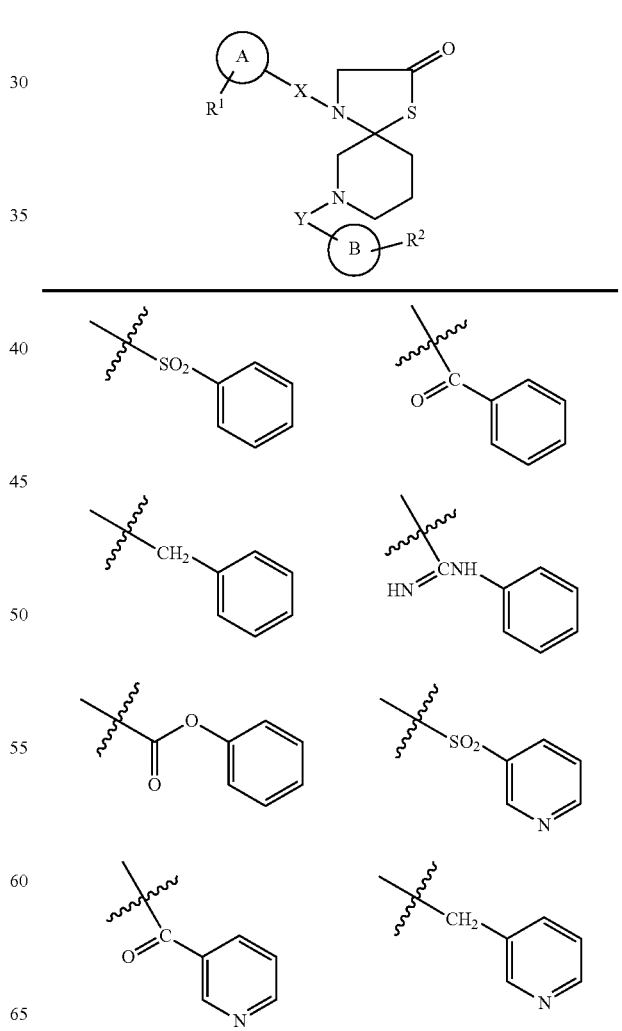

TABLE AE-continued
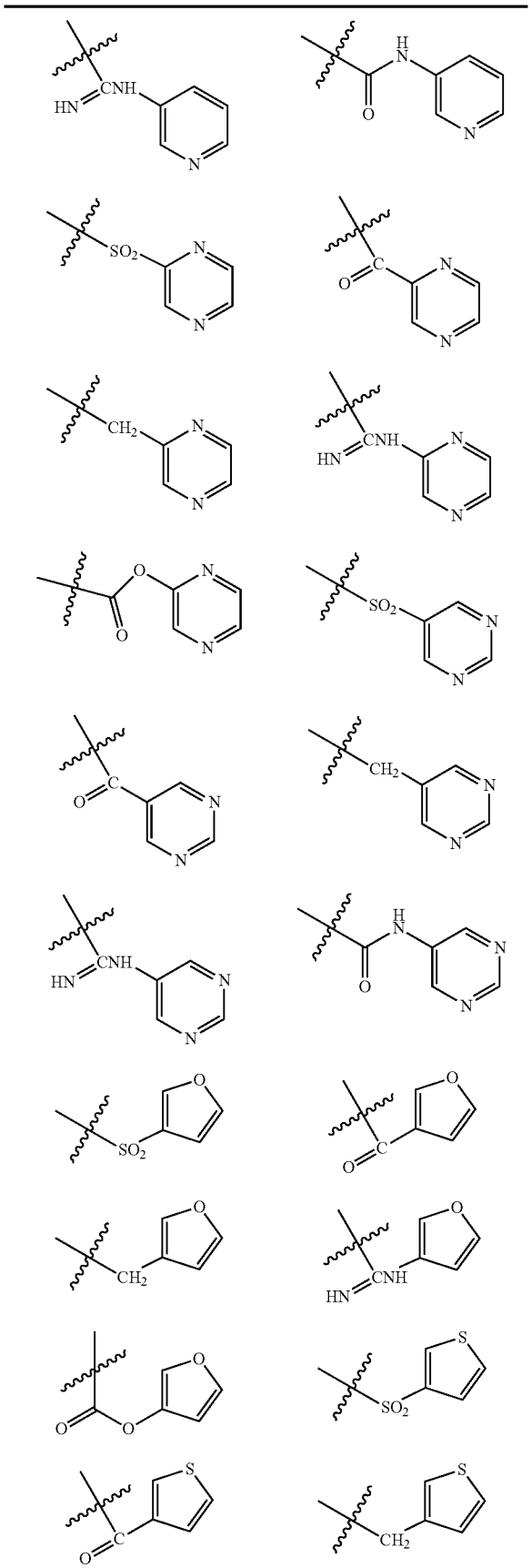
TABLE AE-continued
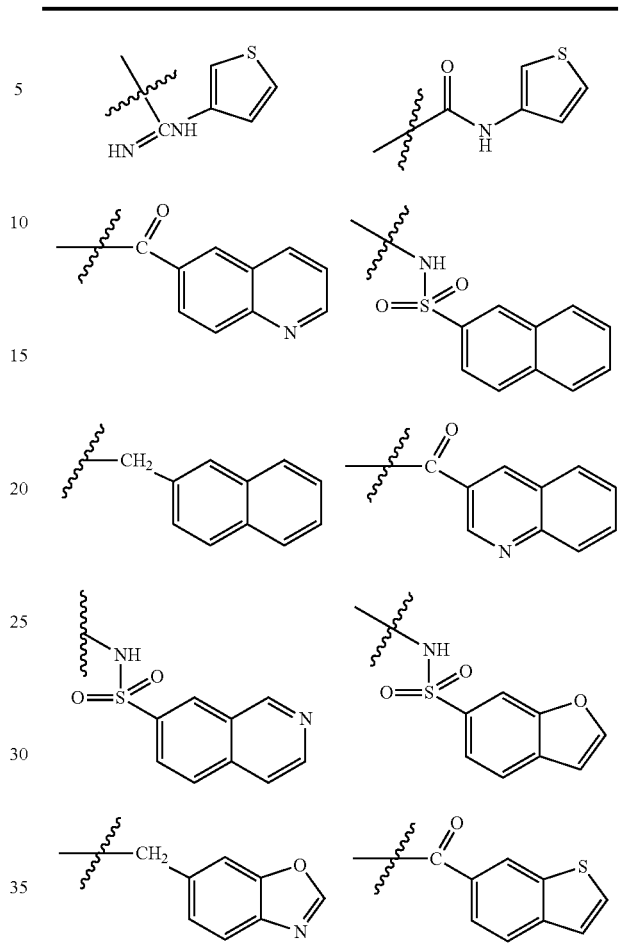
TABLE AF
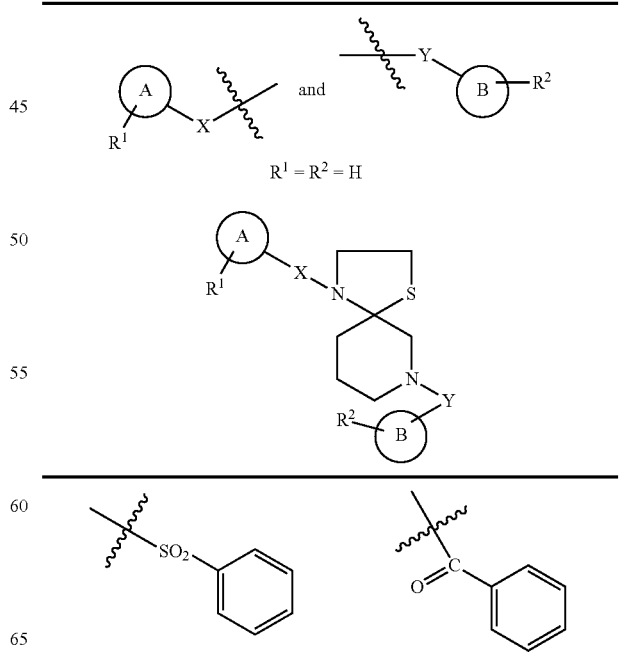
$R^1 = R^2 = H$ TABLE AF-continued
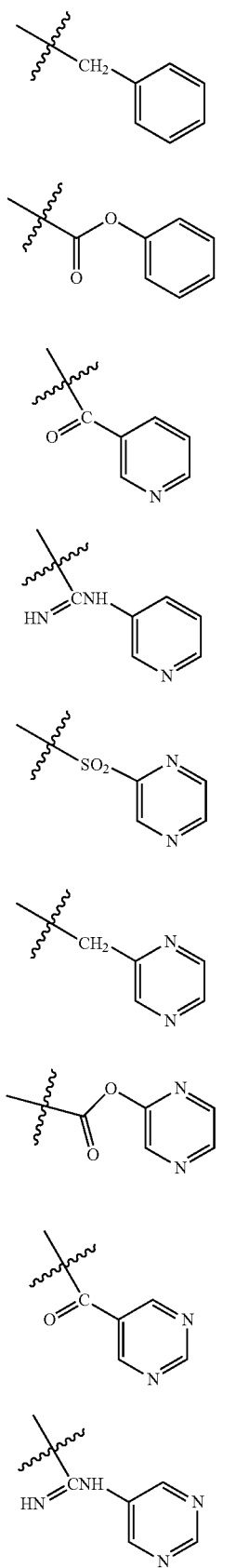
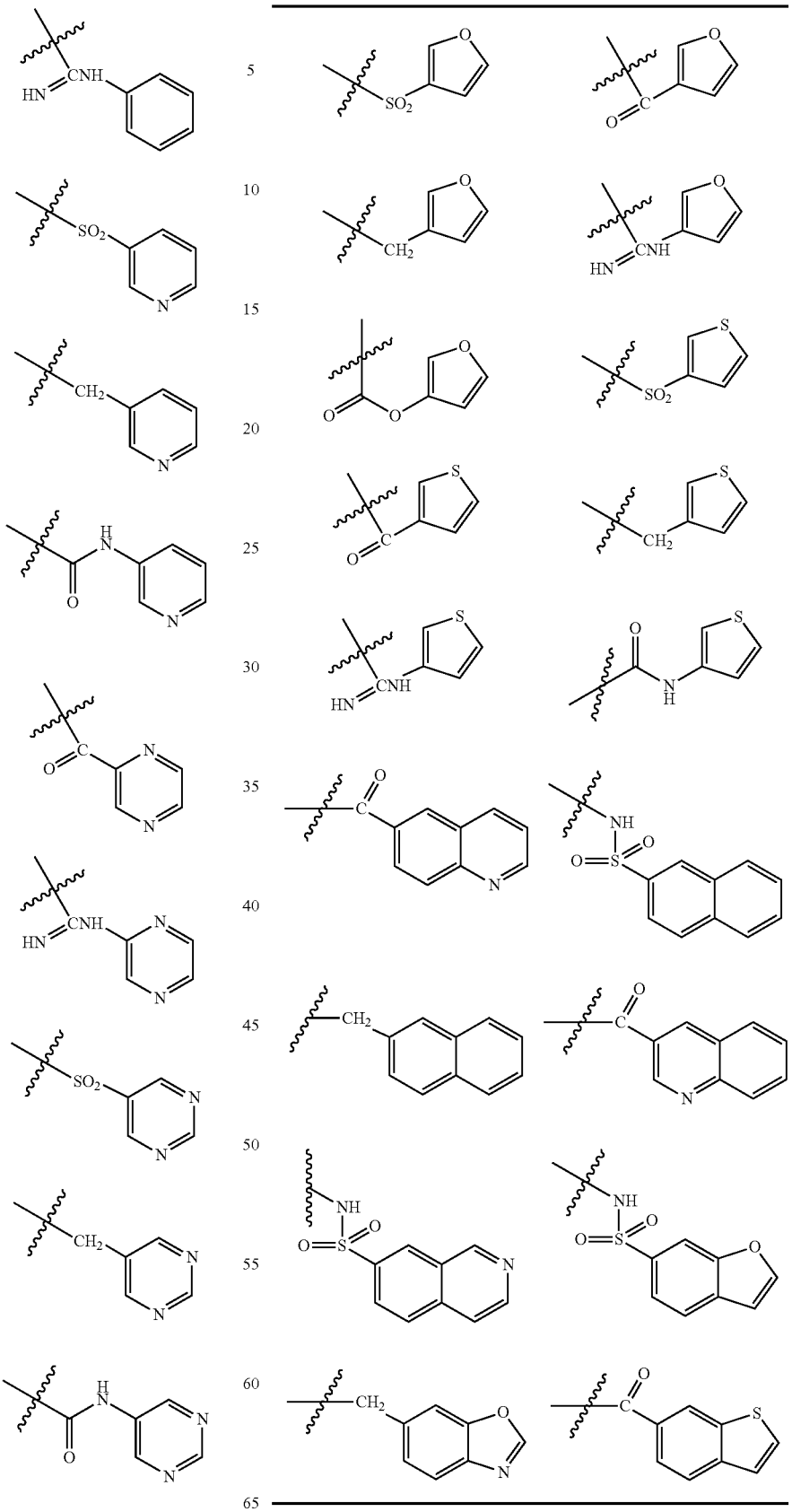

TABLE AG
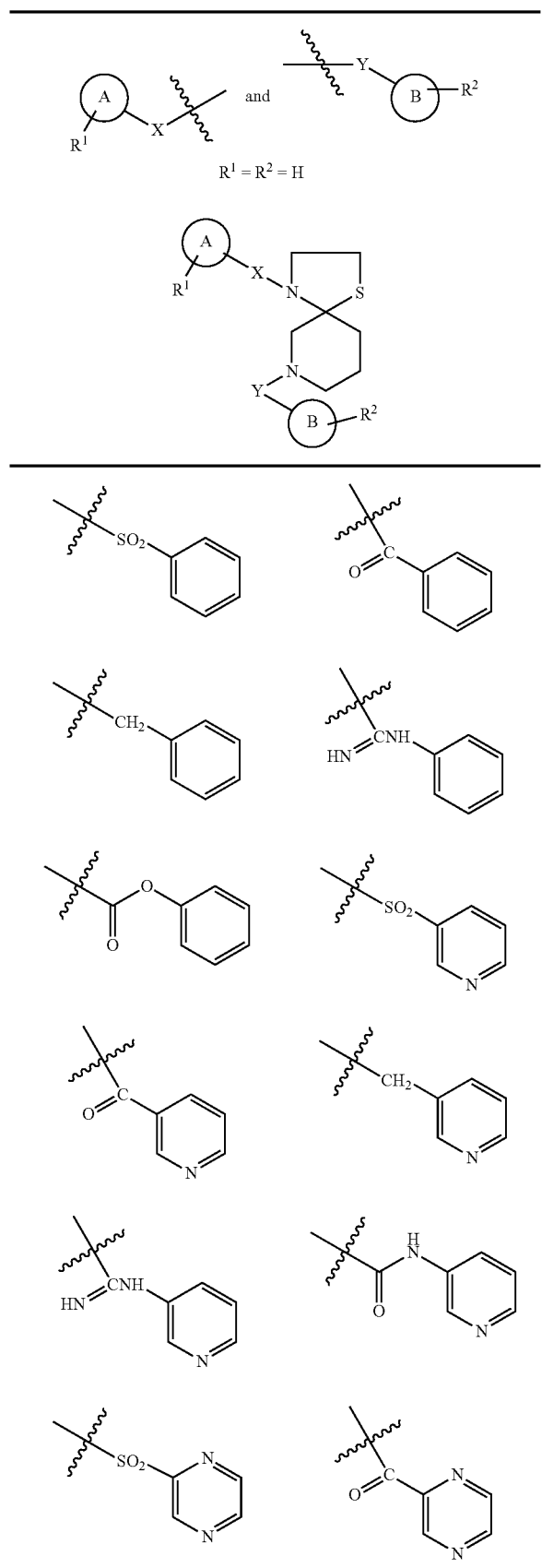
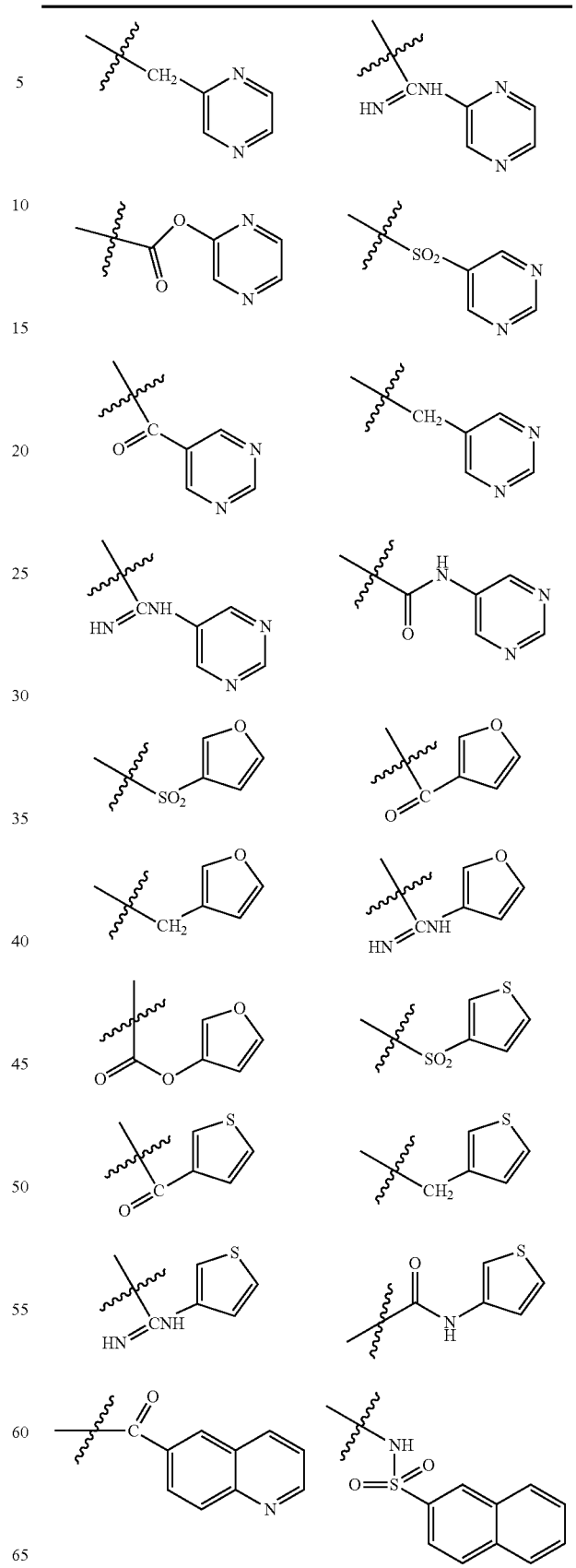

TABLE AG-continued

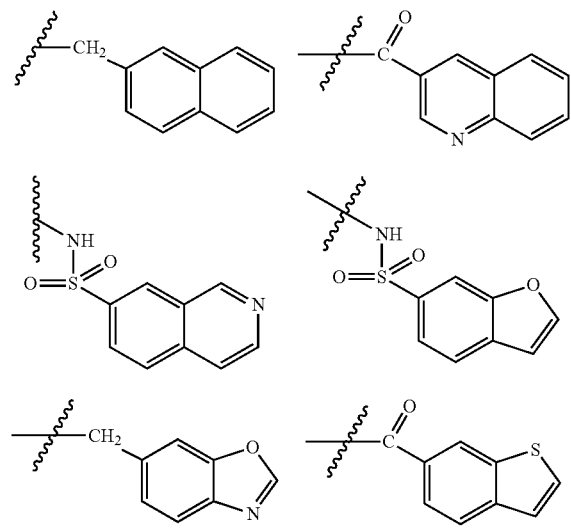

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

Example 1

MOR Agonist Activity Using GTPγS Binding Assay

To assess the mu opiate receptor (MOR) agonist activity of positive compounds from the FLNA screening, compounds were tested in a [$^{35}$S]GTPγS binding assay using striatal membranes. Our previous study has shown that in striatal membranes, activation of MOR leads to an increase in [$^{35}$S]GTPγS binding to Gαo (Wang et al., 2005 Neuroscience 135:247-261).

Striatal tissue was homogenized in 10 volumes of ice cold 25 mM HEPES buffer, pH 7.4, which contained 1 mM EGTA, 100 mM sucrose, 50 µg/ml leupeptin, 0.04 mM PMSF, 2 µg/ml soybean trypsin inhibitor and 0.2% 2-mercaptoethanol. The homogenates were centrifuged at 800×g for 5 minutes and the supernatants were centrifuged at 49,000×g for 20 minutes. The resulting pellets were suspended in 10 volume of reaction buffer, which contained 25 mM HEPES, pH 7.5, 100 mM NaCl, 50 µg/ml leupeptin, 2 µg/ml soybean trypsin inhibitor, 0.04 mM PMSF and 0.02% 2-mercaptomethanol.

The resultant striatal membrane preparation (200 µg) was admixed and maintained (incubated) at 30° C. for 5 minutes in reaction buffer as above that additionally contained 1 mM MgCl$_2$ and 0.5 nM [$^{35}$S]GTPγS (0.1 µCi/assay, PerkinElmer Life and Analytical Sciences) in a total volume of 250 µl and continued for 5 minutes in the absence or presence of 0.1-10 µM of an assayed compound of interest. The reaction was terminated by dilution with 750 µl of ice-cold reaction buffer that contained 20 mM MgCl$_2$ and 1 mM EGTA and immediate centrifugation at 16,000×g for 5 minutes.

The resulting pellet was solubilized by sonicating for 10 seconds in 0.5 ml of immunoprecipitation buffer containing 0.5% digitonin, 0.2% sodium cholate and 0.5% NP-40. Normal rabbit serum (1 µl) was added to 1 ml of lysate and incubated at 25° C. for 30 minutes. Nonspecific immune complexes were removed by incubation with 25 µl of protein A/G-conjugated agarose beads at 25° C. for 30 minutes followed by centrifugation at 5,000×g at 4° C. for 5 minutes. The supernatant was divided and separately incubated at 25° C. for 30 minutes with antibodies raised against Gαo proteins (1:1,000 dilutions).

The immunocomplexes so formed were collected by incubation at 25° C. for 30 minutes with 40 µl of agarose-conjugated protein A/G beads and centrifugation at 5,000×g at 4° C. for 5 minutes. The pellet was washed and suspended in buffer containing 50 mM Tris-HCl, pH 8.0, and 1% NP-40. The radioactivity in the suspension was determined by liquid scintillation spectrometry. The specificity of MOR activation of [$^{35}$S]GTPγS binding to Gαo induced by a selective compound was defined by inclusion of 1 µM β-funaltrexamine (β-FNA; an alkylating derivative of naltrexone that is a selective MOR antagonist). DAMGO (H-Tyr-D-Ala-Gly-N-Me-Phe-Gly-OH; 1 or 10 µM) was used as a positive control.

The results of this study are shown in the Table below.

| FLNA-Binding Compound MOR Agonist Activity | | | | | | |
|---|---|---|---|---|---|---|
| FLNA-Binding Compound | Concentration of FLNA-Binding Compound as Agonist | | | | | |
| | 0.1 µM | 1 µM | 1 µM + BFNA | % DAMGO (0.1 µM) | % DAMGO (1 µM) | % DAMGO + BFNA |
| 7866 | 152.3% | 308.2% | 62.4% | 79.3% | 94.8% | 129.5% |
| C0001 | 129.3% | 184.3% | 33.9% | 75.2% | 66.6% | 52.9% |
| C0002 | 88.4% | 93.8% | 3.9% | 51.4% | 33.9% | 6.1% |
| C0003 | 162.3% | 215.9% | 107.7% | 91.9% | 83.3% | 163.9% |
| C0004 | 122.0% | 228.4% | 65.8% | 72.1% | 85.4% | 99.7% |
| C0005 | 180.4% | 227.2% | 166.4% | 105.4% | 85.1% | 319.4% |
| C0006 | 121.5% | 204.0% | 4.6% | 70.6% | 73.8% | 7.2% |
| C0007 | 79.1% | 195.0% | 10.9% | 46.0% | 70.5% | 17.0% |
| C0008 | 71.2% | 201.6% | 2.8% | 41.4% | 72.9% | 4.4% |
| C0009 | 146.3% | 256.2% | 26.4% | 85.1% | 92.6% | 41.2% |
| C0010 | 136.5% | 307.0% | 89.1% | 80.7% | 114.9% | 135.0% |
| C0011 | 217.0% | 305.0% | 19.0% | 126.8% | 114.3% | 36.5% |
| C0012 | 96.8% | 224.8% | 184.4% | 54.8% | 86.7% | 280.7% |
| C0013 | 156.6% | 301.2% | 39.6% | 91.0% | 108.9% | 61.8% |
| C0014 | 144.9% | 153.5% | 76.3% | 82.0% | 59.2% | 116.1% |
| C0015 | 138.7% | 204.7% | 126.8% | 78.5% | 78.9% | 193.0% |
| C0016 | 172.7% | 230.5% | 96.7% | 100.4% | 83.3% | 150.9% |
| C0017 | 153.8% | 284.5% | 94.1% | 87.1% | 109.9% | 143.2% |
| C0018 | 195.5% | 247.7% | 106.5% | 110.7% | 95.5% | 162.1% |

-continued

FLNA-Binding Compound MOR Agonist Activity

| FLNA-Binding Compound | Concentration of FLNA-Binding Compound as Agonist ||||||
|---|---|---|---|---|---|---|
| | 0.1 μM | 1 μM | 1 μM + BFNA | % DAMGO (0.1 μM) | % DAMGO (1 μM) | % DAMGO + BFNA |
| C0019 | 104.4% | 176.6% | 52.8% | 59.1% | 68.1% | 80.4% |
| C0021 | 159.7% | 192.0% | 90.7% | 94.5% | 87.8% | 546.4% |
| C0022 | 194.3% | 328.7% | 13.4% | 113.5% | 123.2% | 25.7% |
| C0023 | 153.2% | 233.7% | 23.2% | 89.5% | 87.6% | 44.5% |
| C0024 | 178.4% | 229.6% | 59.3% | 92.8% | 84.1% | 135.1% |
| C0025 | 235.7% | 320.7% | 80.2% | 122.6% | 117.5% | 182.7% |
| C0028 | 93.9% | 132.4% | 78.4% | 55.6% | 60.5% | 472.3% |
| C0029 | 175.4% | 308.8% | 16.6% | 91.2% | 113.1% | 37.8% |
| C0030 | 150.3% | 226.8% | 95.0% | 96.0% | 98.0% | 291.4% |
| C0032 | 145.4% | 202.0% | 80.9% | 92.8% | 87.3% | 248.2% |
| C0033 | 134.5% | 186.4% | 76.6% | 85.9% | 80.6% | 235.0% |
| C0034 | 103.6% | 167.9% | 80.1% | 61.3% | 76.7% | 482.5% |
| C0041 | 186.1% | 244.4% | 95.5% | 110.1% | 111.7% | 575.3% |
| C0042 | 167.1% | 260.9% | 110.6% | 98.9% | 119.2% | 666.3% |
| C0047 | 142.2% | 206.1% | 80.1% | 98.1% | 88.5% | 182.0% |
| C0048 | 209.1% | 245.3% | 89.9% | 144.2% | 105.3% | 204.3% |
| C0049 | 106.6% | 210.0% | 81.0% | 73.5% | 90.1% | 184.1% |
| C0051 | 94.4% | 170.4% | 55.9% | 65.1% | 73.1% | 127.0% |
| C0052 | 108.4% | 162.8% | 42.7% | 74.8% | 69.9% | 97.0% |
| C0053 | 104.0% | 157.2% | 93.1% | 71.7% | 67.5% | 211.6% |
| C0054 | 68.2% | 127.0% | 43.5% | 47.0% | 54.5% | 98.9% |
| C0057 | — | — | — | — | — | — |
| C0061 | — | — | — | — | — | — |
| C0062 | 127.8% | 310.5% | 59.8% | 81.9% | 134.7% | 149.9% |
| C0064 | 213.8% | 349.6% | 38.1% | 124.2% | 159.1% | 110.4% |
| C0065 | 198.3% | 279.5% | 47.7% | 127.0% | 121.3% | 119.5% |
| C0067 | 142.7% | 179.0% | 33.5% | 82.9% | 81.5% | 97.1% |
| C0068 | 107.2% | 263.1% | 165.9% | 53.4% | 83.8% | 307.8% |
| C0069 | — | — | — | — | — | — |
| C0070 | 165.6% | 210.8% | 114.2% | 96.2% | 95.9% | 331.0% |
| C0071 | 276.3% | 355.3% | 177.1% | 160.5% | 161.7% | 513.3% |
| C0072 | 172.7% | 259.1% | 67.1% | 100.3% | 117.9% | 194.5% |
| C0073 | — | — | — | — | — | — |
| C0077 | 192.7% | 265.4% | 136.7% | 109.5% | 104.9% | 621.4% |
| C0078 | 138.1% | 236.6% | 170.7% | 82.4% | 106.4% | 359.4% |
| C0080M | 187.9% | 205.4% | 167.1% | 112.1% | 92.4% | 351.8% |
| C0084M | 163.1% | 255.5% | 133.2% | 97.3% | 114.9% | 280.4% |
| C0085M | 211.6% | 246.2% | 43.7% | 105.5% | 78.4% | 112.6% |
| C0138M | 126.9% | 183.9% | 51.5% | 86.3% | 90.9% | 131.0% |
| C0139M | 156.1% | 206.6% | 51.0% | 106.2% | 102.2% | 129.8% |
| C0140M | 126.1% | 215.4% | 83.0% | 85.8% | 106.5% | 211.2% |
| C0141M | 161.5% | 213.9% | 47.9% | 109.9% | 105.8% | 121.9% |
| C0143M | 81.0% | 193.3% | 86.5% | 47.1% | 59.3% | 94.7% |
| C0144M | 186.3% | 295.9% | 125.9% | 108.3% | 90.8% | 137.9% |
| C0145M | 193.0% | 289.2% | 87.0% | 112.2% | 88.7% | 95.3% |
| C0148M | 181.3% | 360.6% | 87.6% | 105.4% | 110.6% | 95.9% |
| C0149M | 209.8% | 406.7% | 93.4% | 122.0% | 124.8% | 102.3% |
| C0150M | 167.1% | 423.1% | 158.1% | 97.2% | 129.8% | 173.2% |
| C0151M | 346.8% | 397.6% | 212.8% | 201.6% | 122.0% | 233.1% |
| C0152M | — | — | — | — | — | — |
| C0154M | — | — | — | — | — | — |
| DAMGO Average | 168.5% | 266.1% | 53.2% | — | — | — |

Example 2

FITC-NLX-Based FLNA Screening Assay

A. Streptavidin-Coated 96-Well Plates

Streptavidin-coated 96-well plates (Reacti-Bind™ NeutrAvidin™ High binding capacity coated 96-well plate, Pierce-ENDOGEN) are washed three times with 200 μl of 50 mM Tris HCl, pH 7.4 according to the manufacturer's recommendation.

B. N-biotinylated VAKGL pentapeptide (Bn-VAKGL) (SEQ ID NO: 1)

Bn-VAKGL peptide (0.5 mg/plate) is dissolved in 50 μl DMSO and then added to 4450 μl of 50 mM Tris HCl, pH 7.4, containing 100 mM NaCl and protease inhibitors (binding medium) as well as 500 μl superblock in PBS (Pierce-ENDOGEN) [final concentration for DMSO: 1%].

C. Coupling of Bn-VAKGL Peptides to Streptavidin-Coated Plate

The washed streptavidin-coated plates are contacted with 5 μg/well of Bn-VAKGL (100 μl) for 1 hour (incubated) with constant shaking at 25° C. [50 μl of Bn-VAKGL peptide solution from B+50 μl binding medium, final concentration for DMSO: 0.5%]. At the end of the incubation, the plate is washed three times with 200 μl of ice-cold 50 mM Tris HCl, pH 7.4.

D. Binding of FITC-Tagged Naloxone [FITC-NLX] to VAKGL.

Bn-VAKGL coated streptavidin plates are incubated with 10 nM fluorescein isothiocyanate-labeled naloxone (FITC-NLX; Invitrogen) in binding medium (50 mM Tris HCl, pH 7.4 containing 100 mM NaCl and protease inhibitors) for 30 minutes at 30° C. with constant shaking. The final assay volume is 100 µl. At the end of incubation, the plate is washed twice with 100 µl of ice-cold 50 mM Tris, pH 7.4. The signal, bound-FITC-NLX is detected using a DTX-880 multi-mode plate reader (Beckman).

E. Screening of Medicinal Chemistry Analogs

The compounds are first individually dissolved in 25% DMSO containing 50 mM Tris HCl, pH 7.4, to a final concentration of 1 mM (assisted by sonication when necessary) and then plated into 96-well compound plates. To screen the medicinal chemistry analogs (new compounds), each compound solution (1 µl) is added to the Bn-VAKGL coated streptavidin plate with 50 µl/well of binding medium followed immediately with addition of 50 µl of FITC-NLX (total assay volume/well is 100 µl). The final screening concentration for each compound is 10 µM.

Each screening plate includes vehicle control (total binding) as well as naloxone (NLX) and/or naltrexone (NTX) as positive controls. Compounds are tested in triplicate or quadruplicate. Percent inhibition of FITC-NLX binding for each compound is calculated [(Total FITC-NLX bound in vehicle−FITC-NLX bound in compound)/Total FITC-NLX bound in vehicle]×100%]. To assess the efficacies and potencies of the selected compounds, compounds that achieve approximately 60-70% inhibition at 10 µM are screened further at 1 and 0.1 µM concentrations.

The results of this screening assay are shown in the table below.

| FLNA Peptide Binding Assay | | | |
|---|---|---|---|
| FLNA-binding | Concentration of FLNA-binding Compound | | |
| Compound | 0.01 µM | 0.1 µM | 1 µM |
| 7866 | 38.5% | 47.9% | 53.4% |
| C0001 | 34.8% | 42.9% | 51.3% |
| C0002 | 38.4% | 45.6% | 42.8% |
| C0003 | 38.3% | 45.3% | 48.8% |
| C0004 | 37.6% | 42.3% | 44.7% |
| C0005 | 35.2% | 44.5% | 51.5% |
| C0006 | 41.6% | 46.8% | 51.8% |
| C0007 | 40.5% | 46.3% | 48.9% |
| C0008 | 42.2% | 52.3% | 54.4% |
| C0009 | 41.7% | 49.0% | 53.9% |
| C0010 | 39.8% | 42.7% | 47.1% |
| C0011 | 37.6% | 41.4% | 46.0% |
| C0012 | 26.3% | 39.5% | 46.4% |
| C0013 | 39.6% | 42.4% | 49.1% |
| C0014 | 29.5% | 38.8% | 40.0% |
| C0015 | 31.2% | 40.6% | 45.5% |
| C0016 | 38.3% | 43.8% | 49.1% |
| C0017 | 28.9% | 35.4% | 40.7% |
| C0018 | 42.3% | 45.9% | 53.4% |
| C0019 | 30.1% | 38.2% | 43.6% |
| C0021 | 34.0% | 38.4% | 40.6% |
| C0022 | 34.5% | 37.6% | 43.9% |
| C0023 | 35.9% | 41.7% | 47.2% |
| C0024 | 37.9% | 46.4% | 50.4% |
| C0025 | 37.2% | 41.4% | 45.1% |
| C0028 | 32.2% | 36.6% | 43.3% |
| C0029 | 38.6% | 43.2% | 50.5% |
| C0030 | 37.4% | 45.4% | 56.0% |
| C0032 | 41.5% | 50.5% | 55.3% |
| C0033 | 43.9% | 48.4% | 51.3% |
| C0034 | 29.6% | 38.3% | 44.8% |
| C0041 | 38.3% | 47.0% | 51.2% |
| C0042 | 42.4% | 49.7% | 56.1% |
| C0047 | 30.8% | 35.2% | 41.4% |
| C0048 | 28.5% | 38.9% | 45.9% |
| C0049 | 25.3% | 27.9% | 30.3% |
| C0051 | 27.0% | 30.4% | 36.4% |
| C0052 | 28.0% | 35.6% | 40.8% |
| C0053 | 28.9% | 33.8% | 39.3% |
| C0054 | 32.9% | 39.4% | 43.3% |
| C0057 | — | — | — |
| C0061 | — | — | — |
| C0062 | 39.5% | 49.5% | 48.0% |
| C0064 | 37.3% | 44.4% | 49.2% |
| C0065 | 37.1% | 44.0% | 47.0% |
| C0067 | 31.3% | 39.7% | 45.0% |
| C0068 | 53.7% | 58.6% | 62.2% |
| C0069 | — | — | — |
| C0070 | 42.6% | 50.6% | 53.6% |
| C0071 | 39.1% | 49.6% | 55.2% |
| C0072 | 28.4% | 37.4% | 44.0% |
| C0073 | — | — | — |
| C0077 | 45.7% | 47.7% | 51.0% |
| C0078 | 46.6% | 48.0% | 50.5% |
| C0080M | 46.8% | 53.3% | 54.6% |
| C0084M | 47.2% | 53.7% | 55.9% |
| C0085M | 45.7% | 53.7% | 60.7% |
| C0138M | 53.0% | 52.0% | 59.5% |
| C0139M | 48.9% | 53.1% | 61.6% |
| C0140M | 42.3% | 49.2% | 54.4% |
| C0141M | 33.1% | 39.0% | 46.9% |
| C0143M | 45.3% | 48.4% | 57.8% |
| C0144M | 46.4% | 50.7% | 55.7% |
| C0145M | 45.1% | 53.7% | 58.3% |
| C0148M | 46.2% | 52.0% | 57.0% |
| C0149M | 48.5% | 52.3% | 62.0% |
| C0150M | 47.3% | 51.8% | 61.4% |
| C0151M | 48.3% | 51.7% | 58.7% |
| C0152M | — | — | — |
| C0154M | — | — | — |
| Naloxone Average | 40.61% | 47.75% | 51.54% |

Example 3

Tail-Flick Test

The mouse "tail flick" test was used to assay the relative antinociceptive activity of compositions containing a compound to be assayed. This assay was substantially that disclosed by Xie et al., 2005 *J. Neurosci* 25:409-416.

The mouse hot-water tail-flick test was performed by placing the distal third of the tail in a water bath maintained at 52° C. The latency until tail withdrawal from the bath was determined and compared among the treatments. A 10 second cutoff was used to avoid tissue damage. Data are converted to percentage of antinociception by the following formula: (response latency−baseline latency)/(cutoff−baseline latency)×100 to generate dose-response curves. Linear regression analysis of the log dose-response curves was used to calculate the $A_{50}$ (dose that resulted in a 50% antinociceptive effect) doses and the 95% confidence intervals (CIs). Relative potency was determined as a ratio of the $A_{50}$ values. The significance of the relative potency and the confidence intervals are determined by applying the t test at p<0.05.

To assess tolerance to the antinociceptive effect, the compound was administered twice daily for 7 days at an $A_{90}$ dose (dose that results in a 90% antinociceptive effect in the 52° C. warm-water tail-flick test), and the tail-flick test was performed daily after the a.m. dose. A significant reduction in tail-flick latency on subsequent days compared to the Day 1 administration of the $A_{90}$ dose indicates antinociceptive tolerance.

Orally administered morphine exhibited an $A_{50}$ value of 61.8 (52.4–72.9) mg/kg, and a mean maximum antinociception amount of about 43% at 56 mg/kg at about 20 minutes. Orally administered compound C0011 exhibited a mean maximum antinociception amount of about 70% at 56 mg/kg at about 10-20 minutes, whereas orally administered compound C0009 exhibited a mean maximum antinociception amount of about 50% at 56 mg/kg at about 10 minutes, compound C0047 exhibited a mean maximum antinociception amount of about 35% at 56 mg/kg at about 20-30 minutes, compound C0052 a mean maximum antinociception amount of about 30% at 56 mg/kg at about 20 minutes, and compound C0022 exhibited a mean maximum antinociception amount of about 40% at 56 mg/kg at about 30 minutes, and compound C0148M exhibited a mean maximum antinociception amount of about 30% at 32 mg/kg at about 10 minutes.

Example 4

Dependence Test

On day 8, 16-20 hours after the last administration of an assay composition, animals were given naloxone to precipitate withdrawal (10 mg/kg, s.c.) before being placed in an observation chamber for 1 hour. A scale adapted from MacRae et al., 1997 *Psychobiology* 25:77-82 was used to quantify four categories of withdrawal behaviors: "wet dog" shakes, paw tremors, mouth movements, and ear wipes. Scores are summed to yield a total withdrawal score across the 1-hour test.

Example 5

Relative Gs/Go Switching

In this set of studies, the rat brain slice organotypic culture methods were modified from those published previously (Adamchik et al., 2000 *Brain Res Protoc* 5:153-158; Stoppini et al., 1991 *J Neurosci Methods* 37:173-182). Striatal slices (200 μM thickness) were prepared using a McIlwain tissue chopper (Mickle Laboratory Engineering Co., Surrey, UK). Slices were carefully transferred to sterile, porous culture inserts (0.4 μm, Millicell-CM) using the rear end of a glass Pasteur pipette. Each culture insert unit contained 2 slices and was placed into one well of the 12-well culture tray. Each well contain 1.5 ml of culture medium composed of 50% MEM with Earl's salts, 2 mM L-glutamine, 25% Earl's balanced salt solution, 6.5 g/l D-glucose, 20% fetal bovine serum, 5% horse serum, 25 mM HEPES buffer, 50 mg/ml streptomycin and 50 mg/ml penicillin. The pH value was adjusted to 7.2 with HEPES buffer.

Cultures were first incubated for 2 days to minimize the impact of injury from slice preparation. Incubator settings throughout the experiment were 36° C. with 5% $CO_2$. To induce tolerance, culture medium was removed and the culture insert containing the slices was gently rinsed twice with warm (37° C.) phosphate-buffered saline (pH 7.2) before incubation in 0.1% fetal bovine serum-containing culture medium with 100 μM morphine for 1 hour twice daily (at 9-10 AM and 3-4 PM) for 7 days.

Slices were returned to culture medium with normal serum after each drug exposure. Tissues were harvested 16 hours after the last drug exposure by centrifugation.

For determination of MOR-G protein coupling, slices were homogenated to generate synaptic membranes. Synaptic membranes (400 μg) were incubated with either 10 μM oxycodone or Kreb's-Ringer solution for 10 minutes before solubilization in 250 μl of immunoprecipitation buffer (25 mM HEPES, pH 7.5; 200 mM NaCl, 1 mM EDTA, 50 μg/ml leupeptin, 10 μg/ml aprotinin, 2 μg/ml soybean trypsin inhibitor, 0.04 mM PMSF and mixture of protein phosphatase inhibitors). Following centrifugation, striatal membrane lysates were immunoprecipitated with immobilized anti-Gαs/olf or -Gαo conjugated with immobilized protein G-agarose beads. The level of MOR in anti-Gαs/olf or -Gαo immunoprecipitates was determined by Western blotting using specific anti-MOR antibodies.

To measure the magnitude of MOR-mediated inhibition of cAMP production, brain slices were incubated with Kreb's-Ringer (basal), 1 μM DAMGO, 1 μM forskolin or 1 μM DAMGO+1 μM forskolin for 10 minutes at 37° C. in the presence of 100 μM of the phosphodiesterase inhibitor IBMX. Tissues were homogenized by sonication and protein precipitated with 1M TCA. The supernatant obtained after centrifugation was neutralized using 50 mM Tris, pH 9.0. The level of cAMP in the brain lysate was measured by a cAMP assay kit (PerkinElmer Life Science, Boston) according to manufacturer's instructions.

| Condition | Gs/olf | Go | Gs/Go-Coupled Ratio |
|---|---|---|---|
| Vehicle | | | |
| Average | 330.7 | 1996.4 | 0.173 |
| SEM | 34.6 | 192.0 | 0.34 |
| Oxycodone, 10 μM | | | |
| Average | 1425.2 | 900.4 | 1.588 |
| SEM | 77.8 | 26.2 | 0.103 |
| C0011, 10 μM | | | |
| Average | 534.3 | 1603.3 | 0.332 |
| SEM | 51.8 | 68.5 | 0.023 |
| C0011, 100 μM | | | |
| Average | 658.2 | 1598.8 | 0.420 |
| SEM | 34.2 | 114.9 | 0.030 |

A compound useful herein can be readily synthesized. An illustrative synthetic scheme is shown below that preparation of compounds containing two sulfonyl linkages and one sulfonyl and one carbonyl linkage. That scheme can be readily adapted for the preparation of compounds containing two carbonyl linkages and one carbonyl and one sulfonyl linkage in the opposite configurations from those shown. More detailed syntheses are set out hereinafter.

Example 6

Carrageenan-Induced Acute Inflammatory Pain

To test the antinociceptive activity of the compounds under acute inflammatory conditions, the latency to paw withdrawal from a noxious thermal stimulus is determined before and 3 hours after injection of a 50 µl solution of 2% carrageenan into the plantar surface of the hindpaw (Mogil et al. 1999 *Pain* 80:67-82). Animals are placed in plexiglas boxes on top of a glass plate maintained at 30° C. and allowed to habituate for two sessions (−24 hours and −1 hour). Each habituation session lasts approximately 45-60 minutes.

For baseline paw withdrawal latencies, an infrared heat source (Ugo Basile model 37370) is applied from under the glass plate onto the plantar surface of the right hind paw with the focus of the light beam no larger than a 3- to 5-mm diameter. The time to withdrawal of the hind paw from the heat source is recorded. A maximum cutoff of 30 seconds is used to prevent tissue damage. The intensity of the beam is set so that baseline latencies are approximately 15 seconds. The post-carrageenan baseline is reestablished 3 hours after the carrageenan injections and only animals with a significant decrease in the latency of hind paw withdrawal from the thermal stimulus (thermal hypersensitivity) are tested. Animals are administered compounds, and hind paw withdrawal latencies are tested at various intervals after injection until the drug response falls below ~20% MPE.

Antihyperalgesia (thermal hypersensitivity) and antinociception are calculated as follows: percentage activity=100 [(test paw withdrawal latency−post-carrageenan baseline paw withdrawal latency)/(pre-carrageenan baseline paw withdrawal latency−post-carrageenan baseline paw withdrawal latency)].

Paw edema is determined by use of a plethysmometer (Ugo Basile) in the mice undergoing the thermal latency testing. Paw volumes for the left and right hind paw are measured at the conclusion of the thermal latency testing (120 minutes after drug administration).

Example 7

LPS-Induced Cytokine Release From Primary Human Astrocytes

The following study was undertaken to investigate whether contemplated compounds and (+)NLX affect LPS-induced release of the pro-inflammatory cytokine (IL-1β, IL-6 and TNF-α) release from primary human astrocytes.

Concentrations used and duration of the treatments:
LPS: 1 mg/ml for 24 hours
C0139M: 100 fM, 10 pM, 1 nM, 100 nM: 2 hours prior to LPS and continue for 24 hours
Experimental Design:

Primary astrocytes culture was prepared according to the provider's instructions (Lonza). The adherent astrocytes were trypsinized by 0.25% trypsin-EDTA, then collected and sub-cultured in 12-well plate (1.2 ml/well). When the cells were 80-85% confluent, cells were treated in an incubator under 5% $CO_2$ for 2 hours with (1) 100 fM, 10 pM, 1 nM or 100 nM C0139M, as well as (2) 10 pM and 1 nM (+)naloxone prior to addition of LPS (1 µg/ml). Vehicle groups were pretreated with 0.1% DMSO only. Following addition of LPS, incubation continued for 24 hours. Culture medium was used as the blank and the levels of cytokines, TNF-α, IL-6 and IL-1β in 200 µl of culture medium were determined. Each well was sampled twice.

To determine the effect of C0139M and (+)NLX on cytokine release, 0.5 µg/well of biotinated mouse monoclonal anti-TNF-α, -IL-6 and -IL-1β were separately coated onto individual streptavidin-coated plates (Reacti-Bind™ NeutrAvidin™ High binding capacity coated 96-well plates), with different antibodies going into different wells. Plates were washed 3 times with ice-cold 50 mM Tris HCl (pH 7.4) and incubated at 30° C. with 200 µl medium derived from the above mentioned conditions. Plates were washed 3 times with ice-cold 50 mM Tris HCl (pH 7.4) and incubated at 30° C. with 0.5 µg/well un-conjugated rabbit anti-anti-TNF-α, -IL-6 and -IL-1β for 1 hour. After two 1 minute washes with 50 mM Tris HCl (pH 7.4), each well was incubated in 0.5 µg/well FITC-conjugated anti-rabbit IgG (human and mouse absorbed) for 1 hour at 30° C. Plates were washed twice with 200 µl ice-cold Tris HCl, pH 7.4 and the residual FITC-A$\beta_{42}$ signals were determined by multimode plate reader, DTX880 (Beckman).

| Compound concentration | TNF-α Average % (±SEM) | IL-6 Average % (±SEM) | IL-1β Average % (±SEM) |
|---|---|---|---|
| C0139M | | | |
| 100 fM | 74.8 (4.3) | 82.6 (1.6) | 84.5 (2.6) |
| 10 pM | 77.0 (3.2) | 76.6 (3.1) | 83.4 (3.0) |
| 1 nM | 77.5 (1.8) | 80.1 (7.0) | 78.2 (0.7) |
| 100 nM | 72.7 (2.5) | 80.2 (6.3) | 70.5 (1.6) |
| (+)Naloxone | | | |
| 10 pM | 58.6 (2.0) | 56.9 (4.4) | 75.9 (4.5) |
| 1 nM | 9.2 (6.0) | 6.8 (4.3) | 10.5 (4.8) |

Compound Syntheses

A compound useful herein can be readily synthesized. An illustrative synthetic scheme is shown below for preparation of compounds containing various X-circle A and Y-circle B groups, as well as two different W atoms. That scheme can be readily adapted for the preparation of compounds containing two carbonyl linkages and one carbonyl and one sulfonyl linkage in the opposite configurations from those shown. More detailed syntheses are set out hereinafter.

General Reaction Scheme
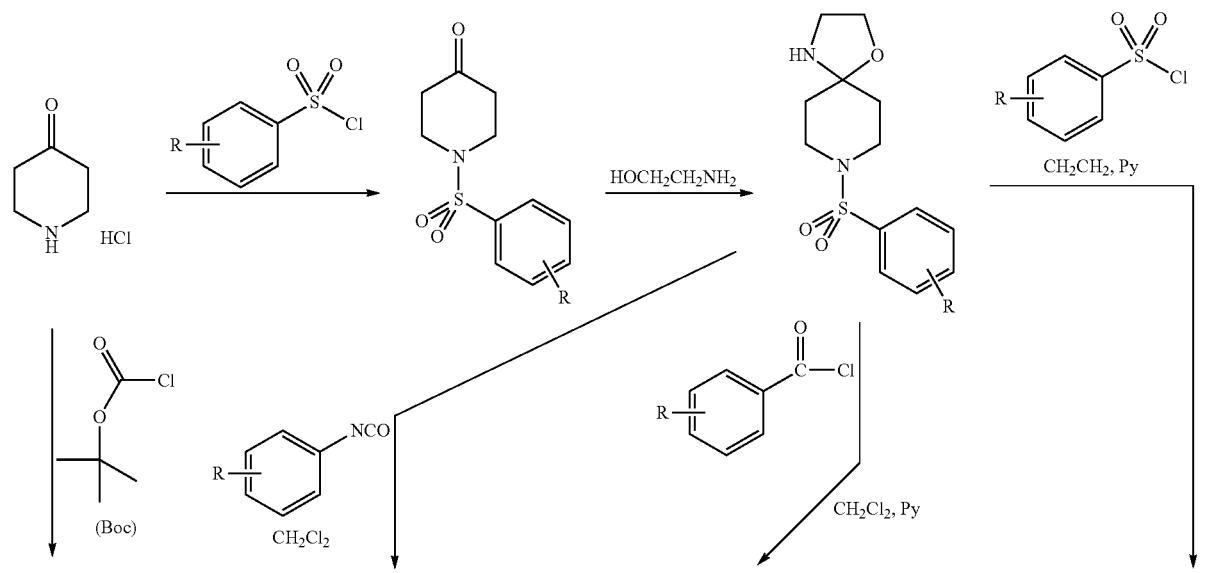
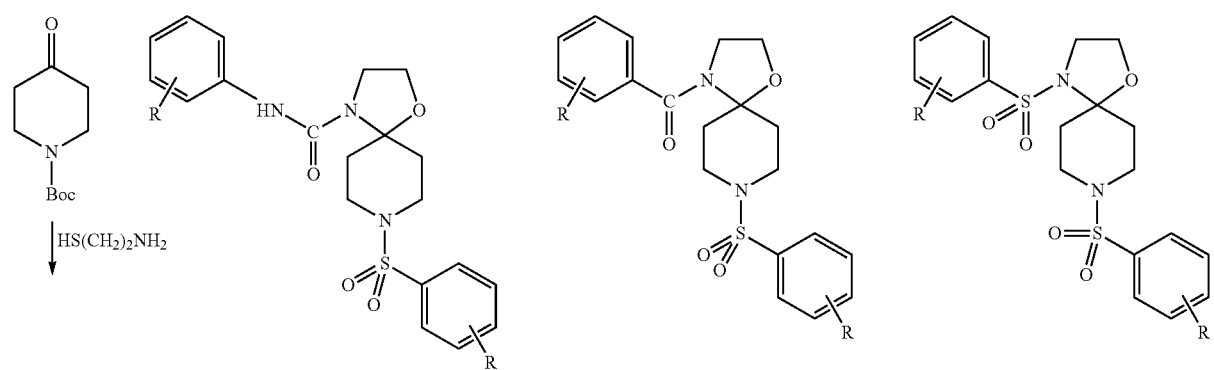
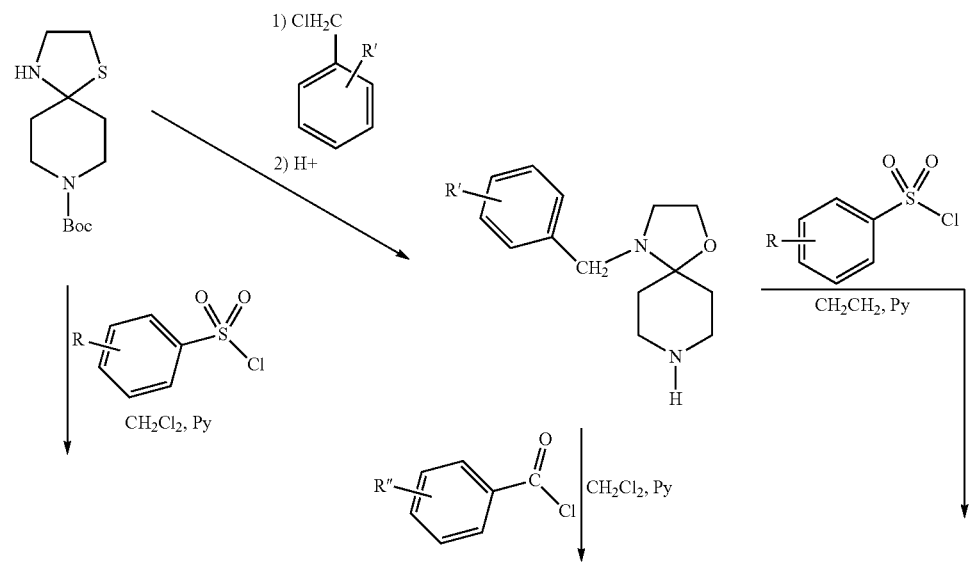

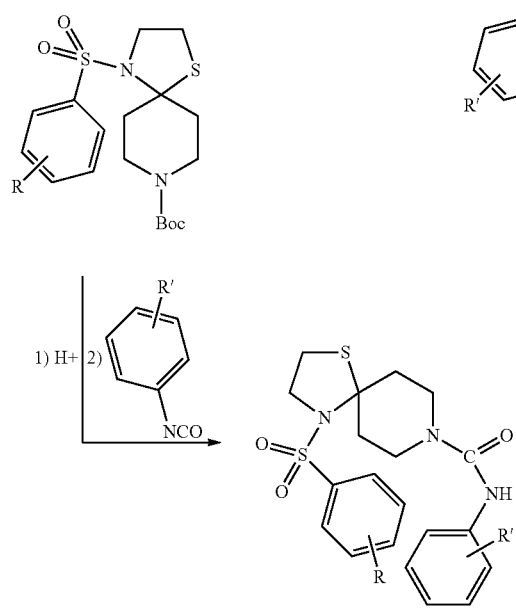
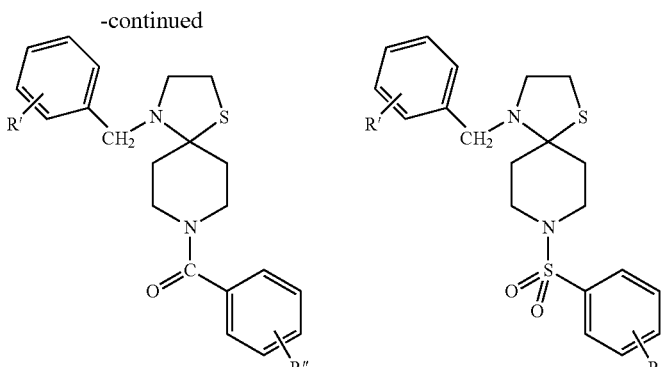

Preparation of Compound C0001

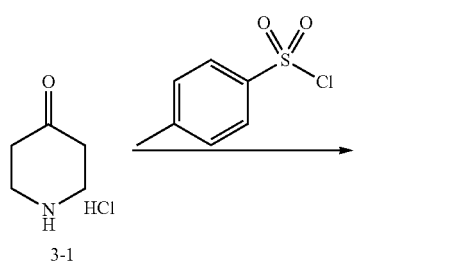

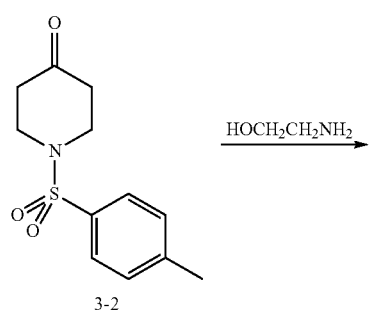

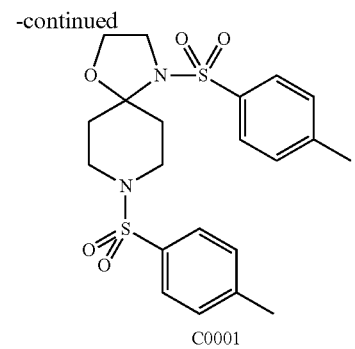

a. Preparation of Compound 3-2

4-Methylbenzene-1-sulfonyl chloride (1.04 g, 5.49 mmol) was added to a solution of compound 3-1 (0.8 g, 5.23 mmol) in pyridine (20 mL) in an atmosphere of $N_2$ and the mixture was allowed to react overnight (about 18 hours) at room temperature. Water was added and the resulting reaction mixture was extracted with $CH_2Cl_2$ (3×). The combined organic layers were washed with 3M HCl and brine and concentrated to give compound 3-2 (0.78 g, yield: 59%, NMR confirmed).

b. Preparation of Compound 3-3

A solution of compound 3-2 (250 mg, 0.99 mmol), p-toluenesulfonic acid monohydrate (20 mg), and 2-aminoethanol (5 mL) in ethanol (20 mL) was stirred overnight (about 18 hours) at room temperature. The solvent was removed under reduced pressure and the residue was partitioned between ethyl acetate and water. The organic layer was washed with water and brine, dried with $Na_2SO_4$ and concentrated to give compound 3-3 (230 mg, yield: 80%, NMR confirmed) as a white solid.

c. Preparation of Compound C0001

4-Methylbenzene-1-sulfonyl chloride (139 mg, 0.73 mmol) was added to a solution of compound 3-3 (180 mg, 0.61 mmol) in pyridine (15 mL) in an atmosphere of $N_2$ and the mixture was allowed to react at room temperature for 4 hours. Water was added and the resulting reaction mixture was extracted with $CH_2Cl_2$ (3×). The combined organic layers were washed with 3M HCl and brine and concentrated to give the crude product (180 mg) as a red solid. Further purification gave compound C0001 (150 mg, yield: 54%, $^1$H NMR confirmed, HPLC 94.5%) as a yellow solid.

$^1$H-NMR (400 MHz, CDCl$_3$) δ: 7.72 (d, J=8.4 Hz, 2H), 7.63 (d, J=8.4 Hz, 2H), 7.33-7.29 (m, 4H), 3.84 (t, J=6.0 Hz, 2H), 3.74 (d, J=9.6 Hz, 2H), 3.48 (t, J=6.0 Hz, 2H), 2.55-2.42 (m, 10H), 1.58 (d, J=11.2 Hz, 2H); MS (ESI) calcd for C$_{21}$H$_{26}$N$_2$O$_5$S$_2$ (m/z): 450.13. found: 473.0 [M+23]$^+$.

Preparation of Compound C0002

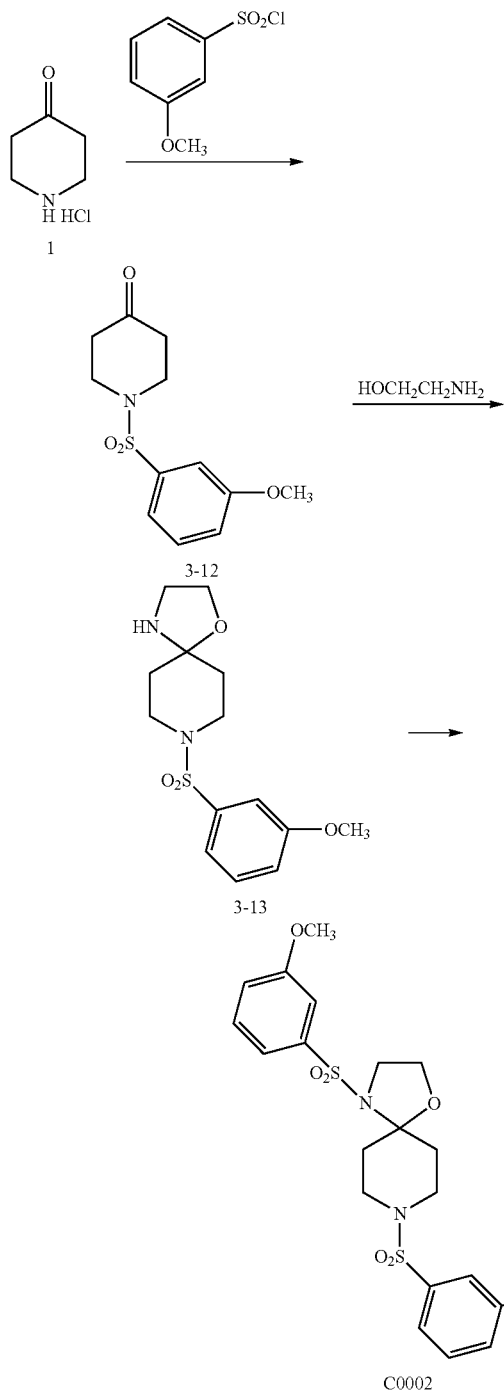

a. Preparation of Compound 3-12

A solution of compound 1 (300 mg, 2.21 mmol) in pyridine (8 mL) was admixed with 4-methoxy-sulfonylbenzene-1-sulfonyl chloride (0.34 mL, 2.21 mmol). The mixture was stirred at room temperature for 3 hours. To the solution was added water and then extracted with dichloromethane for 3 times. The combined organic phase was washed with 3M HCl and concentrated to give 335 mg of white solid ($^1$H NMR confirmed, 56% yield).

b. Preparation of Compound 3-12

A solution of compound 3-12 (335 mg, 1.244 mmol) in ethanol (10 mL) was treated with p-toluenesulfonic acid monohydrate (25 mg) and HOCH$_2$CH$_2$NH$_2$ (2 mL). The mixture was stirred at room temperature overnight (about 18 hours). The ethanol was removed under reduced pressure. The residue was partitioned between dichloromethane and water. The organic phase was washed by saturated NaHCO$_3$ and brine then concentrated to provide 380 mg of colorless oil (yield 97.7%).

c. Preparation of Compound 3-13 p-Toluenesulfonic acid monohydrate (25 mg) and 2-aminoethanol (2 mL) were added to a solution of compound 3-12 (335 mg, 1.244 mmol) in ethanol (10 mL) and the reaction mixture was stirred overnight (about 18 hours) at room temperature. Ethanol was removed under reduced pressure and the residue was partitioned between CH$_2$Cl$_2$ and water. The organic phase was washed with saturated NaHCO$_3$ and brine and concentrated to give compound 3-13 (380 mg, yield: 97.7%) as a colorless oil.

d. Preparation of Compound C0002

4-methoxy-sulfonylbenzene-1-sulfonyl chloride (0.17 mL, 1.216 mmol) was added to a solution of compound 3-13 (380 mg, 1.216 mmol) in pyridine (8 mL). The mixture was stirred at room temperature overnight (about 18 hours). Water was added the solution and then extraction with dichloromethane (3×). The combined organic phase was washed with 3 M HCl and concentrated to give 548 mg of crude product that was then purified to give 450 mg of light yellow powder (MS and $^1$H NMR confirmed, HPLC 95.3%, yield 76.7%).

$^1$H-NMR (400 MHz, CDCl$_3$) δ: 7.46-7.41 (m, 3H), 7.35-7.32 (m, 2H), 7.27-7.25 (m, 1H), 7.13-7.10 (m, 2H), 3.89-3.86 (m, 8H), 3.78-3.76 (m, 2H), 3.51 (t, J=6.4 Hz, 2H), 2.60-2.51 (m, 4H), 1.65-1.60 (m, 2H); MS (ESI) calcd for C$_{21}$H$_{26}$N$_2$O$_7$S$_2$ (m/z): 482.12. found: 483.3 [M+1]$^+$, 505.3 [M+23]$^+$.

Preparation of Compound C0003

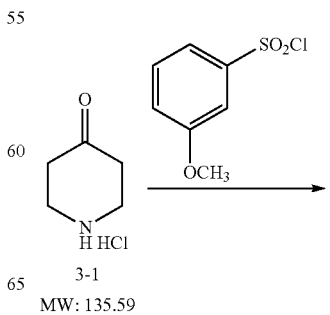

3-1
MW: 135.59

-continued

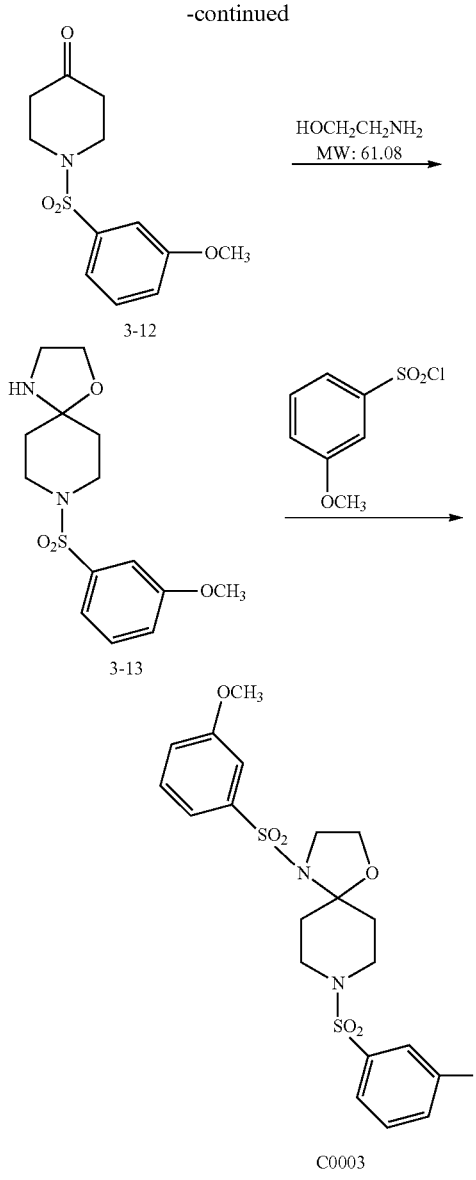

(380 mg, 1.216 mmol) in pyridine (8 mL) and the reaction mixture was stirred overnight (about 18 hours) at room temperature. Water was added and the resulting reaction mixture was extracted with $CH_2Cl_2$ 3 times. The combined organic layers were washed with 3M HCl and concentrated to give the crude product (548 mg) which was further purified to give compound C0003 (450 mg, yield: 76.7%, MS and NMR confirmed, HPLC 95.3%) as a light yellow powder $^1$H-NMR (400 MHz, CDCl$_3$) δ: 7.79-7.72 (m, 2H), 7.46-7.40 (m, 2H), 6.95-6.88 (m, 4H), 3.84-3.81 (m, 8H), 3.75-3.66 (m, 4H), 2.79 (dt, J=12.8, 2.0 Hz, 2H), 2.15 (dt, J=12.8, 4.8 Hz, 2H), 1.38 (d, J=11.2 Hz, 2H). MS (ESI) calcd for $C_{21}H_{26}N_2O_7S_2$ (m/z): 482.12. found: 483.0[M+1]$^+$, 505.1 [M+23]$^+$.

Preparation of Compound C0004

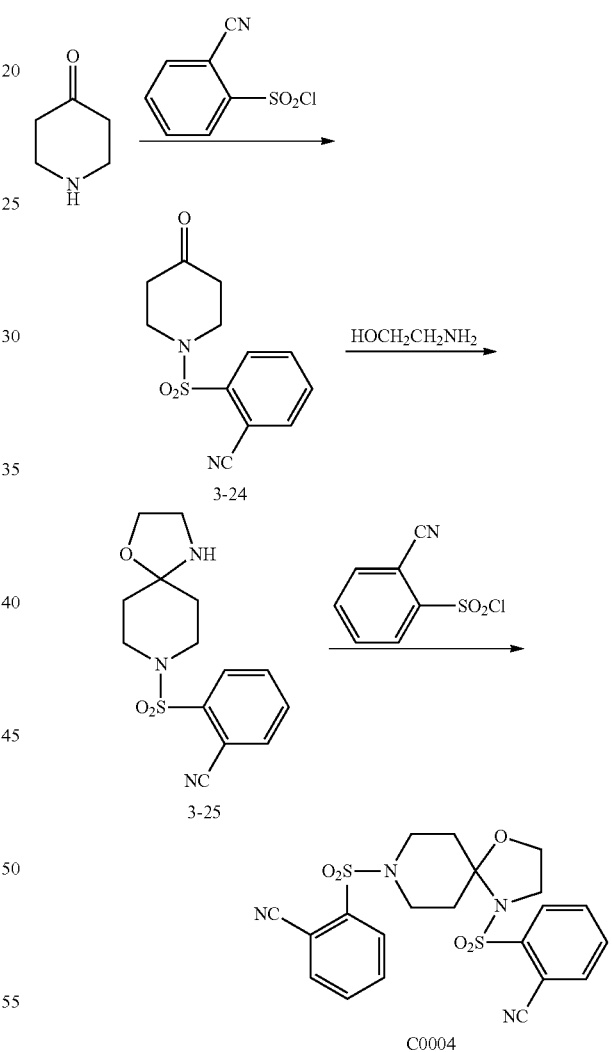

a. Preparation of Compound 3-12

4-Methoxysulfonyl-benzene-1-sulfonyl chloride (0.34 mL, 2.21 mmol) was added to a solution of compound 3-1 (300 mg, 2.21 mmol) in pyridine (8 mL) and the reaction mixture was stirred at room temperature for 3 hours. Water was added and the resulting reaction mixture was extracted with $CH_2Cl_2$ (3×). The combined organic layers were washed with 3M HCl and concentrated to give compound 3-12 (335 mg, yield: 56%, NMR confirmed) as a white solid.

b. Preparation of Compound 3-13 p-Toluenesulfonic acid monohydrate (25 mg) and 2-aminoethanol (2 mL) were added to a solution of compound 3-12 (335 mg, 1.244 mmol) in ethanol (10 mL) and the reaction mixture was stirred overnight (about 18 hours) at room temperature. Ethanol was removed under reduced pressure and the residue was partitioned between $CH_2Cl_2$ and water. The organic phase was washed with saturated $NaHCO_3$ and brine and concentrated to give compound 3-13 (380 mg, yield: 97.7%) as a colorless oil.

c. Preparation of Compound C0003

4-(Methoxy-sulfonyl)benzene-1-sulfonyl chloride (0.17 mL, 1.216 mmol) was added to a solution of compound 3-13 a. Preparation of Compound 3-24

2-Cyanobenzenesulfonyl chloride (100 mg, 0.50 mmol) was added to a solution of piperidin-4-one (92 mg, 0.60 mmol) in pyridine (10 mL). The mixture was stirred at room temperature overnight (about 18 hours). Then pyridine was removed by reduced pressure evaporation. The residue was dissolved in $CH_2Cl_2$ (50 mL) and water (30 mL) was added. The $CH_2Cl_2$ layer was separated and the water phase was extracted with $CH_2Cl_2$ (2×20 mL). The organic layers were combined and washed with 3M HCl (20 mL×2). Then the organic layer was dried over anhydrous $Na_2SO_4$ and concentrated to give the title product as light yellow oil (70 mg, yield: 53.4%, confirmed by MS).

b. Preparation of Compound 3-25

2-Aminoethanol (0.5 mL) and p-toluenesulfonic acid monohydrate were added to a solution of compound 3-24 (35 mg, 0.13 mmol) in ethanol (10 mL) (5 mg). The mixture was stirred at 30° C. overnight (about 18 hours). The solvent was then removed by evaporation under vacuum. To the residue was added $CH_2Cl_2$ (30 mL), then the $CH_2Cl_2$ layer was washed with saturated $Na_2CO_3$ (15 mL×2) and water (20 mL×3), dried over $Na_2SO_4$ and concentrated to give the crude product as yellow oil (33 mg, yield: 80.5%, $^1$H-NMR confirmed).

c. Preparation of Compound C0004 o-Cyanobenzene sulfonyl chloride (26 mg, 0.13 mmol) was added to a solution of compound 3-25 (33 mg, 0.11 mmol) in pyridine (5 mL). The mixture was stirred overnight (about 18 hours) at room temperature. The solvent was removed under reduced pressure. The residue was diluted with $CH_2Cl_2$ (20 mL), washed with 3M HCl (10 mL×3), and the organic layer was dried, and the solvent evaporated to give the crude product as yellow oil. The crude product was purified with silica gel column to give the title product as light yellow solid (8 mg, yield 15.8%, HPLC 95.2%, $^1$H-NMR and MS confirmed).

$^1$H-NMR (400 MHz, $CDCl_3$) δ:8.14 (d, J=8.0 Hz, 1H), 8.03 (d, J=8.0 Hz, 1H), 7.90-7.86 (m, 2H), 7.80-7.69 (m, 4H), 3.98 (t, J=6.0 Hz, 2H), 3.89-3.85 (m, 2H), 3.80 (t, J=6.0 Hz, 2H), 2.88 (dt, J=12.8, 2.0 Hz, 2H,), 2.36 (dt, J=12.8, 4.8 Hz, 2H), 1.68 (d, J=8.8 Hz, 2H). MS (ESI) calcd for $C_{21}H_{20}N_4O_5S_2$ (m/z):472.09. found: 495.1[M+23]$^+$.

Preparation of Compound C0005

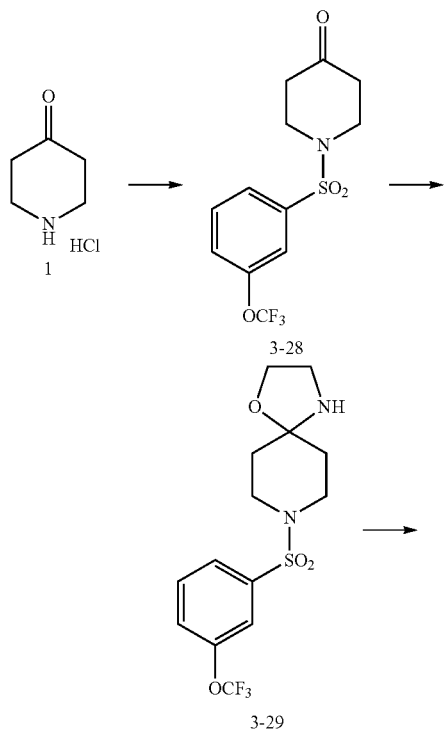

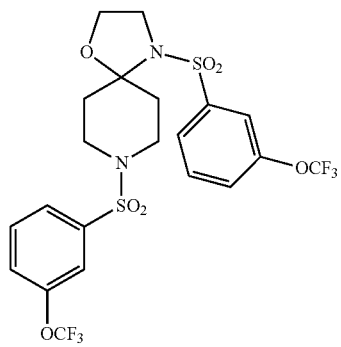

C0005 a. Preparation of Compound 3-28

3-Trifluoromethoxy-benzenesulfonyl chloride (287 mg, 1.1 mmol) was added to compound 1 (150 mg, 1.1 mmol) in pyridine (7 mL). The mixture was stirred at room temperature overnight (about 18 hours). Water was added to the solution and then extracted with dichloromethane for 3 times. The combined organic phase was washed with 3M HCl and concentrated to give 150 mg of the desired product as light yellow solid ($^1$H NMR confirmed, 42% yield).

b. Preparation of Compound 3-29

Compound 3-28 (140 mg, 0.46 mmol) in ethanol (6 mL) was treated with p-toluenesulfonic acid (15 mg) and $HOCH_2CH_2NH_2$ (1.5 mL). The mixture was stirred at room temperature overnight (about 18 hours). Ethanol was removed under reduced pressure. The residue was partitioned between dichloromethane and water. The organic phase was washed by saturated aqueous $NaHCO_3$ and brine. Then the organic layer was concentrated to give 145 mg of compound 3-29 as white liquid (NMR confirmed, yield 85%).

c. Preparation of C0005

3-Trifluoro-methoxybenzenesulfonyl chloride (103 mg, 1.1 mmol) was added to a solution of compound 3-29 (145 mg, 0.4 mmol) in pyridine (2 mL). The mixture was then stirred at room temperature overnight (about 18 hours). Water was added and then the mixture was extracted with dichloromethane (3×). The combined organic phase was washed with 3M HCl and concentrated to get the crude product. The crude product was purified to afford 40 mg of the desired product as white solid ($^1$H NMR and LC-MS confirmed, HPLC 94.4%, 17% yield).

$^1$H-NMR (400 MHz, $CDCl_3$) δ:7.77-7.69 (m, 1H), 7.63-7.59 (m, 2H), 7.53-7.49 (m, 3H), 7.38-7.36 (m, 2H), 3.90 (t, J=5.6 Hz, 2H), 3.80 (d, J=8.4 Hz, 2H), 3.49 (t, J=5.6 Hz, 2H), 2.62-2.53 (m, 4H), 1.64-1.60 (m, 2H). MS (ESI) calcd for $C_{22}H_{20}F_6N_2O_7S_2$ (m/z):590.06. found: 591.0[M+1]$^+$, 613.0 [M+23]$^+$.

Preparation of Compound C0006

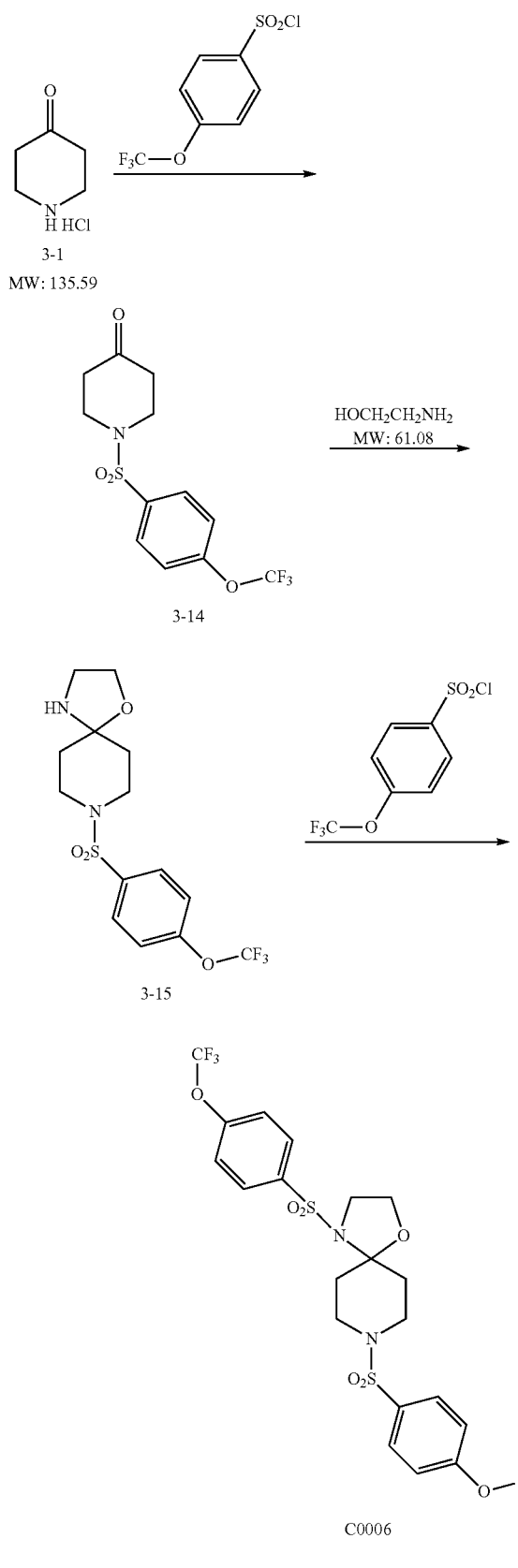

a. Preparation of Compound 3-14

4-Trifluoromethoxybenzene-1-sulfonyl chloride was added to a solution of compound 3-1 (100 mg, 0.7375 mmol) in pyridine (3 mL) (192.38 mg, 0.7375 mmol) and the reaction mixture was stirred at room temperature for 3 hours. Water was added and the resulting reaction mixture was extracted with $CH_2Cl_2$ (3×). The combined organic layers were washed with 3M HCl and concentrated to give compound 3-14 (111 mg, yield: 46.6%, NMR confirmed) as a white solid.

b. Preparation of Compound 3-15 p-Toluenesulfonic acid (10 mg) and 2-aminoethanol (1 mL) was added to a solution of compound 3-14 (111 mg, 0.343 mmol) in ethanol (EtOH) (4 mL) and the reaction mixture was stirred at room temperature for 4 hours. EtOH was removed under reduced pressure and the residue was partitioned between $CH_2Cl_2$ and water. The organic layer was washed with saturated aqueous $NaHCO_3$ and brine and concentrated to give compound 3-15 (128 mg of crude compound, NMR confirmed) as a light yellow liquid.

c. Preparation of Compound C0006

4-Trifluoromethoxybenzene-1-sulfonyl chloride was added (91 mg, 0.349 mmol) to a solution of compound 3-15 (128 mg, 0.349 mmol) in pyridine (2.5 mL) and the reaction mixture was stirred at room temperature for 3 hours. Water was added and the resulting reaction mixture was extracted with $CH_2Cl_2$ (3×). The combined organic layers were washed with 3M HCl and concentrated to give the crude product (132 mg) which was further purified by column chromatography over silica gel to afford compound C0006 (95 mg, yield: 46%, NMR and MS confirmed, HPLC 99%).

$^1$H-NMR (400 MHz, $CDCl_3$) δ:7.92 (dd, J=6.8, 2 Hz, 2H), 7.84 (dd, J=6.8, 1.6 Hz, 2H), 7.38-7.36 (m, 4H), 3.93 (t, J=6 Hz, 2H), 3.81 (d, J=6.4 Hz, 2H), 3.51 (t, J=6 Hz, 2H), 2.61-2.57 (m, 4H), 1.67-1.64 (m, 2H). MS (ESI) calcd for $C_{21}H_{20}F_6N_2O_7S_2$ (m/z):590.06. found: 613.0[M+23]$^+$.

Preparation of Compound C0007

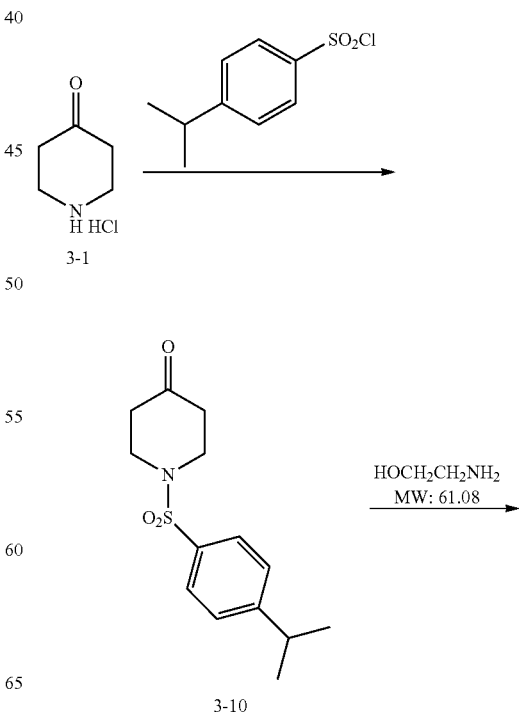

159

-continued

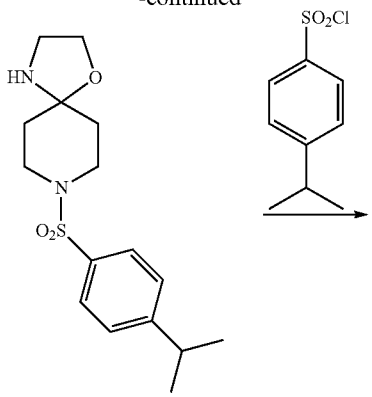

3-11

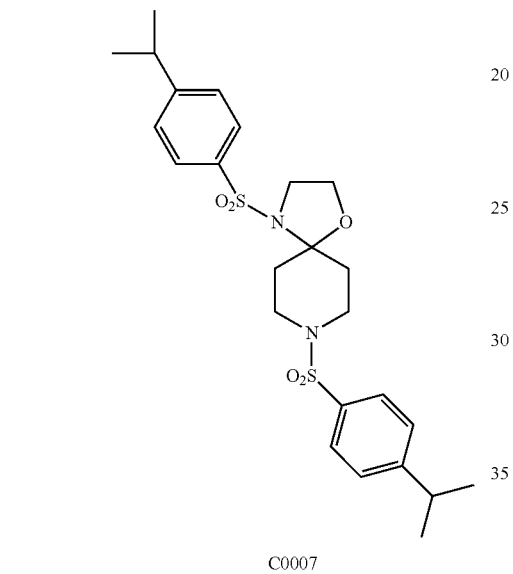

C0007 a. Preparation of Compound 3-10

4-Isopropylsulfonylbenzene-1-sulfonyl chloride (0.13 mL, 0.7375 mmol) was added to a solution of piperidin-4-one hydrochloride hydrate (100 mg, 0.7375 mmol) in pyridine (3 mL) and the reaction mixture was stirred at room temperature for 3 hours. Water was added and the resulting reaction mixture was extracted with $CH_2Cl_2$ (3×). The combined organic layers were washed with 3M HCl and concentrated to give compound 3-10 (105 mg, yield: 50.7%, NMR confirmed) as a white solid.

b. Preparation of Compound 3-11 p-Toluenesulfonic acid monohydrate (15 mg) and 2-aminoethanol (1.5 mL) were added to a solution of compound 3-10 (200 mg, 0.71 mmol) in ethanol (EtOH) (6 mL) and the reaction mixture was stirred overnight (about 18 hours) at room temperature. EtOH was removed under reduced pressure and the residue was partitioned between $CH_2Cl_2$ and water. The organic phase was washed with saturated aqueous $NaHCO_3$ and brine and concentrated to give compound 3-11 (231 mg, yield: 100%) as a white foam.

c. Preparation of Compound C0007

4-Isopropylsulfonylbenzene-1-sulfonyl chloride (0.17 mL, 0.925 mmol) was added to a solution of compound 3-11 (300 mg, 0.925 mmol) in pyridine (8 mL) and the reaction mixture was stirred overnight (about 18 hours) at room temperature. Water was added and the resulting reaction mixture was extracted with $CH_2Cl_2$ (3×). The combined organic lay-

160 ers were washed with 3M HCl and concentrated to give the crude product (384 mg) as a yellow oil (MS confirmed, HPLC 84%, yield: 82.1%). The crude product was triturated in ether/hexane system and filtered to give compound C0007 (240 mg, yield: 51.3%, MS and NMR confirmed, HPLC 95.0%) as a light yellow powder.

$^1$H-NMR (400 MHz, $CDCl_3$) δ: 7.75 (d, J=8.4 Hz, 2H), 7.67 (d, J=8.4 Hz, 2H), 7.37-7.34 (m, 4H), 3.87 (t, J=6.0 Hz, 2H), 3.78-3.76 (m, 2H), 3.49 (t, J=6.0 Hz, 2H), 3.02-2.94 (m, 2H), 2.61-2.51 (m, 4H), 1.63-1.57 (m, 2H), 1.29-1.26 (m, 12H). MS (ESI) calcd for $C_{25}H_{34}N_2O_5S_2$ (m/z):506.19. found: 507.5$[M+1]^+$, 529.4$[M+23]^+$.

Preparation of Compound C0008

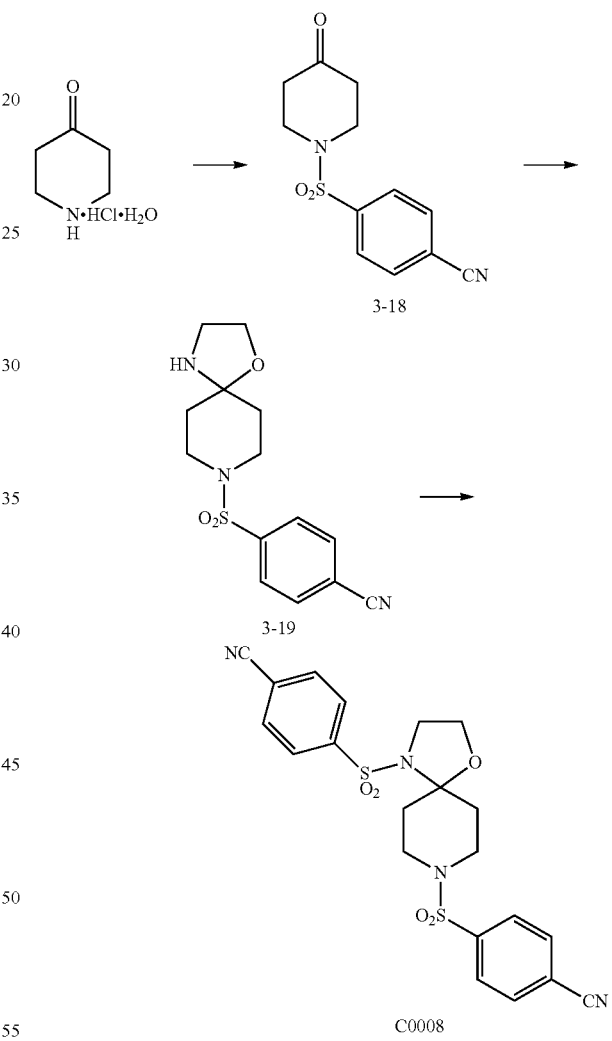

a. Preparation of Compound 3-18

4-Cyanobenzene-1-sulfonyl chloride (310 mg, 1.54 mmol) was added to a solution of piperidin-4-one (354 mg, 2.31 mmol) in pyridine (10 mL). The mixture was stirred overnight (about 18 hours) at room temperature. The solvent was removed under reduced pressure. The residue was diluted with $CH_2Cl_2$ (100 mL), washed with 2 N HCl (50 mL×3), dried over anhydrous $Na_2SO_4$ and concentrated to give the crude product as a yellow solid (138 mg, yield: 34%, TLC confirmed).

b. Preparation of Compound 3-19

2-Aminoethanol (2 mL) and p-toluenesulfonic acid monohydrate (20 mg) was added to a solution of compound 3-18 (138 mg, 0.52 mmol) in ethanol (20 mL). The mixture was stirred at 20° C. overnight (about 18 hours). The solvent was then removed under reduced pressure. The residue was diluted with $CH_2Cl_2$ (60 mL), washed with saturated $Na_2CO_3$ (50 mL×3), dried over anhydrous $Na_2SO_4$ and concentrated to give the title compound as a yellow solid (0.15 g, yield: 94%, TLC confirmed).

c. Preparation of Compound C0008

4-Cyanobenzene-1-sulfonyl chloride (147 mg, 0.73 mmol) was added to a solution of compound 3-19 (150 mg, 0.49 mmol) in pyridine (10 mL). The mixture was stirred at room temperature overnight (about 18 hours). The solvent was removed under reduced pressure. The residue was diluted with $CH_2Cl_2$ (50 mL), washed with 2N HCl (30 mL×3), dried over anhydrous $Na_2SO_4$ and concentrated to give the crude product as a yellow solid. The crude product was purified with a silica gel column to give the pure product as a light yellow solid (100 mg, yield: 43%, TLC confirmed).

$^1$H-NMR (400 MHz, $CDCl_3$) δ:7.96 (d, J=6.8 Hz, 2H), 7.87-7.83 (m, 6H), 3.91 (t, J=6.4 Hz, 2H), 3.82-3.80 (m, 2H), 3.50 (t, J=6.4 Hz, 2H), 2.58-2.54 (m, 4H), 1.64-1.59 (m, 2H). MS (ESI) calcd for $C_{21}H_{20}N_4O_5S_2$ (m/z):472.09. found: 473.1[M+1]$^+$. (LC-MS)

Preparation of Compound C0009

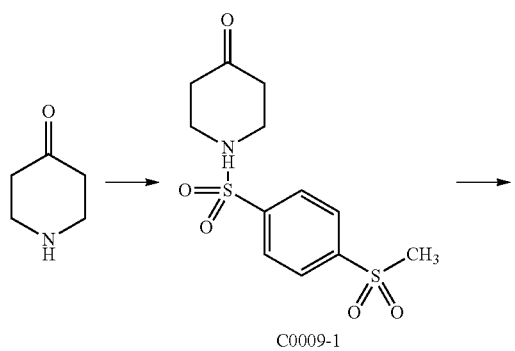

C0009-1

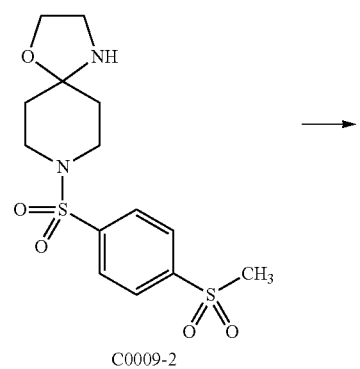

C0009-2

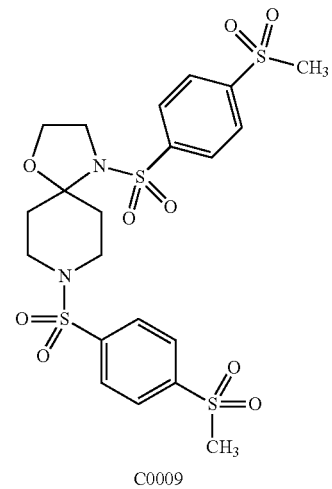

C0009 a. Preparation of C0009-1

4-(Methylsulfonyl)benzene-1-sulfonyl chloride (410 mg, 1.6 mmol) was added to a solution of piperidin-4-one hydrochloride hydrate (247 mg, 1.6 mmol) in pyridine (10 mL). The mixture was stirred at room temperature overnight (about 18 hours). Then the solvent was removed under reduced pressure. To the residue was added $CH_2Cl_2$ (50 mL), then the solution was washed with 1N HCl (20 mL×3), dried over $Na_2SO_4$ and concentrated to give the title product 225 mg as yellow solid (yield: 44%, Confirmed by $^1$H NMR).

b. Preparation of C0009-2 p-Toluenesulfonic acid monohydrate (4 mg) and 2-aminoethanol (0.8 mL, 13.3 mmol) were added to a solution of compound C0009-1 (225 mg, 0.7 mmol) in ethanol (6 mL). The mixture was stirred at room temperature for overnight (about 18 hours). The solvent was removed under reduced pressure. To the residue was added $CH_2Cl_2$ (70 mL) and the resulting solution was washed with saturated $NaHCO_3$ (25 mL×4), then dried over $Na_2SO_4$ and concentrated to give the product 205 mg as white solid (yield: 81%).

c. Preparation of Compound C0009

4-(Methylsulfonyl)benzenesulfonyl chloride (604 mg, 2.37 mmol) was added to a solution of compound C0009-2 (570 mg, 1.58 mmol) in pyridine (20 mL). The mixture was stirred overnight (about 18 hours) at room temperature. The solvent was then removed under reduced pressure. The crude product was then diluted with $CH_2Cl_2$ (250 mL) and washed with 1M HCl (100 mL×2), and the aqueous layer was extracted with $CH_2Cl_2$ (100 mL). The organic phase was then dried over anhydrous $Na_2SO_4$ and concentrated and then the crude product was recrystallized from dichloromethane to give 150 mg purified product as a light yellow solid ($^1$H-NMR and MS confirmed, HPLC: 96%). The solvent was evaporated to give 200 mg of the purified product. The pure product was then re-purified using a silica gel column to give C0009 as a light yellow solid (180 mg, yield: 33%, $^1$H-NMR and MS confirmed, HPLC: 96%).

$^1$H-NMR (400 MHz, DMSO-d$^6$) δ: 8.15-8.00 (m, 8H), 3.85-3.71 (m, 4H), 3.46 (brs, 2H), 3.27 (brs, 8H), 2.18 (brs, 2H), 1.60-1.57 (m, 2H). MS (ESI) calcd for $C_{21}H_{26}N_2O_9S_4$ (m/z):578.05. found: 579.7[M+1]$^+$. (LC-MS)

Preparation of Compound C0010

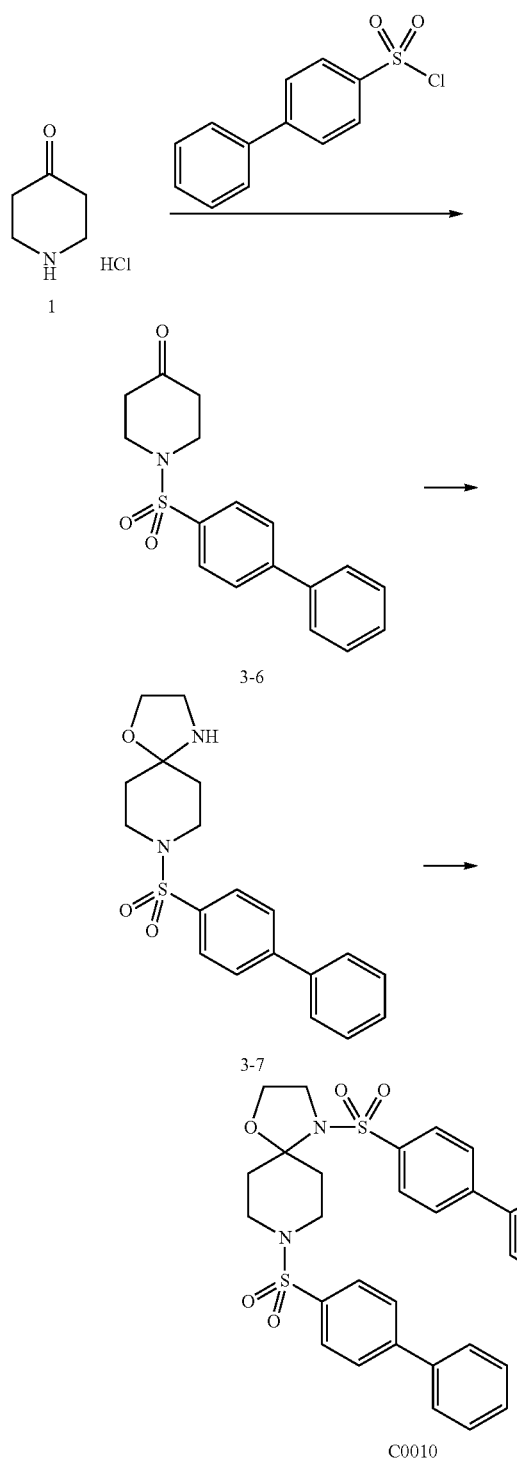

3-7

C0010 a. Preparation of Compound 3-6

4-Phenylsulfonyl chloride (279.2 mg, 1.11 mmol) was added to a solution of compound 1 (150 mg, 1.11 mmol) in pyridine (4 mL). The mixture was stirred at room temperature overnight (about 18 hours). To the solution was added water and the resulting composition was extracted with dichloromethane (3×). The combined organic phase was washed with 3M HCl, and concentrated to give 205 mg of desired product as solid ($^1$H NMR confirmed, 58.6% yield).

b. Preparation of Compound 3-7 p-Toluenesulfonic acid (20 mg) and HOCH$_2$CH$_2$NH$_2$ (2 mL) were added to a solution of compound 3-6 (205 mg, 0.65 mmol) in ethanol (EtOH) (6 mL). The mixture was stirred at room temperature overnight (about 18 hours). The ethanol was removed under reduced pressure. The residue was partitioned between dichloromethane (DCM) and water. The organic phase was washed by saturated aqueous NaHCO$_3$ and brine. The organic layer was concentrated to give 202 mg of crude as white liquid (yield 87%).

c. Preparation of Compound C0010

4-(Phenyl)benzenesulfonyl chloride (142 mg, 0.564 mmol) was added to a solution of compound 3-7 (202 mg, 0.564 mmol) in pyridine (4 mL). The mixture was stirred at room temperature overnight (about 18 hours). Water was added to the solution and then the composition so formed was extracted with dichloromethane (3×). The combined organic phase was washed with 3M HCl then concentrated to give 234 mg of crude product. The crude product was purified by silica gel chromatography to afford 68 mg of pure product (LC-MS and $^1$H NMR showed this is a mixture of compound 3-7 and desired product). Further purification by silica gel column eluted by (CH$_3$OH: CH$_2$Cl$_2$=100:1) gave 55 mg of the desired product with 86% purity. This product was again purified by preparative thin-layer chromatography to give the desired product with 90% purity.

$^1$H-NMR (400 MHz, DMSO-d$^6$) δ:7.81 (d, J=8.4 Hz, 2H), 7.74 (d, J=8.0 Hz, 2H), 7.66-7.62 (m, 4H), 7.53-7.51 (m, 4H), 7.42-7.33 (m, 6H), 3.80 (t, J=6.0 Hz, 2H), 3.74 (d, J=9.2 Hz, 2H), 3.46 (t, J=6.0 Hz, 2H), 2.55-2.48 (m, 4H), 1.59-1.56 (m, 2H). MS (ESI) calcd for C$_{31}$H$_{30}$N$_2$O$_5$S$_2$ (m/z):574.16. found: 575.1[M+1]$^+$ (LC-MS).

Preparation of Compound C0011

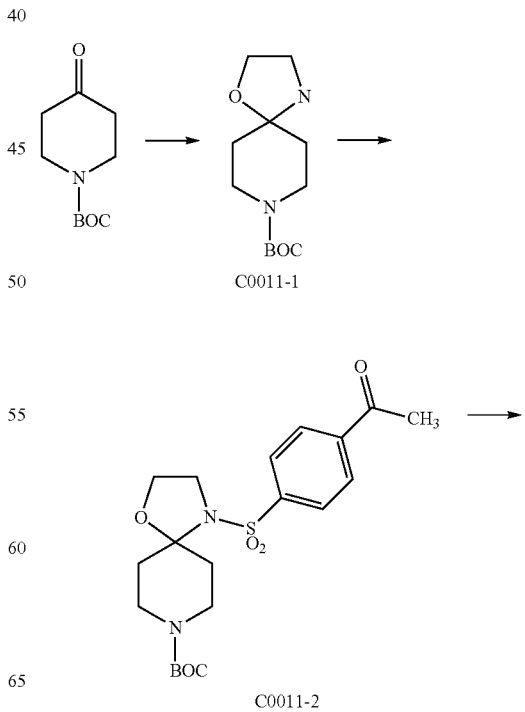

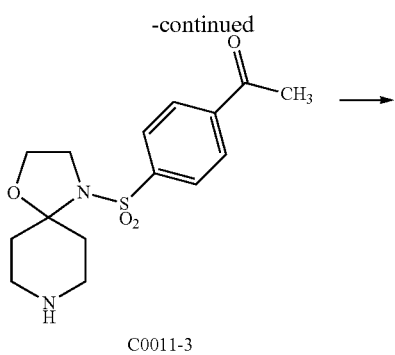

C0011-3

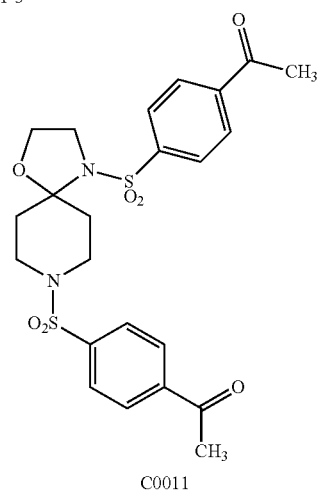

C0011 a. Preparation of Compound C0011-1

2-Ethanolamine (5 mL) was added to a solution of N-Boc-piperidin-4-one (3.014 g, 15.1 mmol) in ethanol (40 mL). The mixture was stirred overnight (about 18 hours) at room temperature. The solvent was removed under reduced pressure. The residue was diluted with CH$_2$Cl$_2$ (100 mL) and washed with saturated aqueous Na$_2$CO$_3$ (100 mL×6). The organic phase was dried over anhydrous Na$_2$SO$_4$, then concentrated to give compound C0011-1 as light yellow oil (2.46 g, yield: 67.2%, $^1$H-NMR confirmed).

b. Preparation of Compound C0011-2

4-Acetylbenzenesulfonyl chloride (1.75 g, 8 mmol) was added to a solution of C0011-1 (2.5 g, 9.7 mmol) in 30 mL of pyridine. The solution was stirred overnight (about 18 hours) at room temperature. The solvent was removed under reduced pressure. The residue was diluted in 100 mL dichloromethane and washed with 0.5 M HCl (50 mL×3), the organic layer was dried and concentrated to provide the crude product as a yellow oil that was purified by silica gel chromatography to provide C0011-2 as yellow solid (1.8 g, yield: 43.8%, confirmed by LCMS).

c. Preparation of Compound C0011-3

CF$_3$COOH (5 mL) was added to a solution of C0011-2 (1.8 g, 4.24 mmol) in 30 mL dichloromethane and the mixture was stirred for 2 hours at room temperature. To the mixture was added 70 mL dichloromethane, and the resulting composition was washed with saturated sodium carbonate solution (50 mL×3). The organic layer was dried and concentrated to provide the crude product as yellow oil. The crude product was used for the next step without any further purification (0.97 g, yield: 70%, confirmed by LCMS).

d) Preparation of C0011

4-Acetylbenzenesulfonyl chloride (0.63 g, 2.88 mmol) was added to the solution of C0011-3 (0.85 g, 2.62 mmol) in 30 mL of pyridine. The mixture was stirred overnight (about 18 hours) at room temperature. The solvent was removed under reduced pressure. The residue was diluted with 150 mL dichloromethane and washed with 3 M HCl (100 mL×3). The organic layer was dried and concentrated to provide the crude product as a yellow solid that was purified by silica gel chromatography to provide C0011 as white solid (0.44 g, yield: 47.3%, confirmed by LCMS, HPLC: 97%).

$^1$H-NMR (400 MHz, CDCl$_3$) δ:8.10~8.07 (m, 4H), 7.92 (d, J=8.8 Hz, 2H), 7.85 (d, J=8.8 Hz, 2H), 3.87 (t, J=6.0 Hz, 2H), 3.81~3.79 (m, 2H), 3.51 (t, J=6.0 Hz, 2H), 2.67 (s, 3H), 2.65 (s, 3H), 2.55~2.52 (m, 4H), 1.61-1.58 (m, 2H); MS (ESI) calcd for C$_{23}$H$_{26}$N$_2$O$_7$S$_2$ (m/z):506.12. found: 507.4 [M+1]$^+$.

Preparation of Compound C0012

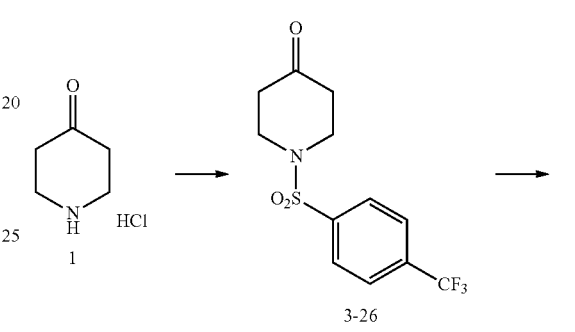

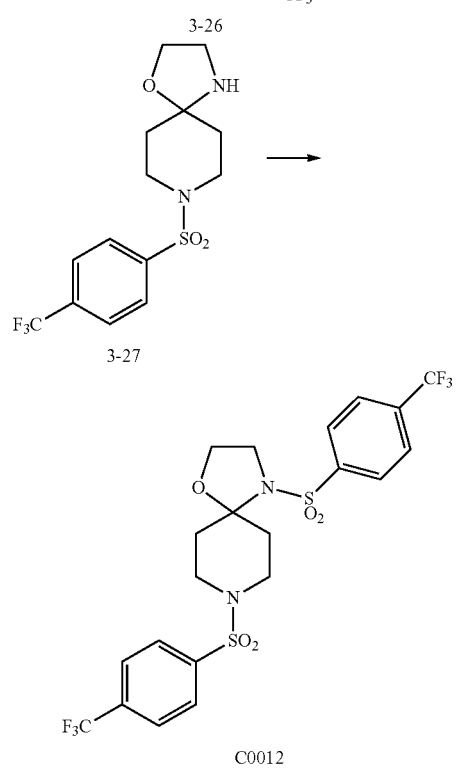

C0012 a. Preparation of Compound 3-26

4-Trifluorobenzenesulfonyl chloride (271 mg, 1.1 mmol) was added to a solution of compound 1 (150 mg, 1.1 mmol) in pyridine (7 mL). The mixture was stirred at room temperature overnight (about 18 hours). To the solution was added water and the resulting composition was then extracted with dichloromethane (3×). The combined organic phase was washed with 3M HCl and concentrated to give 140 mg of the title compound as light yellow solid ($^1$H NMR confirmed, 41% yield).

b. Preparation of Compound 3-27

A solution of compound 3-26 (140 mg, 0.46 mmol) in ethanol (6 mL) was treated with p-toluenesulfonic acid (15 mg) and HOCH$_2$CH$_2$NH$_2$ (1.5 mL). The mixture was stirred at room temperature overnight (about 18 hours). The ethanol was removed under reduced pressure. The residue was partitioned between dichloromethane and water. The organic phase was washed by saturated aqueous NaHCO$_3$ and brine. Then organic layer was concentrated to give 144 mg of compound 3-27 as white liquid ($^1$H NMR confirmed, yield 90%).

c. Preparation of Compound C0012

A solution of compound 3-27 (144 mg, 0.41 mmol) in pyridine (2 mL) was treated with 4-trifluoromethyl-benzene-1-sulfonyl chloride (101 mg, 0.41 mmol). The mixture was stirred at room temperature overnight (about 18 hours). Water was added to that solution and the resulting composition extracted with dichloromethane (3×). The combined organic phase was washed with 3M HCl and concentrated to get the crude product. The crude product was purified to give 40 mg of the desired product ($^1$H NMR confirmed, HPLC 95%, 17.5% yield).

$^1$H NMR (400 MHz, CDCl$_3$) δ:7.88 (d, J=8.0 Hz, 2H), 7.80 (d, J=8.0 Hz, 2H), 7.73-7.71 (m, 4H), 3.82 (t, J=6.0 Hz, 2H), 3.74-3.71 (m, 2H), 3.42 (t, J=6.0 Hz, 2H), 2.50-2.46 (m, 4H), 1.56-1.53 (m, 2H), MS (ESI) calcd for C$_{21}$H$_{20}$F$_6$N$_2$O$_5$S$_2$ (m/z):558.07. found: 581.1[M+23]$^+$ Preparation of Compound C0013

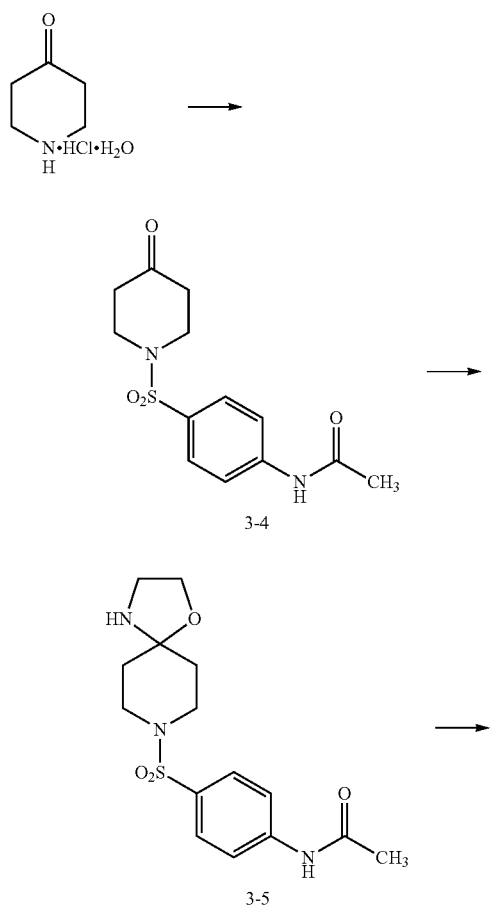

-continued

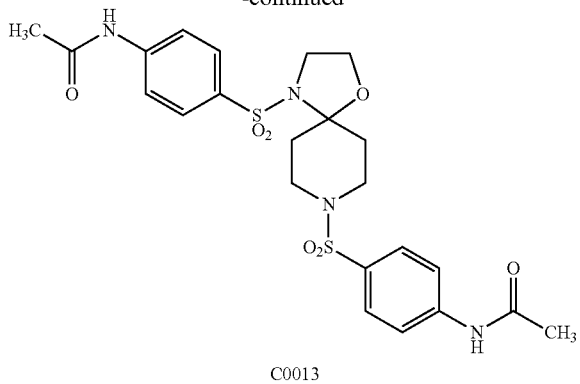

C0013 a. Preparation of Compound 3-4

4-Acetyl-aminobenzene-sulfonyl chloride (0.6 g, 2.57 mmol) was added to a solution of piperidin-4-one (0.47 g, 3.08 mmol) in pyridine (20 mL). The mixture was stirred overnight (about 18 hours) at room temperature. The solvent was removed under reduced pressure. To the residue was added CH$_2$Cl$_2$ (100 mL) and 2N HCl (50 mL). The organic layer was separated and washed with 2N HCl (30 mL×2), then dried over Na$_2$SO$_4$ and concentrated to give the title compound as yellow solid. (0.4 g, yield: 52.6%, TLC confirmed).

b. Preparation of Compound 3-5 p-Toluenesulfonic acid monohydrate (50 mg) and 2-aminoethanol (0.5 g, 8.2 mmol) was added to a solution of compound 3-4 (0.55 g, 1.86 mmol) in ethanol (50 mL). The mixture was stirred overnight (about 18 hours) at 26° C. The solvent was removed under reduced pressure. To the residue was added CH$_2$Cl$_2$ (100 mL) and saturated Na$_2$CO$_3$ (100 mL). The organic layer was separated and washed with saturated Na$_2$CO$_3$ (50 mL×3), then dried over Na$_2$SO$_4$ and concentrated to give the crude product as white powder. (0.59 g, yield: 92.1%, TLC confirmed).

c. Preparation of Compound C0013

4-Acetyl-aminobenzenesulfonyl chloride (0.49 g, 2.09 mmol) was added to a solution of compound 3-5 (0.59 g, 1.74 mmol) in pyridine (50 mL). The mixture was stirred overnight (about 18 hours) at room temperature. The solvent was removed under reduced pressure. To the residue was added CH$_2$Cl$_2$ (100 mL) and 2N HCl (50 mL). The CH$_2$Cl$_2$ layer was separated and washed with 2N HCl (30 mL×2), then dried over anhydrous Na$_2$SO$_4$ and concentrated to give the crude product as yellow solid, which was purified with silica gel column to give the pure product as white solid (320 mg, yield: 34.4%, HPLC: 97%).

$^1$H-NMR (400 MHz, DMSO-d$^6$) δ:10.30-10.28 (m, 2H), 7.78-7.74 (m, 6H), 7.61 (d, J=8.4 Hz, 2H), 3.78 (t, J=6.4 Hz, 2H), 3.56-3.54 (m, 2H), 3.36 (t, J=6.4 Hz, 2H), 2.25-2.20 (m, 4H), 2.05 (s, 3H), 2.04 (s, 3H), 1.57-1.54 (m, 2H); MS (ESI) calcd for C$_{23}$H$_{28}$N$_4$O$_7$S$_2$ (m/z):536.14. found: 537.2 [M+1]$^+$, 559.0[M+23]$^+$.

Preparation of Compound C0014

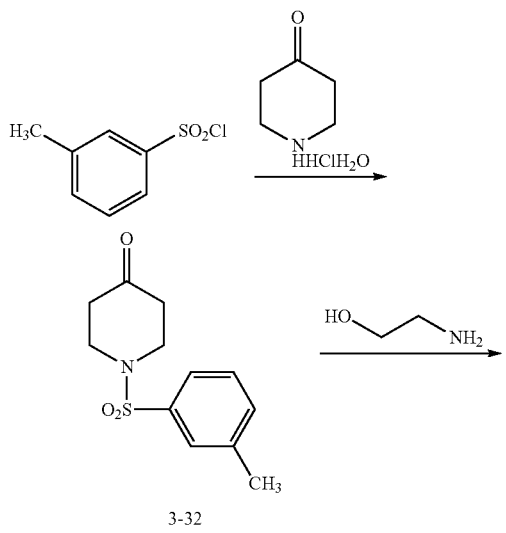

3-32

3-33

C0014 a. Preparation of Compound 3-32

3-methylbenzenesulfonyl chloride (130 mg, 0.69 mmol) was added to a solution of piperidin-4-one (159 mg, 1.03 mmol) in 10 mL pyridine. The mixture was stirred overnight (about 18 hours) at room temperature. The pyridine was removed by evaporation under vacuum. To the residue was added $CH_2Cl_2$ (50 mL), the $CH_2Cl_2$ layer was washed with 3M HCl (30 mL×3), dried over $Na_2SO_4$ and concentrated to give the crude product as light yellow solid (140 mg, yield: 80.5%).

b. Preparation of Compound 3-33

A solution of compound 3-32 (140 mg, 0.55 mmol), p-toluenesulfonic acid (15 mg) and 2-aminoethanol (2 mL) in ethanol (20 mL) was stirred overnight (about 18 hours) at room temperature. The solvent was removed by evaporation under vacuum. To the residue was added ethyl acetate (50 mL) and water (50 mL). The ethyl acetate layer was washed with water (30 mL×3), dried over $Na_2SO_4$ and concentrated to give the crude product as a yellow oil (170 mg, yield: 103.6%).

c. Preparation of Compound C0014 m-Methylbenzenesulfonyl chloride (131 mg, 0.69 mmol) was added to a solution of compound 3-33 (170 mg, 0.57 mmol) in pyridine (2 mL). The mixture was stirred overnight (about 18 hours) at room temperature. To the residue was added $CH_2Cl_2$ (50 mL). The organic solution was washed with 3M HCl (30 mL×3). Next, the $CH_2Cl_2$ layer was evaporated to give the title product as yellow oil. The crude product was purified by silica gel column chromatography to give the pure product as a white powder (30 mg, yield: 11.63%, $^1$H-NMR and MS confirmed, HPLC 95.4%). About 50 mg of compound 3-32 was recovered as white powder.

$^1$H-NMR (400 MHz, $CDCl_3$) δ:7.63-7.60 (m, 2H), 7.56-7.53 (m, 2H), 7.40-7.38 (m, 4H), 3.85 (t, J=6 Hz, 2H), 3.77-3.74 (m, 2H), 3.49 (t, J=6 Hz, 2H), 2.56-2.51 (m, 4H), 2.43 (s, 3H), 2.42 (s, 3H), 1.62-1.58 (m, 2H); MS (ESI) calcd for $C_{21}H_{26}N_2O_5S_2$ (m/z):450.13. found: 451.2[M+1]$^+$, 473.1 [M+23]$^+$ Preparation of Compound C0015

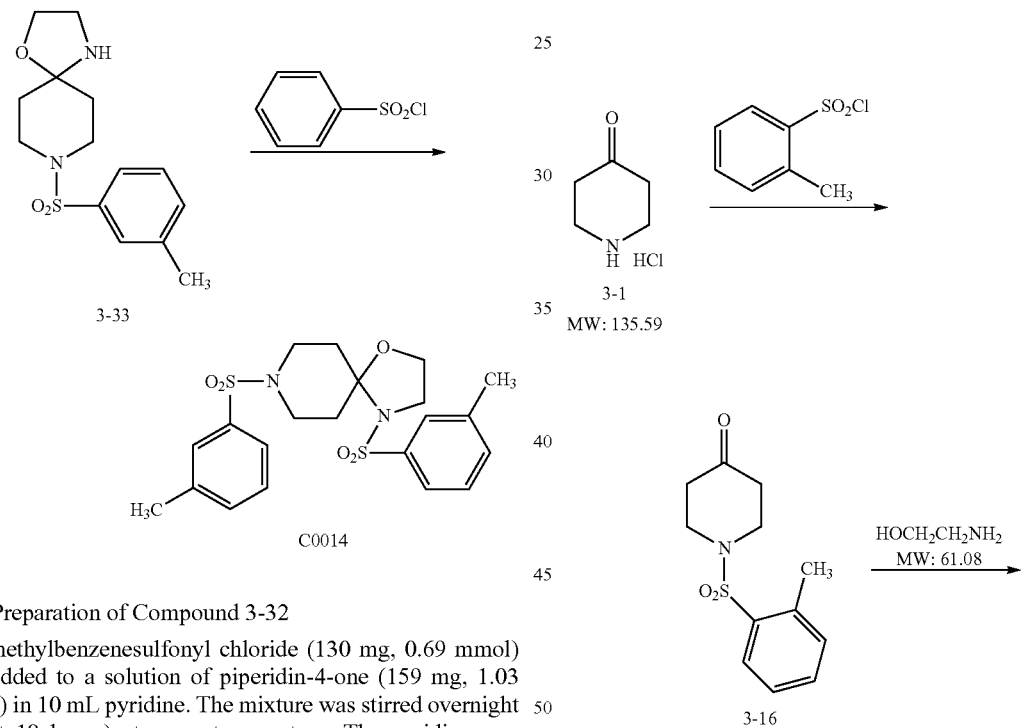

3-1
MW: 135.59

3-16

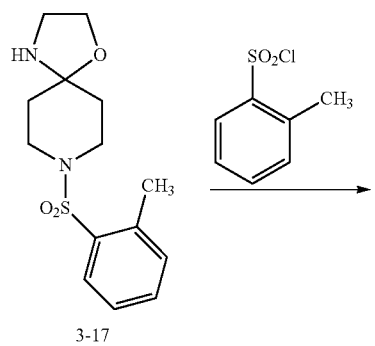

3-17

Preparation of Compound C0016

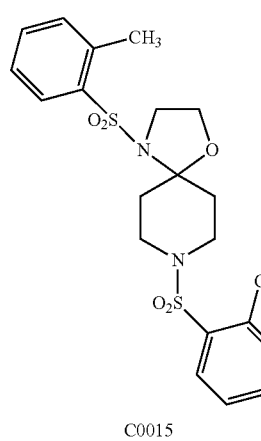

C0015

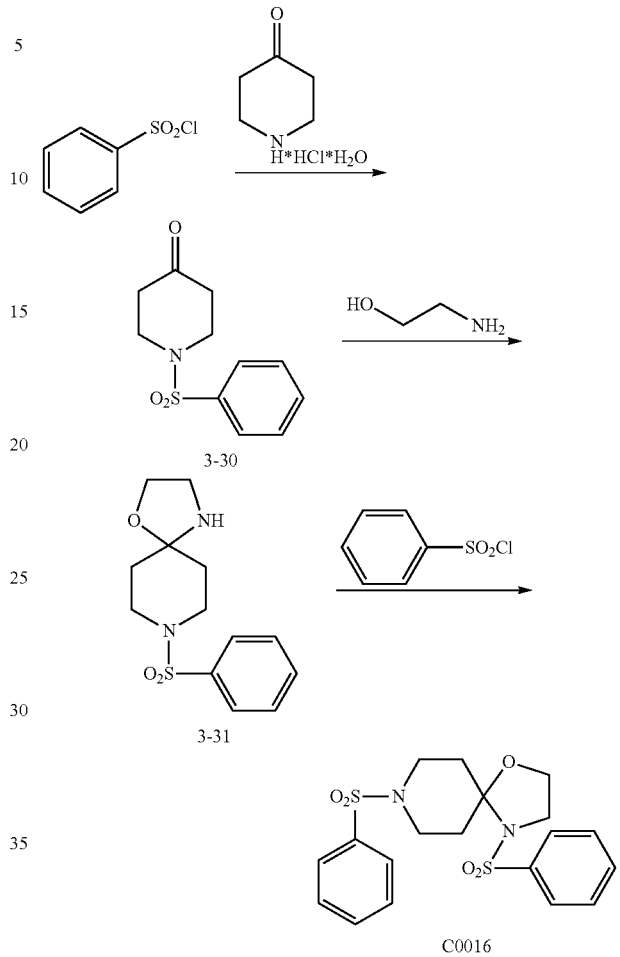

a. Preparation of Compound 3-16

2-Methyl-benzene-1-sulfonyl chloride (140.6 mg, 0.7375 mmol) was added to a solution of compound 3-1 (100 mg, 0.7375 mmol) in pyridine (3 mL) and the reaction mixture was stirred overnight (about 18 hours) at room temperature. Water was added and the resulting reaction mixture was extracted with $CH_2Cl_2$ (3×). The combined organic layers were washed with 3M HCl and concentrated to give compound 3-16 (104 mg, yield: 56%, $^1$H NMR confirmed) as a white solid.

b. Preparation of Compound 3-17 p-Toluenesulfonic acid monohydrate (10 mg) and 2-aminoethanol (1 mL) were added to a solution of compound 3-16 (104 mg, 0.41 mmol) in ethanol (EtOH) (4 mL) and the reaction mixture was stirred overnight (about 18 hours) at room temperature. EtOH was removed under reduced pressure and the residue was partitioned between $CH_2Cl_2$ and water. The organic phase was washed with saturated aqueous $NaHCO_3$ and brine, and concentrated to give the crude compound 3-17 (120 mg, yield: 100%) as a light yellow liquid.

c. Preparation of Compound C0015

2-Methylbenzene-1-sulfonyl chloride (77.2 mg, 0.405 mmol) was added to a solution of compound 3-17 (100 mg, 0.405 mmol) in pyridine (2.5 mL) and the reaction mixture was stirred overnight (about 18 hours) at room temperature. Water was added and the resulting reaction mixture was extracted with $CH_2Cl_2$ (3×). The combined organic layers were washed with 3M HCl and concentrated to give the crude product (97 mg) that was further purified to provide compound C0015 (28 mg, yield: 15%, NMR and MS confirmed, HPLC 91%).

$^1$H-NMR (400 MHz, $CDCl_3$) δ:7.94-7.90 (m, 2H), 7.50-7.44 (m, 2H), 7.35-7.30 (m, 4H), 3.96 (t, J=6.0 Hz, 2H), 3.69 (dt, J=11.6, 2.4 Hz, 2H), 3.35 (t, J=6.0 Hz, 2H), 2.98-2.92 (m, 2H), 2.65 (s, 3H), 2.64 (s, 3H), 2.53-2.47 (m, 2H), 1.85 (d, J=12 Hz, 2H); MS (ESI) calcd for $C_{21}H_{26}N_2O_5S_2$ (m/z): 450.13. found: 451.1[M+1]$^+$, 473.1[M+23]$^+$ a. Preparation of Compound 3-30

A solution of piperidin-4-one (208 mg, 1.36 mmol) in 20 mL of pyridine was treated with benzenesulfonyl chloride (200 mg, 1.13 mmol). The mixture was stirred at room temperature overnight (about 18 hours). The pyridine was then removed by evaporation under vacuum. To the residue was added $CH_2Cl_2$ (50 mL), then the $CH_2Cl_2$ layer was washed with 3M HCl (30 mL×3), dried over $Na_2SO_4$, and concentrated to give the crude product as a light yellow solid (138 mg, yield: 51%).

b. Preparation of Compound 3-31

A solution of compound 3-30 (136 mg, 0.57 mmol), p-toluenesulfonic acid monohydrate (15 mg) and 2-aminoethanol (2 mL) in ethanol (EtOH) (20 mL) was stirred overnight (about 18 hours) at room temperature. The solvent was removed by evaporation under vacuum. To the residue was added ethyl acetate (50 mL) and water (50 mL). The ethyl acetate layer was washed with water (30 mL×3). The water phase was washed with ethyl acetate (20 mL). The combined organic layers were dried over $Na_2SO_4$, filtered and concentrated to give the crude product (151 mg, yield: 92.5%). The crude product was directly used in the next step.

c. Preparation of Compound C0016

A solution of compound 3-31 (150 mg, 0.53 mmol) in pyridine (15 mL) was treated with phenyl sulfonyl chloride (112 mg, 0.64 mmol). The mixture was stirred at room temperature overnight (about 18 hours). The solvent was removed by evaporation under vacuum. To the residue was added $CH_2Cl_2$ (50 mL). The $CH_2Cl_2$ layer was washed with 3M HCl (30 mL×3), dried over $Na_2SO_4$ and concentrated to give the crude product as a light yellow solid. The crude product was purified with a silica gel column using petroleum ether/ethyl acetate 2:1 (petroleum ether/ethyl acetate=2/1) solvent to give the pure product as white solid (97 mg, yield: 43.3%, HPLC: 97% purity, $^1$H-NMR and MS have confirmed).

$^1$H-NMR (400 MHz, $CDCl_3$) δ: 7.84 (d, J=7.2 Hz, 2H), 7.76 (d, J=7.6 Hz, 2H), 7.60-7.50 (m, 6H), 3.86 (t, J=6.4 Hz, 2H), 3.79-3.75 (m, 2H), 3.50 (t, J=6.4 Hz, 2H), 2.58-2.49 (m, 4H), 1.61-1.56 (m, 2H); MS (ESI) calcd for $C_{19}H_{22}N_2O_5S_2$ (m/z):422.1. found: 423.1[M+1]$^+$, 445.2[M+23]$^+$ Preparation of Compounds C0017 and C0018 a. Preparation of Compound 3-34

4-Methoxybenzoyl chloride (0.5 g, 2.93 mmol) was added to a solution of piperidin-4-one (0.37 g, 1.95 mmol) in pyridine (20 mL). The reaction mixture was stirred at room temperature overnight (about 18 hours). The reaction solvent was then removed under reduced pressure. The residue was dissolved in $CH_2Cl_2$ (50 mL), then washed with 3M HCl (50 mL×3). The organic layer was dried over $Na_2SO_4$ and evaporated to give the title compound as a brown oil (330 mg, yield: 61.5%, LC-MS confirmed).

b. Preparation of Compound 3-35

A solution of compound 3-34 (330 mg, 1.42 mmol), 2-aminoethanol (2 mL) and p-toluenesulfonic acid monohydrate (33 mg) in ethanol (20 mL) was stirred at room temperature

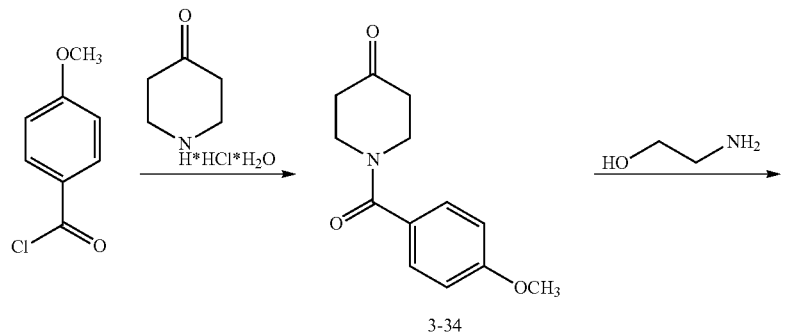

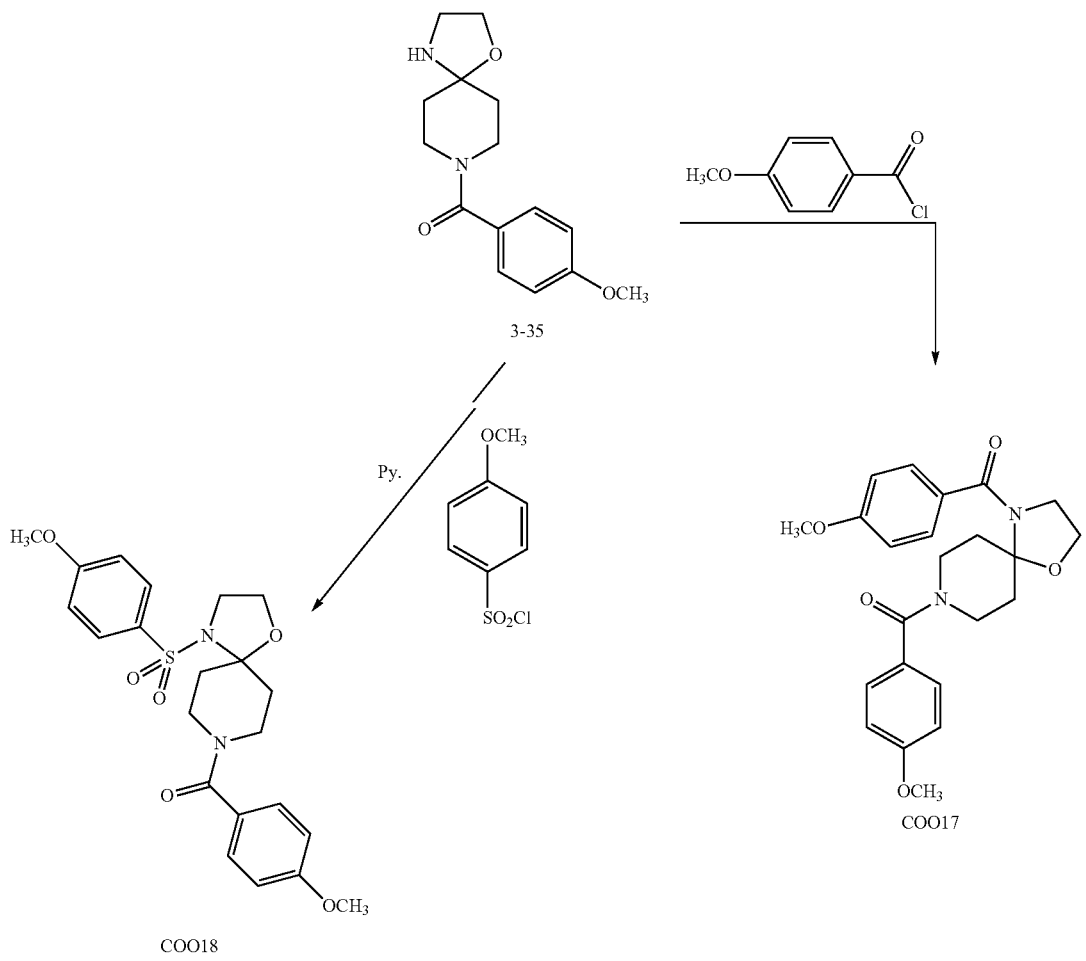

overnight (about 18 hours). The solvent was then removed by evaporation under reduced pressure. The residue was diluted with CH$_2$Cl$_2$ (50 mL), then washed with water (50 mL×3). The organic layer was dried over Na$_2$SO$_4$ and evaporated to give the crude product as a yellow oil (360 mg, yield: 92.1%, $^1$H-NMR and MS confirmed).

c. Preparation of Compound C0017

4-Methoxybenzoyl chloride (160 mg, 0.93 mmol) was added to a solution of compound 3-35 (172 mg, 0.62 mmol) in pyridine (25 mL). The reaction was stirred overnight (about 18 hours) at room temperature. The solvent was then removed under reduced pressure. The residue was diluted with CH$_2$Cl$_2$ (60 mL), then washed with 3M HCl (30 mL×3). The organic layer was dried over Na$_2$SO$_4$ and concentrated to give the crude product as a brown oil. The crude product was purified by silica gel column to give pure product as a white solid (220 mg, yield: 86%, $^1$H NMR and MS confirmed, HPLC: 99.1%).

$^1$H-NMR (400 MHz, CDCl$_3$) δ: 7.48-7.12 (m, 4H), 6.91-6.89 (m, 4H), 4.69 (br, s, 1H), 4.01-3.64 (m, 11H), 3.29-2.92 (m, 4H), 1.71-1.66 (m, 2H); MS (ESI) calcd for C$_{23}$H$_{26}$N$_2$O$_5$ (m/z):410.18. found: 411.2[M+1]$^+$, 433.3[M+23]$^+$.

d. Preparation of Compound C0018

4-Methoxybenzenesulfonyl chloride (220 mg, 1.07 mmol) was added to a solution of compound 3-35 (198 mg, 0.72 mmol) in pyridine (25 mL). The reaction mixture was stirred at room temperature overnight (about 18 hours). The reaction solvent was then removed under reduced pressure. The residue was diluted with CH$_2$Cl$_2$ (50 mL), then washed with 3M HCl (30 mL×3). The organic layer was dried over Na$_2$SO$_4$ and evaporated to give the crude product as brown oil.

$^1$H-NMR (400 MHz, CDCl$_3$) δ:7.79 (d, J=9.6 Hz, 2H), 7.40 (d, J=8.8 Hz, 2H), 6.98 (d, J=8.8 Hz, 2H), 6.92 (d, J=9.2 Hz, 2H), 4.65 (bs, 1H), 3.97 (t, J=6 Hz, 2H), 3.87-3.84 (m, 7H), 3.50 (brs, 2H), 3.20-2.90 (m, 2H), 2.47 (dt, J=5.6, 13.2 Hz, 2H), 1.65-1.62 (m, 2H); MS (ESI) calcd for C$_{22}$H$_{26}$N$_2$O$_6$S (m/z):446.15. found: 447.1[M+1]$^+$ Preparation of Compound C0019

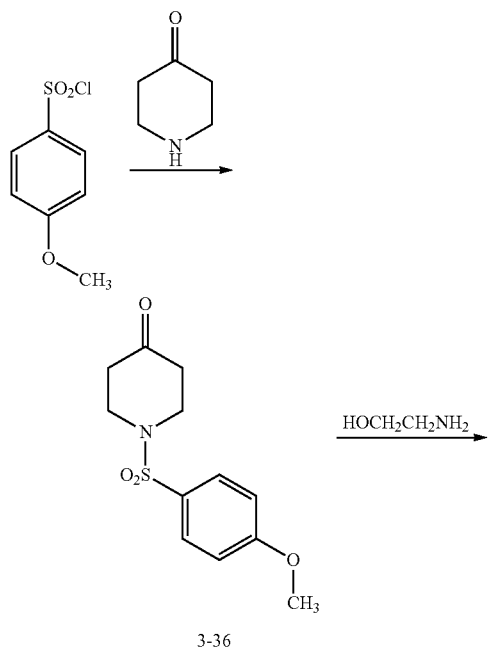

3-36

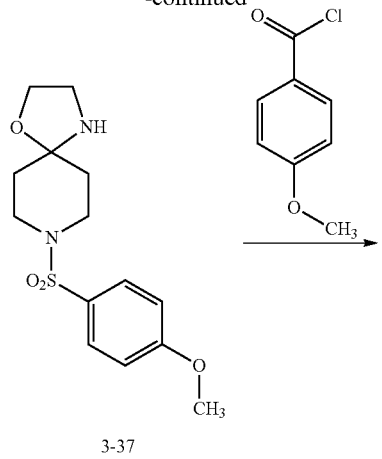

3-37

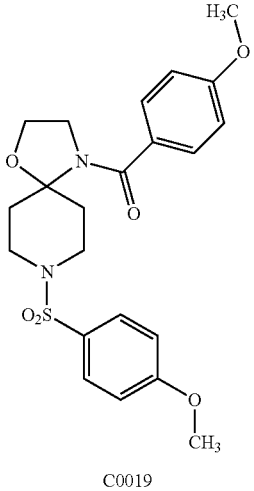

C0019 a. Preparation of Compound 3-36

4-Methoxybenzenesulfonyl chloride (200 mg, 0.97 mmol) was added to a mixture of piperidine-4-one (178 mg, 1.16 mmol) in pyridine (20 mL). The mixture was stirred at room temperature overnight (about 18 hours). The pyridine was then removed under reduced pressure. The residue was diluted with CH$_2$Cl$_2$ (50 mL), then washed with 3M HCl (30 mL×3). The organic layer was dried over anhydrous Na$_2$SO$_4$ and concentrated to give the product as a yellow solid (260 mg, yield: 100%, LC-MS confirmed).

b. Preparation of Compound 3-37

A solution of compound 3-36 (130 mg, 0.48 mmol), 2-aminoethanol (2 mL) and p-toluenesulfonic acid monohydrate (13 mg) in ethanol (20 mL) was stirred at room temperature overnight (about 18 hours). The solvent was removed under reduced pressure. The residue was dissolved in CH$_2$Cl$_2$ (50 mL), then washed with saturated Na$_2$CO$_3$ (50 mL×2) and water (50 mL×2). The organic layer was then dried over Na$_2$SO$_4$ and concentrated to give the product as a white colloid (118 mg, yield: 78.1%, LC-MS confirmed)

c. Preparation of Compound C0019

A solution of compound 3-37 (118 mg, 0.38 mmol) in pyridine (25 mL) was treated with p-methoxybenzoyl chloride (96.7 mg, 0.57 mmol). The mixture was stirred overnight (about 18 hours) at room temperature. The pyridine was removed under reduced pressure. The residue was diluted with CH$_2$Cl$_2$ (50 mL), then washed with 3 M HCl (30 mL×3). The organic layer was dried over Na$_2$SO$_4$ and concentrated to give the crude product as brown oil.

$^1$H-NMR (400 MHz, CDCl$_3$) δ:7.65 (d, J=9.2 Hz, 2H), 7.35 (d, J=8.8 Hz, 2H,), 6.91 (d, J=9.2 Hz, 2H), 6.80 (d, J=8.8 Hz, 2H), 3.79-3.74 (m, 8H), 3.69-3.66 (m, 2H), 3.52 (t, J=6.4 Hz, 2H), 3.00~2.93 (m, 2H), 2.51 (t, J=10.8 Hz, 2H), 1.55-1.49 (m, 2H); MS (ESI) calcd for C$_{22}$H$_{26}$N$_2$O$_6$S (m/z): 446.15. found: 469.2[M+23]$^+$ Preparation of Compound C0021

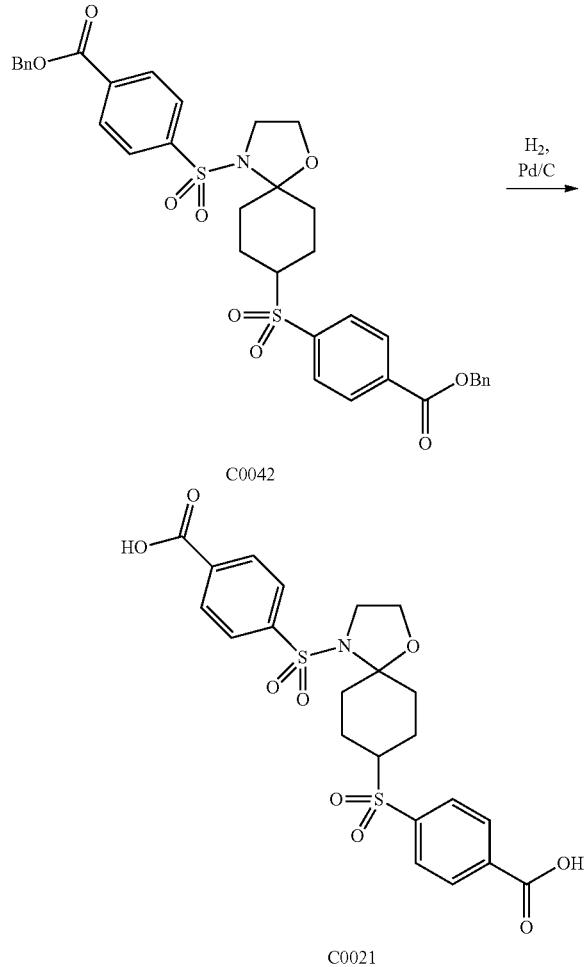

Preparation of Compound C0022

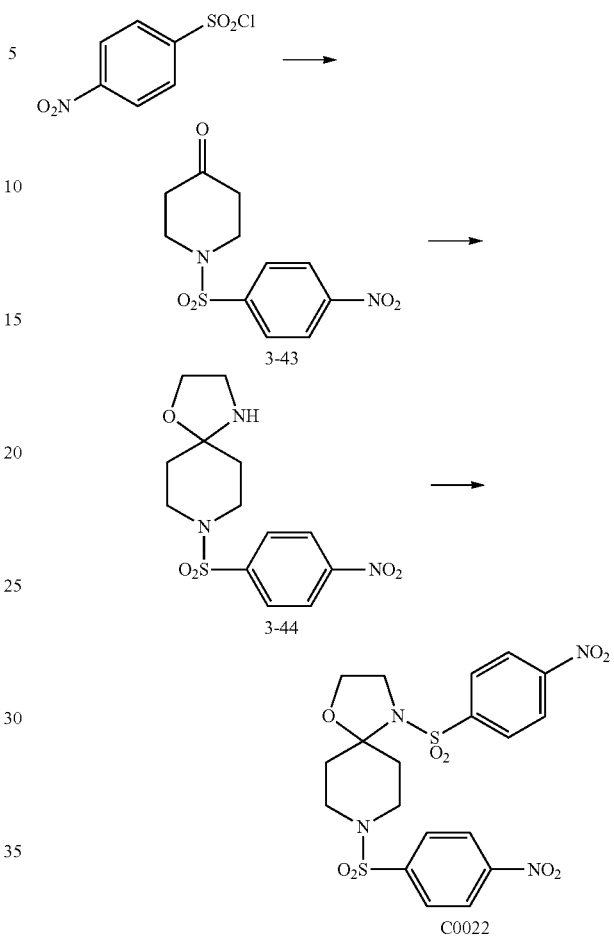

A solution of compound C0042 (110 mg, 0.16 mmol) in 10 mL methanol and 10 mL dichloromethane was added to 45 mg Pd/C, then the mixture was stirred at room temperature for 24 hours under H$_2$. Thin-layer chromatography (TLC) indicated the reaction was not complete, so the mixture was stirred at room temperature under H$_2$ (P=2.5 Mpa) for 2 more days. Later, TLC indicated that the starting material did not react. Next, Pd/C was replaced by Pd(OH)$_2$/C after hydrogenation under P=2.5 Mpa for 20 hours. Next, the mixture was filtered and the solvent was removed under reduced pressure to provide the product as a white solid (60 mg, yield: 74%, confirmed by LC-MS, $^1$H NMR and MASS, 97.8% purity by HPLC).

$^1$H NMR (400 MHz, DMSO-d$^6$) δ:8.16-8.10 (m, 4H), 7.94 (d, J=9.2 Hz, 2H), 7.85 (d, J=9.6 Hz, 2H), 3.83 (brs, 2H), 3.66-3.64 (m, 2H), 3.45 (bs, 2H), 2.34 (t, J=12.4 Hz, 2H), 2.24-2.18 (m, 2H), 1.60-1.57 (m, 2H); MS (ESI) calcd for C$_{21}$H$_{22}$N$_2$O$_9$S$_2$ (m/z):510.54. found: 509.0 [M−1]$^+$.

a. Preparation of Compound 3-43 p-Nitrobenzenesulfonyl chloride (0.5 g, 2.26 mmol) was added to a mixture of piperidine-4-one (0.52 g, 3.38 mmol) in pyridine (10 mL). The reaction mixture was stirred overnight at 30° C., the solvent was removed under the reduced pressure, the residue was diluted with CH$_2$Cl$_2$ (30 mL), washed with 3N HCl (15 mL×3), the organic layer was dried, evaporated to give the crude compound as light yellow solid (200 mg, yield: 31%).

b. Preparation of Compound 3-44

A solution compound 3-43 (0.58 g, 2.04 mmol) in 20 mL of ethanol was treated with 2-aminoethanol (2 mL) and p-toluenesulfonic acid monohydrate (60 mg). The mixture was stirred at 25° C. overnight. Then the solvent was removed under reduced pressure. The residue was diluted with CH$_2$Cl$_2$ (100 mL), washed with saturated Na$_2$CO$_3$ (100 mL×3) and saturated NaHCO$_3$ (50 mL×3). Then the organic phase was dried over anhydrous Na$_2$SO$_4$ and concentrated to give the title compound as yellow solid (0.58 g, yield: 90.6%).

c. Preparation of Compound C0022

To a solution of compound 3-44 (220 mg, 0.67 mmol) in pyridine (15 mL), the compound 4-nitrobenzenesulfonyl chloride (218 mg, 0.99 mmol) was added and the reaction mixture was stirred at 30° C. for 72 hours. The solvent was then removed under reduced pressure and the residue was diluted with CH$_2$Cl$_2$ (30 mL). Next, the residue was washed with 3 N HCl (15 mL×3) and the organic layer was dried then evaporated to give the crude compound as a yellow solid. The crude material was purified with a silica gel column (ethyl acetate:petroleum ether=1:2 to ethyl acetate) to get the pure product (210 mg, yield: 62.5%, HPLC: 97%, $^1$H NMR confirmed).

$^1$H NMR (400 MHz, CDCl$_3$) δ:8.36 (d, J=9.2 Hz, 4H), 8.00 (d, J=9.2 Hz, 2H), 7.92 (d, J=8 Hz, 2H), 3.89 (t, J=6.4 Hz, 2H), 3.83-3.80 (m, 2H), 3.50 (t, J=6 Hz, 2H), 2.56-2.54 (m, 4H), 1.64-1.60 (m, 2H); MS (ESI) calcd for C$_{19}$H$_{20}$N$_4$O$_9$S$_2$ (m/z): 512.07. found: 513.1 [M+1]$^+$, 535.3[M+23]$^+$.

Preparation of Compound C0023

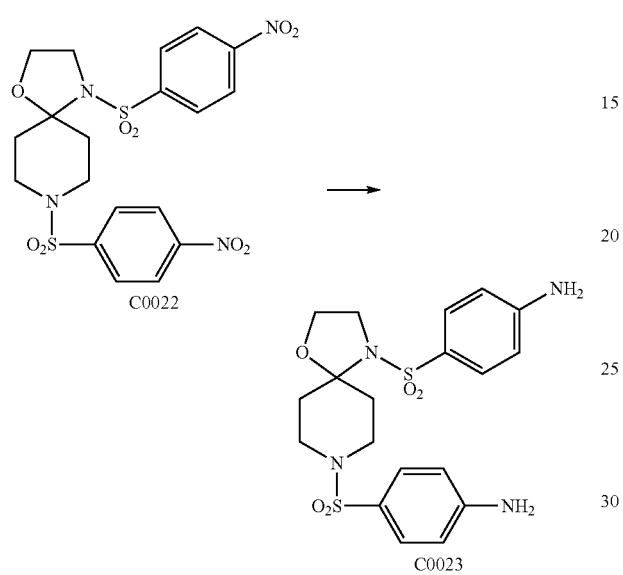

To a solution of C0022 (30 mg, 0.059 mmol) in methanol (MeOH) (10 mL), 10% Pd/C was added (10 mg). The reaction mixture was stirred under H$_2$ overnight (about 18 hours). After the reaction was complete, Pd/C was filtered off, and the filtrate was evaporated to get the crude compound (33 mg). The crude material was purified with a silica gel column (dichloromethane/methanol=100:1) to obtain the desired compound as a white solid (23 mg, yield: 88%, confirmed by $^1$H NMR). HPLC showed that the purity was 92%.

$^1$H NMR (400 MHz, CDCl$_3$) δ: 7.57 (d, J=6 Hz, 2H), 7.50 (d, J=6 Hz, 2H), 6.67-6.64 (m, 4H), 4.08 (d, J=12.8 Hz, 4H), 3.80 (bs, 2H), 3.67 (bs, 2H), 3.41 (bs, 2H), 2.48 (bs, 4H), 1.58-1.55 (m, 2H); MS (ESI) calcd for C$_{19}$H$_{24}$N$_4$O$_5$S$_2$ (m/z): 452.12. found: 475.0 [M+23]$^+$.

Preparation of Compound C0024

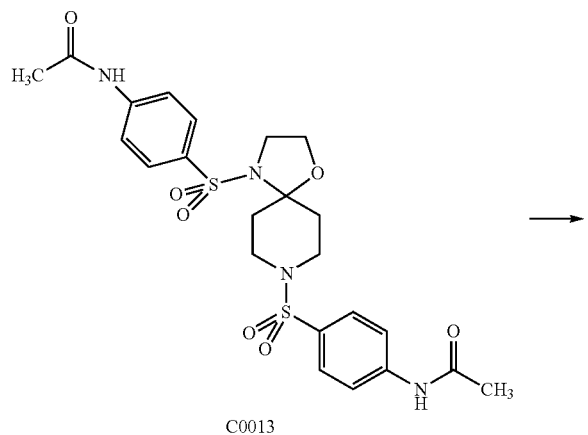

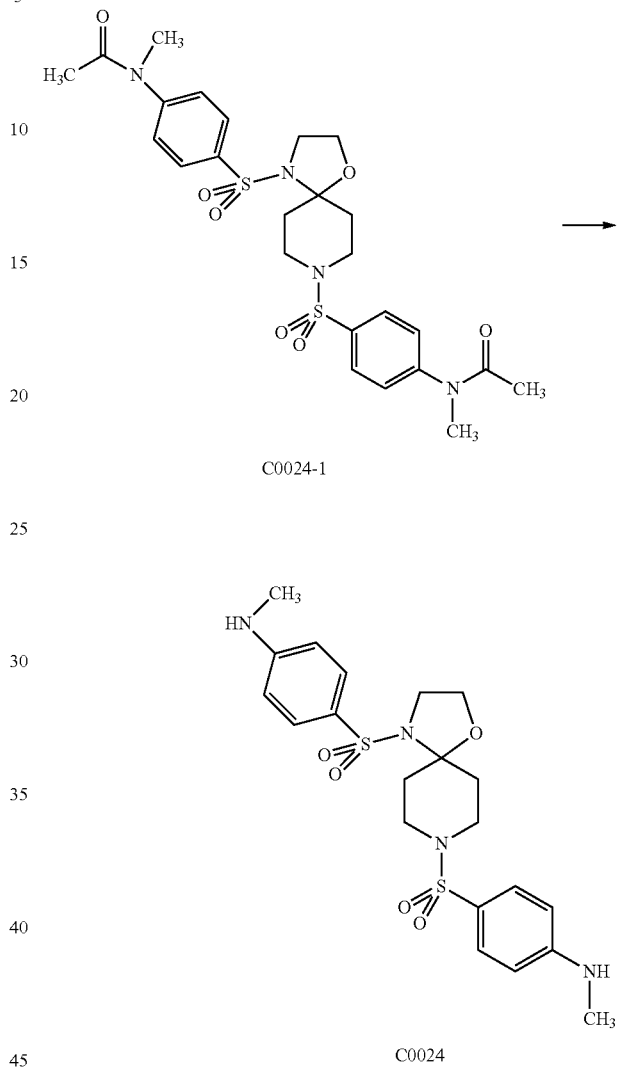

a. Preparation of Compound C0024-1

To a solution of compound C0013 (50 mg, 0.09 mmol) in THF (5 mL), 60% NaH (8.64 mg, 0.36 mmol) was added and the reaction mixture was stirred at room temperature for 0.5 hours. Then CH$_3$I (0.16 mL, 0.54 mmol) was added. The new mixture was stirred at room temperature overnight (about 18 hours). The reaction was quenched with CH$_3$OH. The solvent was removed under reduced pressure. The residue was diluted with water (20 mL), and extracted with CH$_2$Cl$_2$ (15 mL×3). The combined organic layer was dried over anhydrous Na$_2$SO$_4$, filtered, and evaporated to give the crude compound as yellow oil. The crude product was purified with silica gel column (eluted with ethyl acetate:petroleum ether=1:1 to CH$_3$OH:CH$_2$Cl$_2$=1:100) to give three products: C0024, the de-diacetyl product (20 mg) and C0024-2-1 or C0024-2-2, the mono-diacetyl product (15 mg).

b. Preparation of Compound C0024

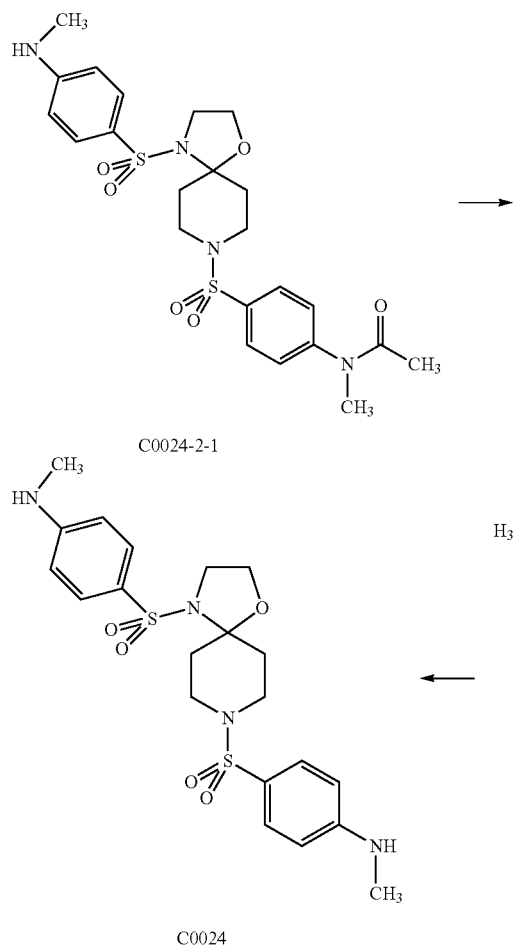

To a solution of compounds C0024-2-1 and C0024-2-2 (15 mg) in CH$_2$OH (10 mL), NaOH was added. The reaction mixture was stirred at room temperature. After the starting material was gone (monitored by TLC), the solvent was removed to obtain the residue, that was diluted with CH$_2$Cl$_2$ (20 mL), washed with water (10 mL×3), the organic layer was dried over anhydrous Na$_2$SO$_4$, filtered, evaporated to give the crude compound. The crude product was purified by silica gel column chromatography (ethyl acetate:petroleum ether=1:2 to 1:1) to get the pure compound (3 mg, HPLC: 98%. MS and $^1$H NMR confirmed).

$^1$H NMR (400 MHz, CDCl$_3$) δ: 7.61 (d, J=10 Hz, 2H), 7.54 (d, J=9.2 Hz, 2H), 6.58 (t, J=9.6 Hz, 4H), 4.27-4.23 (m, 2H), 3.89-3.80 (m, 2H), 3.68 (d, J=8.8 Hz, 2H), 3.45 (t, J=6.4 Hz, 2H), 2.89 (bs, 6H), 2.53-2.43 (m, 4H), 1.60-1.57 (m, 2H); MS (ESI) calcd for C$_{21}$H$_{28}$N$_4$O$_5$S$_2$ (m/z): 480.15. found: 503.0 [M+23]$^+$ Preparation of Compounds C0025

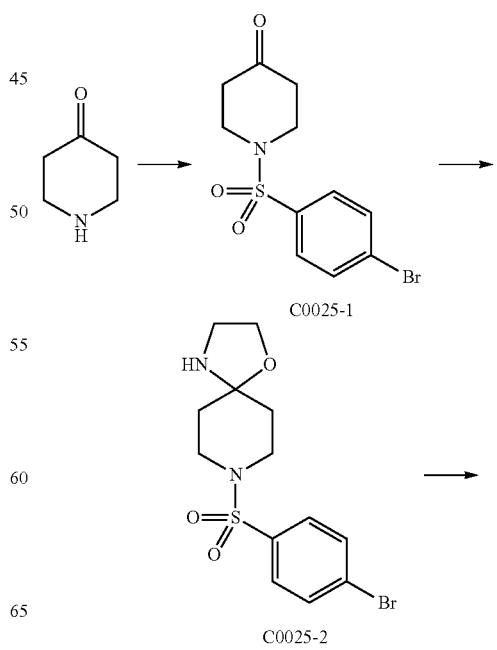

183

-continued

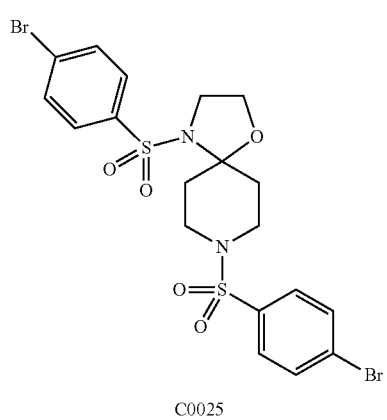

C0025 a. Preparation of Compound C0025-1

4-Bromobenzene-1-sulfonyl chloride (2 g, 7.83 mmol) was added to a solution of piperidin-4-one (1.8 g, 11.74 mmol) in pyridine (30 mL). The mixture was stirred overnight (about 18 hours) at room temperature. The solvent was removed under reduced pressure. The residue was diluted with $CH_2Cl_2$ (100 mL), washed with 3 N HCl (100 mL×2), dried over anhydrous $Na_2SO_4$ and concentrated to give the title compound as a pale solid (1.3 g, yield: 52%, TLC confirmed).

b. Preparation of Compound C0025-2

A solution of C0025-1 (1.3 g, 4.09 mmol), 2-aminoethanol (5 mL), and p-toluenesulfonic acid monohydrate (130 mg) was stirred overnight (about 18 hours) at 25° C. in 60 mL ethanol. The solvent was removed by reduced pressure evaporation. The residue was diluted with 200 mL dichloromethane, washed with water (100 mL×3) and saturated sodium bicarbonate solutions (100 mL×3). Next, the organic layer was dried and concentrated to get the product as a white solid. (1.44 g, yield: 97%, TLC confirmed).

c. Preparation of Compound C0025

To a solution of C0025-2 (1.44 g, 3.99 mmol) in 60 mL of pyridine, 4-bromobenzenesulfonyl chloride (1.53 g, 5.98 mmol) was added with stirring at room temperature overnight (about 18 hours). The solvent was removed under reduced pressure. The residue was diluted with 200 mL dichloromethane, and washed with 1 M hydrochloride (100 mL×3). The organic layer was then dried and concentrated to give the crude product as a yellow solid. The crude product was purified with a silica gel column and solvent of $CH_2Cl_2$: $CH_3OH$=500:1 to give the desired product as a yellow solid (0.3 g pure+0.7 g impure, yield: 43%).

$^1$H-NMR (400 MHz, $CDCl_3$) δ: 7.68-7.60 (m, 8H), 3.87 (t, J=6 Hz, 2H), 3.76 (bs, 2H), 3.47 (t, J=5.6 Hz, 2H), 2.58-2.48 (m, 4H), 1.61-1.55 (m, 2H); MS (ESI) calcd for $C_{19}H_{20}Br_2N_2O_5S_2$ (m/z):579.9. found: 581.0 $[M+1]^+$, 603.1 $[M+23]^+$.

184

Preparation of Compound C0027-1

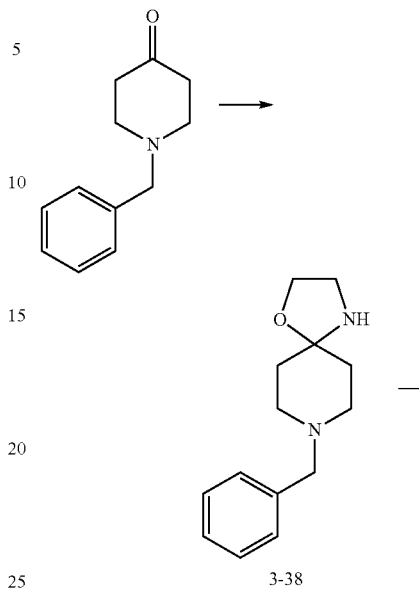

3-38

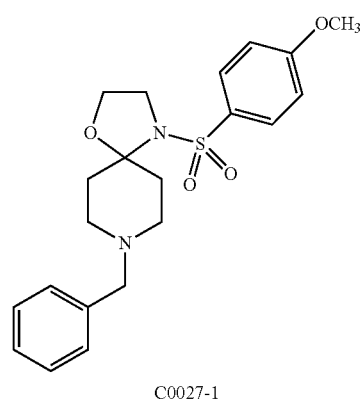

C0027-1 a. Preparation of Compound 3-38 p-Toluenesulfonic acid monohydrate (100 mg) and 2-aminoethanol (5 mL) were added to a solution of N-benzyl-piperidin-4-one (10 g 52.8 mmol) in 80 mL of ethanol. The mixture was stirred at 25° C. overnight (about 18 hours). The solvent was removed under the reduced pressure evaporation, the residue was diluted with 50 mL dichloromethane, and then washed with saturated sodium bicarbonate solutions (30 mL×3), saturated sodium carbonate (30 mL×3), then the organic layer was dried and concentrated to get the product as yellow oil (11.5 g, yield: 93.8).

b. Preparation of Compound C0027-1

4-Methoxy-benzene-1-sulfonyl chloride (1.83 g, 8.85 mmol) was added to the solution of compound 3-38 (1.37 g, 5.91 mmol) in pyridine (20 mL). The reaction mixture was stirred overnight (about 18 hours) at room temperature. The solvent was removed under reduced pressure. The residue (brown oil) was purified with silica gel column to give yellow foam (410 mg, yield: 17%, confirmed by LC-MS).

Preparation of Compound C0028

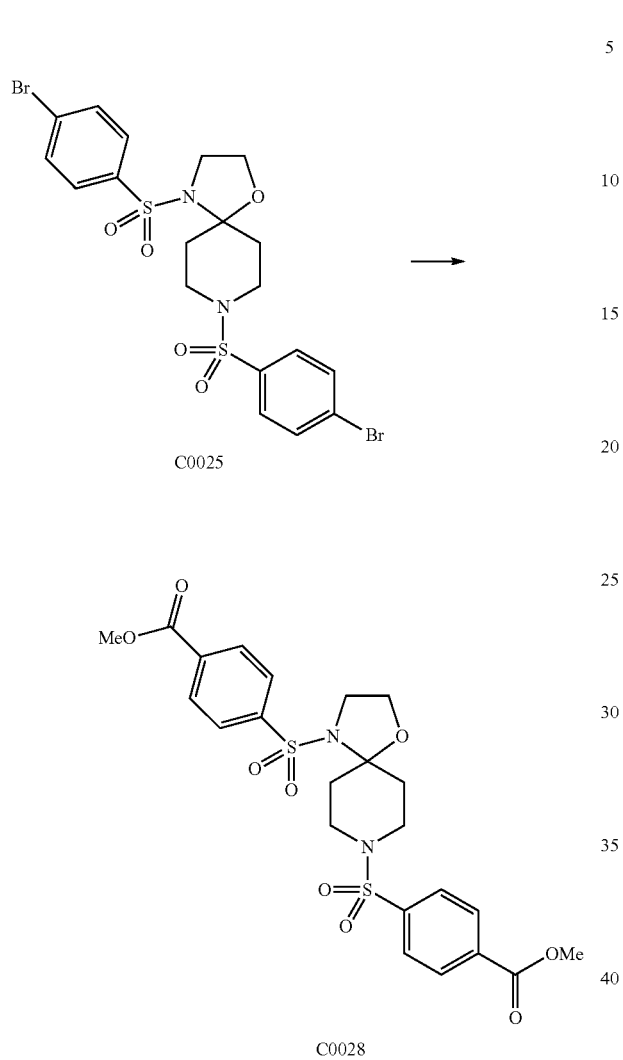

A solution of compound C0025 (100 mg, 0.17 mmol) in 20 mL dimethylformamide (DMF) was treated with Pd(PPh$_3$)$_4$ (60 mg), triethylamine (0.1 mL) and methanol (8 mL), with stirring at 130° C. overnight (about 18 hours) under carbon monoxide (p=2 Mpa). The mixture was quenched with 5 mL water, and the solvent was removed under reduced pressure evaporation. The residue was diluted with 50 mL dichloromethane and washed with water (50 mL×3). The organic layer was dried and concentrated to obtain the crude product as a green solid. After purification with a silica gel column and solvent of dichloromethane to CH$_2$Cl$_2$:CH$_2$OH=500:1, the purified product was obtained as a yellow solid (85 mg, yield: 91%, $^1$H-NMR confirmed).

$^1$H NMR (400 MHz, CDCl$_3$) δ: 8.31-8.18 (m, 4H), 7.92 (d, J=8.8 Hz, 2H), 7.85 (d, J=8.4 Hz, 2H), 4.00 (s, 3H), 3.98 (s, 3H), 3.89 (t, J=5.8 Hz, 2H), 3.81 (m, 2H), 3.53 (t, J=5.6 Hz, 2H), 2.61-2.49 (m, 4H), 1.60 (bs, 2H); MS (ESI) calcd for C$_{23}$H$_{26}$N$_2$O$_9$S$_2$ (m/z):538.59. found: 539.2 [M+1]$^+$.

Preparation of Compound C0029

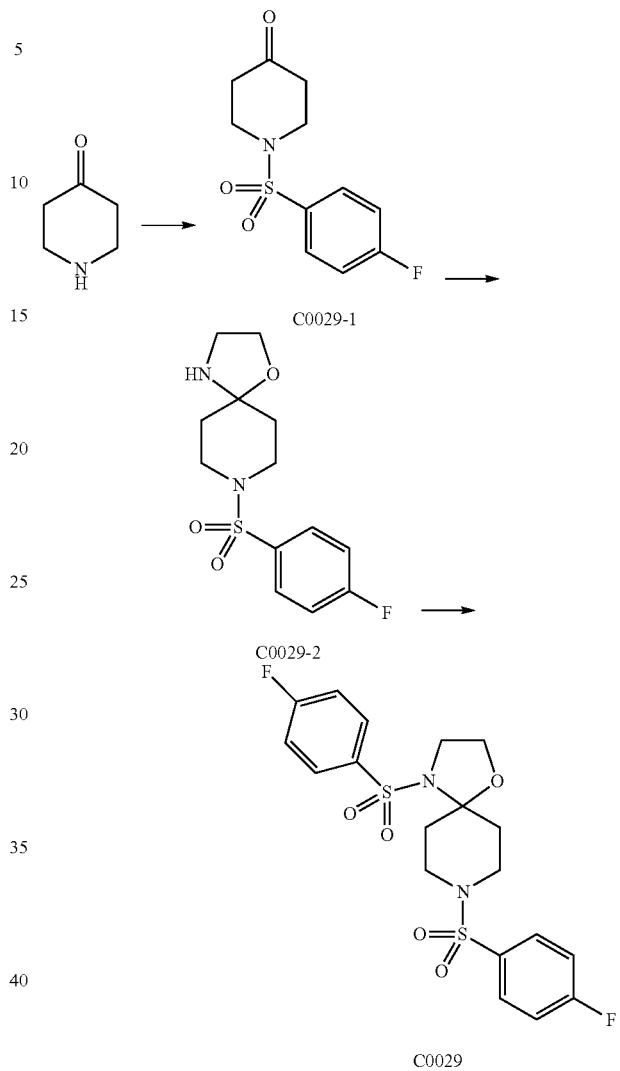

a. Preparation of Compound C0029-1

A stirred solution of piperidine-4-one (1.47 g, 7.71 mmol) in pyridine (20 mL) was treated with 4-flurobenzenesulfonyl chloride (1 g, 5.14 mmol) and the reaction mixture was stirred at room temperature overnight (about 18 hours). The solvent was removed under the reduced pressure and the residue was diluted with CH$_2$Cl$_2$ (20 mL). The diluted mixture was washed with 3N HCl (15 mL×3) and the organic layer was dried over anhydrous Na$_2$SO$_4$, filtered, and evaporated to give the crude compound as white solid (0.72 g, yield: 54.5%, $^1$H NMR confirmed).

b. Preparation of Compound C0029-2

To a solution of compound C0029-1 (0.72 g, 2.8 mmol), 2-aminoethanol (0.26 g, 4.2 mmol) and p-toluenesulfonic acid monohydrate (100 mg) in ethanol (20 mL) was added and stirred at 25° C. overnight (about 18 hours). The solvent was removed under the reduced pressure. The residue was diluted with CH$_2$Cl$_2$ (20 mL), washed with NaHCO$_3$ solution (20 mL×3), the organic layer was dried over anhydrous Na$_2$SO$_4$, filtered, evaporated to give the crude compound as white solid (0.81 g, yield: 96%, $^1$H NMR confirmed).

$^1$H NMR (400 MHz, CDCl$_3$) δ: 7.81~7.75 (m, 2H), 7.20~7.14 (m, 2H), 3.67 (t, J=6.4 Hz, 2H), 3.31~3.26 (m, 2H), 3.12 (t, J=6.4 Hz, 2H), 2.97~2.94 (m, 2H), 1.76~1.74 (m, 4H).

c. Preparation of Compound C0029

4-Fluorobenzenesulfonyl chloride (0.79 g, 4.06 mmol) was added to a solution of C0029-2 (0.81 g, 2.7 mmol) in pyridine (20 mL). The reaction mixture was stirred at room temperature overnight (about 18 hours). The solvent was removed under reduced pressure. The residue was diluted with $CH_2Cl_2$ (30 mL) and washed with 3 N HCl (20 mL×3). Next, the organic layer was dried over anhydrous $Na_2SO_4$, filtered, and evaporated to give the crude compound as an orange solid. The crude product was further purified by silica gel column to get the desired compound as a white solid (179 mg pure product, HPLC 97%, confirmed by $^1$H-NMR and MS; 500 mg of mixture, yield: 50%).

$^1$H NMR (400 MHz, $CDCl_3$) δ: 7.83 (dd, J=4.8, 8.8 Hz, 2H), 7.74 (dd, J=5.2, 8.8 Hz, 2H), 7.18 (dt, J=2.0, 8.4 Hz, 4H), 3.85 (t, J=6.0 Hz, 2H), 3.74-3.72 (m, 2H), 3.44 (t, J=6.0 Hz, 2H), 2.54-2.48 (m, 4H), 1.60-1.57 (m, 2H); MS (ESI) calcd for $C_{19}H_{20}F_2N_2O_5S_2$ (m/z):458.08. found: 459.1 $[M+1]^+$.

Preparation of Compound C0030

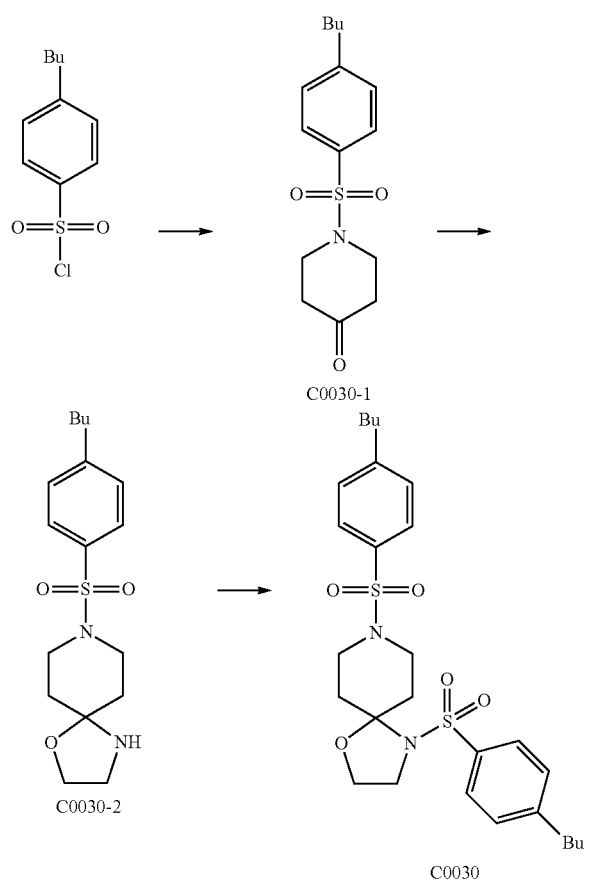

C0030-1

C0030-2

C0030 a. Preparation of Compound C0030-1

A solution of piperdin-4-one (594 mg, 3.9 mmol) in 20 mL of pyridine was treated with 4-n-butylbenzenesulfonyl chloride (600 mg, 2.6 mmol). The mixture was stirred overnight (about 18 hours) at room temperature. The solvent was removed under reduced pressure. The residue was then diluted with 50 mL of dichloromethane, washed with 1N hydrochloride (30 mL×3). Next, the organic layer was dried and concentrated to give the crude product as a white solid (501 mg, yield: 66%, $^1$H NMR confirmed).

b. Preparation of Compound C0030-2

A solution of C0030-1 (500 mg, 1.7 mmol), 2-aminoethanol (5 mL) and p-toluenesulfonic acid monohydrate (100 mg) in 30 mL of ethanol was stirred at 25° C. overnight (about 18 hours). The solvent was removed by reduced pressure evaporation. The residue was diluted with 50 mL dichloromethane, washed with water (50 mL×3) and saturated sodium bicarbonate aqueous (50 mL×3). The organic layer was dried and concentrated to give the product as a yellow solid (200 mg, yield: 89%, $^1$H-NMR confirmed).

c. Preparation of Compound C0030

At room temperature, a solution of C0030-2 (512 mg, 1.5 mmol) in 20 mL of pyridine was treated with 4-n-butylbenzene-sulfonyl chloride (528 mg, 2.3 mmol) and allowed to stir overnight (about 18 hours). The solvent was then removed under reduced pressure. The residue was diluted with 50 mL dichloromethane and washed with 1N hydrochloride (30 mL×3). Next, the organic layer was dried and concentrated to get the crude product as brown oil (796 mg).

$^1$H-NMR (400 MHz, $CDCl_3$) δ:7.87 (d, J=8.8 Hz, 2H), 7.80 (d, J=8 Hz, 2H), 7.47-7.44 (m, 4H), 4.00 (t, J=6 Hz, 2H), 3.91-3.89 (m, 2H), 3.63 (t, J=6 Hz, 2H), 2.82 (dt, J=7.4 Hz, 2.4 Hz, 4H), 2.74-2.62 (m, 4H), 1.80-1.72 (m, 6H), 1.56-1.46 (m, 4H), 1.10-1.06 (m, 6H); MS (ESI) calcd for $C_{27}H_{38}N_2O_5S_2$ (m/z):534.22. found: 535.3 $[M+1]^+$ Preparation of Compound C0031

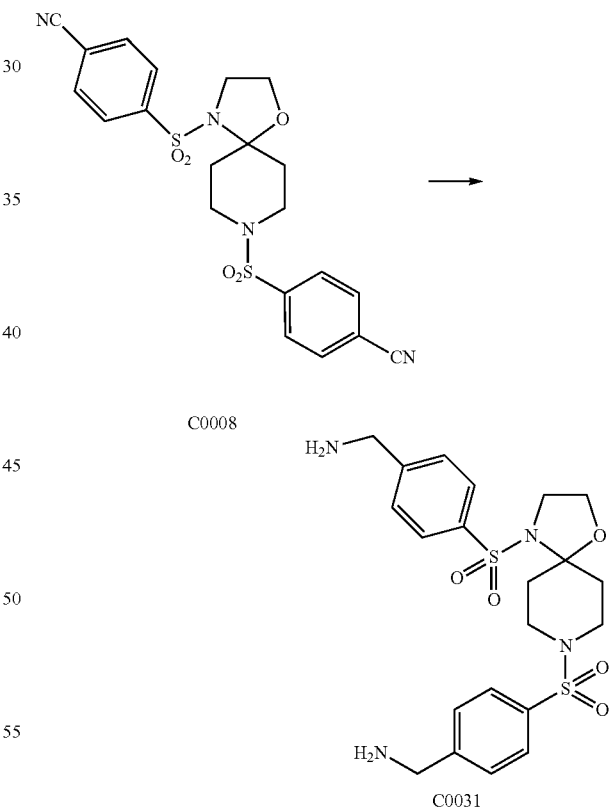

C0008

C0031

A mixture of Raney Ni (wet, 600 mg) and C0008 (40 mg, 0.085 mmol) was in ethanolamine (30 mL). The mixture was hydrogenated under 1.5 MPa of $H_2$ and stirred at 50° C. overnight (about 18 hours).

The reaction mixture was filtered. The filtrate was concentrated to obtain the crude product. The crude product was purified by silica gel to obtain the title product as yellow solid (15 mg; yield: 36%).

¹H NMR (400 MHz, CDCl₃): 7.79 (d, J=8.0 Hz, 2H); 7.72 (d, J=8.4 Hz, 2H); 7.48 (m, 4H); 3.96 (s, 2H); 3.97 (s, 2H); 3.84 (t, J=6.4 Hz, 2H); 3.78-3.72 (m, 2H); 3.48 (t, J=6.4 Hz, 2H); 2.51 (m, 4H); 1.53 (m, 2H); LCMS (ESI) calcd for C$_{21}$H$_{28}$N$_4$O$_5$S$_2$ (m/z): 480.6. found: 481.2[M+1]$^+$.

Preparation of Compound C0032

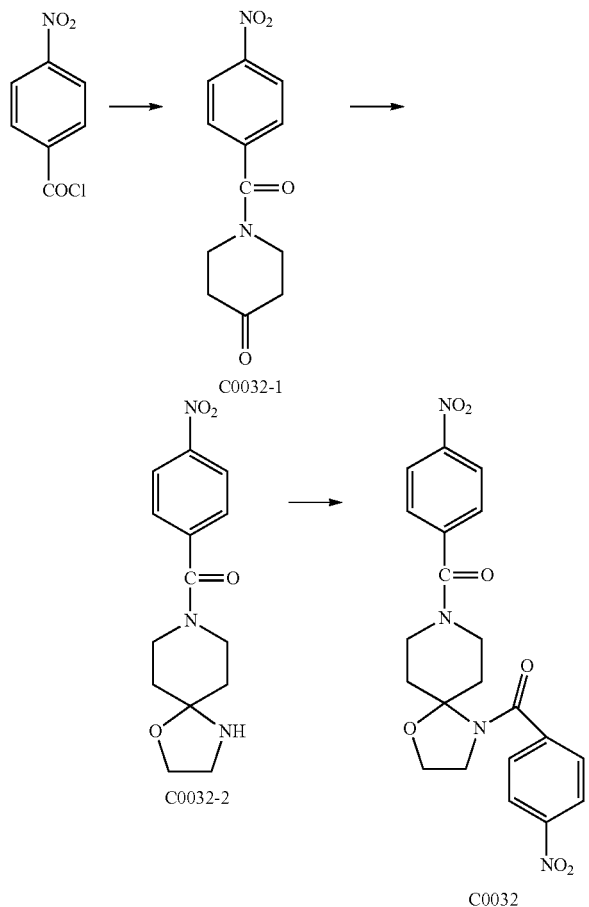

a. Preparation of Compound C0032-1 p-Nitrobenzoyl chloride (2 g, 10.87 mmol) was added to a solution of piperidine-4-one (3.15 g, 10.17 mmol) in pyridine (30 mL). The reaction mixture was stirred at room temperature overnight (about 18 hours). The solvent was removed under reduced pressure. The residue was diluted with CH$_2$Cl$_2$ (30 mL) and washed with 3 N HCl (20 mL×3). The organic layer was dried over anhydrous Na$_2$SO$_4$, filtered, and evaporated to give the crude compound as a yellow solid (1.49 g, yield: 55.9%, confirmed by ¹H-NMR and LCMS).

b. Preparation of Compound C0032-2

A solution of compound C0032-1 (2 g, 8.06 mmol), 2-aminoethanol (0.73 g) and p-toluenesulfonic acid monohydrate (200 mg) in ethanol (40 mL) was stirred at 25° C. overnight (about 18 hours). The solvent was removed under reduced pressure. The residue was diluted with CH$_2$Cl$_2$ (30 mL) and washed with NaHCO$_3$ (30 mL×3). Next, the organic layer was dried over anhydrous Na$_2$SO$_4$, filtered, and evaporated to give the crude compound as an orange solid. (2.2 g, yield: 93.7%, confirmed by ¹H NMR and LCMS).

c. Preparation of Compound C0032

4-Nitrobenzoyl chloride (1.02 g, 5.52 mmol) was added to a solution of compound C0032-2 (1.07 g, 3.68 mmol) in pyridine (30 mL). The reaction mixture was stirred overnight (about 18 hours) at room temperature.

¹H NMR (400 MHz, CDCl₃) δ: 8.27-8.23 (m, 4H), 7.64-7.59 (m, 4H), 4.75-4.73 (m, 1H), 4.04-3.99 (m, 2H), 3.57-3.54 (m, 3H), 3.37 (t, J=12.4 Hz, 1H), 3.08 (t, J=12.8 Hz, 1H), 2.98-2.81 (m, 2H), 1.78 (d, J=13.2 Hz, 1H), 1.58 (d, J=13.2 Hz, 1H). MS (ESI) calcd for C$_{21}$H$_{20}$N$_4$O$_7$ (m/z):440.13. found: 441.1[M+1]$^+$. (LC-MS)

Preparation of Compound C0033

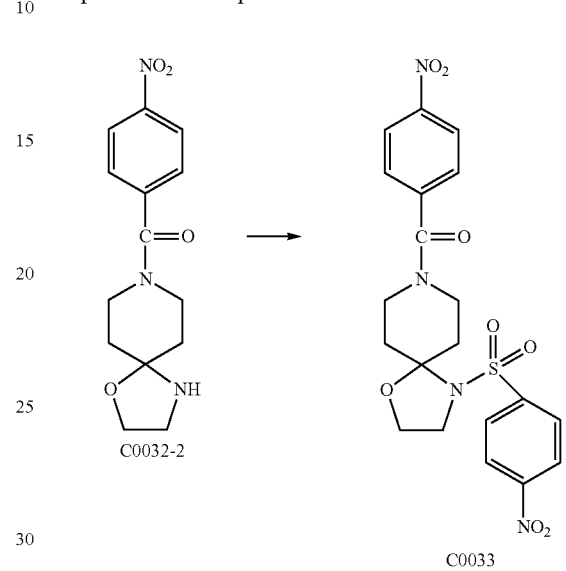

4-Nitrobenzene-sulfonyl chloride (1.28 g, 5.77 mmol) was added to a solution of compound C0032-2 (1.12 g, 3.85 mmol) in pyridine (30 mL). The reaction mixture was stirred overnight (about 18 hours) at room temperature.

¹H-NMR (400 MHz, CDCl₃) δ:8.39 (d, J=8.4 Hz, 2H), 8.31 (d, J=8.8 Hz, 2H), 8.06 (d, J=8.4 Hz, 2H), 7.61 (d, J=8.8 Hz, 2H), 4.75-4.72 (m, 1H), 4.05 (t, J=6 Hz, 2H), 3.62-3.50 (m, 3H), 3.32 (t, J=12.4 Hz, 1H), 2.99 (t, J=12.4 Hz, 1H), 2.51-2.42 (m, 2H), 1.70-1.67 (m, 2H). MS (ESI) calcd for C$_{20}$H$_{20}$N$_4$O$_8$S (m/z):476.10. found: 477.2[M+1]$^+$.

Preparation of Compound C0034

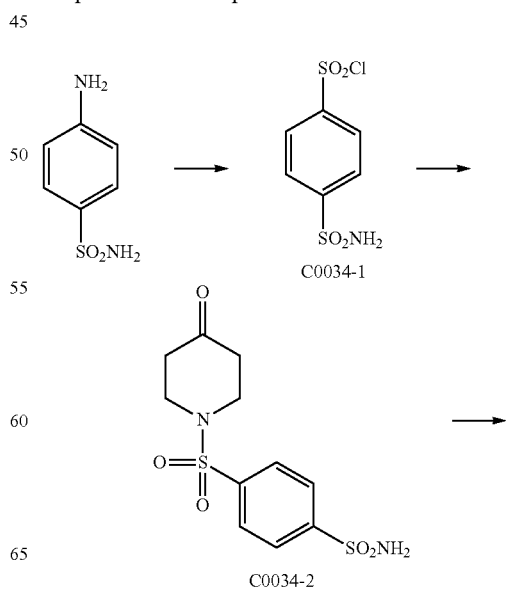

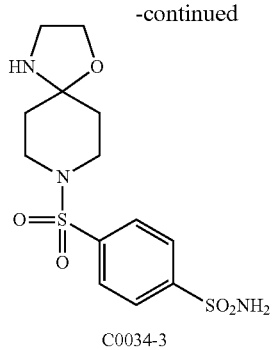

C0034-3

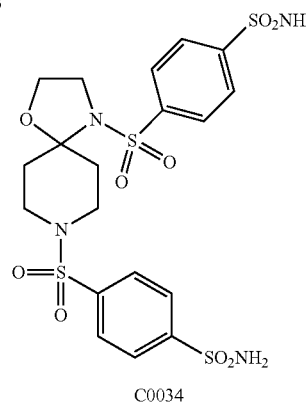

C0034 a. Preparation of Compound C0034-1

Cupric chloride (5 g) was added to a saturated solution of sulfur dioxide in $CH_3COOH$ (200 mL) and sulfur dioxide gas (from the reaction of $NaHSO_4$ and $H_2SO_4$). The gas was slowly bubbled into the solution for 4 hours until the solution became a blue-green hue. Next, 4-aminobenzene-1-sulfonamide (20 g, 116 mmol) was added to a solution of concentrated HCl (40 mL) and $H_2O$ (50 mL) with stirring for 1 hour at 0° C. To this mixture was added a solution of sodium nitrate (8 g, 116 mmol) at such a rate of addition that the temperature did not rise above 0° C. The mixture was stirred for 0.5 hours then quenched with the $SO_2/CuCl_2$ solution made earlier. The mixture was then stirred for 1 hour at room temperature. Next, $H_2O$ (500 mL) was added, and stirring continued for an additional 30 minutes. The product was collected by suction filtration, washed with $H_2O$, dried in vacuo at 60° C. to give the title product as a light yellow solid (LC-MS confirmed). After drying, about 10 g crude product as a light yellow solid was obtained (10 g, yield: 33%, confirmed by LC-MS).

b. Preparation of Compound C0034-2

A solution of piperidine-4-one (1.4 g, 9.4 mmol) in 30 mL of pyridine was added to compound C0034-1 (2.00 g, 7.8 mmol). The mixture was stirred overnight (about 18 hours) at room temperature. The solvent was removed under reduced pressure and the residue was diluted with $CH_2Cl_2$. The crude product was washed with 2N HCl (50 mL×3). The aqueous layer was extracted with $CH_2Cl_2$. The organic phase was combined and concentrated to give the crude product as a light yellow solid (0.65 g, yield: 37%, TLC confirmed)

c. Preparation of C0034-3

A solution of compound C0034-2 (0.5 g, 1.58 mmol) in 10 mL ethanol was treated with ethanolamine (5 mL) and 4-methylbenzenesulfonic acid monohydrate (0.1 g). The mixture was stirred overnight (about 18 hours) at 25° C. Then the solvent was removed under reduced pressure. The residue was diluted with $CH_2Cl_2$ (100 mL), and washed with saturated $NaHCO_3$ (50 mL×6), there was much dissolved solid. Then the organic phase was dried over anhydrous $Na_2SO_4$ and concentrated to give few yellow solid. The aqueous layer was filtered to provide a white solid. The aqueous layer was extracted with $CH_2Cl_2$ until there was no fluorescence under UV in the new extraction. The white solid was confirmed to be the product, which was purified with silica gel column to give the pure product as white solid (0.25 g, yield: 43.9%, $^1$H NMR confirmed).

d. Preparation of Compound C0034

A solution of compound C0034-3 (0.245 g, 0.68 mmol) in 20 mL of pyridine was treated C0034-1 (0.257 g, 1.01 mmol). The mixture was stirred at room temperature overnight (about 18 hours). The solvent was removed and the residue was diluted with $CH_2Cl_2$ (50 mL), washed with 2N HCl (50 mL×3). There was some solid dissolved in both aqueous phase and organic phase. The two phases were combined and filtered, to provide a yellow solid. The aqueous phase was extracted with $CH_2Cl_2$ (50 mL×3), and then concentrated to give some white solid. The NMR showed that the yellow solid contained compound C0034. The yellow solid was purified by chromatography on silica gel ($CH_2Cl_2:CH_3OH=200:1$) to give compound C0034 as a white solid (50 mg, yield: 12.7%, $^1$H NMR and MS confirmed, HPLC 97%).

$^1$H NMR (400 MHz, $CD_3OD$) δ: 8.01 (t, J=9.2 Hz, 4H), 7.93 (d, J=7.6 Hz, 2H), 7.85 (d, J=8.0 Hz, 2H), 3.80 (t, J=6.4 Hz, 2H), 3.69-3.66 (m, 2H), 3.43 (t, J=6 Hz, 2H), 2.46-2.30 (m, 4H), 1.57-1.54 (m, 2H). MS (ESI) calcd for $C_{19}H_{24}N_4O_9S_4$ (m/z):580.04. found: 579.0[M−1]$^+$.

Preparation of Compound C0038

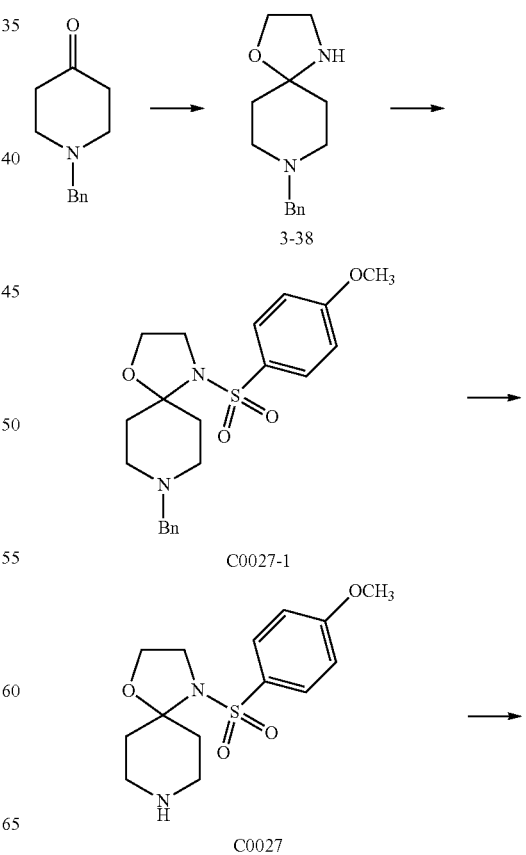

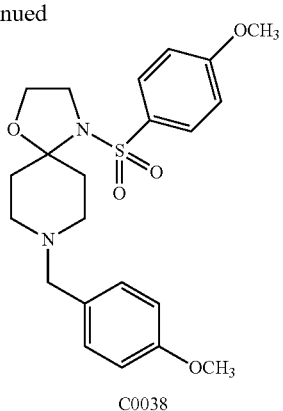

C0038 a. Preparation of Compound 3-38 p-Toluenesulfonic acid monohydrate (100 mg) and 2-aminoethanol (5 mL) were added to a solution of N-benzyl-piperidin-4-one (10 g 52.8 mmol) in 80 mL of ethanol. The mixture was stirred at 25° C. overnight (about 18 hours). The solvent was removed under the reduced pressure evaporation, the residue was diluted with 50 mL dichloromethane, and then washed with saturated sodium bicarbonate solutions (30 mL×3), saturated sodium carbonate (30 mL×3), then the organic layer was dried and concentrated to get the product as yellow oil (11.5 g, yield: 93.8).

b. Preparation of Compound C0027-1

4-Methoxybenzene-1-sulfonyl chloride (1.83 g, 8.85 mmol) was added to the solution of compound 3-38 (1.37 g, 5.91 mmol) in pyridine (20 mL). The reaction mixture was stirred overnight (about 18 hours) at room temperature. The solvent was removed under reduced pressure. The residue (brown oil) was purified with silica gel column to give yellow foam (410 mg, yield: 17%, confirmed by LC-MS).

c. Preparation of Compound C0027

To the solution of C0027-1 (410 mg, 1.02 mmol) in $CH_3OH:CH_2Cl_2=2:1$ (30 mL), 10% Pd/C (0.2 g) was added and the reaction mixture was stirred at room temperature overnight under $H_2$. The solvent was filtered to remove Pd/C. The solvent was removed under the reduced pressure to give the white foam as product (310 mg, yield: 98%, confirmed by LCMS).

d. Preparation of Compound C0038

Acetic acid (16.8 mg, 0.28 mmol), $NaBH(OAc)_3$ (89 mg, 0.42 mmol), 4-methoxybenzaldehyde (75.24 mg, 0.56 mmol) was added to the solution of C0027 (87 mg, 0.28 mmol) in dry dichloromethane. The reaction mixture was stirred at room temperature for 48 hours. The solvent was removed under the reduced pressure. The residue was diluted with $CH_2Cl_2$, washed with water (10 mL). The organic layer was dried, evaporated to get crude product as yellow oil, then purified with silica gel column to get desired compound as colorless oil (26 mg, yield: 22%, confirmed by LCMS and $^1H$ NMR, HPLC 97%).

Preparation of Compound C0041

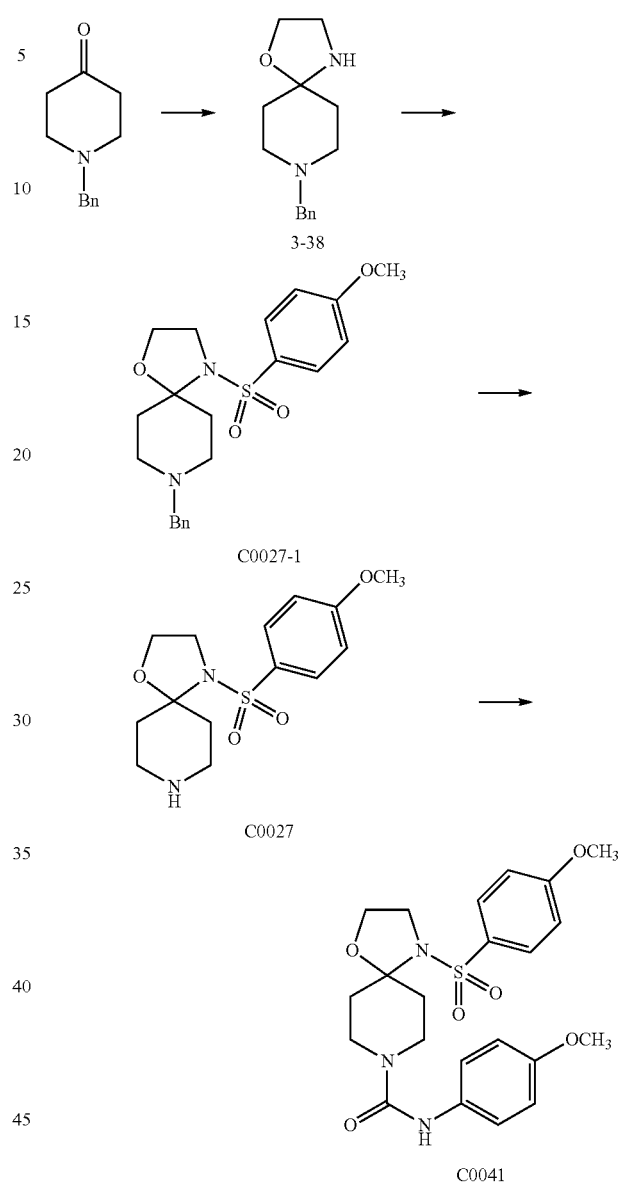

4-Methoxyphenyl isocyanate (0.06 mL, 0.43 mmol) was added dropwise to the solution of C0027 (90 mg, 0.29 mmol) in $CH_2Cl_2$ (5 mL). The reaction mixture was stirred at room temperature overnight (about 18 hours). The reaction mixture was evaporated to remove the solvent and the residue was purified with silica gel column chromatography (methanol/dichloromethane=40:1+$NH_3H_2O$) to obtain the compound with 87% purity by HPLC. The compound was further purified with preparative HPLC to get the desired compound with HPLC 98% (42 mg, yield 52%).

$^1H$ NMR (400 MHz, $CDCl_3$) δ: 7.70 (d, J=8.8 Hz, 2H), 7.15 (d, J=9.2 Hz, 2H), 6.88 (d, J=8.8 Hz, 2H), 6.76 (d, J=8.4 Hz, 2H), 6.17 (brs, 1H), 3.93-3.87 (m, 5H), 3.78 (s, 3H), 3.70 (s, 3H), 3.42 (t, J=6 Hz, 2H), 2.99 (t, J=12 Hz, 2H), 2.38 (dt, J=12, 6 Hz, 2H), 1.57-1.54 (m, 2H). MS (ESI) calcd for $C_{22}H_{27}N_3O_6S$ (m/z):461.16. found: 462.4[M+1]$^+$, 484.4[M+23]$^+$.

Preparation of Compound C0042

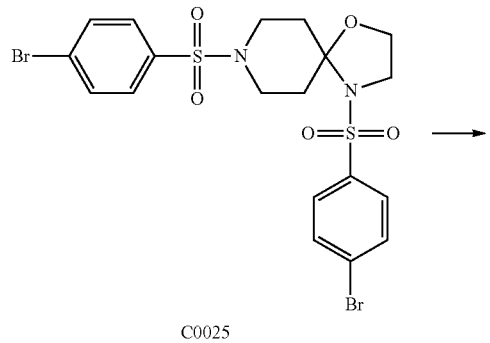

C0025

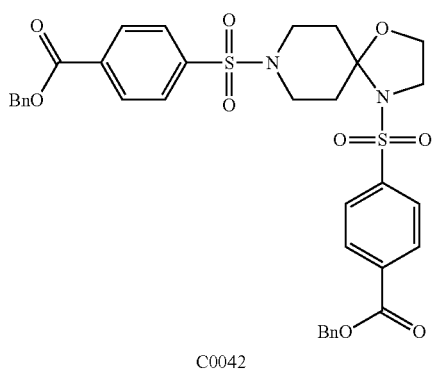

C0042

A solution of compound C0025 (400 mg, 0.69 mmol) in 20 mL of dimethylformamide was treated Pd(PPh$_3$)$_4$ (239 mg, 0.21 mmol), triethylamine (0.3 mL, 2.07 mmol) and 8 mL of benzyl alcohol. The mixture was stirred at 130° C. for 2 days under CO gas (P=2.5 Mpa). The solvent was removed under reduced pressure, the residue was diluted with methanol (25 mL) and filtered to get the product as a yellow solid. After purification with a silica gel column chromatography, using dichloromethane solvent, the desired product was obtained as a yellow solid (399 mg, Yield: 83.7%, confirmed by LC-MS, the purity of 99% is confirmed by HPLC).

$^1$H-NMR (400 MHz, CDCl$_3$) δ: 8.20 (d, J=8.0 Hz, 4H), 7.88 (d, J=8.0 Hz, 2H), 7.80 (d, J=8.0 Hz, 2H), 7.46-7.33 (m, 10H), 5.39 (d, J=5.6 Hz, 2H), 3.84 (t, J=6.6 Hz, 2H), 3.78-3.75 (m, 2H), 3.49 (t, J=6.4 Hz, 2H), 2.53-2.44 (m, 4H), 1.56-1.52 (m, 2H). MS (ESI) calcd for C$_{35}$H$_{34}$N$_2$O$_9$S$_2$ (m/z): 690.17. found: 691.4[M+1]$^+$.

Preparation of Compound C0047

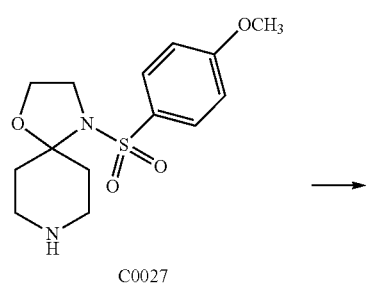

C0027

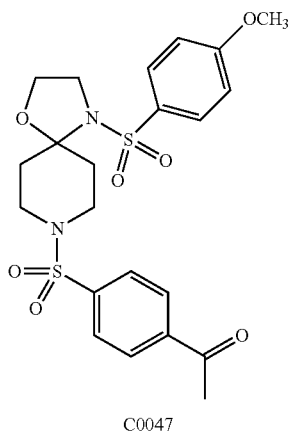

C0047

4-Acetylbenzenesulfonyl chloride (0.162 g, 0.74 mmol) was added to the solution of C0027 (0.21 g, 0.67 mmol) in 20 mL pyridine. The mixture was stirred at room temperature overnight (about 18 hours). The solvent was removed under reduced pressure. The residue was diluted with 50 mL dichloromethane and washed with 1M HCl three times (30 mL). The organic layer was dried over anhydrous Na$_2$SO$_4$ then concentrated to give the crude product as a yellow solid. After purification on a silica gel column chromatography (CH$_2$Cl$_2$: CH$_2$OH=500:1 to 250:1), the product was obtained as a white solid (0.224 g, yield: 67.5%, confirmed by LC-MS, $^1$H NMR and MASS, HPLC 99%).

$^1$H-NMR (400 MHz, CDCl$_3$) δ: 8.09 (d, J=8 Hz, 2H), 7.85 (d, J=8 Hz, 2H), 7.75 (d, J=8 Hz, 2H), 6.98 (d, J=8.4 Hz, 2H), 3.88 (s, 3H), 3.84 (t, J=6.4 Hz, 2H), 3.79 (d, J=7.2 Hz, 2H), 3.45 (t, J=6 Hz, 2H), 2.66 (s, 3H), 2.54 (d, J=8.4 Hz, 4H), 1.60 (d, J=9.6 Hz, 2H). MS (ESI) calcd for C$_{22}$H$_{26}$N$_2$O$_7$S$_2$ (m/z): 494.12. found: 495.1[M+1]$^+$.

Preparation of Compound C0048

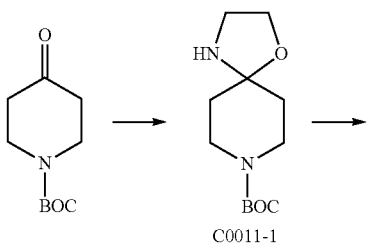

C0011-1

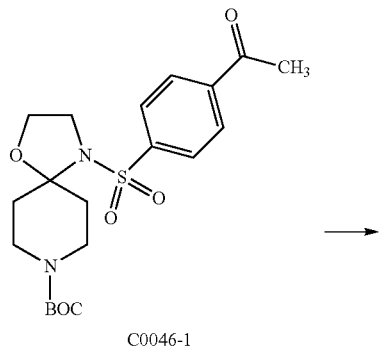

C0046-1

-continued

C0046

C0048

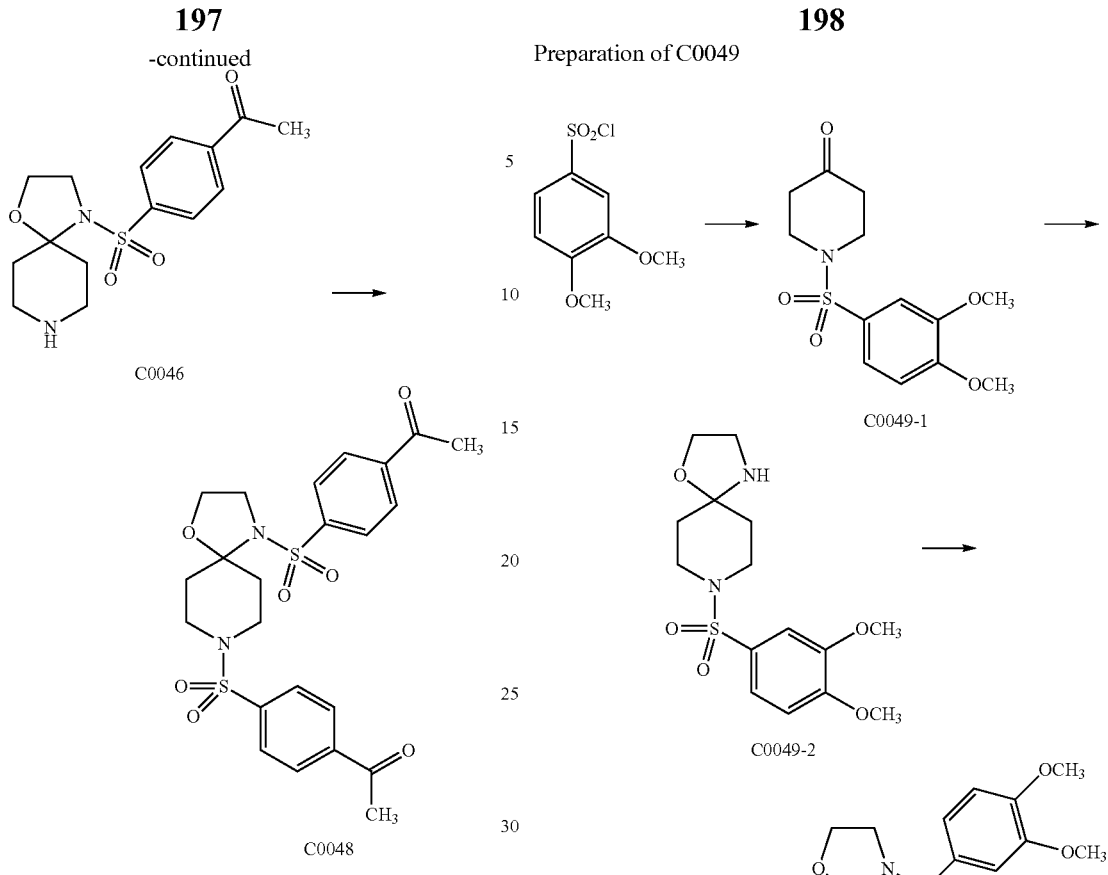

Preparation of C0049

C0049-1

C0049-2

C0049 a. Preparation of Compound C0046-1

4-Acetylbenzene-1-sulfonyl chloride (2 g, 9.1 mmol) was added to a solution of C0011-1 (2.63 g, 10.9 mmol) in pyridine (20 mL). The mixture was stirred at room temperature overnight (about 18 hours). Then the solvent was removed under reduced pressure. The residue was diluted with $CH_2Cl_2$ (100 mL) and washed with saturated $NaHCO_3$ (100 mL×3). The organic phase was dried over anhydrous $Na_2SO_4$ and concentrated to give the crude product as yellow solid, which was purified with silica gel column chromatography (eluted with $CH_2Cl_2$:$CH_3OH$=80:1) to give the title compound as a white solid (3.3 g, yield: 71.7%, $^1$H NMR confirmed).

b. Preparation of Compound C0046

A solution of C0046-1 (3.26 g, 11.48 mmol) in dichloromethane (DCM) (20 mL) was treated with $CF_3COOH$ (5 mL). The mixture was stirred overnight (about 18 hours) at room temperature. Thin-layer chromatography indicated that the material reacted completely. DCM (30 mL) was added and the organic layer was washed with saturated sodium carbonate solution (50 mL×3). The organic layer was dried and evaporated to get yellow oil, which was purified with silica gel column to give the product as yellow oil (1.1 g, yield: 44%, confirmed by LCMS, MS, and NMR, HPLC: 98.2%).

c. Preparation of Compound C0048

4-Methoxybenzene-1-sulfonyl chloride (74 mg, 0.36 mmol) was added to the solution of C0046 (100 mg, 0.3 mmol) in pyridine (5 mL). The mixture was stirred for two days at room temperature. The solvent was removed under reduced pressure. The residue was diluted with 50 mL of dichloromethane and washed with 2M HCl (30 mL×3). The organic layer was dried over anhydrous $Na_2SO_4$ and concentrated to give the crude product as white solid (120 mg, yield: 78.7%, confirmed by MS and $^1$H NMR, HPLC: 97.4%)

a. Preparation of Compound C0049-1

3,4-Dimethoxybenzene-1-sulfonyl chloride (500 mg, 2.1 mmol) was added to a solution of piperdin-4-one (486 mg, 3.2 mmol) in 20 mL of pyridine. The mixture was stirred overnight (about 18 hours) at room temperature. The solvent was removed under reduced pressure. The residue was diluted with dichloromethane (50 mL) and washed with 1N HCl (30 mL×3). The organic layer was dried and concentrated to give the product as yellow solid (260 mg, yield: 41.2%, confirmed by LC-MS).

b. Preparation of Compound C0049-2

A solution of compound C0049-1 (260 mg, 0.87 mmol), p-toluenesulfonic acid monohydrate (26 mg), and 2-aminoethanol (5 mL) in 10 mL of ethanol was stirred at 25° C. overnight (about 18 hours). The solvent was removed by reduced pressure evaporation. The residue was diluted with 50 mL of dichloromethane, and then washed with saturated sodium bicarbonate solutions (20 mL×3). The organic layer was dried and concentrated to give the product as yellow solid (297 mg, yield: 100%, confirmed by $^1$H NMR). a composition containing that compound c. Preparation of C0049

3,4-Dimetheoxybenzenesulfonyl chloride (308 mg, 1.3 mmol) was added to a solution of compound C0049-2 (297 mg, 0.87 mmol) in 20 mL pyridine and the reaction mixture was stirred overnight (about 18 hours) at room temperature. The solvent was removed under reduced pressure evaporation; the residue was diluted with 50 mL dichloromethane, and then washed with 1M HCl (30 mL×3). The organic layer was dried and concentrated to give the crude product as yellow solid (380 mg), after purified with silica gel column (CH$_2$Cl$_2$ to CH$_2$Cl$_2$:CH$_2$OH=500:1), then get the product as white solid (180 mg, yield: 38.3%, confirmed by $^1$H NMR, HPLC: 99%)

Preparation of C0051

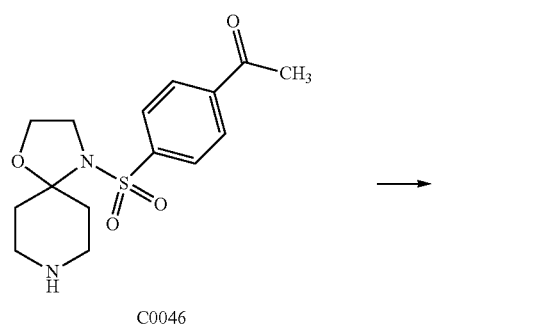

C0046

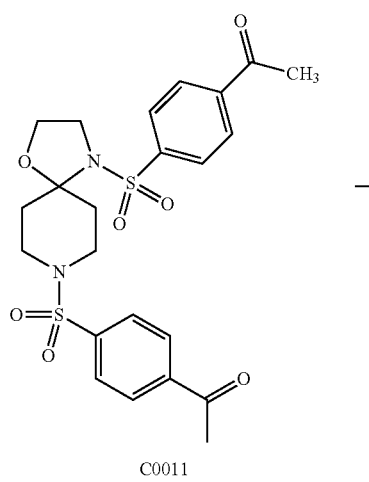

C0011

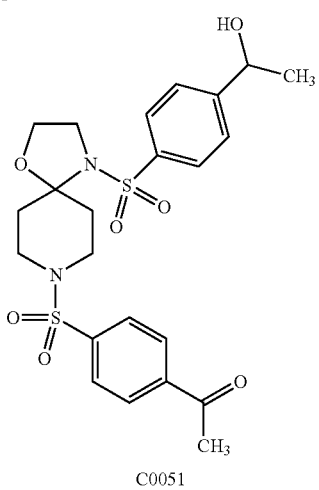

C0051

A solution of C0011 (120 mg) in CH$_2$OH/CH$_2$Cl$_2$ (10 mL/20 mL) was treated with Pd(OH)$_2$/C (30 mg). The mixture was stirred overnight (about 18 hours) at room temperature under H$_2$. Pd(OH)$_2$/C was removed by filtration and the filtrate was evaporated under reduced pressure to give the crude product as white solid, which was purified with silica gel column to give compound C0051 as white solid (91 mg, yield: 75.2%, confirmed by MS and NMR, HPLC: 95.9%).

Preparation of Compound C0052

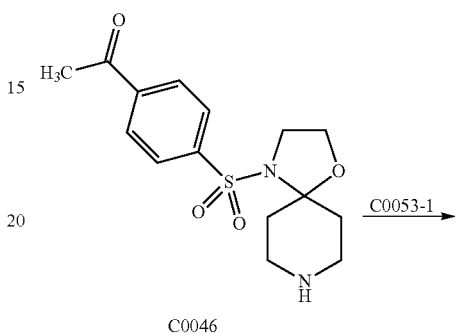

C0046

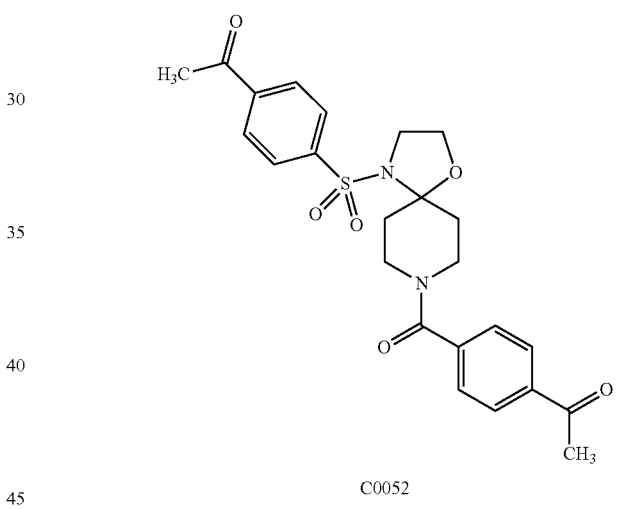

C0052

A solution of C0046 (190 mg, 0.586 mmol) in dry CH$_2$Cl$_2$ (20 mL) and diisopropylethylamine (0.5 mL) at 0° C. was treated with a solution of 4-acetylbenzoyl chloride (128 mg, 0.703 mmol) in dry CH$_2$Cl$_2$ (8 mL) added dropwise. After the addition, the mixture was stirred overnight (about 18 hours) at room temperature. The mixture was then washed with water (30 mL×3). The organic layer was dried and evaporated to give the crude product as a yellow solid. The crude product was purified with silica gel column to yield the pure product as white solid (135 mg, yield: 49%, confirmed by LCMS, NMR and MS, HPLC: 98.7%).

$^1$H-NMR (400 MHz, CDCl$_3$) δ: 8.09 (d, J=7.2 Hz, 2H), 8.02 (d, J=8 Hz, 2H), 7.97 (d, J=8 Hz, 2H), 7.53 (d, J=7.6 Hz, 2H), 4.73 (d, J=8.8 Hz, 1H), 4.01 (t, J=7.2 Hz, 2H), 3.61-3.5 (m, 3H), 3.27 (t, J=12.8 Hz, 1H), 2.96 (t, J=12.4, 1H), 2.67 (s, 3H), 2.64 (s, 3H), 2.50-2.43 (m, 2H), 1.65 (d, J=12.8 Hz, 2H). MS (ESI) calcd for C$_{24}$H$_{26}$N$_2$O$_6$S (m/z):470.15. found: 471.2 [M+1]$^+$, 493.2[M+23]$^+$.

Preparation of Compound C0053

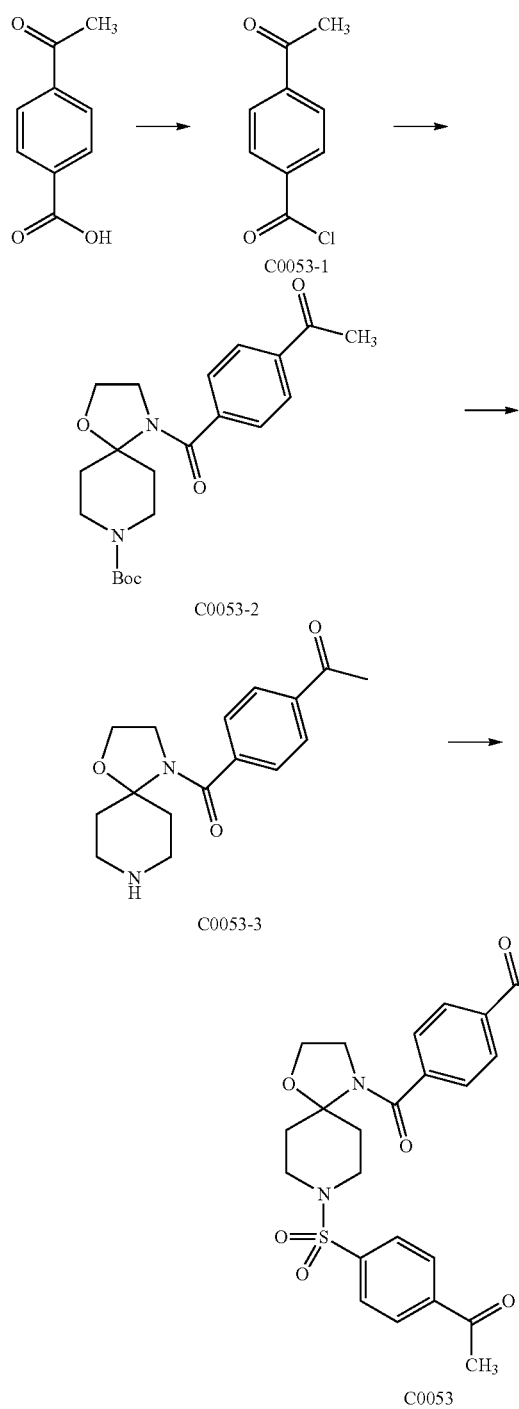

a. Preparation of Compound C0053-1

Oxalyl chloride (570 mg, 4.5 mmol) was added dropwise to a solution of 4-acetylbenzoic acid (250 mg, 1.52 mmol) in dry CH$_2$Cl$_2$ (20 mL) and dimethylformamide (0.1 mL) at 0° C. After addition, the mixture was stirred for 2 hours at room temperature. The solvent and excess oxalyl chloride was removed by reduced pressure evaporation to give the product as a yellow solid (270 mg, yield: 97%, confirmed by LCMS dissolved with CH$_2$OH.

b. Preparation of Compound C0053-2

C0053-1 (500 mg, 2.74 mmol solution in 20 mL dry CH$_2$Cl$_2$) was added to a solution of C0011-1 (727 mg, 23 mmol) and diisopropylethylamine (1 mL) in dry CH$_2$Cl$_2$ (20 mL) dropwise at 0° C. Next, the mixture was stirred at room temperature for 3 days. The mixture was then washed three times with water (50 mL), the organic layer was dried then evaporated to get the product as brown oil (1.28 g, yield: 100%, confirmed by LCMS).

c. Preparation of Compound C0053-3

A solution of C0053-2 (1 g, 2.58 mmol) and CF$_3$COOH (5 mL) in CH$_2$Cl$_2$ (20 mL) was stirred overnight (about 18 hours) at room temperature. The mixture was washed with saturated Na$_2$CO$_3$ solution and the organic layer was dried and evaporated to give the crude product as a brown oil. The crude product was purified on a silica gel column to provide the purified product as a brown oil (360 mg, yield: 48.3%, confirmed by LCMS).

d. Preparation of Compound C0053

4-Acetylbenzene-1-sulfonyl chloride (120 mg, 0.55 mmol) was added to a solution of C0053-3 (160 mg, 0.55 mmol) in pyridine (20 mL). The mixture was stirred overnight (about 18 hours) at room temperature. The solvent was removed by reduced pressure evaporation. The crude product was diluted with 50 mL CH$_2$Cl$_2$ and washed three times with 1N HCl (30 mL). The organic layer was dried and evaporated to give the crude product as a yellow solid. Purification with silica gel column gave the pure product as a white solid (102 mg, yield: 39%, confirmed by LCMS, MS and NMR; HPLC: 95.26%).

$^1$H-NMR (400 MHz, CDCl$_3$) δ:8.10 (d, J=8.4, 2H), 7.98 (d, J=7.6 Hz, 2H), 7.88 (d, J=8 Hz, 2H), 7.73 (d, J=8.4 Hz, 2H), 3.88-3.85 (m, 4H), 3.50 (t, J=6 Hz, 2H), 3.04 (bs, 2H), 2.66-2.62 (m, 8H), 1.67 (s, 2H). MS (ESI) calcd for C$_{24}$H$_{26}$N$_2$O$_6$S (m/z):470.15. found: 471.4[M+1]$^+$, 493.4[M+23]$^+$. (LC-MS)

Preparation of Compound C0054

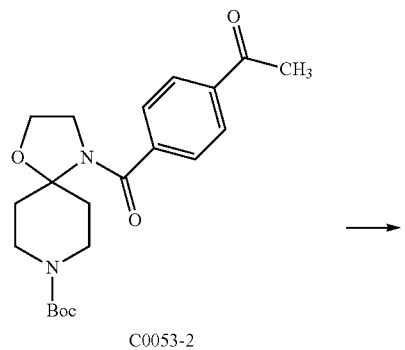

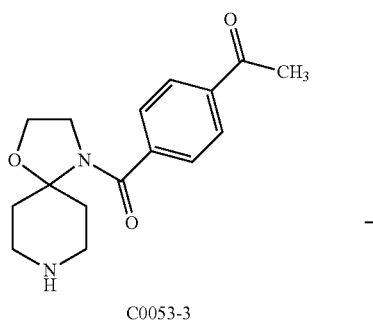

C0053-3

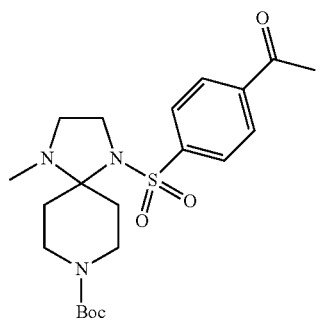

C0057-2

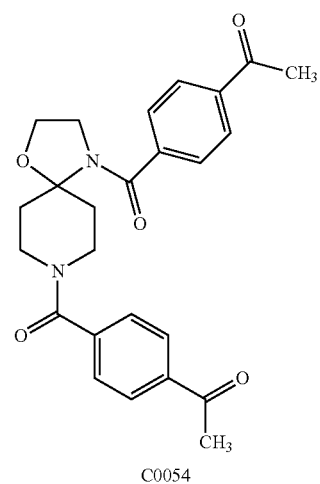

C0054

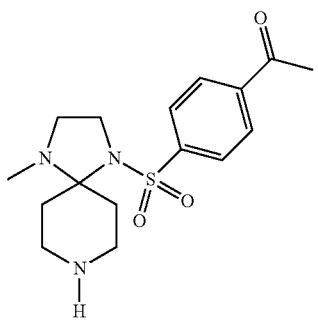

C0057-3

A solution of 4-acetylbenzoyl chloride (111 mg, 0.61 mmol) in dry dichloromethane (CH$_2$Cl$_2$) (8 mL) was added dropwise to a solution of C0053-3 (160 mg, 0.55 mmol) and diisopropylethylamine (0.3 mL) in dry CH$_2$Cl$_2$ (20 mL) at 0° C. After the addition, the mixture was stirred at room temperature for 2 days. To this mixture, 20 mL of CH$_2$Cl$_2$ was added and the mixture was washed with water (40 mL×3). The organic layer was dried and evaporated to give the crude product as yellow oil. Purification with silica gel column chromatography gave the pure product as white solid (110 mg, yield: 45.7%, confirmed by LCMS, MS and NMR. HPLC: 99.74%).

$^1$H-NMR (400 MHz, CDCl$_3$) δ: 8.01 (dd, J=4.4 Hz, 8 Hz, 4H), 7.55 (dd, J=3.6 Hz, 7.6 Hz, 4H), 4.79 (d, J=10.4 Hz, 1H), 4.01 (d, J=6.4 Hz, 2H), 3.66~3.58 (m, 3H), 3.35 (s, 1H), 3.09~2.93 (m, 3H), 2.64 (s, 3H), 2.63 (s, 3H), 1.78 (d, J=11.6 Hz, 1H), 1.59 (s, 1H). MS (ESI) calcd for C$_{25}$H$_{26}$N$_2$O$_5$ (m/z): 434.18. found: 435.3[M+1]$^+$, 457.4[M+23]$^+$.

Preparation of Compound C0057

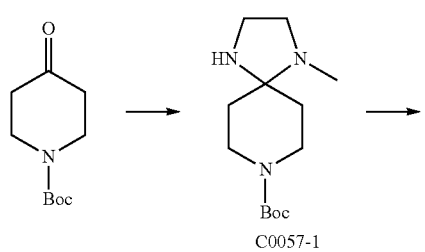

C0057-1

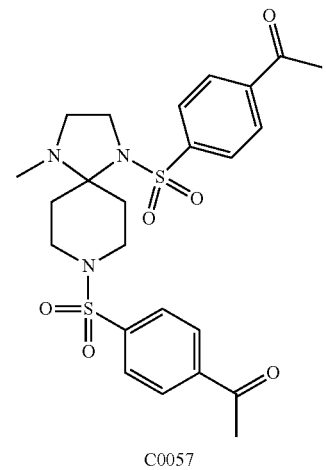

C0057 a. Preparation of Compound C0057-1

To N-Boc-piperidin-4-one (2.0 g, 10.1 mmol) in toluene (40 ml), N-methylethane-1,2-diamine (1.33 ml, 15.3 mmol) was added. The mixture was refluxed overnight (about 18 hours) with water-separator. Toluene was removed under reduced pressure. The residue was dissolved with CHCl$_3$ and washed with water. The organic layer was dried with anhydrous Na$_2$SO$_4$, concentrated under vacuum to obtain 2.2 g of C0057-1 as yellow oil (yield: 86%).

205

Preparation of Compound C0061

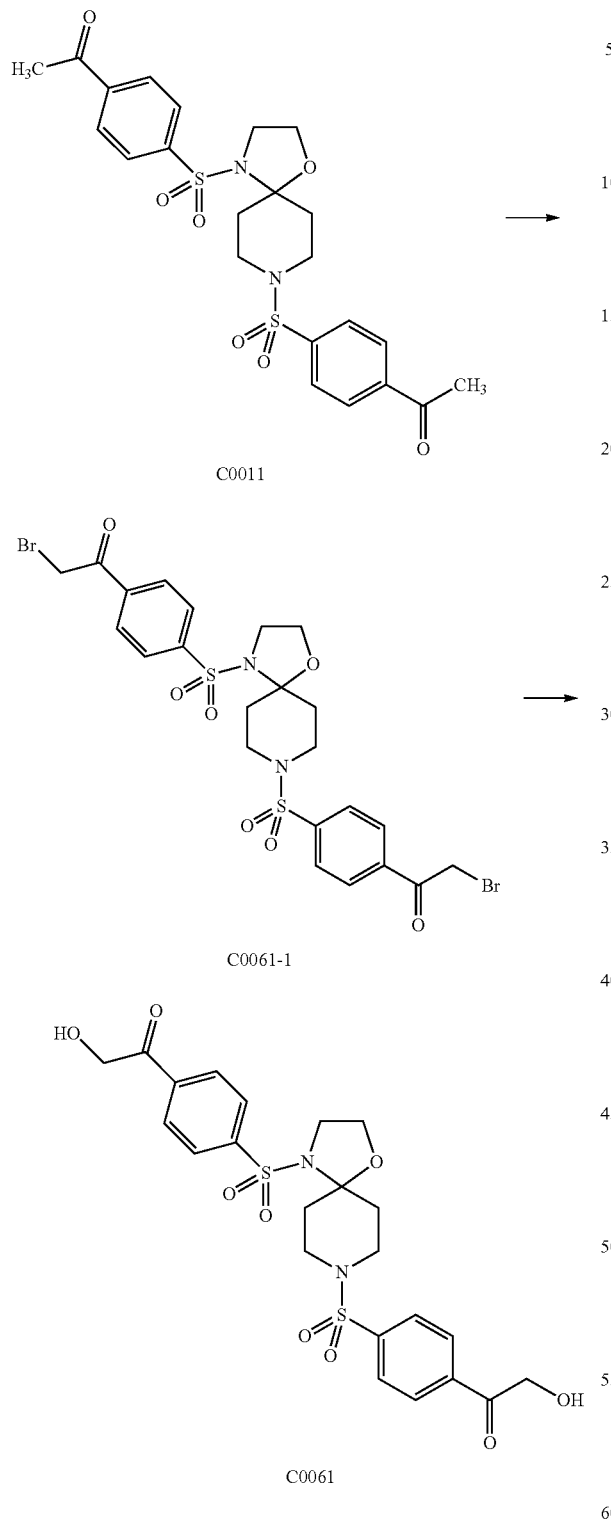

a. Preparation of C0061-1

To the solution of C0011 (20 mg, 0.0395 mmol) in pyridine (0.6 mL) was added NBS (14 mg, 0.079 mmol). The mixture was stirred overnight (about 18 hours) at room temperature. LCMS showed that C0011 did not react. The reaction was warmed to 80° C. and stirred for 2 days.

206

Preparation of Compound C0062

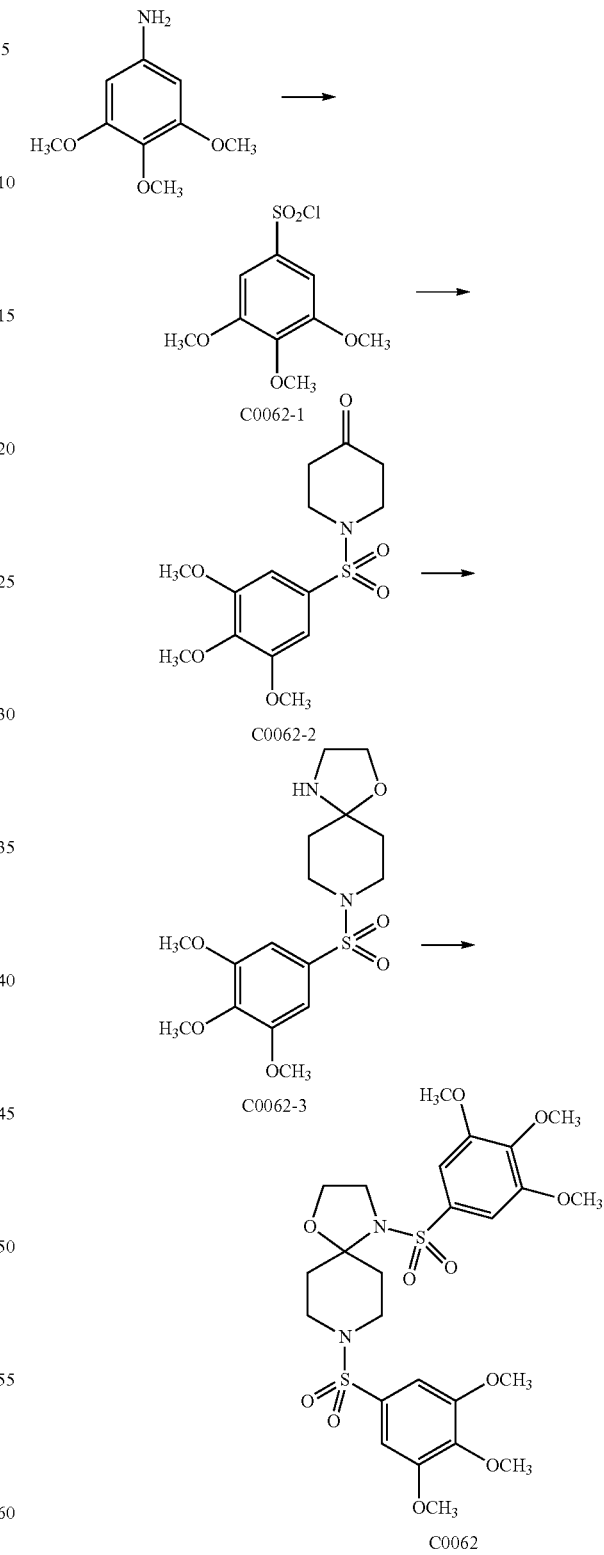

a. Preparation of Compound C0062-1

CuCl$_2$ (2.5 g) was added to a saturated solution of SO$_2$ [from the reaction of NaHSO$_3$ and H$_2$SO$_4$) in glacial acetic acid (200 mL) and SO$_2$ gas was slowly bubbled into the solution for 2 hours. 3,4,5-Trimethoxyaniline (10 g, 54.6 mmol) was added to a solution of concentrated HCl (40 mL) and H$_2$O (50 mL) and the mixture was stirred for 1 hour at 0° C. To this solution was added a solution of NaNO$_2$ (3.77 g, 54.6 mmol) in H$_2$O (20 mL) at such a rate that the temperature did not rise above 0° C. The mixture was stirred for 0.5 hours and then added dropwise to the SO$_2$ and CuCl$_2$ saturated solution. The reaction was then stirred for 1 hour. H$_2$O (1000 mL) was added and continued stirring for 0.5 hour. Then the product was collected by suction filtration, washed with H$_2$O, dried in vacuum at 50° C.

b. Preparation of Compound C0062-2

Compound C0062-1 (300 mg, 1.12 mmol) was added to a solution of piperidin-4-one hydrochloride (229 mg, 1.68 mmol) in pyridine (10 mL). The reaction mixture was stirred overnight (about 18 hours) at room temperature. To the reaction mixture, 20 mL of water was added and the reaction mixture was extracted with dichloromethane (3×). The organic layers were combined and washed with 1N HCl (2×) and brine (1×). The crude product was dried and then concentrated under vacuum to afford 279 mg of crude product (yield: 75.7).

c. Preparation of Compound C0062-3 p-Toluenesulfonic acid monohydrate (4.51 mg, 0.024 mmol) and 2-aminoethanol (0.9 mL) were added to a solution of C0062-2 (279 mg, 0.848 mmol) in ethanol (5 mL). The reaction mixture was stirred overnight (about 18 hours) at room temperature. The reaction mixture was dissolved in CH$_2$Cl$_2$ (30 mL) and washed with aqueous of NaHCO$_3$ and brine, dried, concentrated under vacuum to afford 226 mg of crude product. (yield: 71.6%).

d. Preparation of Compound C0062

Compound C0062-1 (189 mg, 0.709 mmol) was added to a solution of C0062-3 (220 mg, 0.591 mmol) in pyridine (6 mL). The reaction mixture was stirred overnight (about 18 hours) at room temperature. The solvent was removed and the residue was dissolved in CH$_2$Cl$_2$ and washed with 1N HCl and brine, dried, and concentrated under vacuum to afford 335 mg of crude product. (yield: 94.2%). 94 mg of the crude product was purified via preparation TLC (petroleum ether: ethyl acetate=1:1) to afford 35 mg of final product. (yield: 37.2%).

Preparation of Compound C0064

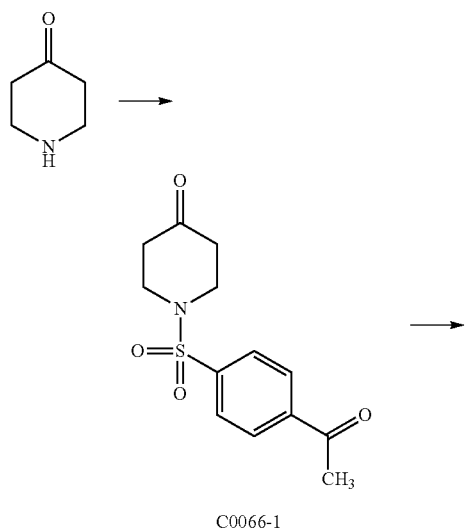

C0066-1

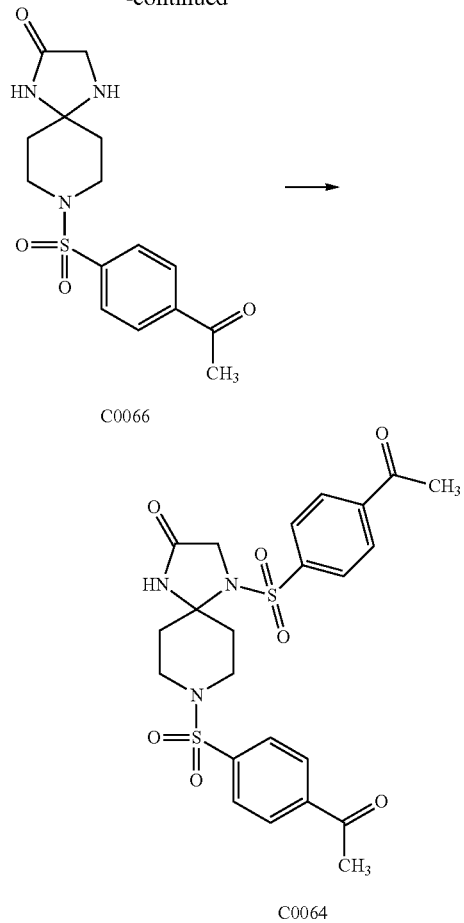

C0066

C0064 a. Preparation of Compound C0066-1

Triethylamine (606 mg, 6.0 mmol) and piperidin-4-one (297 mg, 3.0 mmol) were added to a solution of 4-acetylbenzene-1-sulfonyl chloride (656 mg, 3.0 mmol) in CH$_2$Cl$_2$ (10 mL). The mixture was stirred at room temperature overnight (about 18 hours). The solution was washed with water, dried over anhydrous Na$_2$SO$_4$ and concentrated to obtain the title product as yellow solid (643 mg, Yield: 76%).

b. Preparation of Compound C0066

Triethylamine (230 mg, 2.28 mmol) and C0066-1 (643 mg, 2.28 mmol) were added to a solution of 2-aminoacetamide hydrochloride (252 mg, 2.28 mmol) in CH$_3$OH (20 mL). Then the mixture was heated to reflux overnight (about 18 hours). Then the solution was cooled and filtered to obtain C0066 as white solid (550 mg, Yield: 72%).

c. Preparation of Compound C0064

4-Acetylbenzene-1-sulfonyl chloride (175 mg, 0.8 mmol) was added to a solution of C0066 (135 mg, 0.4 mmol) in pyridine (4.0 mL) at 60° C. The mixture was stirred at 60° C. overnight (about 18 hours). Thin-layer chromatography suggested there was the product we needed. The mixture was concentrated and purified by silica gel to obtain the title product as white solid (30 mg, Yield: 14%).

$^1$H NMR (400 MHz, DMSO): 9.51 (s, 1H); 8.18 (d, J=8.0 Hz, 2H); 8.13 (d, J=8.4 Hz, 2H); 8.02 (d, J=7.2 Hz, 2H); 8.02 (d, J=8.4 Hz, 2H); 3.89 (s, 2H); 3.70 (d, J=6.8 Hz, 2H); 2.65 (s, 6H); 2.64-2.45 (m, 4H); 1.65 (d, J=10.8 Hz, 2H); MS (ESI) calcd for C$_{23}$H$_{25}$N$_3$O$_7$S$_2$ (m/z): 519.59. found: 520.3 [M+1]$^+$.

Preparation of Compound C0065

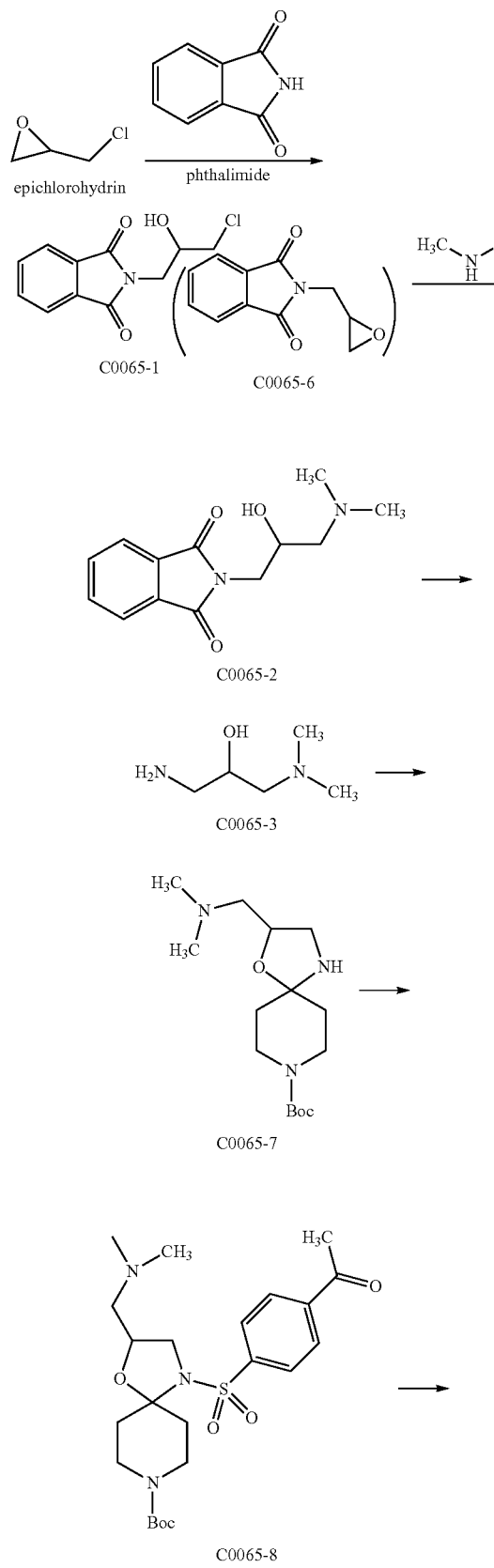

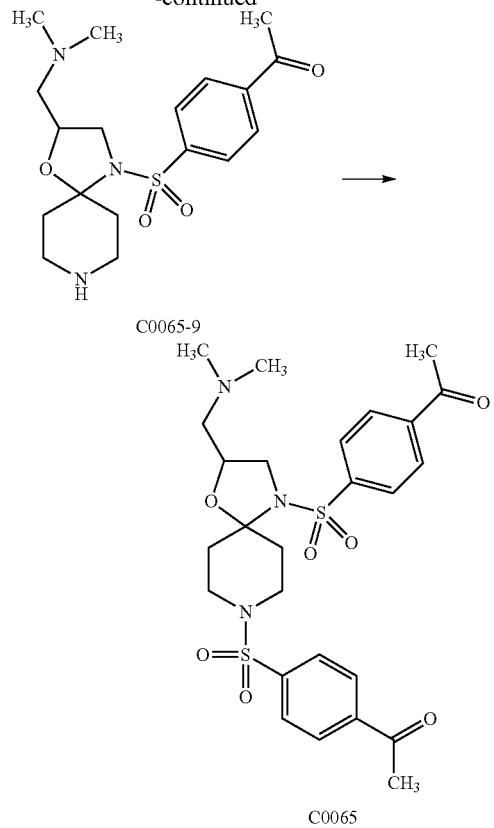

a. Preparation of Compound C0065-1

A suspension of phthalimide (7.35 g, 50 mmol) in epichlorohydrin (15.7 mL, 200 mmol) was boiled under reflux for 10 hours. The mixture was allowed to cool and concentrated to brown oil. The crude product was purified by silica gel to obtain 4.7 g of C0065-6 (structure showed in the above scheme) as white solid (yield: 46%) and 4.1 g of C0065-1 as white solid.

b. Preparation of Compound C0065-2

The mixture of compound C0065-1 and C0065-6 (3.1 g, 15 mmol) and aqueous dimethylamine (10.3 g) was stirred overnight (about 18 hours) at room temperature. Thin-layer chromatography suggested the reaction complete. The reaction mixture was washed with $CH_2Cl_2$ for 3 times and the water was removed under reduced pressure to obtain the crude product of C0065-2.

c. Preparation of Compound C0065-3

The compound C0065-2 was added into 20% hydrochloric acid (20 mL) and refluxed for 4 hours. The mixture was cooled to room temperature and then, phthalic acid was separated. The aqueous solution was washed by ether and concentrated. The residue was dissolved in NaOH (20%) and extracted with $CH_2Cl_2$ (3×). The combined organic layers were dried over $Na_2SO_4$ and concentrated to obtain 1.1 g of the product as yellow oil (yield: 62%).

d. Preparation of Compound C0065-7

A solution of N-Boc-piperidin-4-one (420 mg, 2.1 mmol) in ethanol (4 mL) was treated with compound C0065-3 (500 mg, 4.2 mmol). The mixture was stirred overnight (about 18 hours) at room temperature. The solvent was removed under reduced pressure. The residue was diluted with $CH_2Cl_2$ (30 mL) and washed with saturated aqueous $Na_2CO_3$ (30 mL×6).

The organic phase was dried over anhydrous Na₂SO₄, then concentrated to give 600 mg of compound C0065-4 as a yellow oil (yield: 95%)

e. Preparation of Compound C0065-8

4-Acetylbenzene-1-sulfonyl chloride (200 mg, 0.9 mmol) was added to a solution of compound C0065-7 (600 mg, 2.0 mmol) in pyridine (4 mL). The mixture was stirred at room temperature for 4 hours. The solvent was removed under reduced pressure. The residue was purified with silica gel to obtain 220 mg of the title compound as a white solid (yield: 50%)

f. Preparation of Compound C0065-9

A solution of compound C0065-8 (220 mg, 0.45 mmol) in 3 mL of CH₂Cl₂ and 0.5 mL CF₃COOH and the mixture were stirred for 1 hour at room temperature. The mixture was added 30 mL of CH₂Cl₂ and washed with saturated sodium carbonate solution (30 mL×3). The organic layer was dried and concentrated to get the crude product 150 mg as white solid. The crude product was used for the next step without any further purification.

e. Preparation of Compound C0065

4-Acetylbenzene-1-sulfonyl chloride (103 mg, 0.47 mol) was added to the solution of compound C0065-9 (150 mg, 0.39 mmol) in pyridine (3 mL). The mixture was stirred overnight (about 18 hours) at room temperature. The solvent was removed under reduced pressure. The residue was purified with silica gel to obtain the 150 mg of title compound as a white solid (yield: 68%). The structure was confirmed by ¹H NMR & LC-MS. Purity 94.4% by HPLC, shown as follows.

¹H NMR (400 MHz, CDCl₃): 8.02 (m, 4H); 7.83 (d, J=8.4 Hz, 2H); 7.82 (d, J=8.4 Hz, 2H); 4.15-3.98 (m, 1H); 3.75-3.66 (m, 2H); 3.65 (dd, J=8.8, 5.6 Hz, 1H); 3.01 (t, J=8.8 Hz, 1H); 2.61 (s, 3H); 2.60 (s, 3H); 2.56-2.49 (m, 3H); 2.42-2.33 (m, 1H); 2.30 (d, J=6.0 Hz, 2H); 2.09 (s, 6H); 1.69 (dd, J=13.2, 2.1 Hz, 1H); 1.39 (d, J=7.8 Hz, 1H); MS (ESI) calcd for C₂₆H₃₃N₃O₇S₂ (m/z): 563.69. found: 564.4[M+1]⁺.

C0065 HCl Salt

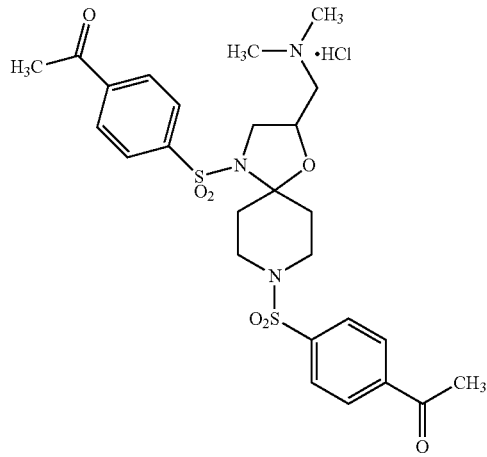 [SMILES: CC(=O)c1ccc(S(=O)(=O)N2CCC3(CC2)OC(CN(C)C)CN3S(=O)(=O)c2ccc(C(C)=O)cc2)cc1 ; Cl]

¹H NMR (400 MHz, CDCl₃): 8.22 (m, 4H); 8.01 (m, 4H); 4.81 (br, m, 1H); 4.03-3.85 (m, 3H); 3.40-3.07 (m, 2H); 2.98-2.86 (m, 1H); 2.80 (s, 3H); 2.79 (s, 3H); 2.73 (m, 9H); 2.49 (td, J=13.4, 4.6 Hz, 1H); 1.88 (d, J=14.0 Hz, 1H); 1.70 (d, J=9.9 Hz, 1H); LCMS (ESI) calcd for C₂₆H₃₄ClN₃O₇S₂ (m/z): 600.15. found: 564.3[M+1-HCl]⁺.

Preparation of Compound C0067

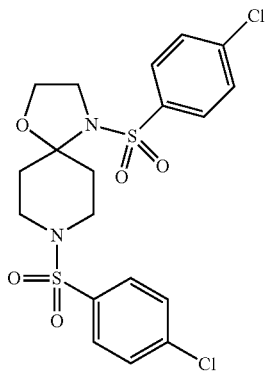

C0067

This compound was made using conditions and procedures discussed elsewhere herein.

Preparation of Compound C0068

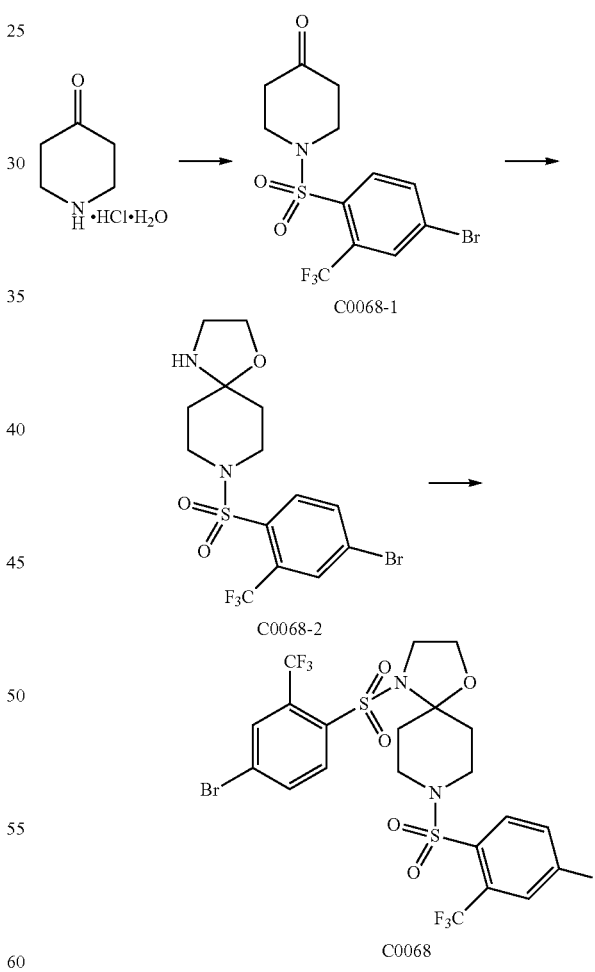

a. Preparation of Compound C0068-1

Piperidin-4-one hydrochloride hydrate (92 mg, 0.6 mmol) in pyridine (2 mL) was treated with 4-bromo-2-(trifluoromethyl)benzene-1-sulfonyl chloride (194 mg, 0.6 mmol). The mixture was stirred at room temperature overnight (about 18 hours). The solvent was removed under reduced pressure. To the residue was added CH$_2$Cl$_2$ (50 mL), then the solution was washed with 1N HCl (20 mL×3), dried over Na$_2$SO$_4$, and concentrated to give the title product as yellow solid (117 mg; yield: 50.5%).

b. Preparation of Compound C0068-2 p-Toluenesulfonic acid monohydrate (1.59 mg) and 2-aminoethanol (0.32 mL, 5.54 mmol) were added to a solution of compound C0068-1 (107 mg, 0.28 mmol) in ethanol (4 mL). The mixture was stirred at room temperature overnight (about 18 hours). The solvent was removed under reduced pressure. CH$_2$Cl$_2$ (70 mL) was added to the residue and washed with saturated NaHCO$_3$ (25 mL×4), then dried over Na$_2$SO$_4$ and concentrated to give the product as yellow oil (110 mg, yield: 91.6%).

c. Preparation of Compound C0068

A solution of C0068-2 (110 mg, 0.26 mmol) in pyridine (1.5 mL) was treated with 4-bromo-2-(trifluoromethyl)benzene-1-sulfonyl chloride (100 mg, 0.31 mmol). The mixture was stirred at room temperature overnight (about 18 hours). The reaction mixture was concentrated in vacuo to remove the pyridine and the residue was dissolved with CH$_2$Cl$_2$, washed with saturated NaHCO$_3$. The organic layer was dried over Na$_2$SO$_4$ and concentrated in vacuo to obtain the crude product. The crude product was purified by silica gel and then preparative thin-layer chromatography to give the title product as yellow solid (30 mg, yield: 12.7%).

$^1$H NMR (400 MHz, CDCl$_3$): 8.03-7.98 (m, 4H); 7.87 (m, 2H); 4.02 (t, J=6.8 Hz, 2H); 3.78 (m, 2H); 3.52 (t, J=6.8 Hz, 2H); 3.00 (t, J=12.8 Hz, 2H); 2.47 (dt, J=4.8, 13.2 Hz, 2H); 1.85-1.77 (m, 2H); MS (ESI) calcd for C$_{21}$H$_{18}$N$_2$O$_5$S$_2$Br$_2$F$_6$ (m/z): 716.31. found: 717.0 [M+1]$^+$.

Preparation of Compound C0069

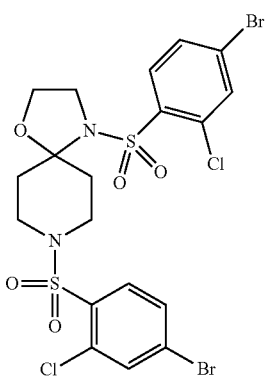

C0069

This compound was made using conditions and procedures discussed elsewhere herein.

Preparation of Compound C0070

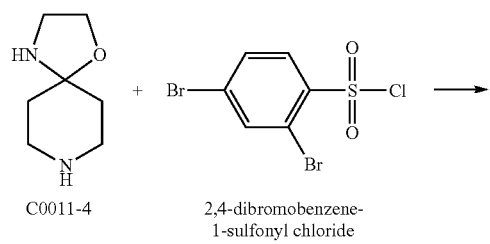

C0011-4    2,4-dibromobenzene-1-sulfonyl chloride

-continued

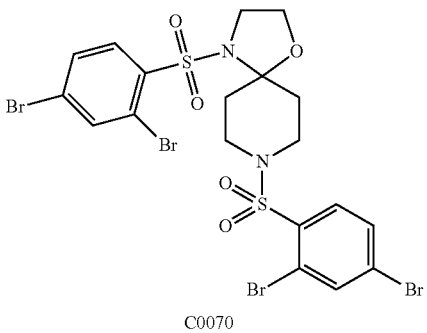

C0070

2,4-Dibromobenzene-1-sulfonyl chloride (502 mg, 1.5 mmol) was added to the solution of compound C0011-4 (71 mg, 0.5 mmol) in pyridine (2 mL). The mixture was stirred overnight (about 18 hours) at room temperature. The reaction mixture was concentrated in vacuo to remove the pyridine and the residue was dissolved with dichloromethane, and washed with 1N HCl. The organic layer was dried over Na$_2$SO$_4$ and concentrated in vacuo to obtain the crude product. The crude product was purified by preparative thin-layer chromatography to obtain 50 mg of the title product as white solid (yield: 13%). The crude product was further purified by preparative thin-layer chromatography to obtain compound C0070 as white product (24 mg; yield: 6.5%). The structure was confirmed by NMR & LC-MS. Purity: 96.8% by HPLC, shown as follows:

$^1$H NMR (400 MHz, CDCl$_3$): 8.00-7.89 (m, 4H); 7.62-7.55 (m, 2H); 3.98 (t, J=6.8 Hz, 2H); 3.72 (m, 4H); 3.01 (m, 2H); 2.36-2.20 (m, 2H); 1.72 (d, J=13.2 Hz, 2H); MS (ESI) calcd for C$_{19}$H$_{18}$Br$_4$N$_2$O$_5$S$_2$ (m/z): 738.1. found: 739.0[M+1]$^+$.

Preparation of Compound C0071

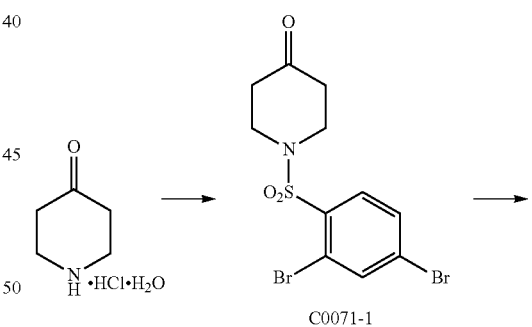

C0071-1

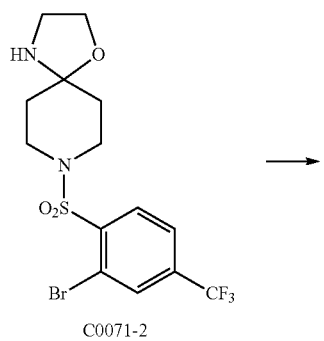

C0071-2

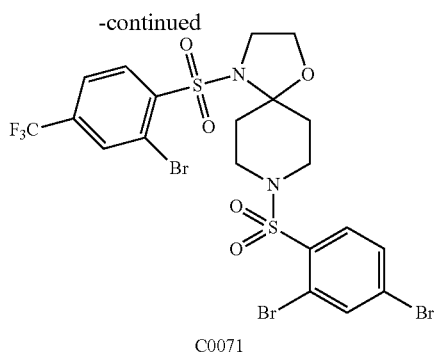

C0071

Preparation of Compound C0072

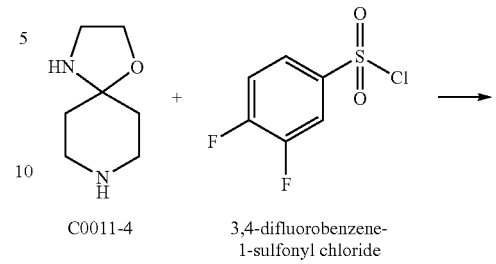

C0011-4    3,4-difluorobenzene-
           1-sulfonyl chloride a. Preparation of Compound C0071-1

Piperidin-4-one hydrochloride hydrate (95 mg, 0.62 mmol) in pyridine (3 mL) was treated with 2-bromo-4-(trifluoromethyl)benzene-1-sulfonyl chloride (200 mg, 0.62 mmol). The mixture was stirred at room temperature overnight (about 18 hours). The solvent was removed under reduced pressure. The residue was diluted with $CH_2Cl_2$ (30 mL) and washed with 1N HCl (30 mL×3). The organic phase was dried over anhydrous $Na_2SO_4$, and concentrated to give the crude product as yellow solid (150 mg; yield: 62.6%)

b. Preparation of Compound C0071-2 p-Toluenesulfonic acid monohydrate (2 mg, 0.01 mmol) and 2-aminoethanol (0.44 mL) were added to the solution of compound C0071-1 (145 mg, 0.376 mmol) in ethanol (3 mL). The mixture was stirred overnight (about 18 hours) at room temperature. The solvent was removed under reduced pressure. The residue was diluted with $CH_2Cl_2$ (30 mL) and washed with saturated aqueous $NaHCO_3$ (30 mL×6). The organic phase was dried over anhydrous $Na_2SO_4$, then concentrated to give compound C0071-2 as yellow oil (140 mg; yield: 86%).

c. Preparation of Compound C0071

A solution of compound C0071-2 (140 mg, 0.326 mmol) in pyridine (3 mL) was treated with 2-bromo-4-(trifluoromethyl)benzene-1-sulfonyl chloride (127 mg, 0.391 mmol). The mixture was stirred overnight (about 18 hours) at room temperature overnight (about 18 hours). The solvent was removed under reduced pressure. The residue was diluted with $CH_2Cl_2$ (30 mL) and washed with 1N HCl (30 mL×3). The organic phase was dried over anhydrous $Na_2SO_4$, and then concentrated to give the crude product. The crude product was purified with preparative thin-layer chromatography to obtain the title product as white solid (30 mg; yield: 12.8%).

$^1$H NMR (400 MHz, $CDCl_3$): 8.25 (d, J=7.6 Hz, 1H); 8.20 (d, J=8.4 Hz, 1H); 8.01 (s, 1H), 8.00 (s, 1H); 7.75 (d, J=8.8 Hz, 1H), 7.71 (d, J=9.2 Hz, 1H); 4.03 (t, J=6.3 Hz, 2H); 3.81 (dd, J=7.6, 5.2 Hz, 2H); 3.74 (t, J=6.3 Hz, 2H); 3.08 (dt, J=12.8, 6.8 Hz, 2H); 2.35 (td, J=12.8, 4.8 Hz, 2H); 1.77 (d, J=12.4 Hz, 2H); MS (ESI) calcd for $C_{21}H_{18}Br_2F_6N_2O_5S_2$ (m/z): 716.31. found: 738.9[M+Na]$^+$.

3,4-Difluorobenzene-1-sulfonyl chloride (319 mg, 1.5 mmol) was added to the solution of compound C0011-4 (71 mg, 0.5 mmol) in pyridine (2 mL). The mixture was stirred overnight (about 18 hours) at room temperature. The reaction mixture was concentrated in vacuo to remove the pyridine and the residue was dissolved with $CH_2Cl_2$, washed with 1N HCl and then the organic layer was dried over $Na_2SO_4$, concentrated in vacuo to obtain the crude product. The crude product was purified by preparative thin layer chromatography to obtain the title product. (53 mg, yield: 21.5%). The product was recrystallized with $CH_2Cl$ and petroleum ether to obtain 25 mg of C0072 as white solid (25 mg, yield: 10.1%).

$^1$H NMR (400 MHz, $CDCl_3$): 7.62 (m, 4H); 7.34 (m, 2H); 3.91 (t, J=6.0 Hz, 2H); 3.77 (m, 2H); 3.48 (t, J=6.0 Hz, 2H); 2.63-2.47 (m, 4H); 1.70-1.60 (m, 2H); MS (ESI) calcd for $C_{19}H_{18}F_4N_2O_5S_2$ (m/z): 494.48. found: 495.0 [M+1]$^+$.

Preparation of Compound C0073

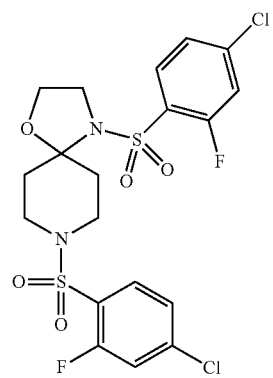

This compound was made using conditions and procedures discussed elsewhere herein.

Preparation of Compound C0077

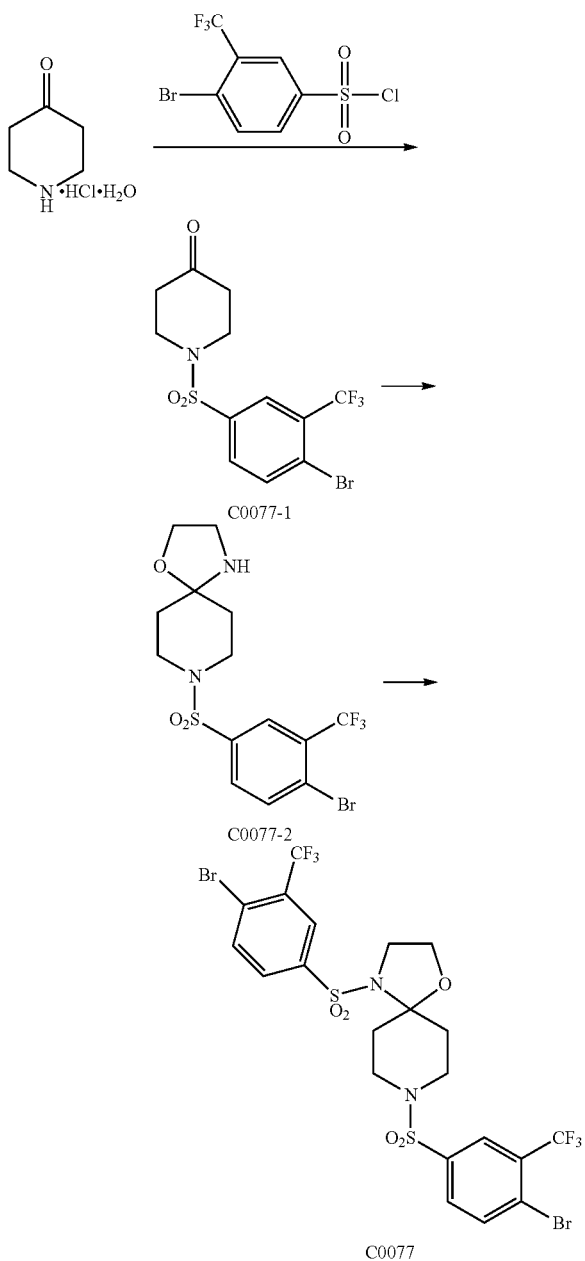

a. Preparation of Compound C0077-1

Piperidin-4-one hydrochloride hydrate (153.5 mg, 1 mmol) in pyridine (2 mL) was treated with 4-bromo-3-(trifluoromethyl)benzene-1-sulfonyl chloride (323.5 mg, 1 mmol). The mixture was stirred at room temperature overnight (about 18 hours). The solvent was removed under reduced pressure. CH$_2$Cl$_2$ (50 mL) was added to the residue, then the solution was washed with 1N HCl (20 mL×3), dried over Na$_2$SO$_4$ and concentrated to give the title product as white solid (216 mg; yield: 56%).

b. Preparation of Compound C0077-2 p-Toluenesulfonic acid monohydrate (3.1 mg) and 2-aminoethanol (0.62 mL, 10.7 mmol) was added to a solution of compound C0077-1 (207 mg, 0.54 mmol) in ethanol (5 mL). The mixture was stirred at room temperature overnight (about 18 hours). The solvent was removed under reduced pressure. CH$_2$Cl$_2$ (70 mL) was added to the residue and washed with saturated NaHCO$_3$ (25 mL×4), then dried over Na$_2$SO$_4$ and concentrated to give the product as yellow oil (210 mg, yield: 90.7%).

c. Preparation of Compound C0077

A solution of C0077-2 (110 mg, 0.26 mmol) in pyridine (1.5 mL) was treated with 4-bromo-3-(trifluoromethyl)benzene-1-sulfonyl chloride (100 mg, 0.31 mmol). The mixture was stirred at room temperature overnight (about 18 hours). The reaction mixture was concentrated in vacuo to remove the pyridine and the residue was dissolved with CH$_2$Cl$_2$, washed with saturated NaHCO$_3$ and then the organic layer was dried over Na$_2$SO$_4$, concentrated in vacuo to obtain the crude product. The crude product was purified by silica gel to obtain the crude product as white solid (180 mg, yield: 51.3%). Further, purification by preparative HPLC gave the title product as white solid (87 mg, yield: 24.8%).

$^1$H NMR (400 MHz, CDCl$_3$): 8.11 (d, J=2.4 Hz, 1H), 8.06 (d, J=2.0 Hz, 1H); 7.92 (d, J=8.4 Hz, 2H); 7.87 (dd, J=2.4, 8.0 Hz, 1H); 7.78 (dd, J=2.0, 8.0 Hz, 1H); 3.95 (t, J=6.0 Hz, 2H); 3.84-3.83 (m, 2H); 3.50 (t, J=6.4 Hz, 2H); 2.61-2.56 (m, 4H); 1.68 (m, 2H); MS (ESI) calcd for C$_{21}$H$_{18}$N$_2$O$_5$S$_2$Br$_2$F$_6$ (m/z): 716.31.

Preparation of Compound C0078

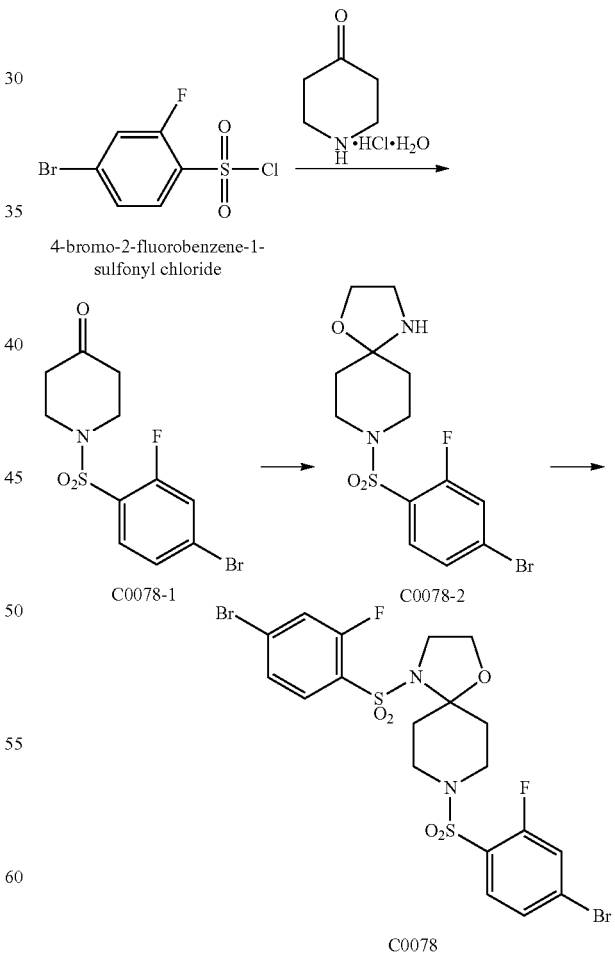

a. Preparation of Compound C0078-1

4-Bromo-2-fluorobenzene-1-sulfonyl chloride (300 mg, 1.1 mmol) was added to a solution of piperidin-4-one hydrochloride hydrate (169 mg, 1.1 mmol) in pyridine (2 mL). The mixture was stirred at room temperature overnight (about 18 hours). The solvent was removed under reduced pressure. The residue was diluted with $CH_2Cl_2$ (30 mL) and washed with 1N HCl (30 mL×3). The organic phase was dried over anhydrous $Na_2SO_4$, and concentrated to give the crude product as white solid (230 mg, yield: 62.4%)

b. Preparation of Compound C0078-2

2-Aminoethanol (0.78 mL, 13.39 mmol) and p-toluenesulfonic acid monohydrate (3.8 mg, 0.02 mmol) were added to the solution of compound C0078-1 (225 mg, 0.67 mmol) in ethanol (7 mL). The mixture was stirred overnight (about 18 hours) at room temperature. The solvent was removed under reduced pressure. The residue was diluted with $CH_2Cl_2$ (30 mL) and washed with saturated aqueous $NaHCO_3$ (30 mL×6). The organic phase was dried over anhydrous $Na_2SO_4$, and concentrated to give compound C0078-2 as yellow oil (260 mg)

c. Preparation of Compound C0078

4-Bromo-2-fluorobenzene-1-sulfonyl chloride (216 mg, 0.79 mmol) was added to a solution of compound C0078-2 (250 mg, 0.66 mmol) in pyridine (2 mL). The mixture was stirred at room temperature overnight (about 18 hours). Diethyl ether was added and the resulting precipitate was collected by filtration to obtain 180 mg of the crude product and purified by chromatography (petroleum ether:ethyl acetate=10:1 to 3:1) to obtain 40 mg of the product (40 mg; yield: 10%). The structure was confirmed by $^1H$ NMR & MS, purity 98.5%.

$^1H$ NMR (400 MHz, $CDCl_3$): 7.79 (dd, J=8.4, 7.6 Hz, 1H); 7.71 (dd, J=8.4, 7.6 Hz, 1H); 7.45 (m, 4H); 3.97 (t, J=6.4 Hz, 2H); 3.82 (dd, J=10.0, 2.8 Hz, 2H); 3.75 (t, J=6.4 Hz, 2H); 2.81 (t, J=12.8 Hz, 2H); 2.39 (dt, J=12.8, 4.8 Hz, 2H); 1.61 (d, J=10.8 Hz, 2H); MS (ESI) calcd for $C_{19}H_{18}Br_2F_2N_2O_5S_2$ (m/z):616.29. found: 619.1 $[M+1]^+$.

Preparation of Compound C0079M

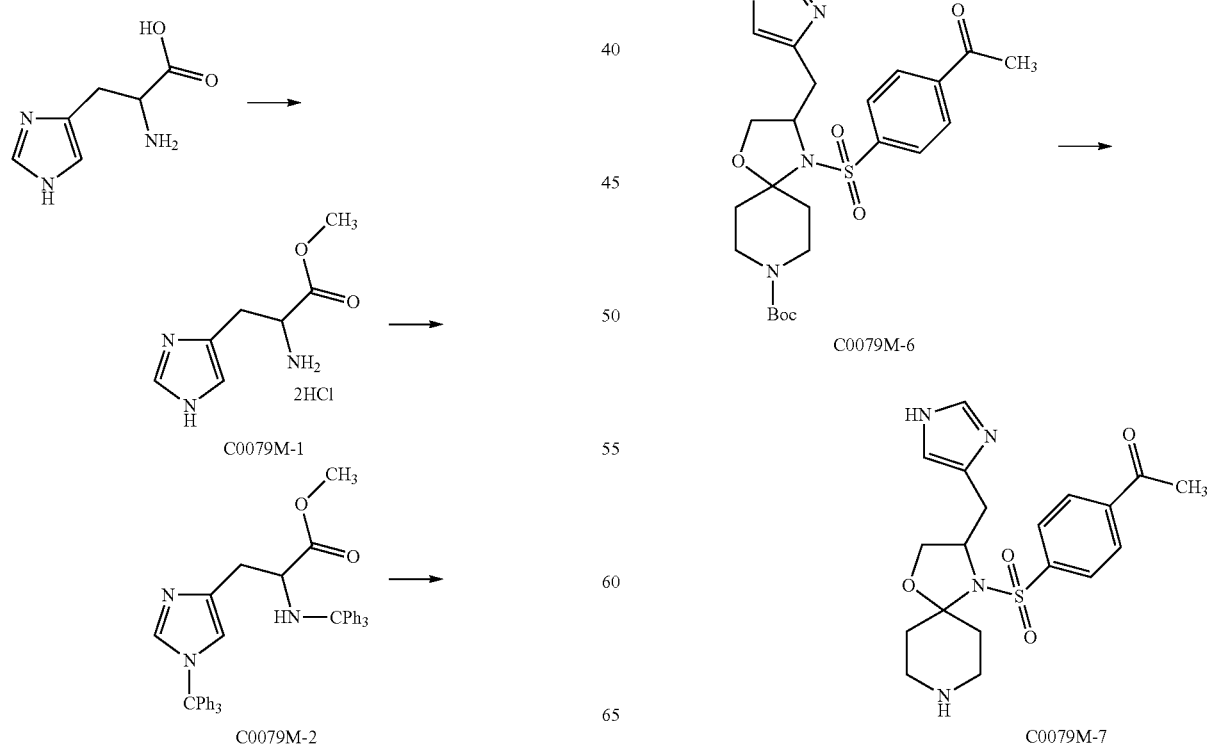

221

-continued

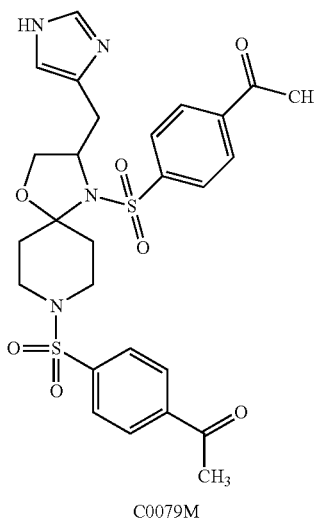
C0079M a. Preparation of Compound C0079M-5

Compound C0079M-4·2HCl (311 mg, 1.44 mmol) was dissolved in water (20 ml) and was added saturated aqueous NaHCO₃ to pH=7 and washed with dichloromethane. The water phase was concentrated and the residue was dissolved in ethanol. The mixture was filtered and the filtrate was concentrated to afford 270 mg of compound C0079M-4. A mixture of C0079M-4 and t-butyl-4-oxopiperidine-1-carboxylate (344 mg, 1.73 mmol) in ethanol (5 ml) was stirred overnight (about 18 hours) at room temperature.

b. Preparation of Compound C0079M-6

The mixture of compound C0079M-5 (967 mg, 2.48 mmol) and 4-acetylbenzene-1-sulfonyl chloride (597 mg, 2.73 mmol) in pyridine (10 ml) was stirred overnight at room temperature. TLC suggested the reaction complete. The mixture was concentrated to remove the solvent. The residue was dissolved in dichloromethane and was washed with 0.1 N HCl and brine, dried, concentrated to afford 854 mg of crude product. The crude product was purified via column chromatography (CH₂Cl₂—CH₂Cl₂/CH₃OH=10/1) to afford a product (440 mg, yield: 40%).

Preparation of Compound C0080M

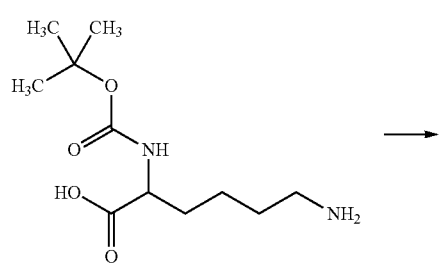

222

-continued

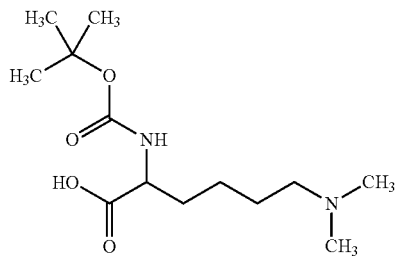
C0080-1

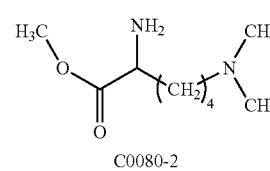
C0080-2

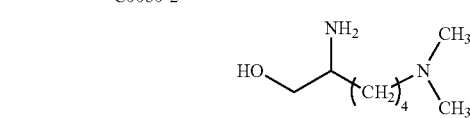
C0080-3

C0080-4

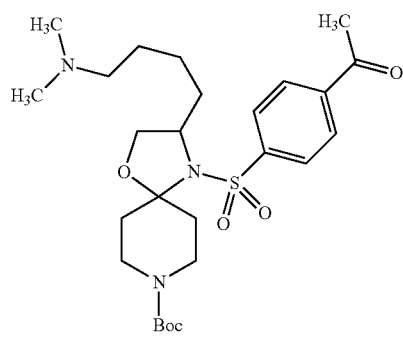
C0080-5

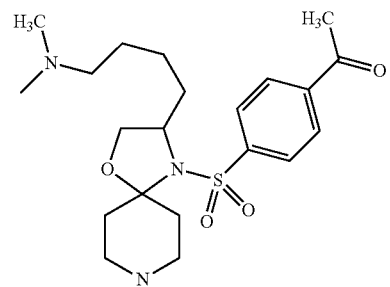
C0080-6

-continued

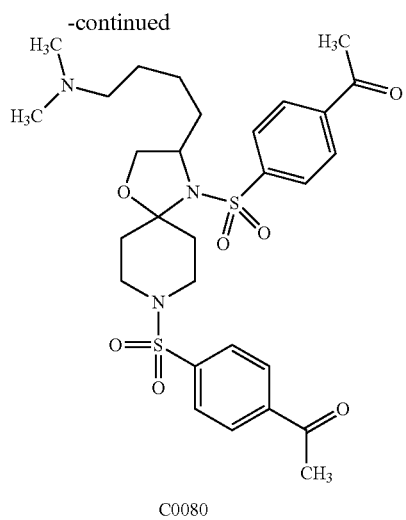

C0080 a. Preparation of Compound C0080-1

Boc-D-lys-OH (2.46 g, 9.4 mmol), suspended in CH$_2$OH (80 mL), was treated with 40% aq HCHO (1.6 mL, 19 mmol) followed by 10% Pd/C (200 mg). The reaction mixture was stirred under H$_2$ for 2 days. The catalyst was filtered off, and the filtrate was concentrated to dryness. Diethyl ether (100 mL) was added to the resulting oil, and stirring was continued to obtain a white solid, which was filtered off and washed with diethyl ether (2.6 g, yield: 100%, confirmed by $^1$H NMR).

b. Preparation of Compound C0080-2

C0080-1 (375 mg, 1.44 mmol) was dissolved in HCl/CH$_2$OH (8 mL), and the reaction mixture was stirred at reflux for 3 hours. Then the mixture was concentrated in vacuo to remove the solvent to obtain the HCl salt of the title product as white solid (354 mg, yield: 99.5%, confirmed by $^1$H NMR). Because the yield was low, the aqueous part was concentrated in vacuo to obtain yellow oil (57 mg, yield: 55.8%). $^1$H NMR also suggested it was the desired product.

c. Preparation of Compound C0080-2

C0080-2 (354 mg, 1.43 mmol) was suspended in THF (10 mL) and LiAH$_4$ (326 mg, 8.60 mmol) was added slowly at 0° C., and the reaction mixture was stirred at 0° C. to room temperature for 1.5 hours. Saturated Na$_2$SO$_4$ was added to quench the reaction and the mixture was filtered, then the organic layer was concentrated in vacuo to obtain the title product as yellow oil (150 mg, yield: 71.8%, confirmed by $^1$H NMR).

d. Preparation of Compound C0080-4

Compound C0080-3 (120 mg, 0.75 mmol) was added to a solution of N-Boc-piperidin-4-one (150 mg, 0.75 mmol) in ethanol (2 mL). The mixture was stirred at room temperature for overnight (about 18 hours). The solvent was removed under reduced pressure. CH$_2$Cl$_2$ (70 mL) was added to the residue and washed with saturated NaHCO$_3$ (25 mL×4), then dried over Na$_2$SO$_4$ and concentrated to give the product as yellow oil (234 mg, yield: 91.5%).

e. Preparation of Compound C0080-5

4-Acetylbenzenesulfonyl chloride (180 mg, 0.82 mmol) in pyridine (2 mL) was added to a solution of compound C0080-4 (234 mg, 0.69 mmol). The mixture was stirred at room temperature overnight (about 18 hours). The solvent was removed under reduced pressure. To the residue was added CH$_2$Cl$_2$ (70 mL) and washed with saturated NaHCO$_3$ (25 mL×4), then dried over Na$_2$SO$_4$ and concentrated to give the crude product. The crude product was purified by chromatograph with CH$_2$Cl$_2$:CH$_2$OH=50:1 to 3:1 to obtain the title product as yellow oil (80 mg, yield: 22.2%).

f. Preparation of Compound C0080-6

CF$_3$COOH (0.2 mL) was added to a solution of compound C0080-5 (80 mg, 0.15 mmol) in CH$_2$Cl$_2$ (3 mL). The mixture was stirred at room temperature for 2 hours. Then, CH$_2$Cl$_2$ was added and the mixture was washed with saturated Na$_2$CO$_3$. The organic layer was dried over Na$_2$SO$_4$, concentrated in vacuo to obtain the product as yellow oil (67 mg)

g. Preparation of Compound C0080

4-Acetylbenzenesulfonyl chloride (40 mg, 0.18 mmol) was added to a solution of compound C0080M-6 (mixture) (65 mg, 0.15 mmol) in pyridine (1.5 mL). The mixture was stirred at room temperature overnight (about 18 hours). The solvent was removed under reduced pressure. CH$_2$Cl$_2$ (70 mL) was added to the residue and washed with saturated NaHCO$_3$ (25 mL×4), then dried over Na$_2$SO$_4$ and concentrated to give the crude product. The crude product was purified by preparative thin-layer chromatography with CH$_2$Cl$_2$:CH$_2$OH=9:1 to obtain the title product as yellow oil (10 mg, yield: 11%).

$^1$H NMR (400 MHz, CDCl$_3$): 8.09 (d, J=8.0 Hz, 2H), 8.07 (d, J=8.4 Hz, 2H), 7.93 (d, J=8.4 Hz, 2H); 7.84 (d, J=8.0 Hz, 2H); 3.81 (m, 2H); 3.69-3.61 (m, 3H); 2.66-2.38 (m, 12H); 2.33 (s, 6H); 1.74 (m, 2H); 1.54-1.39 (m, 4H); 1.39-1.24 (m, 2H); MS (ESI) calcd for C$_{29}$H$_{39}$N$_3$O$_7$S$_2$ (m/z): 605.22. found: 606.5 [M+1]$^+$.

Preparation of Compound C0084

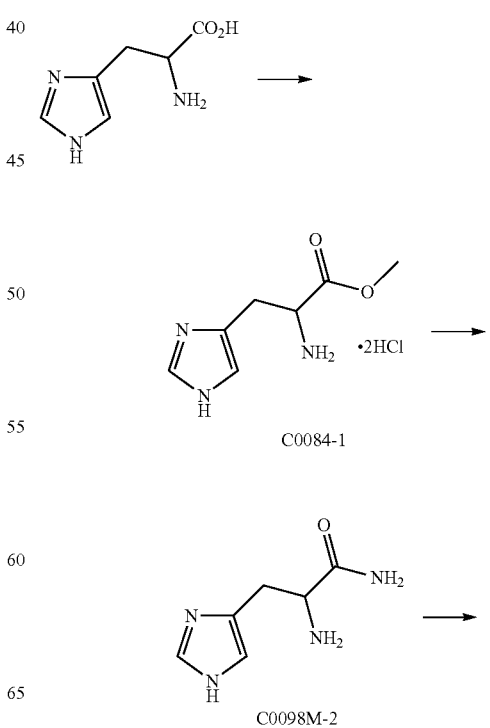

-continued

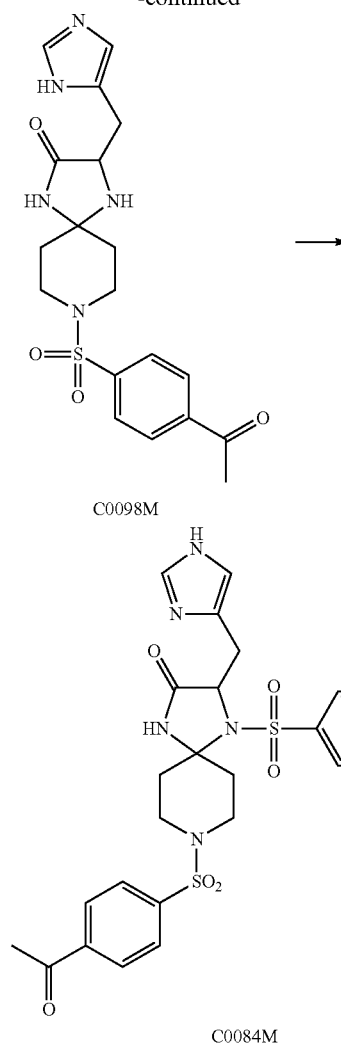

a. Preparation of Compound C0084-1

2-Amino-3-(1H-imidazol-4-yl)propanoic acid (5 g, 32.26 mmol) in HCl/CH$_3$OH (1N, 100 mL) was heated at reflux for 3 hours. The reaction mixture was concentrated to remove the solvent to obtain 7.5 g of the title product as white solid.

b. Preparation of Compound C0098M-2

220 mg of C0084-1 was dissolved in 10 mL of saturated NH$_4$OH (aq). The solution was stirred at room temperature overnight (about 18 hours). The solution was extracted with CHCl$_3$:CH$_2$OH=4:1 (6×) and the water was evaporated. The residue was washed with acetone and CHCl$_3$ to obtain the crude product (the mixture of the product and NH$_4$Cl) as white solid (210 mg). The structure was confirmed by $^1$H NMR & LC-MS (target M+1=155, material M+1=170).

c. Preparation of Compound C0098M 1-(4-Acetylphenylsulfonyl)-piperidin-4-one (365 mg, 1.3 mmol) in methanol (10 mL) was treated with C0098M-2 (200 mg, 1.3 mmol). The reaction was stirred at room temperature overnight (about 18 hours) and heated at reflux for 3 hours after which the solvent was removed in vacuo. The residue was purified by column chromatography to obtain the title product as white solid (65 mg; yield: 17%).

d. Preparation of Compound C0084

4-Acetylbenzene-1-sulfonyl chloride (32 mg, 0.14 mmol) and triethylamine (1 mL) was added to the solution of compound C0098M (50 mg, 0.12 mmol) in CHCl$_3$ (2 mL). The mixture was stirred at reflux for 8 hours, and then stirred at room temperature overnight (about 18 hours). The crude product was purified by chromatography eluted with CH$_2$Cl$_2$:CH$_2$OH Preparation of Compound C0085

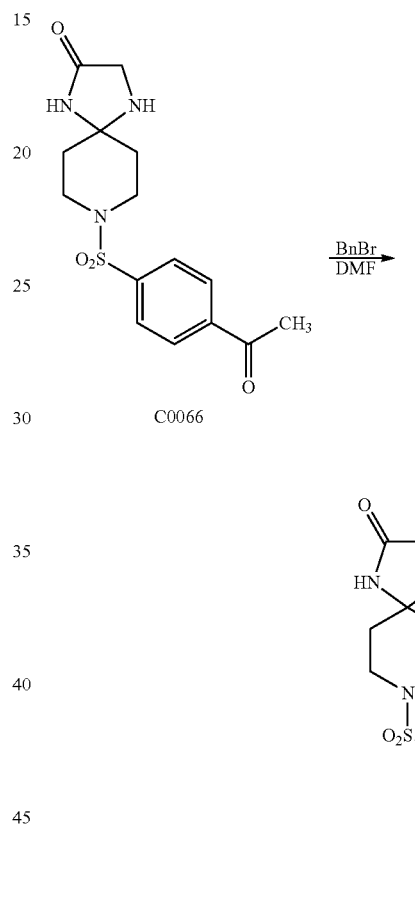

K$_2$CO$_3$ (30 mg, 0.22 mmol) and 1-(bromomethyl)benzene (38 mg, 0.22 mmol) in dimethylformamide (0.5 mL) was added to a solution of C0066 (67 mg, 0.2 mmol) in dimethylformamide (1.5 mL). The mixture was stirred at room temperature for 3 hours. Then the mixture was stirred at room temperature overnight (about 18 hours). Water was added and yellow solid was formed. The mixture was filtered and the collected solid was washed with water. The solid was dried to obtain the title product as yellow solid (24 mg, Yield: 28%, HPLC: 95%).

$^1$H NMR (400 MHz, CDCl$_3$): 8.66 (s, 1H); 7.99 (d, J=8.4 Hz, 2H); 7.81 (d, J=8.8 Hz, 2H); 7.37-7.26 (m, 5H); 3.86 (m, 2H); 3.67 (s, 2H); 2.88 (s, 2H); 2.49 (t, J=11.2 Hz, 2H); 2.37 (s, 3H); 2.13-2.06 (m, 2H); 1.66 (d, J=12.4 Hz, 2H); MS (ESI) calcd for C$_{22}$H$_{25}$N$_3$O$_4$S (m/z): 427.52. found: 428.2 [M+1]$^+$.

Preparation of Compound C0138M

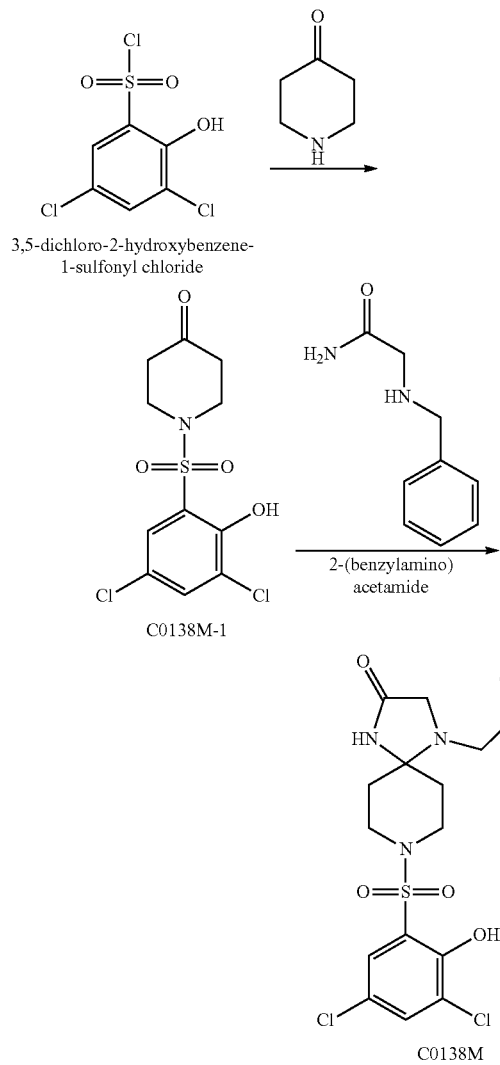

a. Preparation of Compound C0138M-1

The mixture of piperidin-4-one (266 mg, 2.68 mmol), 3,5-dichloro-2-hydroxybenzene-1-sulfonyl chloride (700 mg, 2.68 mmol) and triethylamine (0.7 mL, 5.36 mmol) in CHCl$_3$ (7.5 mL) was stirred at room temperature overnight (about 18 hours). The reaction mixture was diluted in CHCl$_3$ (30 mL) and washed with water, followed by 0.1 N HCl and brine. The organic layer was dried and concentrated to obtain the final product. (760 mg, yield: 87%).

b. Preparation of Compound C0138M

The mixture C0138M-1 (400 mg, 1.23 mmol), 2-(benzylamino)acetamide (202 mg, 1.23 mmol) and p-toluenesulfonic acid (6 mg) in CH$_3$OH (15 mL) was heated at reflux overnight (about 18 hours). A precipitate formed while the reaction refluxed. The solid was filtered and washed with methanol and ether. The solid was dried to obtain the final product (340 mg, yield: 60%).

$^1$H NMR (400 MHz, DMSO): 10.72 (s, 1H); 9.07 (s, 1H); 7.90 (s, 1H); 7.60 (s, 1H); 7.33-7.23 (m, 5H); 3.76 (d, J=10 Hz, 2H); 3.67 (s, 2H); 2.86-2.90 (m, 4H); 1.96 (m, 2H); 1.61 (d, J=12.4 Hz, 2H); MS (ESI) calcd for C$_{20}$H$_{21}$Cl$_2$N$_3$O$_4$S (m/z): 470.37. found: 468.1 [M−2]$^+$.

Preparation of Compound C0139M

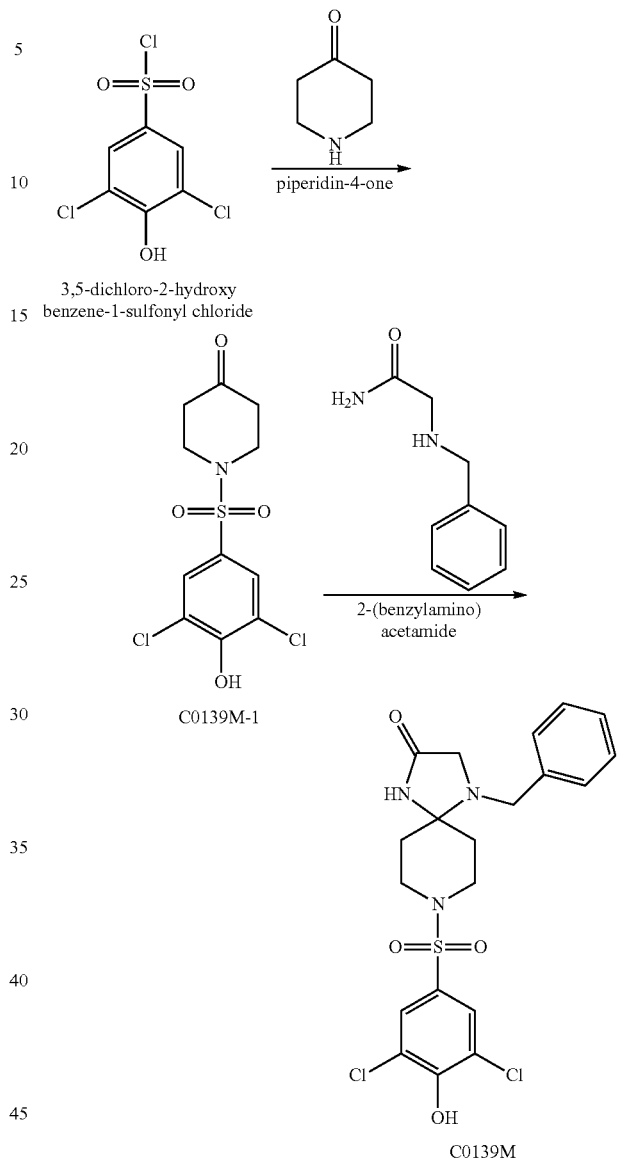

a. Preparation of Compound C0139M-1

The mixture of piperidin-4-one (114 mg, 1.15 mmol) in triethylamine (0.4 mL, 2.30 mmol), 3,5-dichloro-4-hydroxybenzene-1-sulfonyl chloride (300 mg, 1.15 mmol), and CHCl$_3$ (3.2 mL) was stirred at room temperature overnight (about 18 hours). The reaction mixture was diluted in CHCl$_3$ and the mixture was washed with water and 0.1 N HCl and brine. The organic layer was dried and concentrated to obtain the target product. (320 mg, yield: 86%).

b. Preparation of Compound C0139M

The solution of C0139M-1 (310 mg, 0.96 mmol), 2-(benzylamino)acetamide (157 mg, 0.96 mmol) and p-tolunesulfonic acid monohydrate (9 mg, 0.048 mmol) in CH$_3$OH (10 mL) was heated at reflux overnight (about 18 hours). The reaction solution was cooled to room temperature and the white solid was filtered and washed with CH$_3$OH and dried in vacuo to obtain 155 mg of the impure product as white solid. The impure product was washed with CH$_3$OH and dichloromethane to obtain title product as white solid (80 mg, yield:

16%). The structure was confirmed by $^1$H NMR & LC-MS, (target M+1=470), purity: 96.6%.

$^1$H NMR (400 MHz, CD$_3$OD): 7.63 (s, 2H); 7.26-7.13 (m, 5H); 3.74 (d, J=12.4 Hz, 2H); 3.66 (s, 2H); 3.03 (s, 2H); 2.55 (t, J=12.4 Hz, 2H); 2.05 (dt, J=13.6, 4.8 Hz, 2H); 1.68 (d, J=12.4 Hz, 2H); MS (ESI) calcd for C$_{20}$H$_{21}$Cl$_2$N$_3$O$_4$S (m/z): 470.37. found: 470.3 [M+1]$^+$.

Second Synthesis of C0139

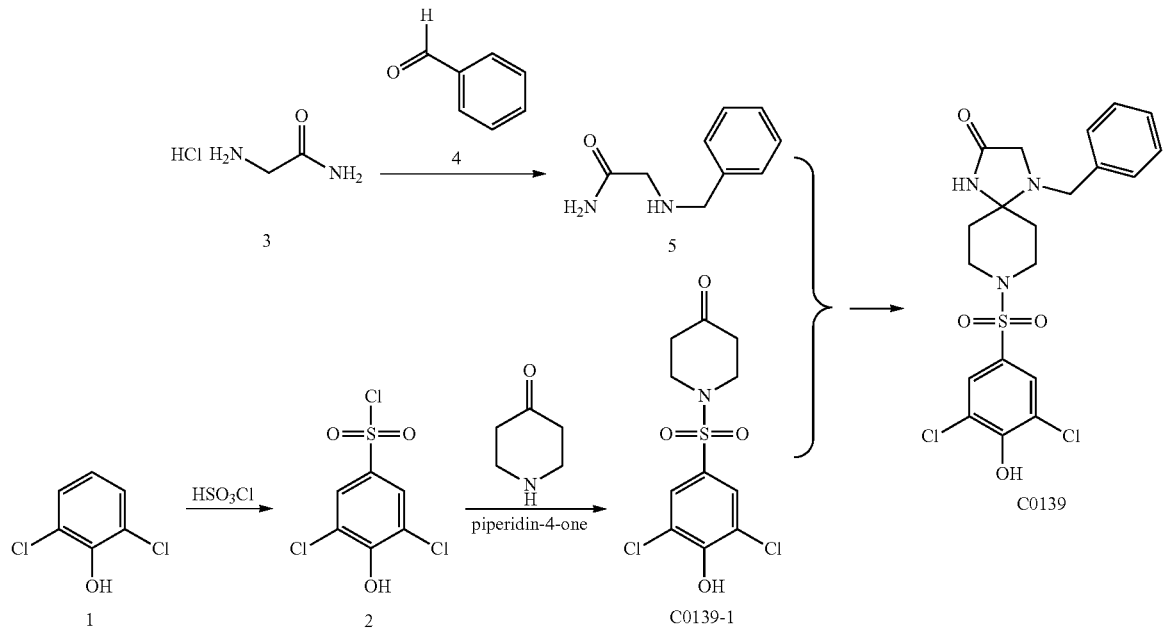

a. Preparation of Compound 5

Triethylamine (265 mL, 1.9 mol) was added to a suspension of compound 3 (210.5 g, 1.9 mol) in 2.5 L methanol at room temperature. Compound 4 (200 mL, 1.9 mol) was added dropwise at room temperature to the suspension of compound 3 and triethylamine. The mixture was stirred at room temperature for 3 hours (107.7 g, 2.85 mol). NaBH$_4$ was added at 0° C. and the resulting mixture was stirred overnight (about 18 hours). The solution was poured through a filter to remove a white solid and the filtrate was concentrated by removing the solvent. 1.0 L of water was added and the solution was extracted with ethyl acetate (500 mL×4). The organic phase was collected and dried over NaSO$_4$ overnight (about 18 hours). The solvent was removed by evaporation. 500 mL of ethyl acetate and 500 mL of ether was added to the residue and the resulting mixture was stirred for 30 minutes. The mixture was filtered and washed with ether, then dried under vacuum at 40° C. to provide the desired product as white solid (244 g, yield 69%).

$^1$H-NMR (400 MHz, CDCl$_3$): 3.29 (s, 2H); 3.77 (m, 2H); 5.68 (brs, 1H); 7.05 (brs, 1H); 7.23~7.31 (m, 5H).

b. Preparation of Compound 2

In an ice/water bath, HSO$_3$Cl (52 mL, 790 mmol) was added dropwise to a solution of compound 1 (20 g, 123 mmol) in 40 ml CS$_2$. The solution was stirred overnight (about 18 hours). The mixture was poured into 40 g of ice and filtered to obtain a white solid. The solid was washed with ice-water and dried to provide a white solid (30 g, yield 93%, TLC and LCMS confirmed it was compound 2, target M-1=258.8).

c. Preparation of Compound C0139-1

Piperidin-4-one (57 g, 0.42 mol) was added to a solution of compound 2 (50 g, 0.19 mol) and ethyl acetate (106 ml) in 500 ml of CHCl$_3$. The solution was stirred at 40° C. overnight (about 18 hours). The mixture was washed with water, 1N HCl, brine, and concentrated to provide a white solid (50 g, yield 81.9%, TLC and $^1$H-NMR showed it was C0139-1 and some ethyl acetate).

$^1$H-NMR (400 MHz, CDCl$_3$): 7.56 (s, 2H); 3.36 (t, J=6.4 Hz, 4H); 2.53 (t, J=6.4 Hz, 4H);

d. Preparation of C0139

The mixture of compound C0139-1 (50 g, 154 mmol), compound 5 (38 g, 231 mmol), and toluenesulfonic acid monohydrate (1.46 g) in 150 mL of methanol was refluxed overnight (about 18 hours). The mixture was cooled to room temperature and filtered to provide a white solid (20 g, crude yield 27%). The white solid was recrystallized in methanol to obtain the pure title compound as a white solid (10.6 g, yield 14%, $^1$H-NMR and MS confirmed, 98% by HPLC).

$^1$H-NMR (400 MHz, CD$_3$OD): 7.61 (s, 2H); 7.14~7.22 (m, 5H); 3.71 (d, J=9.6 Hz, 2H); 3.64 (s, 2H); 3.01 (s, 2H); 2.50~2.56 (t, J=12.4 Hz, 2H); 2.03~2.05 (td, J=12.4 Hz, 4.4 Hz, 2H); 1.65 (d, J=6.8 Hz, 2H). MS (ESI) calcd. for C$_{20}$H$_{21}$Cl$_2$N$_3$O$_4$S (m/z): 469.06. found: 468.0 [M-1]$^-$, 469.8 [M+1]$^+$.

Preparation of Compound C0140M

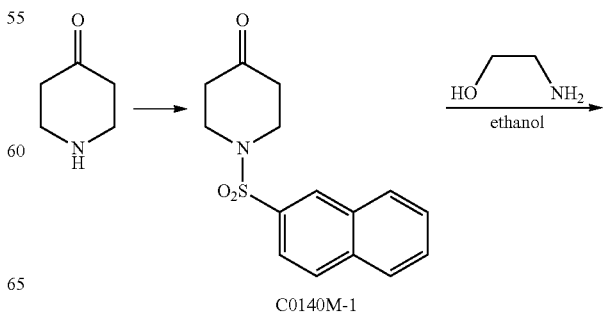

a. Preparation of Compound C0140M-1

Naphthalene-2-sulfonyl chloride (816 mg, 3.6 mmol) and triethylamine (606 mg, 6 mmol) was added to a solution of piperidin-4-one (300 mg, 3 mmol) in CHCl₃ (20 mL). The mixture was stirred at room temperature overnight (about 18 hours). The mixture was diluted with CHCl₃, and washed with H$_2$O (10 mL×3) and 0.1N HCl (10 mL×3), dried over Na$_2$SO$_4$ and concentrated to give the title product as white solid (832 mg, yield: 96%).

b. Preparation of Compound C0140M-2 p-Toluenesulfonic acid monohydrate (10 mg) and 2-aminoethanol (1 mL, 17.3 mmol) was added to a solution of compound C0140M-1 (500 mg, 1.73 mmol) in ethanol (20 mL). The mixture was stirred at room temperature for 2 hours. The precipitate formed was filtered off to give the product as white solid (420 mg, yield: 73%).

$^1$H NMR (400 MHz, CDCl$_3$): 8.38 (s, 1H), 8.33 (s, 1H); 7.99-7.90 (m, 6H); 7.79-7.74 (m, 2H); 7.67-7.61 (m, 4H); 3.86-3.79 (m, 4H); 3.53 (t, J=6.0 Hz, 2H); 2.66-2.55 (m, 4H); 1.64-1.58 (m, 2H); calcd for C$_{27}$H$_{26}$N$_2$O$_5$S$_2$ (m/z):522.13. found: 523.5 [M+1]$^+$.

Preparation of Compound C0141M a. Preparation of Compound C0141M-1

0.5 g of piperidin-4-one was dissolved in 25 mL of CHCl$_3$ and 1.4 mL of triethylamine was added. Then 915 mg of thiophene-2-sulfonyl chloride was added and the mixture was stirred at 70° C. overnight (about 18 hours). The solution was diluted with 50 mL of CHCl$_3$ and washed 0.1 M HCl (aq, 50 mL×3) and brine. The organic layer was dried over Na$_2$SO$_4$ and evaporated to obtain the title product as yellow solid (1.025 g, yield: 83.7%).

b. Preparation of Compound C0141M-2

The solution of C0141M-1 (1.02 g, 4.18 mmol), 2-aminoethanol (4.8 mL, 83.6 mmol), and p-toluenesulfonic acid monohydrate (24 mg, 0.125 mmol) in ethanol (30 ml) was stirred at room temperature for 2 days. The reaction solution was evaporated and the residue was dissolved in CHCl$_3$, and washed with saturated NaHCO$_3$ (aq) for (6×) and brine. The organic layer was dried over Na$_2$SO$_4$ and evaporated to obtain the title product as yellow oil. (1.175 g, yield: 98%)

c. Preparation of Compound C0141M 576 mg of C0141M-2 was dissolved in 10 mL of CHCl$_3$ and 0.56 mL of triethylamine was added. Thiophene-2-sulfonyl chloride (438 mg) was added and the mixture was stirred at 70° C. overnight (about 18 hours). The solution was diluted with 50 mL of CHCl$_3$ and washed 0.1 M HCl (aq, 50 mL×3) and brine. The organic layer was dried over Na$_2$SO$_4$ and evaporated to obtain 600 mg of the crude product as yellow solid. The crude product was purified by chromatography eluted with petroleum ether:ethyl acetate=20:1 to 2:1 to obtain 40 mg of the impure product as yellow solid, then recrystallized with CHCl$_3$ and petroleum ether to obtain 11 mg of the title product as white solid (11 mg, yield: 1.3%). The structure was confirmed by $^1$H NMR & LC-MS (target M+1=435), purity: 96.3% by HPLC, shown as follows.

$^1$H NMR (400 MHz, CDCl$_3$): 7.63-7.60 (m, 3H); 7.53 (d, J=4.0 Hz, 1H); 7.15 (t, J=4.0 Hz, 1H); 7.11 (t, J=4.0 Hz, 1H); 3.92 (t, J=6.0 Hz, 2H); 3.80-3.78 (m, 2H); 3.58 (t, J=6.0 Hz, 2H); 2.65-2.56 (m, 4H); 1.68 (d, J=10.2 Hz, 2H); MS (ESI) calcd for C$_{15}$H$_{18}$N$_2$O$_5$S$_4$ (m/z): 434.01 found: 435.1 [M+1]$^+$.

Preparation of Compound C0143M

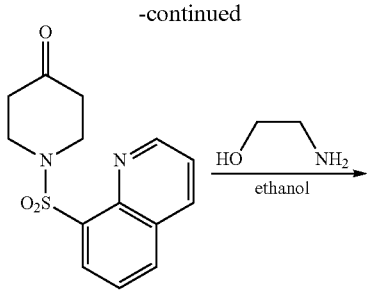

C0143M-1

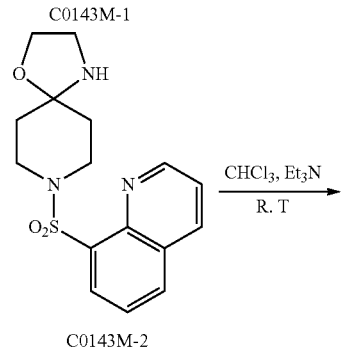

C0143M-2

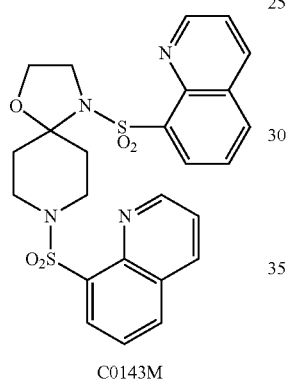

C0143M a. Preparation of Compound C0143M-1

8-Quinolinesulfonyl chloride (1.1 g, 4.8 mmol) and triethylamine (808 mg, 8 mmol) was added to a solution of piperidin-4-one (400 mg, 4 mmol) in CHCl$_3$ (20 mL). The mixture was stirred at room temperature overnight (about 18 hours). The mixture was diluted with CHCl$_3$, and washed with H$_2$O (10 mL×3) and 0.1N HCl (10 mL×3), dried over Na$_2$SO$_4$ and concentrated to give the title product as yellow solid (1.01 g, yield: 87%).

b. Preparation of Compound C0143M-2 p-Toluenesulfonic acid monohydrate (20 mg) and 2-aminoethanol (2.13 g, 35 mmol) was added to a solution of compound C0143M-1 (1.01 g, 3.5 mmol) in ethanol (30 mL). The mixture was stirred at room temperature overnight (about 18 hours). The mixture was concentrated in vacuo to dryness; the residue was diluted with dichloromethane, washed with saturated Na$_2$CO$_3$, dried over Na$_2$SO$_4$ and concentrated in vacuo to give the crude product as yellow solid (783 mg, yield: 67.2%).

c. Preparation of Compound C0143M

8-Quinolinesulfonyl chloride (588 mg, 2.59 mmol) and triethylamine (475 mg, 4.7 mmol) were added to a solution of compound C0143M-2 (783 mg, 2.35 mmol) in CHCl$_3$ (20 mL). The mixture was stirred at room temperature overnight (about 18 hours). The mixture was diluted with CHCl$_3$, and washed with H$_2$O (10 mL×3) and 0.1N HCl (10 mL×3), dried over Na$_2$SO$_4$ and concentrated to give the crude product. The crude product was purified by chromatography eluted with petroleum ether:ethyl acetate=5:1 to 2:1 to obtain 285 mg of C0134M-1 and 100 mg of the desired product with impurity. The crude product was purified by Pre-HPLC to obtain 30 mg of the title product as white solid (30 mg, yield: 2.4%). The structure was confirmed by NMR & LC-MS (target M+1=525), purity: 97.5% by HPLC.

$^1$H NMR (400 MHz, CDCl$_3$) δ 9.09-9.02 (m, 2H), 8.44 (d, J=7.6 Hz, 1H), 8.38 (d, J=7.6 Hz, 1H), 8.30-8.25 (m, 2H), 8.04 (d, J=8.0 Hz, 2H), 7.70-7.50 (m, 4H), 4.44 (t, J=6.0 Hz, 2H), 3.99 (d, J=11.6 Hz, 2H), 3.85 (t, J=6.0 Hz, 2H), 2.89 (t, J=12.4 Hz, 2H), 2.26 (dt, J=12.8, 4.4 Hz, 2H), 1.35 (d, J=12.4 Hz, 2H). LC-MS (ESI) calcd for C$_{25}$H$_{24}$N$_4$O$_5$S$_2$ (m/z): 524.12. found: 525.3 [M+1]$^+$.

Preparation of Compound C0144M

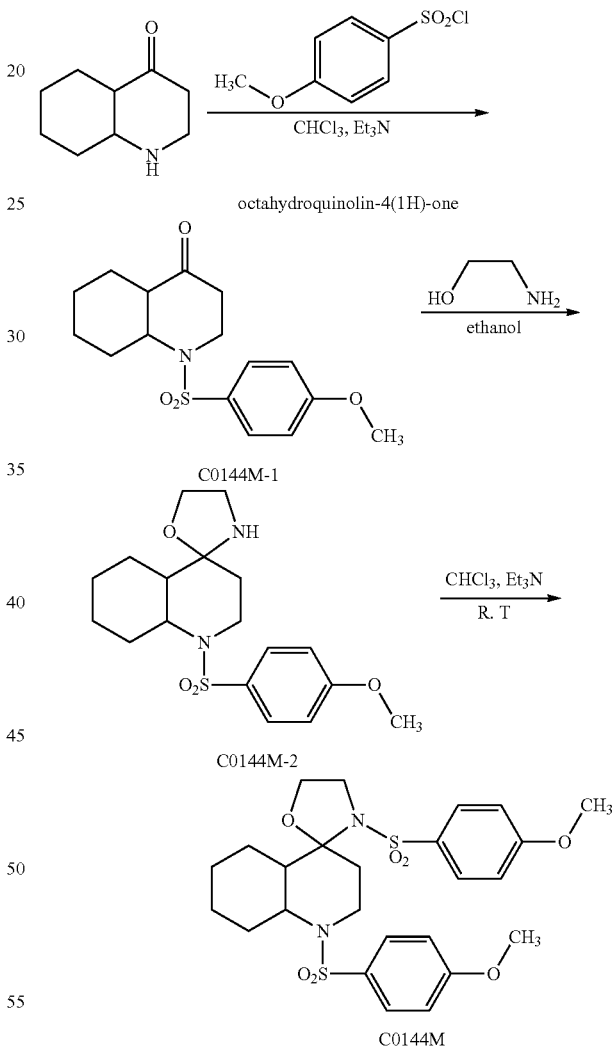

a. Preparation of Compound C0144M-1

4-Methoxybenzenesulfonyl chloride (453 mg, 2.2 mmol) and triethylamine (404 mg, 4 mmol) were added to a solution of octahydroquinolin-4(1H)-one (306 mg, 2 mmol) in CHCl$_3$ (15 mL). The mixture was stirred at room temperature overnight (about 18 hours). The mixture was diluted with CHCl$_3$, and washed with H$_2$O (10 mL×3) and 0.1N HCl (10 mL×3), dried over Na$_2$SO$_4$ and concentrated to give the title product as yellow oil (612 mg, yield: 95%).

b. Preparation of Compound C0144M-2 p-Toluenesulfonic acid monohydrate (10 mg) and 2-aminoethanol (1.15 g, 18.9 mmol) were added to a solution of compound C0144M-1 (612 mg, 1.89 mmol) in ethanol (20 mL). The mixture was stirred at room temperature overnight (about 18 hours). The mixture was concentrated in vacuo to dryness, the residue was diluted with dichloromethane, washed with saturated $Na_2CO_3$, dried over $Na_2SO_4$ and concentrated in vacuo to give the crude product as yellow gum (556 mg, yield: 80.4%).

c. Preparation of Compound C0144M

4-Methoxybenzenesulfonyl chloride (344 mg, 1.67 mmol) and triethylamine (303 mg, 3 mmol) was added to a solution of compound C0144M-2 (556 mg, 1.5 mmol) in $CHCl_3$ (15 mL). The mixture was stirred at room temperature overnight (about 18 hours). The mixture was diluted with $CHCl_3$, and washed with $H_2O$ (10 mL×3) and 0.1 N HCl (10 mL×3), dried over $Na_2SO_4$ and concentrated to give the crude product. The crude product was purified by chromatography eluted with petroleum ether:ethyl acetate=10:1 to 5:1 to obtain 98 mg of product as white solid.

$^1$H NMR (400 MHz, $CDCl_3$) δ 7.82 (d, J=6.8 Hz, 2H), 7.63 (d, J=6.8 Hz, 2H), 7.02 (d, J=6.8 Hz, 2H), 6.95 (d, J=6.8 Hz, 2H), 4.02-3.97 (m, 2H), 3.88 (s, 3H), 3.86 (s, 3H) 3.78-3.74 (m, 2H), 3.55-3.54 (m, 1H), 3.31-3.25 (m, 2H), 2.54-2.52 (m, 1H), 2.18 (dt, J=4.8, 13.2 Hz, 1H), 1.72-1.70 (m, 1H), 1.63-1.59 (m, 3H), 1.30-1.2 (m, 3H), 1.20-0.90 (m, 2H). LC-MS (ESI) calcd for $C_{25}H_{32}N_2O_7S_2$ (m/z): 536.17. found: 537.3 $[M+1]^+$.

Preparation of Compound C0145M

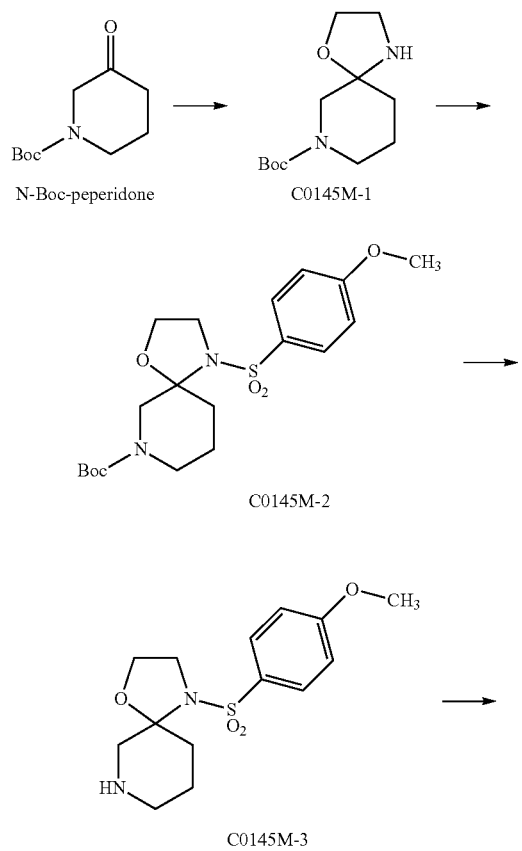

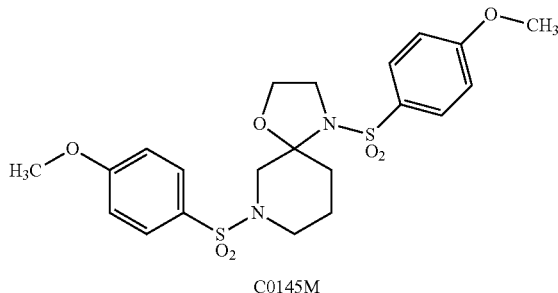

C0145M a. Preparation of Compound C0145M-1

A solution of N-Boc-piperidin-4-one (500 mg, 2.67 mmol) and 2-aminoethanol (0.55 mL, 9.34 mmol) in ethanol (4 mL) was stirred at room temperature overnight (about 18 hours). The solvent was removed under reduced pressure. The residue was diluted with $CH_2Cl_2$ (50 mL) and washed with saturated aqueous $Na_2CO_3$ (30 mL×6). The organic phase was dried over anhydrous $Na_2SO_4$, then concentrated to give target product as yellow oil (614 mg; yield: 95%).

b. Preparation of Compound C0145M-2

4-Methoxybenzene-1-sulfonyl chloride (626 mg, 3.04 mmol) and triethylamine (0.7 mL) were added to a solution of compound C0145M-1 (614 mg, 2.53 mmol) in chloroform (5 mL). The mixture was stirred at room temperature overnight (about 18 hours). The solvent was removed under reduced pressure. The residue was purified by column chromatography (petroleum ether:dichloromethane=1:1) to obtain target product as white solid (500 mg; yield: 48%).

c. Preparation of Compound C0145M-3

$CF_3COOH$ (0.6 mL) was added to the solution of compound C0145M-2 (500 mg, 1.21 mmol) in 6 mL dichloromethane and the mixture was kept stirring for 0.5 hour at room temperature. Then $CH_3CH_2OH/NH_3$ (20 mL) was added to the reaction mixture. The solvent was removed under reduced pressure. The residue was diluted with dichloromethane (20 mL) and the white solid was precipitated. TLC showed that the solid was $CF_3COONH_4$. Then the mixture was filtered and the filtrate was concentrated. The residue was purified by column chromatography ($CH_2Cl_2:CH_3OH=10:1$) to obtain the product as yellow solid (290 mg; yield: 76%).

d. Preparation of Compound C0145M

4-Methoxybenzene-1-sulfonyl chloride (214 mg, 1.0 mmol) and triethylamine (0.25 mL) were added to a solution of compound C0145M-3 (270 mg, 0.865 mmol) in chloroform (5 mL). The mixture was stirred at room temperature overnight (about 18 hours). The solvent was removed under reduced pressure. The residue was diluted in dichloromethane (DCM) (30 mL). The solution was washed by 0.1 N HCl (30 mL×2) and brine. The organic phase was dried over anhydrous $Na_2SO_4$ and concentrated. The residue was purified by column chromatography (dichloromethane) to obtain compound 4 as white solid (250 mg; yield: 60%).

$^1$H NMR (400 MHz, $CDCl_3$): 7.75-7.70 (m, 4H); 7.02-6.96 (m, 4H); 4.05-3.98 (m, 2H); 3.89 (s, 3H); 3.88 (s, 3H); 3.75 (t, J=11.5 Hz, 2H); 3.60-3.50 (m, 1H); 3.41 (dd, J=15.2, 7.6 Hz, 1H); 2.86 (d, J=12.0 Hz, 1H); 2.35-2.24 (m, 2H); 1.99-1.78 (m, 1H); 1.68 (t, J=12.2 Hz, 2H); LCMS (ESI) calcd for $C_{21}H_{26}N_2O_7S_2$ (m/z): 482.12 found: 483.3$[M+1]^+$.

Preparation of Compound C0146M

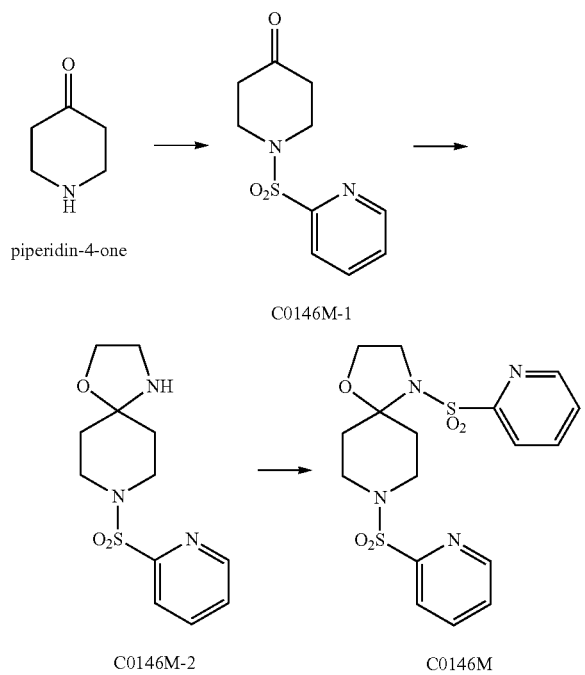

a. Preparation of Compound C0146M-1

Pyridine-2-sulfonyl chloride (20 mg, 0.11 mmol) was added to a solution of piperidin-4-one (14 mg, 0.136 mmol) in pyridine (0.6 ml). The mixture was stirred at room temperature overnight (about 18 hours). TLC showed that there was no new product. Alternate reaction conditions are being sought.

Preparation of Compound C0149M

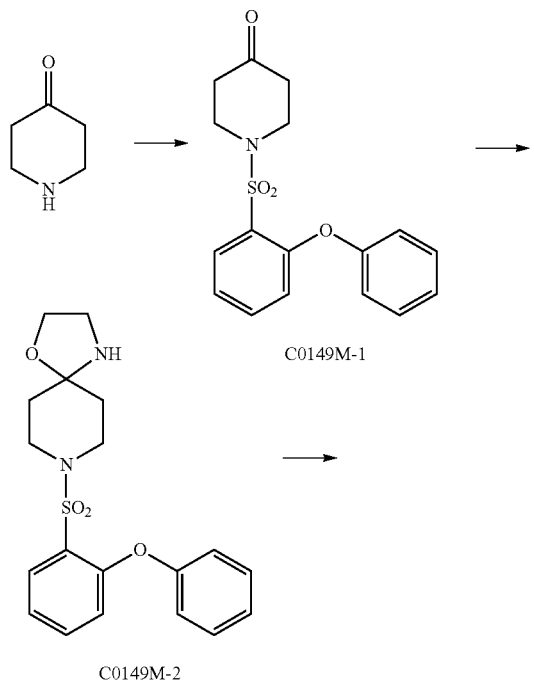

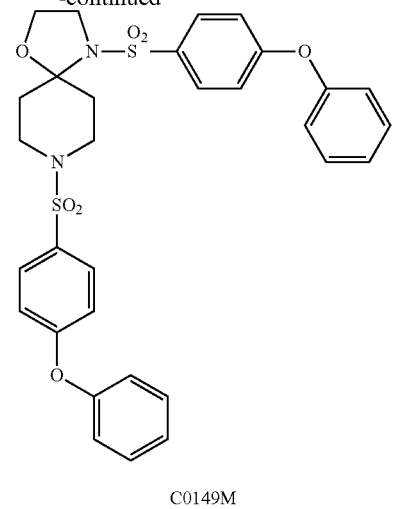

a. Preparation of Compound C0149M-1

4-Phenoxybenzenesulfonyl chloride (500 mg, 1.86 mmol) and triethylamine (404 mg, 4 mmol) was added to a solution of piperidin-4-one (202 mg, 2.05 mmol) in CHCl₃ (7 mL). The mixture was stirred at room temperature overnight (about 18 hours). The mixture was diluted with CHCl₃, and washed with H₂O (10 mL×3) and 0.1N HCl (10 mL×3), dried over Na₂SO₄ and concentrated to give 417 mg of the title product (67.8% yield).

b. Preparation of Compound C0149M-2 p-Toluenesulfonic acid monohydrate (10 mg) and 2-aminoethanol (769 mg, 12.6 mmol) were added to a solution of C0149M-1 (417 mg, 1.26 mmol) in ethanol (15 mL). The mixture was stirred at room temperature overnight (about 18 hours). The mixture was concentrated in vacuo to dryness, the residue was diluted with dichloromethane, washed with saturated Na₂CO₃, dried over Na₂SO₄ and concentrated in vacuo to give the crude product as white solid (434 mg, yield: 92.3%).

c. Preparation of Compound C0149M

4-Phenoxybenzenesulfonyl chloride (223 mg, 0.83 mmol) was added to a solution of compound C0149M-2 (282 mg, 0.75 mmol) in pyridine (3 mL). The mixture was stirred at room temperature overnight (about 18 hours). The mixture was concentrated in vacuo, the residue was diluted with dichloromethane, and washed with 1N HCl (10 mL×3), dried over Na₂SO₄ and concentrated to give the crude product. The crude product was purified by chromatography eluted with petroleum ether:ethyl acetate=10:1 to 1:1 to obtain the title product (60 mg, white solid, purity: 94%) and an impure product (168 mg, yellow gum, purity: 88.9%). The product was recrystallized with CHCl₃ and hexane to obtain 45 mg of the title product.

¹H NMR (400 MHz, CDCl₃) δ 7.78 (d, J=8.8 Hz, 2H), 7.71 (d, J=8.8 Hz, 2H), 7.42 (m, 4H), 7.26-7.19 (m, 2H), 7.14-7.01 (m, 8H), 3.89 (t, J=6.4 Hz, 2H), 3.78-3.75 (m, 2H), 3.49 (t, J=6.0 Hz, 2H), 2.66-2.49 (m, 4H), 1.62 (d, J=10.6 Hz, 2H). LC-MS (ESI) calcd for $C_{31}H_{30}N_2O_2S_2$ (m/z): 606.71. found: 607.3 [M+1]⁺.

Preparation of Compound C0150M

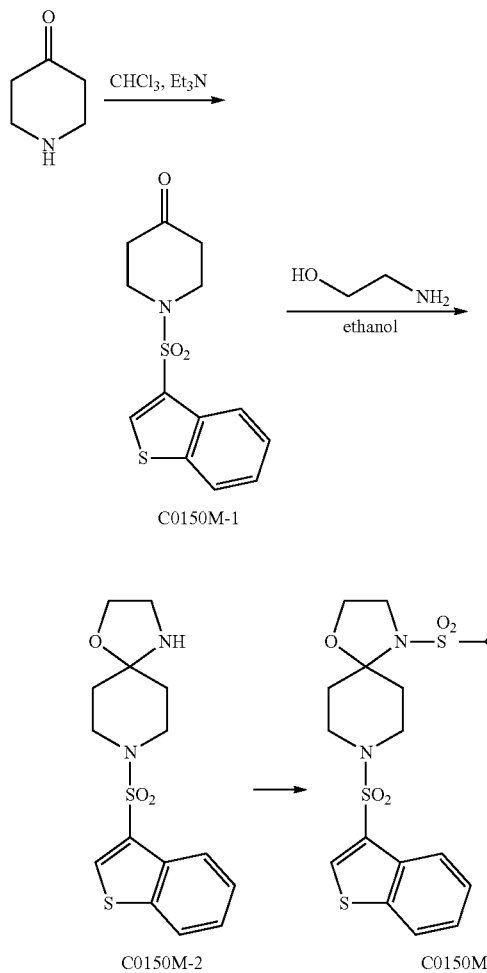

C0150M-1

C0150M-2        C0150M a. Preparation of Compound C0150M-1

A solution of piperidin-4-one (47 mg, 0.47 mmol) in chloroform (3 mL) was treated with 1-benzothiophene-3-sulfonyl chloride (100 mg, 0.43 mmol) and triethylamine (0.12 mL). The mixture was stirred at room temperature overnight (about 18 hours). The solvent was removed under reduced pressure. The residue was diluted in dichloromethane (30 mL). The solution was washed by 0.1 N HCl (30 mL×2) and brine. The organic phase was dried over anhydrous $Na_2SO_4$ and concentrated to obtain target product as light yellow solid (120 mg; yield: 94%).

b. Preparation of Compound C0150M-2

A solution of C0150M-1 (217 mg, 0.74 mmol) in ethanol (10 mL) was treated with p-toluenesulfonic acid monohydrate (6 mg) and 2-aminoethanol (452 mg, 7.4 mmol). The mixture was stirred at room temperature for 5 hours. The mixture was concentrated in vacuo to dryness, the residue was diluted with dichloromethane, washed with saturated $Na_2CO_3$, dried over $Na_2SO_4$ and concentrated in vacuo to give the crude product as light yellow solid (228 mg, yield: 91.2%)

c. Preparation of Compound C0150M

A solution of compound C0150M-2 (228 mg, 0.67 mmol) in pyridine (3 mL) was treated with 4-benzothiophene-3-sulfonyl chloride (173 mg, 0.74 mmol). The mixture was stirred at room temperature overnight (about 18 hours). The mixture was concentrated in vacuo, the residue was diluted with dichloromethane, and washed with 1N HCl (10 mL×3), dried over $Na_2SO_4$ and concentrated to give the crude product. The crude product was purified by chromatography eluted with petroleum ether:ethyl acetate=5:1 to 1:1 to obtain the title product (200 mg, white solid).

$^1$H NMR (400 MHz, CDCl$_3$) δ 8.28 (d, J=7.6 Hz, 1H), 8.18-8.21 (m, 2H), 8.08 (s, 1H), 7.90 (t, J=8.4 Hz, 2H), 7.47-7.52 (m, 4H), 3.93 (dt, J=1.6, 12.0 Hz, 2H), 3.83 (t, J=6.4 Hz, 2H), 3.53 (t, J=6.0 Hz, 2H), 2.72 (t, J=12.0 Hz, 2H), 2.58 (dt, J=4.4, 12.8 Hz, 2H), 1.68 (d, J=12.4 Hz, 2H). LC-MS (ESI) calcd for $C_{23}H_{22}N_2O_5S_4$ (m/z): 534.69. found: 535.3 [M+1]$^+$.

Preparation of Compound C0151M

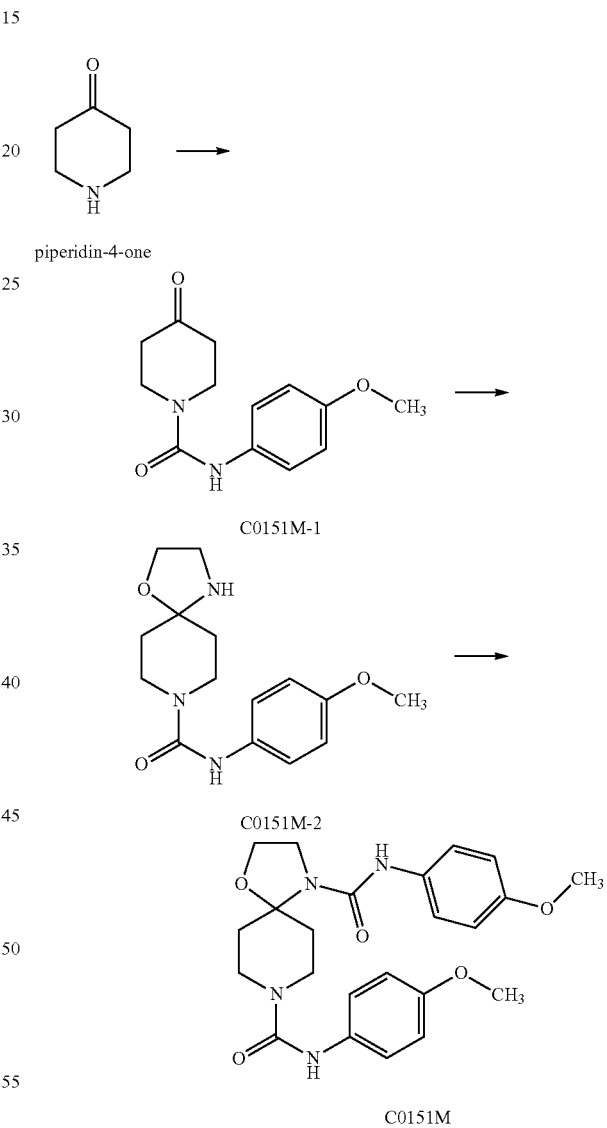

piperidin-4-one

C0151M-1

C0151M-2

C0151M a. Preparation of Compound C0151M-1

The mixture of piperidin-4-one (643 mg, 6.5 mmol) and 1-isocyanato-4-methoxybenzene (500 mg, 3.4 mmol) and $K_2CO_3$ (1.1 g, 8.0 mmol) in dichloromethane (20 mL) was stirred overnight (about 18 hours) at room temperature. To the reaction mixture was added 5 mL water and the water phase was extracted with dichloromethane. The combined organic layer was washed with 1N HCl and brine, dried, concentrated to obtain the product (800 mg, yield: 96%).

b. Preparation of Compound C0151M-2

Ethanolamine (0.4 mL) was added to a solution of C0151M-1 (0.5 g, 2.0 mmol) in ethanol (5.0 mL). The mixture was stirred at room temperature for 4 hours. The solvent was removed under reduced pressure. The residue was diluted with $CH_2Cl_2$ and washed with saturated aqueous $Na_2CO_3$. The organic phase was dried over anhydrous $Na_2SO_4$, concentrated to obtain the title product as white solid (530 mg, yield: 90%).

c. Preparation of Compound C0151M

1-Isocyanato-4-methoxybenzene (268 mg, 1.8 mmol) and $K_2CO_3$ (373 mg, 2.7 mmol) were added to a solution of compound C0151M-2 (530 mg, 1.8 mmol) in dichloromethane (10 mL). The mixture was stirred at room temperature overnight (about 18 hours). The mixture was filtered and the solvent was removed under reduced pressure. The residue was washed with diethyl ether and then diluted with $CH_2Cl_2$. The organic layer was washed with water and dried over anhydrous $Na_2SO_4$, concentrated to obtain the title product as white solid (759 mg, yield: 95.2%).

$^1$H NMR (400 MHz, CDCl3): 7.25-7.19 (m, 4H); 6.86-6.81 (m, 4H); 6.29 (s, 1H); 6.19 (s, 1H); 4.10 (t, J=5.6 Hz, 2H); 4.10 (d, J=12.4 Hz, 2H); 3.78 (s, 3H); 3.77 (s, 3H); 3.16 (dt, J=2.0, 13.2 Hz, 2H); 2.79 (dt, J=5.6, 13.6 Hz, 2H); 1.61 (d, J=12.8 Hz, 2H); MS (ESI) calcd for $C_{23}H_{28}N_4O_5$ (m/z): 440.49. found: 441.1 [M+1]$^+$.

Preparation of Compound C0152M

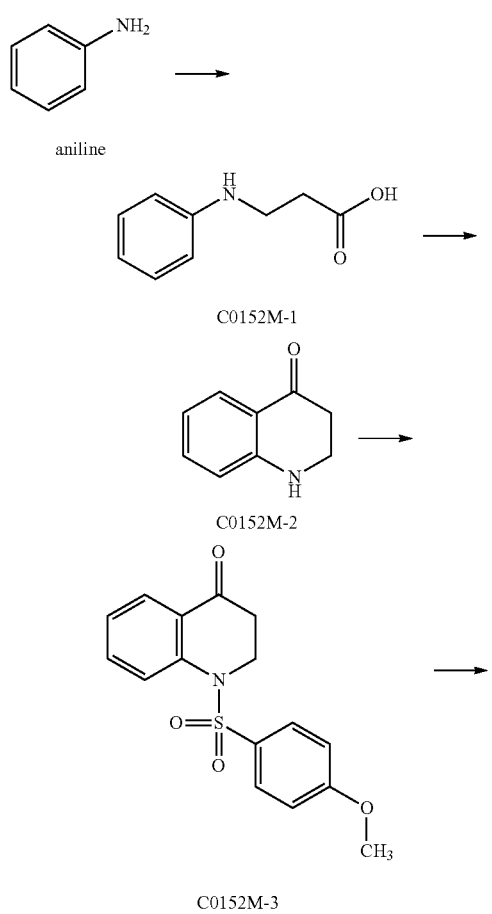

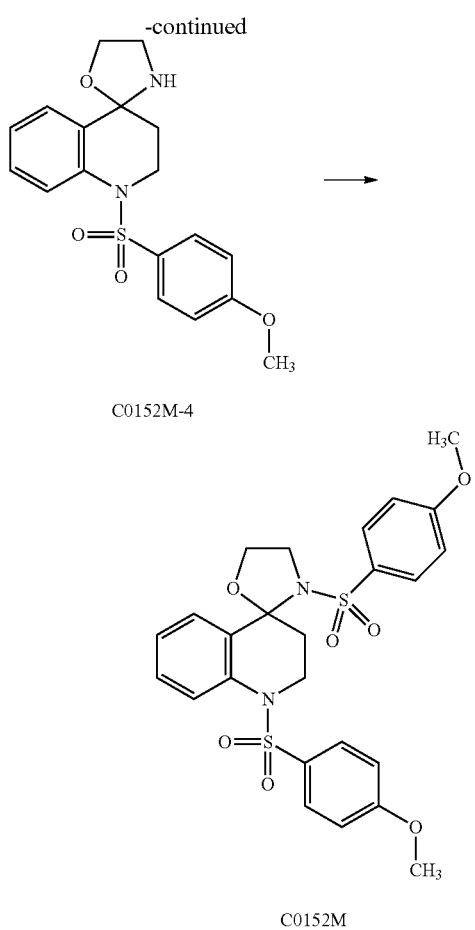

a. Preparation of Compound C0152M-1

A mixture of aniline (5 g, 53.8 mmol), 3-bromopropanoic acid (8.2 g, 53.8 mmol), triethylamine (10.8 g, 107.6 mmol), sodium iodide (0.05 g), and tetrahydrofuran (50 mL) was stirred at reflux overnight (about 18 hours). The reaction mixture was cooled down and filtered. The filtrate was concentrated under reduced pressure. The residue was diluted with dichloromethane (DCM) (100 mL) and washed with water once. The organic phase was dried over anhydrous $Na_2SO_4$ and concentrated. The residue was purified by column chromatography ($CH_2Cl_2$:$CH_3OH$:$CH_3COOH$=200:1:1) to obtain compound C0152M-1 as brown oil (3 g; yield: 33%)

b. Preparation of Compound C0152M-2

Compound C0152M-1 (1.5 g, 9 mmol) and polyphosphoric acid (1.5 g) were heated at 100° C. for 1 hour. After cooling to 0° C., ice-water was added into the reaction mixture. The aqueous phase was neutralized to pH 7 with saturated aqueous $KHCO_3$ at 0° C. and basified to pH 12 with saturated aqueous $K_2CO_3$. The aqueous layer was extracted with dichloromethane (150 mL×4). The organic layer were dried over anhydrous $Na_2SO_4$, filtered, and evaporated under reduced pressure to give a crude product which was purified by column chromatography (petroleum ether:ethyl acetate=5:1) to give product as yellow oil (94 mg; yield: 7.1%)

c. Preparation of Compound C0152M-3

4-Methoxybenzene-1-sulfonyl chloride (159 mg, 0.77 mmol) was added to a solution of compound C0152M-2 (160 mg, 1.08 mmol) in pyridine (5 mL). The mixture was stirred at room temperature overnight (about 18 hours). The solvent was removed under reduced pressure. The residue was diluted in dichloromethane (30 mL) and washed with 0.1 N HCl (30 mL×3) and brine. The organic phase was dried over anhydrous $Na_2SO_4$ and concentrated to obtain the crude product. The crude product was purified by column chromatography (petroleum ether:ethyl acetate=5:1) to obtain the title product as white solid (130 mg; yield: 64%)

d. Preparation of Compound C0152M-4

To a solution of C0152M-3 (170 mg, 0.536 mmol) and 2-aminoethanol (327 mg, 5.36 mmol) in ethanol (10 mL) was add 4-methylbenzenesulfonic acid mono-hydrate (3 mg, 0.016 mmol). The reaction was stirred at room temperature overnight (about 18 hours). The solvent was removed under reduced pressure. The residue was diluted with $CH_2Cl_2$ (50 mL) and washed with saturated aqueous $Na_2CO_3$ (30 mL×6). The organic phase was dried over anhydrous $Na_2SO_4$, then concentrated to give compound C0152M-4 as yellow solid (175 mg; yield: 90%).

e. Preparation of Compound C0152M

4-Methoxybenzene-1-sulfonyl chloride (85 mg, 0.41 mmol) was added to a solution of compound C0152M-4 (123 mg, 0.34 mmol) in chloroform (5 mL) and triethylamine (69 mg, 0.68 mmol)). The mixture was stirred under reflux for 4 hours. The reaction mixture was cooled down and diluted with chloroform (40 mL). The organic layer was washed with 0.1 N HCl (30 mL×3), water (1×) and brine (2×). Then it was dried over anhydrous $Na_2SO_4$ and concentrated to obtain the crude product.

Preparation of Compound C0154M

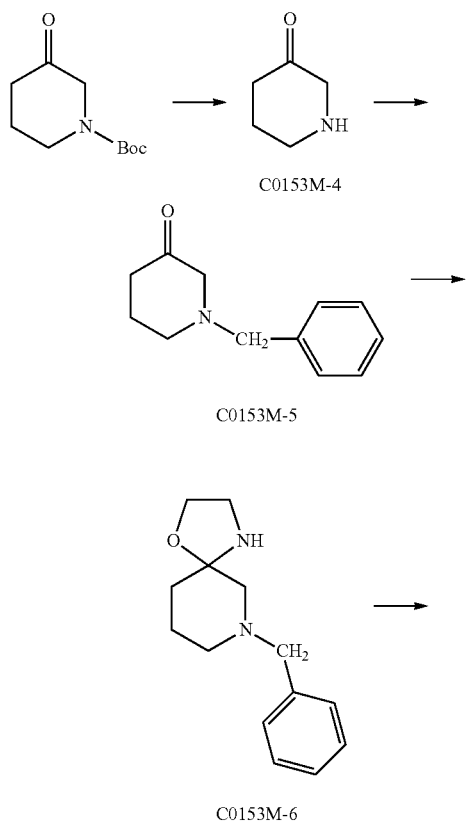

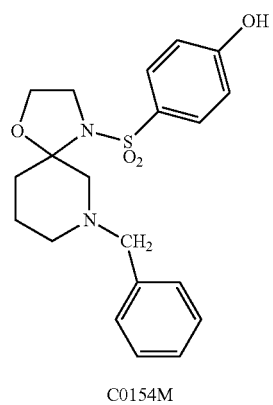

C0154M a. Preparation of Compound C0153M-4 t-Butyl-3-oxopiperidine-1-carboxylate (500 mg, 2.51 mmol) in $HCl/CH_3OH$ (12.5 mL) was heated to reflux for 0.5 hours. The solution was cooled to room temperature and evaporated to dryness to obtain the HCl salt of the title compound as yellow solid (330 mg, yield: 97%).

b. Preparation of Compound C0153M-5

Piperidin-3-one hydrochloride (330 mg) was added to 10 mL of acetonitrile. Then, 1.38 g of $K_2CO_3$ and 855 mg of benzyl bromide were added to the solution. The mixture was heated at reflux overnight (about 18 hours). The mixture was filtered and the filtrate was evaporated to dryness. The residue was purified by chromatography eluted with dichloromethane:methanol=30:1 to obtain the title product as yellow oil (260 mg, yield: 58.3%).

c. Preparation of Compound C0153M-6

The solution of C0153M-5 (250 mg, 1.32 mmol), 2-aminoethanol (282 mg, 4.62 mmol) in $CH_3CH_2OH$ (3 mL) was stirred at room temperature overnight (about 18 hours). The reaction solution was evaporated to dryness and the residue was dissolved in dichloromethane and washed with saturated $Na_2CO_3$ (aq) (6×) and brine. The organic layer was dried over $Na_2SO_4$ and evaporated to dryness to obtain the title product as a yellow oil (301 mg, yield: 98%).

d. Preparation of Compound C0154M

This compound is made using conditions and procedures discussed elsewhere herein.

Each of the patents, patent applications and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

What is claimed:

1. A compound or its pharmaceutically acceptable salt that is

[chemical structure]

or

[chemical structure]

-continued

[chemical structure]

said compound binding to the biotinylated pentapeptide of filamin A (Bn-FLNA) of SEQ ID NO: 1, and inhibiting about 60-70 percent of the FITC-labeled naloxone binding when present at a 10 µM concentration and using unlabeled naltrexone as the control inhibitor at the same concentration.

2. A pharmaceutical composition comprising an analgesic effective amount of a compound of claim 1 or its pharmaceutically acceptable salt dissolved or dispersed in a physiologically tolerable carrier.

3. A method of reducing one or both of inflammation and pain in a host mammal in need thereof that comprises administering to that host mammal a pharmaceutical composition containing an analgesic effective amount of a compound of claim 1 or its pharmaceutically acceptable salt, optionally including both individual enantiomeric forms, a racemate, diastereomers and mixtures thereof, dissolved or dispersed in a physiologically tolerable carrier.

4. The method according to claim 3, wherein said host mammal is selected from the group consisting of a primate, a laboratory rodent, a companion animal, and a food animal.

5. The method according to claim 3, wherein said composition is administered a plurality of times over a period of days.

6. The method according to claim 5, wherein said composition is administered a plurality of times in one day.

7. The method according to claim 3, wherein said composition is administered perorally.

8. The method according to claim 3, wherein said composition is administered parenterally.

* * * * *